US009493845B2

(12) United States Patent
Cao et al.

(10) Patent No.: US 9,493,845 B2
(45) Date of Patent: Nov. 15, 2016

(54) METHODS FOR IDENTIFYING COMPOUNDS THAT MODULATE UNTRANSLATED REGION-DEPENDENT GENE EXPRESSION AND METHODS OF USING SAME

(71) Applicant: PTC Therapeutics, Inc., South Plainfield, NJ (US)

(72) Inventors: Liangxian Cao, Parlin, NJ (US); Panayiota Trifillis, Piscataway, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 0 days.

(21) Appl. No.: 13/873,543

(22) Filed: Apr. 30, 2013

(65) Prior Publication Data
US 2013/0347133 A1 Dec. 26, 2013

Related U.S. Application Data

(63) Continuation of application No. 10/543,033, filed as application No. PCT/US2004/001643 on Jan. 21, 2004, now Pat. No. 8,460,864.

(60) Provisional application No. 60/441,637, filed on Jan. 21, 2003.

(51) Int. Cl.
C12Q 1/68 (2006.01)
C07K 14/52 (2006.01)
G01N 33/50 (2006.01)

(52) U.S. Cl.
CPC ............. *C12Q 1/6897* (2013.01); *C07K 14/52* (2013.01); *C12Q 1/6886* (2013.01); *G01N 33/5011* (2013.01); *G01N 33/5023* (2013.01); *C12Q 2600/136* (2013.01); *C12Q 2600/158* (2013.01); *G01N 2333/515* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 3,346,381 A | 10/1967 | Grieg | |
| 5,439,797 A | 8/1995 | Tsien et al. | |
| 5,444,149 A | 8/1995 | Keene et al. | |
| 5,518,885 A | 5/1996 | Raziuddin et al. | |
| 5,587,300 A | 12/1996 | Malter | |
| 5,691,145 A | 11/1997 | Pitner et al. | |
| 5,698,427 A | 12/1997 | Keene et al. | |
| 5,700,660 A | 12/1997 | Leonard et al. | |
| 5,731,343 A | 3/1998 | Feng et al. | |
| 5,734,039 A * | 3/1998 | Calabretta et al. ......... 536/24.5 |
| 5,776,738 A | 7/1998 | Dell'Orco, Sr. et al. | |
| 5,843,770 A | 12/1998 | Ill et al. | |
| 5,849,520 A | 12/1998 | Leonard et al. | |
| 5,859,227 A | 1/1999 | Giordano et al. | |
| 5,908,779 A | 6/1999 | Carmichael et al. | |
| 5,928,888 A | 7/1999 | Whitney | |
| 5,990,298 A | 11/1999 | Carmichael et al. | |
| 6,004,749 A | 12/1999 | Giordano et al. | |
| 6,010,856 A | 1/2000 | Ulevitech et al. | |
| 6,057,437 A | 5/2000 | Kamiya et al. | |
| 6,107,029 A | 8/2000 | Giordano | |
| 6,117,848 A * | 9/2000 | Monia et al. ............... 514/44 A |
| 6,159,709 A | 12/2000 | Korneluk et al. | |
| 6,171,821 B1 | 1/2001 | Korneluk et al. | |
| 6,203,976 B1 * | 3/2001 | Foulkes et al. ............. 435/6.12 |
| 6,203,982 B1 | 3/2001 | Nunokawa et al. | |
| 6,214,563 B1 | 4/2001 | Negulescu et al. | |
| 6,221,587 B1 | 4/2001 | Ecker et al. | |
| 6,221,612 B1 | 4/2001 | Knapp et al. | |
| 6,232,070 B1 | 5/2001 | Shuman | |
| 6,265,167 B1 | 7/2001 | Carmichael et al. | |
| 6,265,546 B1 | 7/2001 | Cohen et al. | |
| 6,284,882 B1 | 9/2001 | Wu-Wong et al. | |
| 6,303,295 B1 | 10/2001 | Taylor et al. | |
| 6,331,170 B1 | 12/2001 | Ordway | |
| 6,331,396 B1 | 12/2001 | Silverman et al. | |
| 6,399,373 B1 | 6/2002 | Bougueleret | |
| 6,448,007 B1 | 9/2002 | Giordano et al. | |
| 6,455,280 B1 | 9/2002 | Edwards et al. | |
| 6,465,176 B1 | 10/2002 | Giordano et al. | |
| 6,476,208 B1 | 11/2002 | Cohen et al. | |
| 6,528,060 B1 | 3/2003 | Nicolette | |
| 6,617,493 B1 | 9/2003 | Fader | |
| 6,627,797 B1 | 9/2003 | Duvick et al. | |
| 6,630,589 B1 | 10/2003 | Giordano et al. | |

(Continued)

FOREIGN PATENT DOCUMENTS

EP 1 176 196 1/2002
EP 1 604 011 12/2005

(Continued)

OTHER PUBLICATIONS

Bakheet et al. (Nucleic Acids Research, 2001, vol. 29, No. 1, p. 246-254).*

(Continued)

*Primary Examiner* — Stephanie K Mummert

(74) *Attorney, Agent, or Firm* — Jones Day

(57) ABSTRACT

The present invention relates to methods for identifying compounds that modulate untranslated region-dependent expression of a target gene. The invention particularly relates to using untranslated regions of a target gene or fragments thereof linked to a reporter gene to identify compounds that modulate untranslated region-dependent expression of a target gene. The methods of the present invention provide a simple, sensitive assay for high-throughput screening of libraries of compounds to identify pharmaceutical leads.

20 Claims, 11 Drawing Sheets

(56) References Cited

U.S. PATENT DOCUMENTS

Figure 1:
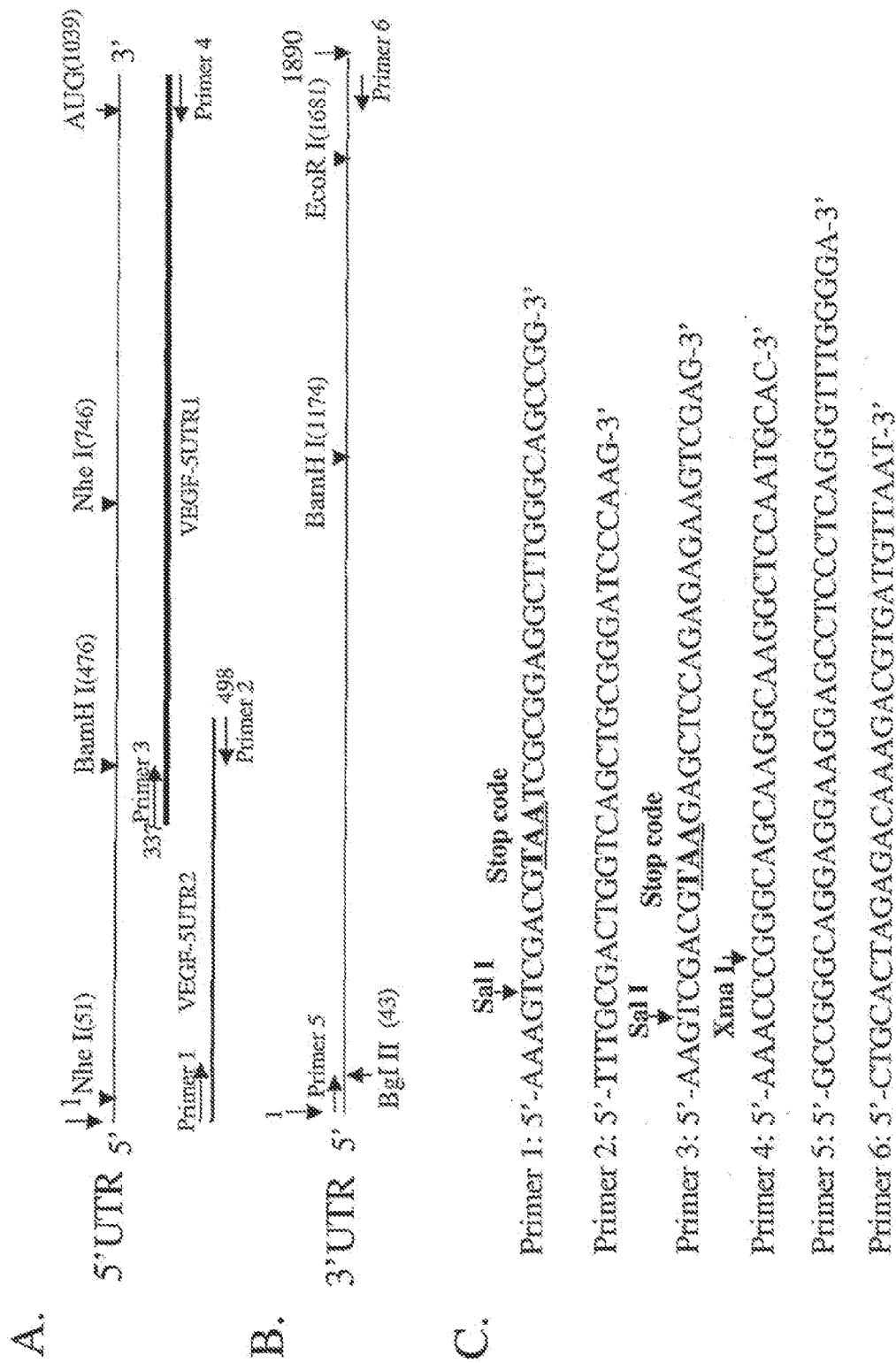

| | | |
|---|---|---|
| 6,635,671 B1 | 10/2003 | Kastelic et al. |
| 6,638,522 B1 | 10/2003 | Mulye |
| 6,645,747 B1 | 11/2003 | Hallahan et al. |
| 6,653,132 B1 | 11/2003 | Keshet et al. |
| 6,667,152 B2 | 12/2003 | Miles et al. |
| 6,872,850 B2 | 3/2005 | Giordano et al. |
| 7,078,171 B2 | 7/2006 | Giordano et al. |
| 7,371,726 B2 | 5/2008 | Junker et al. |
| 7,598,079 B2 | 10/2009 | Kastelic et al. |
| 7,598,361 B2 | 10/2009 | Cheikh et al. |
| 7,601,840 B2 | 10/2009 | Moon et al. |
| 7,767,689 B2 | 8/2010 | Moon et al. |
| 8,076,352 B2 | 12/2011 | Cao et al. |
| 8,076,353 B2 | 12/2011 | Cao et al. |
| 8,283,115 B1 | 10/2012 | Friesen et al. |
| 8,283,116 B1 | 10/2012 | Friesen et al. |
| 8,426,194 B2 | 4/2013 | Cao et al. |
| 8,460,864 B2 | 6/2013 | Cao et al. |
| 2002/0006661 A1 | 1/2002 | Green et al. |
| 2002/0132257 A1 | 9/2002 | Giordano et al. |
| 2003/0135870 A1 | 7/2003 | Cheikh et al. |
| 2003/0199453 A1 | 10/2003 | Giordano et al. |
| 2004/0063120 A1 | 4/2004 | Beer et al. |
| 2004/0091866 A1 | 5/2004 | Giordano et al. |
| 2004/0138282 A1 | 7/2004 | Greig et al. |
| 2004/0152117 A1 | 8/2004 | Giordano et al. |
| 2004/0231007 A1 | 11/2004 | Kastelic et al. |
| 2005/0048549 A1 | 3/2005 | Cao et al. |
| 2007/0072186 A1 | 3/2007 | Mehta et al. |
| 2009/0068654 A1 | 3/2009 | Kastelic et al. |

FOREIGN PATENT DOCUMENTS

| | | |
|---|---|---|
| EP | 1 761 638 | 3/2007 |
| GB | 9828707.1 | 12/1998 |
| GB | 9828709.7 | 12/1998 |
| JP | 2001/46086 A | 2/2001 |
| JP | 2008/507271 | 3/2008 |
| WO | WO 95/28485 | 10/1995 |
| WO | WO 95/33831 | 12/1995 |
| WO | WO 97/25860 | 7/1997 |
| WO | WO 97/25860 A | 7/1997 |
| WO | WO 98/39484 | 9/1998 |
| WO | WO 93/20212 | 10/1999 |
| WO | WO 00/04051 | 1/2000 |
| WO | WO 00/05356 | 2/2000 |
| WO | WO00/39314 | 7/2000 |
| WO | WO 00/46247 | 8/2000 |
| WO | WO 01/84155 | 8/2001 |
| WO | WO 02/48150 | 6/2002 |
| WO | WO 02/077609 | 10/2002 |
| WO | WO 02/083953 | 10/2002 |
| WO | WO 03/087815 | 10/2003 |
| WO | WO 2004/065561 | 8/2004 |
| WO | WO 2005/049868 | 6/2005 |
| WO | WO 2005/095615 | 10/2005 |
| WO | WO 2005/118857 | 12/2005 |
| WO | WO 2006/022712 | 3/2006 |

OTHER PUBLICATIONS

Lowe et al. (Nucleic Acids Research, 1990, 18(7):1757-1761).*
U.S. Appl. No. 12/143,697, filed Jun. 20, 2008, Friesen et al.
Adams et al., 1991, "Fluorescence ratio imaging of cyclic AMP in single cells." Nature 349:694-697.
Afounda et al., 1999, "Localized XId3 mRNA activation in Xenopus embryos by cytoplasmic polyadenylation." Mech Dev 88(1):15-31.
Aharon & Schneider, 1993, "Selective destabilization of short-lived mRNAs with the granulocyte-macrophage colony-stimulating factor AU-rich 3' noncoding region is mediated by a cotranslational mechanism" Mol. Cell. Biol. 13: 1971.
Amara et al., 1999, "TGF-beta(1), regulation of alzheimer amyloid precursor protein mRNA expression in a normal human astrocyte cell line: mRNA stabilization." Brain Res. Mol. Brain Res. 71(1):42-49.
Banholzer et al., 1997, "Rapamycin destabilizes interleukin-3 mRNA in autocrine tumor cells by a mechanism requiring an intact 3' untranslated region." Molecular and Cellular Biology 17: 3254-3260.
Bardoni & Mandel, 2002, "Advances in understanding of fragile X pathogenesis and FMRP function, and in identification of X linked mental retardation genes." Curr. Opin. Genet. Dev. 12(3):284-293.
Barkoff et al., 2000, "Translational control of cyclin B1 mRNA during meiotic maturation: coordinated repression and cytoplasmic polyadenylation" Dev Biol. 220(1):97-109.
Bashaw & Baker, 1995, "The msl-2 dosage compensation gene of Drosophila encodes a putative DNA-binding protein whose expression is sex specifically regulated by Sex-lethal." Develop. 121(10):3245-3258.
Beelman & Parker, 1994, "Differential effects of translational inhibition in cis and in trans on the decay of the unstable yeast MFA2 mRNA." J. Biol. Chem, 269:9687-9692.
Bergsten & Gavis, 1999, "Role for mRNA localization in translational activation but not spatial restriction of nanos RNA." Develop. 126(4):659-669.
Bock et al., 1992, "Selection of single-stranded DNA molecules that bind and inhibit human thrombin." Nature 355:564-566.
Brennab & Seitz, 2001, "HuR and mRNA stability." Cell. Mol. Life. Sci. 58:266.
Cao, "Develop New cancer drugs that control VEGF expression: VEGF is an endothelial cell specific mitogen." Grant application (no date provided).
Cao, "Targeting VEGF 5'-and 3'-UTRs for tumor therapy: generation of stable cell lines for High Throughput screening." (no date provided).
Carballo et al., 1998, "Feedback inhibition of macrophage tumor necrosis factor-alpha production by tristetraprolin." Science 281:1001.
Castagnetti et al., 2000, "Control of oskar mRNA translation by Bruno in a novel cell-free system from Drosophila ovaries." Develop. 127(5):1063-1068.
Charlesworth et al., 2000, "The temporal control of Wee1 mRNA translation during Xenopus oocyte maturation is regulated by cytoplasmic polyadenylation elements within the 3'-untranslated region." Dev. Biol. 227(2): 706-719.
Chen et al., 1994, "Interplay of two functionally and structurally distinct domains of the c-fos AU-rich element specifies its mRNA-destabilizing function." Mol. Cell. Biol. 14:416-426.
Chen et al., 1995, "AU-rich elements: characterization and importance in mRNA degradation" Trends Biochem. Sci 20:465-470.
Chen et al., 1995, "mRNA decay mediated by two distinct AU-rich elements from c-fos and granulocyte-macrophage colony-stimulating factor transcripts: different deadenylation kinetics and uncoupling from translation." Mol. Cell. Biol. 15:5777.
Chen et al., 2001, "AU Binding Proteins Recruit the Exosome to Degrade ARE-Containing mRNAs" Cell 107:451.
Claffey et al., 1998, "Identification of a human VPF/VEGF 3' untranslated region mediating hypoxia-induced mRNA stability." Mol. Biol. of Cell. 9:469-481.
Clark et al., 2000, "Synthesis of the posterior determinant Nanos is spatially restricted by a novel cotranslational regulatory mechanism." Curr. Biol. 10(20):1311-1314.
Clark et al., 2002, "A common translational control mechanism functions in axial patterning and neuroendocrine signaling in Drosophila ." Develop. 129(14): 3325-3334.
Cohen et al., 1996, "CN1-1493 inhibits monocyte/macrophaae tumor necrosis factor by suppression of translation efficiency." Proc. Natl. Acad. Sci. USA 93:3967-3971.
Crosio et al., 2000, "La protein has a positive effect on the translation of TOP mRNAs in vivo." Nucl. Acids. Res. 28(15):2927-34.
Crucs et al.. 2000, "Overlapping but distinct RNA elements control repression and activation of nanos translation." Mol. Cell. 5(3):457-467.

(56) References Cited

OTHER PUBLICATIONS

Curatola et al., 1995, "Rapid degradation of AU-rich element (ARE) mRNAs is activated by ribosome transit and blocked by secondary structure at any position 5' to the ARE." Mol. Cell. Biol. 15:6331.
Dahanukar & Wharton, 1996. "The Nanos gradient in *Drosophila* embryos is generated by translational regulation," Genes Dev 20:2610-2620.
Dias et al., 1994, "Chemical Probe for Glycosidic Conformation in Telomeric DNAs" J. Am. Chem. Soc. 116:4479-4480.
Diener & Moore, 1998, "Solution Structure of a Substrate for the Archael Pre-tRNA Splicing Endonucleases: The Bulge-Helix-Bulge Motif." Mol. Cell. 1:883-894.
Dominski & Marzluff, 1999, "Formation of the 3' end of histone mRNA." Gene 239(1):1-14.
Fruscoloni et al., 2001, "Cleavage of non-tRNA substrates by eukaryal tRNA splicing endonucleases." EMBO Rep 2(3):217-221.
Gan et al., 1998, "Functional characterization of the internal ribosome entry site of eIF4G mRNA" J. Biol. Chem. 273:5006-5012.
Gavis et al., 1996, "A conserved 90 nucleotide element mediates translational repression of nanos RNA. Development. Sep. 1996; 122(9):2791-800." Develop. 122(9):2791-2800.
Gebauer et al., 1998, "The *Drosophila* splicing regulator sex-lethal directly inhibits translation of malespecific-lethal 2 mRNA" RNA 4(2):142-150.
Genbank Accession No. NM_0017 ev 25, 2006.
Genbank Accession No. NM_0029 ev 25, 2006.
Genbank Accession No. NM_006536, 2006.
Genbank Accession No. AF022375, 2006.
Genbank Accession No. AJ131730, 2006.
Genbank Accession No. M11567, 2006.
Genbank Accession No. M14745, 2006.
Genbank Accession No. M14758, 2006.
Genbank Accession No. M33680, 2006.
Genbank Accession No. M54968, 2006.
Genbank Accession No. M90100, 2006.
Genbank Accession No. NM_0002 30, 2006.
Genbank Accession No. NM_0017 28, 2006.
Genbank Accession No. NM_0027 74, 2006.
Genbank Accession No. NM_0052 51, 2006.
Genbank Accession No. NM_0807 06, 2006.
Genbank Accession No. NM_0001 62, 2006.
Genbank Accession No. NM_0002 08, 2006.
Genbank Accession No. NM_0002 47, 2006.
Genbank Accession No. NM_0003 21, 2006.
Genbank Accession No. NM_0004 18, 2006.
Genbank Accession No. NM_0005 27, 2006.
Genbank Accession No. NM_0005 72, 2006.
Genbank Accession No. NM_0005 89, 2006.
Genbank Accession No. NM_0006 65, 2006.
Genbank Accession No. NM_000600, 2006.
Genbank Accession No. NM_0007 58, 2006.
Genbank Accession No. NM_0007 84, 2006.
Genbank Accession No. NM_0007 91, 2006.
Genbank Accession No. NM_0007 99, 2006.
Genbank Accession No. NM_0008 99, 2006.
Genbank Accession No. NM_0008 ev 75, 2006.
Genbank Accession No. NM_0009 48, 2006.
Genbank Accession No. NM_0011 45, 2006.
Genbank Accession No. NM_001168, 2006.
Genbank Accession No. NM_0012 40, 2006.
Genbank Accession No. NM_0015 65, 2006.
Genbank Accession No. NM_0015 67, 2006.
Genbank Accession No. NM_001917, 2006.
Genbank Accession No. NM_0020 06, 2006.
Genbank Accession No. NM_002006, 2006.
Genbank Accession No. NM_002087, 2006.
Genbank Accession No. NM_0021 11, 2006.
Genbank Accession No. NM_0021 51, 2006.
Genbank Accession No. NM_002231, 2006.
Genbank Accession No. NM_002392, 2006.
Genbank Accession No. NM_0026 ev 32, 2006.
Genbank Accession No. NM_0029 63, 2006.
Genbank Accession No. NM_0029 86, 2006.
Genbank Accession No. NM_0029 ev 64, 2006.
Genbank Accession No. NM_0032 55, 2006.
Genbank Accession No. NM_0032 56, 2006.
Genbank Accession No. NM_0033 55, 2006.
Genbank Accession No. NM_0036 42, 2006.
Genbank Accession No. NM_0038 ev 83, 2006.
Genbank Accession No. NM_004364, 2006.
Genbank Accession No. NM_004395, 2006.
Genbank Accession No. NM_0047 95, 2006.
Genbank Accession No. NM_0047 97, 2006.
Genbank Accession No. NM_0052 52, 2006.
Genbank Accession No. NM_0054 ev 17, 2006.
Genbank Accession No. NM_0059 31, 2006.
Genbank Accession No. NM_007310, 2006.
Genbank Accession No. NM_000794, 2006.
Genbank Accession No. NM_000134, 2006.
Genbank Accession No. NM_0187 ev 27, 2006.
Genbank Accession No. NM_0204 15, 2006.
Genbank Accession No. NM_0326 11, 2006.
Genbank Accession No. NM_053056, 2006.
Genbank Accession No. NM_0784 67, 2006.
Genbank Accession No. NM_0807 04, 2006.
Genbank Accession No. NM_0807 05, 2006.
Genbank Accession No. NM_080881, 2006.
Genbank Accession No. NM_138712, 2006.
Genbank Accession No. NM_389 92, 2006.
Genbank Accession No. NM_1393 ev 17, 2006.
Genbank Accession No. S48568.
Genbank Accession No. U22431.
Genbank Accession No. U25676.
Genbank Accession No. X16302.
Genbank Accession No. XM_589987.
Genbank Accession No. XM_001831.
Genbank Accession No. XM_003061.
Genbank Accession No. XM_003751.
Genbank Accession No. XM_015547.
Genbank Accession No. X01394.
Genbank Accession No. X00588.1.
Goodwin et al., 1993, "Translational regulation of tra-2 by its 3' untranslated region controls sexual identity in C. elegans." Cell 75:329-339.
Goodwin et al., 1997, "A genetic pathway for regulation of tra-2 translation" Develop. 124:749-758.
Green et al., 2002, "Crystallization and characterization of Smaug: a novel RNA-binding motif." Biochem. Biophys. Res. Commun. 297(5):1085-1088.
Guhaniyogi & Brewer, 2001, "Regulation of mRNA stability in mammalian cells." Gene 265(1-2):11-23.
Haag & Kimble. 2000, "Regulatory elements required for development of caenorhabditis elegans hermaphrodites are conserved in the tra-2 homologue of C. remanei, a male/female sister species" Genetics 155(1):105-116.
Hubert et al., 1996, "RNAs mediating cotranslational insertion of selenocysteine in eukaryotic selenoproteins" Biochimi 78(7):590-596.
Ikeniura, 1985, "Codon Usage and tRNA Content in Unicellular and Multicellular Organisms." Mol. Biol. Evol., 2(1):13-34.
Ikemura and Okeki, 1983, "Codon usage and transfer RNA contents: organism-specific codon-choice patterns in reference to the isoacceptor contents." Cold Spring Harbor Symp. Quant. Biol. 47:1087-1097.
Jan et al., 1997, "Conservation of the C.elegans tra-2 3'UTR translational control." EMBO J 16(20):6301-6313.
Jan et al., 1999, "The Star protein, GLD-1, is a translational regulator of sexual identity in Caenorhabditis elegans." EMBO J. 18:258-269.
Kakegawa et al., 2002, "Rapamycin induces binding activity to the terminal oligopyrimidine tract of ribosomal protein mRNA in rats." Arch Biochem Biophys 402(1):77-83.

(56) References Cited

OTHER PUBLICATIONS

Kastelic et al., 1996, "Induction of rapid IL-1 beta mRNA degradation in THP-1 cells mediated through the AU-rich region in the 3'UTR by a radicicol analogue." Cytokine 8: 751-761.
Keene & Tenenbaum, 2002, "Eukaryotic mRNPs may represent posttranscriptional operons" Mol. Cell. 9:1161.
Kelly et al., 1996, "Reconciliation of the X-ray and NMR structures of the thrombin-binding aptamer d(GGTTGGTGTGGTTGG)." J. Mol. Biol. 256:417-422.
Kim et al., 2002, "The human elongation factor 1 alpha (EF-1 alpha) first intron highly enhances expression of foreign genes from the murine cytomegalovirus promoter." J. Biotechnol. 93(2):183-187.
Kimble, 1988, "fog-2, a germ-line-specific sex determination gene required for hermaphrodite spermatogenesis in Caenorhabditis elegans." Genetics, 119:43-61.
Kleman-Leyer et al., 1997, "Properties of H. volcanii tRNA Intron Endonuclease Reveal a Relationship between the Archaeal and Eucaryal tRNA Intron Processing Systems." Cell., 89:839-847.
Koeller et al., 1991, "Translation and the stability of mRNAs encoding the transferrin receptor and c-fos." Proc. Natl. Acad. Sci. 88:7778.
Le & Maizel, 1989, "A method for assessing the statistical significance of RNA folding" J. Theor Biol. 138:495-510.
Li & Abelson, 2000, "Crystal Structure of a Dimeric Archaeal Splicing Endonuclease." J. Mol. Biol. 302:639-648.
Li et al., 1998, "Crystal structure and evolution of a transfer RNA splicing enzyme" Science 280(5361):279-284.
Lykke-Andersen, J. & Garrett, R.A.., 1997, "RNA-protein interactions of an archaeal homotetrameric splicing endoribonuclease with an exceptional evolutionary history." EMBO J 16(20):6290-6300.
Macaya et al., 1993, "Thrombin-binding DNA aptamer forms a unimolecular quadruplex structure in solution." Proc. Natl. Acad. Sci. 90:3745-3749.
Muhlrad et al., 1995. "Turnover mechanisms of the stable yeast PGK1 mRN." Mol. Cell. Biol. 15(4):2145-2156.
Mukherjee et al., 2002, "The mammalian exosome mediates the efficient degradation of mRNAs that contain AU-rich elements." EMBO J. 21:165.
Nanbru et al., 1995, "Alternative translation of the proto-oncogene c-myc by an internal ribosome entry site." J. Biol. Chem. 272:32061-32066.
Oh et al.. 1992, "Homeotic gene Antennapedia mRNA contains 5'-noncoding sequences that confer translational initiation by internal ribosome binding." Genes Dev 6:1643-1653.
Ostareck-Lederer et al., 2002, "c-Src-mediated phosphorylation of hnRNP K drives translational activation of specifically silenced mRNAs" Mol. Cell. Biol. 22(13):4535-4543.
Paynton & Bachvarova, 1994, "Polyadenylation and deadenylation of maternal mRNAs during oocyte growth and maturation in the mouse" Mol. Reprod. Dev 37(2): 172-180.
Peterlin et al., 1993, "Tat Trans-Activator." In Human Retroviruses; Cullen Ed.; Oxford University Press: New York, pp. 75-100.
Pettetier & Soneberg, 1988, "Internal initiation of translation of eukaryotic mRNA directed by a sequence derived from poliovirus RNA" Nature 334:320-325.
Piecyk et al., 2000, "TIA-1 is a translational silencer that selectively regulates the expression of TNF-alpha" EMBO J. 19:4154.
Qin & Pyle, 1999, "Site-specific labeling of RNA with fluorophores and other structural probes." Methods 18 (1):60-70.
Rajagopalan & Malter, 2000, "Growth factor-mediated stabilization of amyloid precursor protein mRNA is mediated by a conserved 29-nucleotide sequence in the 3'-untranslated region." J. Neurochem. 74(1):52-59.
Raught et al. 2000, "Translational Control of Gene Expression." Sonenberg, Hershey and Mathews, eds. Cold Spring Harbor Laboratory Press.
Reinmann et al., 2002, "Suppression of 15-lipoxygenase synthesis by hnRNP E1 is dependent on repetitive nature of LOX mRNA 3'-UTR control element Dice." J. Mol. Biol 315(5):965-974.

Reyes & Abelson 1988, "Substrate Recognition and Splice Site Determination in Yeast tRNA Splicing." Cell, 55:719-730.
Rogers et al., 2002, "An iron-responsive element type II in the 5'-untranslated region of the Alzheimer's amyloid precursor protein transcript." J. Biol. Chem. 277(47):45518-45528.
Sarkar & Hopper., 1998, "tRNA Nuclear Export in *Saccharomyces cerevisiae*: In Situ Hybridization Analysis." Mol. Biol. of the Cell 9:3041-3055.
Savant-Bhonsale et al., 1992, "Evidence for instability of mRNAs containing AUUUA motifs mediated through translation-dependent assembly of a > 20S degradation complex" Genes Dev. 6:1927.
Saxena et al., 1992, "Angiogenin is a Cytotoxic, tRNA-specific Ribonuclease in the RNase A Superfamily." J. Biol. Chem. 267(30):21982-21986.
Schlatter & Fussenegger, 2003, "Novel CNBP- and La-based translation control systems for mammalian cells." Biotechnol Bioeng. 81(1):1-12.
Schultze et al., 1994, "Three-dimensional solution structure of the thrombin-binding DNA aptamer d(GGTTGGTGTGGTIGG)." J. Mol. Biol. 235:1532-1547.
Stebbins-Boaz et al., 1996, "CPEB controls the cytoplasmic polyadenylation of cyclin, Cdk2 and c-mos mRNAs and is necessary for oocyte maturation in Xenopus." EMBO J. 15(10):2582-2592.
Stein et al., 1998, "Translation of vascular endothelial growth factor mRNA by internal ribosome entry: implications for translation under hypoxia" Mol. Cell. Biol. 18:3112-3119.
Stoneley, 1998. "C-Myc 5' untranslated region contains an internal ribosome entry segment" Oncogene 16:423-428.
Tay et al., 2000, , "The control of cyclin B1 mRNA translation during mouse oocyte maturation." Dev. Biol. 221(1):1-9.
Thiele et al., 1999, "Expression of leukocyte-type 12-lipoxygenase and reticulocyte-type 15-lipoxygenase in rabbits" Adv Exp Med Biol. 447:45-61.
Tholanikunnel & Malborn, 1997, "A 20-nucleotide (A + U)-rich element of beta2-adrenergic receptor (beta2AR) mRNA mediates binding to beta2AR-binding protein and is obligate for agonist-induced destabilization of receptor mRNA." J. Biol. Chem. 272:11471.
Thompson et al., 2000, "Rapid deadenylation and Poly(A)-dependent translational repression mediated by the Caenorhabditis elegans tra-2 3' untranslated region in Xenopus embryos." Mol. Cell. Biol. 20(6):2129-2137.
Trifillis et al., 1999, "Finding the right RNA: identification of cellular mRNA substrates for RNA-binding proteins." RNA 5:1071-1082.
Trotta et al., 1997, "The yeast tRNA splicing endonuclease: a tetrameric enzyme with two active site subunits homologous to the archaeal tRNA endonucleases." Cell 89:849-858.
Trotta, "Gene Expression" Revised Background Draft.
Trotta., 1999, "The Composition, Function and Evolution of he tRNA Splicing Endonuclease." Thesis, California Institute of Technology, pp. 1-147.
Vagner et al., 1995, "Alternative translation of human fibroblast growth factor 2 mRNA occurs by internal entry of ribosomes." Mol. Cell. Biol. 15:35-44.
Vagner et al., 2001, "Irresistible IRES. Attracting the translation machinery to internal ribosome entry sites." EMBO Reports 2:893.
Volarevic et al., 2000, "Proliferation, But not Growth Blocked by Conditional Deletion of 40S Ribosomal Protein S6." Science 288:2045-2047.
Wang et al., 1993, "A DNA aptamer which binds to and inhibits thrombin exhibits a new structural motif for DNA." Biochem. 32(8): 1899-1904.
Wells et al., 1998, "Circularization of mRNA by eukaryotic anslation initiation factors." Mol. Cell. 2:135-140.
Westmark & Malter, 2001, "Extracellular-regulated kinase controls beta-amyloid precursor protein mRNA decay" Brain Res Mol. Brain. Res 90(2):193-201.
Wilkund et al., 2002, "Inhibition of translation by UAUUUAU and UAUUUUUAU motifs of the AU-rich RNA instability element in the HPV-1 late 3' untranslated region." J. Biol. Chem. 277:40462.

(56) References Cited

OTHER PUBLICATIONS

Worthington et al., 2002, "RNA binding properties of the AU-rich element-binding recombinant Nup475/TIS11/tristetraprolin protein." J. Biol. Chem. 277: 48558-48564.
Ye et al., 1997, "Ultrabithorax and Antennapedia 5' untranslated regions promote developmentally regulated internal translation initiation" Mol. Cell. Biol. 17:1714-1721.
Zaldi & Malter, 1995. "Nucleolin and heterogeneous nuclear ribonucleoprotein C proteins specifically interact kith the 3'-untranslated region of amyloid protein precursor mRNA," J. Biol. Chem, 271(29):1 7292-17298.
Zhang et al.. 1997, "Gene Expression Profiles in Normal and Cancer Cells." Science 276:1268-1272.
Zhu et al., 2001, "Binding of the La autoantigen to the 5' untranslated region of a chimeric human translation elongation factor 1A reporter mRNA inhibits translation in vitro." Biochim. Biophys Acta 1521(1-3):19-29.
Kemeny et al., 1998, "The tetravalent guanylhydrazone CNI-1493 blocks the toxic effects of interleukin-2 without diminishing anti-tumor efficacy." Proc. Natl. Acad. Sci. USA 95: 4561-4566.
Danner et al., 1998, "Agonist regulation of human beta2-adrenergic receptor mRNA stability occurs via a specific AU-rich element." J. Biol. Chem. 273(6):3223-9.
Zubiaga et al., 1995, "The nonamer UUAUUUAUU is the key AU-rich sequence motif that mediates mRNA degradation." Mol. Cell. Biol. 15(4):2219-30.
Akashi et al., 1994, "Number and Location of AUUUA Motifs: Role in Regulating Transiently Expressed RNAs." Blood 83:3182-3187 Am soc. of Hemat.
Auwerx et al., 1991, "The human leukemia cell line, THP-I : A multifaceted model for the study of monocyte-macrophage differentiation." Experientia 47:22-31 Birkhauser Verlag Basel.
Beutler et al., 1988, "Assay of Ribonuclease that preferentially hydrolyses mRNAs Containing Cytokine-Derived UA-Rich Instability Sequences." Biochem. Biophys Res. Commun. 152:973-980.
Brenchley, 1998, "Antagonizing the expression of VEGF in pathological angiogenesis." Exp. Opin Ther. Patents 8(12): 1695-1706.
Chen et al., 1994, "Selective Degradation of Early-Response-Gene mRNAs: Functional Analyses of Sequence Features of the AU-rich elements." Mol. Cell. Biol. 14: 8471-8482.
Chen et al., 1995, "AU-rich elements: characterization and importance in mRNA degradation." TIBS 20:465-470.
Cho et al.. 2002, "Emerging techniques for the discovery and validation of therapeutic targets for skeletal diseases" Expert Opin. Ther. Targets 6(6):679-689.
Crawford et al., 1997, "The Role of 3' Poly (A) Tail Metabolism in Tumor Necrosis Factor-α Regulation." J Biol. Chem. 272:21120-21127. The Am Soc of Biochem. and Molec. Biol.
Fan et al., 1998, "Overepxression of HuR, a nuclear-cytoplasmic shuttling protein, increases in vivo stability of ARE-containing mRNAS." EMBO J 17:3448-3460.
Forsysthe et al., 1996, "Activation of Vascular Endothelial Growth factor Gene Transcription by Hypoxia-Inducible Factor 1." Mol and Cell. Biol. 16(9):4604-4613.
Gil et al., 1996, "Multiple regions of the *Arubidopsis* Saur-AC1 gene control transcript abundance: the 3' untranslated region functions as an mRNA instability determinant." EMBO J 15:1678-1686.
Heaton et al., 1998, "Cyclic Nucleotide Regulation of Type-1 Plasminogen Activator-nhibitor mRNA stability in Rat Hepatoma Cells." J Biol. Chem. 273:14261-14268.
Hyder et al., 2000, "Identification of Functional Estrogen Response Elements in the Gene Coding for the Potent Angiogenic Factor Vascular Endothelial Growth Factor." Cancer Res 60:3183-3190.
Iida et al., 2002, "Vascular endothelial growth factor gene expression in a retinal pigmented cell is up-regulated by glucose deprivation through 3' UTR." Life Sciences 71:1607-1614.
Klausner et al., 1993, "Regulating the Fate of mRNA: The control of Cellular Iron Metabolism" Cell 72:19-28.

Kobayashi et al., 1998, "Characterization of the 3' Untranslated region of mouse DNA topoisomerase IIα mRNA." Gene 215:329-337.
Lagnado et al., 1994, "AUUUA is Not sufficient to promote Poly(A) Shortening and Degradation of mRNA: the Functional Sequence within the AU-rich elements may be UUAUUUA(U/A) (U/A)" Mol. Cell. Biol. 14: 7984-7995.
Levy et al., 1995, "Sequence and functional characterization of the terminal exon of the human insulin receptor gene." Biochem Biophys Acta 1263:253-257.
Levy et al., 1996, "Post-transcriptional Regulation of Vascular Endothelial Growth Factor by Hypoxia." J. Biol. Chem. 271:2746-2753.
Levy et al., 1998, "Hypoxic Stabilization of Vascular Endothelial Growth Factor mRNA by the RNA-binding Protein HuR." J Biol. Chem. 273(11):6417-6423.
Lewis et al., 1998, "Mapping of a Minimal AU-rich Sequence Required for Lipopolysaccharide-induce binding of a 55-kDA protein on tumor necrosis Factor-α mRNA." J Biol. Chem. 273:13781-13786.
Nanbu et al., 1994, "Multiple Instability-Regulating Sites in the 3'Untranslated Region of the Urokinase-Type Plasminogen activator mRNA." Mol. Cell. Biol. 14:4920-4928.
Sachs et al., 1993, "Messenger RNA Degradation in Eukaryotes." Cell 74:413-421.
Sambrook et al., 1989, "Standard protocol for calcium phosphate-mediated transfection of adherent cells." Molec. cloning 16:3316-37.
Shaw & Kamen, 1986, "A conserved AU sequence from the 3' Untranslated Region of GM-CSF mRNA mediates selective mRNA degradation." Cell 46:659-667.
Shyu et al., 1991, "Two distinct destabilizing elements in the c-fos message trigger deadenylation as a first step in rapid mRNA decay." Genes Dev 5:221-231.
Stoecklin et al., 1994, "Functional Hierarchy of AUUUA Motifs in Mediating Rapid Interleukin-3 MRNA decay." J Biol. Chem. 269:28591-28597.
Stolle et al., 1988, "Cellular Factor affecting the stability of β-globin mRNA." Gene 62:65-74.
Sullivan et al., 1996, "Mutational analysis of the DST element in tobacco cells and transgenic plants: Identification of residues critical for mRNA instability." RNA 2:308-315.
Winstall et al., 1995, "Rapid mRNA Degradation Mediated by the c-fos 3' AU-Rich element and that mediated by the Granulocyte-Macrophage Colony-Stimulating Factor 4' AU-Rich Element occur through similar Polysome-Associated Mechanisms" Mol. Cell. Biol. 15:3796-3804.
Xu et al., 1997, "Modulation of the Fate of Cytoplasmic mRNA by AU-Rich elements key sequence Features Controlling mRNA Deadenylation and Decay." Mol. Cell. Biol. 17:4611-4621.
Zhang et al., 1996. "An enhanced green fluorescent protein allows sensitive detection of gene transfer in mammalian cells." BBRC 227:707-11.
Zhang et al., 1995, "Identification and Characterization of a Sequence motif involved in nonsense-mediated mRNA decay" Mol. Cell. Biol, 15:2231-2244.
Written Opinion of the International Searching Authority dated Jul. 14, 2008 in the PCT Application No. PCT/U504/01643 filed Jan. 21, 2004.
International Search Report dated Jul. 14, 2008 in the PCT Application No. PCT/US04/01643 filed Jan. 21, 2004.
Benjamin et al., 1997, "Conditional switching of vascular endothelial growth factor (VEGF) expression in tumors: induction of endothelial cell shedding and regression of hemangioblastoma-like vessels by VEGF withdrawal." Proc. Natl. Acad Sci 94:8761-8766.
Bornes et al., 2004, "Control of the Vascular Endothelial growth factor internal ribosme entry site (IRES) Activity and translation initation by Alternativey Spliced Coding seqences." J Biol. Chem. 279(18):18717-18726.
Child et al., 1999, "Cell type-dependent and -independent control of HER-2/neu translation" Int Journal of Biochem & Cell Biol 31:201-213.

(56) References Cited

OTHER PUBLICATIONS

Database WPI Week, 2002, "Screening drug improving insulin resistance without exacerbating diabetic retinopathy, by detechig expression of reporter gene fused to promoter region of human vascular endothelial growth factor gene in mammal cell." JP 2001 340080 A.
De Jong et al., 2002, "RNA and RNA-protein complexes as targets for therapeutic intervention." Curr. Topics Medicinal Chem. 2:289-302.
De Wet et al., 1987, "Firefly Luciferase Gene: Structure and Expression in Mammalian Cells." Mol Cell. Biol. 7(2):725-737.
Dreyfuss et al., 2002 "Messenger-RNA-Binding Proteins and the Messages they Carry." Nature Rev Molec Cell Biol. 3:195-205.
Eibl et al., 1999, "In vivo analysis of plastid psbA, rbcL and rpl32 UTR elements by chloroplast transformation: tobacco plastid gene expression is controlled by modulation of transcript levels and translation efficiency." Plant J. 19:333-345.
Fortes et al., 2003, "Inhibiting expression of specific genes in mammalian cells with 5' end-mutated u 1 small nuclear RNAs targeted to terminal exons of pre-mRNA" Proc. Natl. Acad. Sci 100(14):8264-8269.
Genbank Accession No. AF022375, dated Oct. 7, 1998.
Genbank Accession No. AJ131730, dated Oct. 7, 2008.
Genbank Accession No. M11567, dated Oct. 30, 1994.
Genbank Accession No. M14745, dated Apr. 27, 1993.
Genbank Accession No. MI4758, dated Dec. 3, 1999.
Genbank Accession No. M33680, dated Aug. 3, 1993.
Genbank Accession No. M54968, dated Oct. 17, 2008.
Genbank Accession No. M90100, dated Dec. 31, 1994.
Genbank Accession No. NM_000230, dated Apr. 19, 2009.
Genbank Accession No. NM_000162, dated Apr. 9, 2009.
Genbank Accession No. NM_000134, dated Apr. 12, 2009.
Genbank Accession No. NM_000208, dated Mar. 29, 2009.
Genbank Accession No. NM_000247, dated Apr. 12, 2009.
Genbank Accession No. NM_000321, dated Apr. 19, 2009.
Genbank Accession No. NM_000418, dated Apr. 12, 2009.
Genbank Accession No. NM_000527, dated Apr. 26, 2009.
Genbank Accession No. NM_000572, dated Apr. 19, 2009.
Genbank Accession No. NM_000589, dated Apr. 12, 2009.
Genbank Accession No. NM_000665, dated Apr. 12, 2009.
Genbank Accession No. NM_000600, dated Apr. 19, 2009.
Genbank Accession No. NM_000758, dated Apr. 19, 2009.
Genbank Accession No. NM_000784. dated Mar. 29, 2009.
Genbank Accession No. NM_000791, dated Mar. 29, 2009.
Genbank Accession No. NM_000799, dated Apr. 5, 2009.
Genbank Accession No. NM_000794, dated Apr. 10, 2009.
Genbank Accession No. NM_000899. dated Mar. 29, 2009.
Genbank Accession No. NM_000875, dated Apr. 10, 2009.
Genbank Accession No. NM_000948, dated Mar. 22, 2009.
Genbank Accession No. NM_001145, dated Apr. 5, 2009.
Genbank Accession No. NM_001168, dated Apr. 19, 2009.
Genbank Accession No. NM_001240, dated Feb. 24, 2009.
Genbank Accession No. NM_001565, dated Apr. 12, 2009.
Genbank Accession No. NM_001567, dated Mar. 22, 2009.
Genbank Accession No. NM_001728, dated Apr. 5, 2009.
Genbank Accession No. NM_001725, dated Oct. 22, 2006.
Genbank Accession No. NM_001917, dated Apr. 5, 2009.
Genbank Accession No. NM_002006. dated Mar. 15, 2009.
Genbank Accession No. NM_002087, dated Mar. 29, 2009.
Genbank Accession No. NM_002111, dated Apr. 19, 2009.
Genbank Accession No. NM_002151, dated Apr. 23, 2009.
Genbank Accession No. NM_002231, dated Mar. 15, 2009.
Genbank Accession No. NM_002392, dated Apr. 19, 2009.
Genbank Accession No. NM_002632, dated Apr. 19, 2009.
Genbank Accession No. NM_002774, dated Apr. 11, 2009.
Genbank Accession No. NM_002963, dated Apr. 19, 2009.
Genbank Accession No. NM_002986, dated Mar. 29, 2009.
Genbank Accession No. NM_002925, dated Aug. 20, 2006.
Genbank Accession No. NM_002964, dated Mar. 29, 2009.
Genbank Accession No. NM_003255, dated Mar. 22, 2009.
Genbank Accession No. NM_003256, dated Apr. 5, 2009.
Genbank Accession No. NM_003355, dated Apr. 19, 2009.
Genbank Accession No. NM_003642, dated Oct. 22, 2008.
Genbank Accession No. NM_003883, dated Apr. 12, 2009.
Genbank Accession No. NM_004364. dated Apr. 5, 2009.
Genbank Accession No. NM_004395, dated Dec. 21, 2008.
Genbank Accession No. NM_004795, dated Apr. 12, 2009.
Genbank Accession No. NM_004797, dated Apr. 12, 2009.
Genbank Accession No. NM_005251, dated Apr. 5, 2009.
Genbank Accession No. NM_005252, dated Apr. 5, 2009.
Genbank Accession No. NM_005417. dated Apr. 19, 2009.
Genbank Accession No. NM_005931, dated Apr. 5, 2009.
Genbank Accession No. NM_006536, dated Sep. 17, 2006.
Genbank Accession No. NM_007310, dated Apr. 12, 2009.
Genbank Accession No. NM_018727, dated Mar. 1, 2009.
Genbank Accession No. NM_020415, dated Mar. 29, 2009.
Genbank Accession No. NM_032611, dated Mar. 29, 2009.
Genbank Accession No. NM_053056, dated Apr. 19, 2009.
Genbank Accession No. NM_078467, dated Apr. 19, 2009.
Genbank Accession No. NM_080704, dated Mar. 1, 2009.
Genbank Accession No. NM_080705 , dated Mar. 1, 2009.
Genbank Accession No. NM_080706, dated Mar. 1, 2009.
Genbank Accession No. NM_080881, dated Dec. 21, 2008.
Genbank Accession No. NM_138712, dated Apr. 12, 2009.
Genbank Accession No. NM_138992, dated Apr. 5, 2009.
Genbank Accession No. NM_139317, dated Apr. 5, 2009.
Genbank Accession No. S48568, dated Apr. 17, 2002.
Genbank Accession No. U22431, dated Jun. 28, 1995.
Genbank Accession No. U25676, dated Jul. 20, 1995.
Genbank Accession No. X005881, dated Oct. 7, 2008.
Genbank Accession No. X01394, dated Oct. 7, 2008.
Genbank Accession No. X16302, dated Apr. 18, 2005.
Genbank Accession No. XM_001831, dated May 8, 2002.
Genbank Accession No. XM_003061, dated May 8, 2002.
Genbank Accession No. XM_003751, dated Oct. 16, 2001.
Genbank Accession No. XM_015547, dated Aug. 1, 2002.
Genbak Accession No. XM_589987, dated Sep. 30, 2005.
Huang et al., 1990, "Intervening sequences increase efficiency of RNA 3' processing and accumulation of cytoplasmic RNA." Nucl. Acids Res. 18(4):937-947.
Huez et al., 1998. "Two Independent Internal Ribosome Entry Sites are Involved in Translation Initiation of Vascular Endothelial Growth Factor mRNA." Mol. Cell. Biol. 18(11):6178-6190.
Ismail et al,. 2000. "Split-intron retroviral vectors: enhanced expression with improved safety." J. Virol. 74 (5):2365-2371.
Kozak et al., 1986, "Influences of mRNA secondary structure on intiation by eukaryotic ribosomes" Proc. Natl. Acad Sci 83:2850-2854.
Lai et al., 1999, "Evidence that Tristetraprolin binds to AU-Rich Elements and promotes the Deadenylation and Destabilitzation of Tumor Necrosi Factor Alpha mRNA" Mol. Cell. Biol. 19(6):4311-4323.
Lemm et al., 2002, "Regulation of c-myc mRNA decay by translational pausing in a coding region instability determinant." Mol. Cell. Biol. 22(12):3959-3969.
Mehta et al, 2006, "Derepression of the Her-2 uORF is mediated by a novel post-transcriptional control mechanism in cancer cells." Genes & Dev. 20:939-953.
Nishimori et al., 2004, "Involvement of the 3'-untranslated region of cyclooxygenase-2 gene in its post-transcriptional regulation through the glucocorticoid receptor." Life Sciences 74:2505-2513.
Sachs & Geballe, 2006, "Downstream control of upstream open reading frames." Genes & Dev. 20:915-921.
Tischer et al., 1991, "The human gene for vascular endothelial growth factor." The J Biol Chem. 266(18):11947-11954.
Wang et al., 2003, "Human SP-A 3'-UTR variants mediate differential gene expression in basal levels and in response to dexamethasone." Am J Physio, Lung Cell & Mol. Physio. 284(5):L738-L748.
Office Action, mailed Oct. 4, 2007, in U.S. Appl. No. 10/895,393.
Response to Notice of Non-Compliant Amendment, filed Jul. 9, 2007, in U.S. Appl. No. 10/895,393.

(56) References Cited

OTHER PUBLICATIONS

Restriction Requirement, mailed Dec. 28, 2006, in U.S. Appl. No. 10/895,393.
Amendment, filed Apr. 3, 2008, in U.S. Appl. No. 10/895,393.
Response to Restriction Requirement, filed Apr. 25, 2007, in U.S. Appl. No. 10/895,393.
Final Office Action, mailed Dec. 16, 2008, in U.S. Appl. No. 10/895,393.
Request for Continued Examination and Amendment, dated Jun. 16, 2009, in U.S. Appl. No. 10/895,393.
Restriction/Election Requirement, dated Jan. 26, 2009, in U.S. Appl. No. 10/579,500.
Response to Restriction/ElectionRequirement, dated Jun. 26, 2009, in U.S. Appl. No. 10/579,500.
Requirement for Restriction/Election, dated Jan. 11, 2007, in U.S. Appl. No. 10/851,074.
Amendment and Response to Restriction/Election, dated May 11, 2007, in U.S. Appl. No. 10/851,074.
Non Final Office Action, dated Sep. 7, 2007, in U.S. Appl. No. 10/851,074.
Amendment and Response to Non-Final Rejection, dated Apr. 13, 2008, in U.S. Appl. No. 10/851,074.
Non Final Rejection, dated Jul. 10, 2008, in U.S. Appl. No. 10/851,074.
Non Final Rejection, dated Oct. 23, 2008, in U.S. Appl. No. 10/851,074.
Amendment and Response to Non-Final Rejection, dated Apr. 22, 2009, in U.S. Appl. No. 10/851,074.
Supplemental European Search Report, dated Nov. 19, 2008, issued in EP 04809465.0 (EP1761638).
Supplemental Partial European Search Report, dated May 30, 2008, issued in EP 04781055.1 (EP 1786933).
International Preliminary Report on Patentability, dated Jan. 23, 2007, in the PCT Application No. PCT/US04/26309.
International Search Report, dated Jul. 13, 2005, in the PCT Application No. PCT/US04/26309.
Written Opinion of the International Searching Authority, dated Jul. 13, 2005, in the PCT Application No. PCT/US04/26309.
International Preliminary Report on Patentability, dated Nov. 19, 2007, in the PCT Application No. PCT/US04/020751.
Written Opinion of the International Searching Authority, dated Nov. 6, 2007, in the PCT Application No. PCT/US04/020751.
International Search Report, dated Mar. 7, 2005, in the PCT Application No. PCT/US04/038496.
International Preliminary Report on Patentability, dated Jul. 17, 2008, in the PCT Application No. PCT/US04/038496.
Written Opinion, dated May 17, 2006, in the PCT Application No. PCT/US04/038496.
Cohen et al., 1996, "Interleukin 6 induces the expression of vascular endothelial growth factor." J. Biol Chem. 271(12):736-741.
Yamazaki et al., 2003, "HIF-1-dependent VEGF reporter gene assay by a stable transformant of CHO cells." Biol & Pharm Bull. 26(4): 417-420.
Zhang et al., 2000, "Wild-type p53 suppresses angiogenesis in human leiomyosarcoma and synovial sarcoma by transcriptional suppression of vascular endothelial growth factor expression." Cancer Res 60:3655-3661.
Supplemental Partial European Search Report, dated Nov. 5, 2009, issued in EP 04704085.2 (EP 1604011).
Restriction Requirement mailed Sep. 3, 2009 in U.S. Appl. No. 10/895,393.
Response to Restriction/Election Requirement, dated Dec. 2, 2009 in U.S. Appl. No. 10/895,393.
Non-Final Rejection, dated Feb. 18, 2010 in U.S. Appl. No. 10/895,393.
Restriction/Election Requirement, dated Aug. 6, 2009, in U.S. Appl. No. 10/579,500.
Response to Restriction/Election Requirement, dated Sep. 4, 2009, in U.S. Appl. No. 10/579,500.
Non-Final Rejection, dated Jan. 5, 2010, in U.S. Appl. No. 10/579,500.
Final Rejection, dated Aug. 24, 2009, in U.S. Appl. No. 10/851,074.
Response to Final Rejection and Request for Continued Examination, dated Nov. 24, 2009, in U.S. Appl. No. 10/851,074.
Non-Final Rejection, dated Jun. 24, 2010, in U.S. Appl. No. 10/851,074.
Communication from the Examining Division, dated Jan. 29, 2010, issued in EP 04704085.2 (EP 1604011).
Horvath et al., "Multiple elements in the 5' untranslated region down-regulate c-sis messenger RNA translation." Cell Growth & Diff., 6: 1103-1110.
Kowalski and Mager, 1998, "A human endogenous retrovirus suppresses translation of an associated fusion transcript, PLA2L." J. Virol., 72(7):6164-8.
Hoover et al., 1997, "Pim-1 protein expression is regulated by its 5'-untranslated region and translation initiation factor eIF-4E." Cell Growth Differ., 8: 1371-1380.
Pontrelli et al., 2004, "Translational control of apolipoprotein B mRNA: regulation via cis elements in the 5' and 3' untranslated regions." Biochemistry, 43(21):6734-44.
Bhattacharyya et al., 2007, "Mining the GEMS—a novel platform technology targeting post-transcriptional control mechanisms." Drug Discov Today, 12(13-14):553-60.
Final Rejection, dated Jan. 25, 2011 in U.S. Appl. No. 10/851,074.
Amendment, dated Jun. 27, 2011 in U.S. Appl. No. 10/851,074.
Non-Final Rejection, dated Feb. 15, 2011 in U.S. Appl. No. 10/895,393.
Adams et al., 1998, "Localized infusion of IGF-I results in skeletal muscle hypertrophy in rats." J Appl Physiol, 84:1716-1722.
Barton et al., 2002, "Muscle-specific expression of insulin-like growth factor 1 counters muscle decline in mdx mice." J. Cell Biol., 157:137-148.
Barton-Davis, 1998, "Viral mediated expression of insulin-like growth factor I blocks the aging-related loss of skeletal muscle function." PNAS, 95:15603-15607.
Bogdanovich et al., 2004, "Therapeutics for Duchenne muscular dystrophy: current approaches and future directions." J Mol Med., 82(2):102-15.
Burkin and Kaufman, 1999, "The α7β1 integrin in muscle development and disease." Cell Tissue Res., 296:183-190.
Chakkalakal et al., 2005, "Molecular, cellular, and pharmacological therapies for Duchenne/Becker muscular dystrophies." FASEB J., 19(8):880-91.
Coleman et al., 1995, "Myogenic Vector Expression of Insulin-like Growth Factor I Stimulates Muscle Cell Differentiation and Myofiber Hypertrophy in Transgenic Mice." J. Biol. Chem., 270:12109-12116.
Davies and Nowak, 2006, "Molecula Mechanisms of Muscular Dystrophies: Old and New Players." Nature, 7:762-773 (Supplementary Information Included).
Engvall et al., 2003, "The new frontier in muscular dystrophy research: booster genes." FASEB J., 17:1579-1584.
Graniolini et al., 2001, "Distinct reaions in the 3' untranslated region are responsible fo argetina and stabilizing utrophin transcripts in skeletal muscle cells." J Cell Biol. 154:1173-1183.
Gramolini, 2001, "Increased expression of utrophin in a slow vs. a fast muscle involves posttranscriptional events." Am J Physiol Cell Physiol., 281(4):C1300-9.
Kambadur et al., 1997, "Mutations in myostatin (GDF8) in double-muscled Belgian Blue and Piedmontese cattle." Genome Res., 7(9):910-6.
Karin et al., 2006, "Role for IKK2 in muscle: waste not, want not." J Clin Invest., 116: 2866-2868.
Krag et al., 2004, "Heregulin ameliorates the dystrophic phenotype in mdx mice." PNAS, 101: 13856-13860.
Nowak and Davies, 2004, "Duchenne Muscular Dystrophy and dystrophin: pathogenesis and opportunities for treatment." EMBO Reports, 5:872-876.
Ohlendieck and Campbell, 1991, "Dystrophin-associated proteins are greatly reduced in skeletal muscle from mdx mice." J Cell Biol, 115:1685-1694.

(56) References Cited

OTHER PUBLICATIONS

Patel et al, 2005, "Molecular mechanisms involving IGF-1 and myostatin to induce muscle hypertrophy as a therapeutic strategy for Duchenne Muscular Dystrophy." Acta Myol., 24(3):230-41.
Tobin et al., 2005, "Myostatin, a negative regulator of muscle mass: implications for muscle degenerative diseases." Curr Opin Pharmacol., 5(3):328-32.
Vachon et al.,1997, "Integrins (alpha7betal) in muscle function and survival. Disrupted expression in merosin-deficient congenital muscular dystrophy." J Clin Invest., 100(7):1870-81.
Veyrune et al., 1996, "A localisation signal in the 3' untranslated region of c-myc mRNA targets c-myc mRNA and beta-globin reporter sequences to the perinuclear cytoplasm and cytoskeletal-bound polysomes." J Cell Sci, 109:1185-1194.
Avila et al., 2007 "Trichostatin A increases SMN expression and survival in a mouse model of spinal muscular atrophy." J Clin Invest.;117(3):659-71.
Bertini et al., 2005, "134th ENMC International Workshop: Outcome Measures and Treatment of Spinal Muscular Atrophy, Feb. 11-13, 2005, Naarden, The Netherlands." Neuromuscul Disord. 15(11):802-16.
Boda et al., 2004, "Survival motor neuron SMN1 and SMN2 gene promoters: identical sequences and differential expression in neurons and non-neuronal cells." Eur J Hum Genet.; 12(9):729-37.
Brahe et al., 2005, "Phenylbutyrate increases SMN gene expression in spinal muscular atrophy patients." Eur J Hum Genet.; 13(2):256-9.
Echaniz-Laguna et al., 1999, "The promoters of the survival motor neuron gene (SMN) and its copy (SMNc) share common regulatory elements." Am J Hum Genet; 64(5):1365-70.
Germain-Desprez et al., 2001, "The SMN genes are subject to transcriptional regulation during cellular differentiation." Gene, 279:109-117.
Iannaconne et al., 2002 "Outcome Measures for Pediatric Spinal Muscular Atrophy." Arch Neurol. 59:1445-1450.
Iannaconne et al., 2003, "Reliability of 4 Outcome Measures in Pediatric Spinal Muscular Atrophy." Arch Neurol; 60:1130-1136.
Jarecki et al,. 2005 "Diverse small-molecule modulators of SMN expression found by high-throughput compound screening: early leads towards a therapeutic for spinal muscular atrophy." Hum Mol Genet.; 14(14):2003-18.
Kolb et al., 2006, "A novel cell immunoassay to measure survival of motor neurons protein in blood cells." BMC Neurology, 6:6.
Lunn et al., 2004, "Indoprofen upregulates the survival motor neuron protein through a cyclooxygenase-independent mechanism." Chem Biol.; 11(11):1489-93.
Merlini et al., 2003, "Role of gabapentin in spinal muscular atrophy: results of a multicenter, randomized Italian study." J Child Neurol.; 18(8):537-41.
Monani et al., 1999, Promoter analysis of the human centromeric and telomeric survival motor neuron genes (SMNC and SMNT). Biochim Biophys Acta; 1445(3):330-6.
Sumner., 2006, "Therapeutics development for spinal muscular atrophy." NeuroRx.; 3(2):235-45.
Wan, 2005, "The survival of motor neurons protein determines the capacity for snRNP assembly: biochemical deficiency in spinal muscular atrophy." Molec & Cell Biol, 25(13): 5543-5551.
Wolstencroft et al., 2005, "A non-sequence-specific requirement for SMN protein activity: the role of aminoglycosides in inducing elevated SMN protein levels." Hum Mol Genet, 14(9):1199-1210.
Zhang et al., 2001, "An in vivo reporter system for measuring increased inclusion of exon 7 in SMN2 mRNA: potential therapy of SMA." Gene Ther., (20):1532-1538.
Gubitz et al., 2004 "The SMN complex." Exp Cell Res.; 296:51-6.
Paushkin et al.., 2002 "The SMN complex, an assemblyosome of ribonucleoproteins" Curr Opin Cell Biol., 14:305-12.
Sumner et al., 2006, "SMN mRNA and protein levels in peripheral blood: biomarkers for SMA clinical trials." Neurology, 66:1067-1073.

Yong et al., 2004, "Why do cells need an assembly machine for RNA-protein complexes?" Trends Cell Biol.; 15(5):226-32.
Akin et al., 1998, "Regulation of Vascular Endothelial Growth Factor (VEGF) Expression is Mediated by Internal Initiation of Translation and Alternative Initiation of Transcription." Oncogene, 17:227-236.
Asano et al, 1997, "The translation initiation factor eIF3-p48 subunit is encoded by int-6, a site of frequent integration by the mouse mammary tumor virus genome." J. Biol. Chem., 272(38): 23477-23480.
DeJong, Eric S., et al., 2002, "RNA and RNA-Protein Complexes as Targets for Therapeutic Intervention." Current Topics in Medicinal Chemistry, 2(3):289-302.
Ge et al., 2002, "Regulation of Promoter Activity of the APP Gene by Cytokines and Growth Factors." Ann. N.Y. Acad. Sci 973:463-467.
Grens et al., 1990, "The 5' and 3'Untranslated Regions of Ornithine Decarboxylase mRNA Affect the Translational Efficiency." The Journal of Biological Chemistry, 265(20): 11810-11816.
Han et al. Interactive effects of the tumor necrosis factor promoter and 3'-untranslated regions. J Immunol. Mar. 15, 1991;146(6):1843-8.
Hudziak et al., 2000, "Antiproliferative effects of steric blocking phoshorodiamiade morpholino an sense agents directed against c-myc." Antisense Nucleic Acid Drug Dev., 10(3): 163-174.
Nyder et al., 1996, Cancer Research, 56 3954-3960.
Ismail et al., 2000, "Split-intron retroviral vectors: enhanced expression with improved safety." J Virol., 75(5):2365-2371.
Kedersha et al., 2002, "Stress Granules: Sites of mRNA Triage that Regulate mRNA Stability and Translatability." Biochemical Society Transactions, 30(6):963-969.
Lal et al., 2004, "Concurrent Versus Individual Binding of HuR and AUF1 to Common Labile Target mRNAs." The EMBO Journal 23:3092-3102.
Levy et al., 1996 "Hypoxia-inducible Protein Binding to Vascular Endothelial Growth Factor mRNA and Its Modulation by the von Hippel-Lindau Protein." J. Biol. Chem., 271(41): 25492-25497.
Li et al., 2001, "Targeting HER-2/new-overexpressing breast cancer cells by an antisense iron responsive element-directed gene expression." Cancer Letters, 174(2): 151-158.
McTiernan et al., 1999, "Characterization of proximal transcription regulatory elements in the rat phospholamban promoter." J. Molecular & Cellular Cardiology, 31(12:2137-2153.
Millard et al., 2000, "A U-Rich Element in the 5' Untranslated Region if necessary for the Translation of p27mRNA." Molec & Cell. Biol. 20(16):5947-5959.
Miller et al, 1998, "The Vascular Endothelial Growth Factor mRNA Contains an Internal Ribosome Entry Site." FEBS Letters, 434:417-420.
Morris et al., 2000, "Upstream Open Reading Frames as Regulators of mRNA translation." Molec & Cell. Biol. 20(23):8635-8642.
Nunokawa et al., Expression of human inducible nitric oxide synthase is regulated by both promoter and 3'-regions. Biochem Biophys Res Commun. Apr. 17, 1997;233(2):523-6.
Rapella et al., 2002, "Flavopiridol inhibits vascular endothelial growth factor production induced by hypoxia or picolinic acid in human neuroblastoma" Int. J. Cancer 99:658-664.
Pesole et al., 2001, "Structural and Functional Features of Eukaryotic mRNA Untranslated Regions." Gene 276:73-81.
Stoecklin et al., 2003, "A Constitutive Decay Element Promotes Tumor Necrosis Factor Alpha mRNA Degradation via AU-Rich Element-Independent Pathway." Molecular and Cellular Biology, 23(10):3506-3515.
Trotta et al., 2003, "BCR/ABL Activates mdm2 mRNA Translation via the La Antigen." Cancer Cell, 3:145-160.
Wickstrom E. Oligonucleotide treatment of ras-induced tumors in nude mice. Mol Biotechnol. May 2001;18(1):35-55.
Zwicky et al., 2003 "Exploring the Role of 5' Alternative Splicing and of the 3'-Untranslated region of Cathepsin B MRNA." Biological Chemistry 384(7): 1007-1018.
Canadian Office Action issued Aug. 30, 2010 in Application No. 2,514,184.

(56) References Cited

OTHER PUBLICATIONS

Canadian Office Action issued Aug. 18, 2011 in Application No. 2,514,184.
Canadian Office Action issued Jul. 11, 2012 in Application No. 2,514,184.
Canadian Office Action issued Apr. 29. 2013 in Application No. 2,514,184.
Supplementary European Search Report dated Oct. 27, 2009 issued in EP 04704085 (EP1604011).
Article 94(3) EPC Communication dated Jul. 14, 2011 issued in EP 04704085 (EP1604011).
Hong Kong Publication No. 1176383 issued Jul. 27, 2013 in Application No. HK13103422.7.
Partial European Search Report dated Jul. 24, 2012 issued in EP 12152322.9 (EP2500437).
European Search Report dated Nov. 9, 2012 issued in EP 12152322.9 (EP2500437).
Article 04(3) EPC Communication dated Aug. 19, 2013 issued in EP 12152322.9 (EP2500437).
Written Opinion of the International Searching Authority dated Mar. 7, 2005 in the PCT Application No. PCT/US04/038496 filed Nov. 17, 2004 (WO 2005/049868).
International Search Report dated Feb. 16, 2005 in the PCT Application No. 1 PCT/US04/038496 (WO 2005/049868).
Notice of Abandonment issued Aug. 31, 2010 in U.S. Appl. No. 10/579,500.
Amendment filed Aug. 17, 2010 in U.S. Appl. No. 10/895,393.
Final Rejection dated Oct. 27, 2010 in U.S. Appl. No. 10/895,393.
Amendment filed Jan. 26, 2011 in U.S. Appl. No. 10/895,393.
Non-Final Rejection dated Feb. 15, 2011 in U.S. Appl. No. 10/895,393.
Amendment filed Jul. 15, 2011 in U.S. Appl. No. 10/895,393.
Final Rejection dated Oct. 13, 2011 in U.S. Appl. No. 10/895,393.
Amendment Under 37 CFR 1.11 filed Apr. 13, 2012 in U.S. Appl. No. 10/895,393.
Non-Final Rejection dated Dec. 17, 2013 in U.S. Appl. No. 10/895,393.
International Search Report dated Nov. 6, 2011, issued in PCT/US04/20751 (WO 2005/118857).
Notice of Allowance Fees Due issued Dec. 27, 2012 in U.S. Appl. No. 10/851,074.
Issue Notification dated Apr. 1, 2013 in U.S. Appl. No. 10/851,074.
Genbank Accession No. AJ131730, dated Apr. 15, 2005, accessed Jan. 28, 2014.
Genbank Accession No. M54968, dated Feb. 4, 1997, accessed Jan. 28, 2014.
Genbank Accession No. NM_000794, dated Sep. 17, 2006, accessed Jan. 28, 2014.
Genbank Accession No. NM_000899, dated Nov. 27, 2005, accessed Jan. 28, 2014.
Genbank Accession No. NM_002087, dated Oct. 18, 2005, accessed Jan. 28, 2014.
Genbank Accession No. NM_002231, dated Nov. 27, 2005, accessed Jan. 28, 2014.
Genbank Accession No. NM_002986, dated Nov. 6, 2005, accessed Jan. 28, 2014.
Genbank Accession No. NM_003642, dated Sep. 24, 2005, accessed Jan. 28, 2014.
Genbank Accession No. NM_004364, dated Jan. 29, 2006, accessed Jan. 28, 2014.
Genbank Accession No. NM_004395, dated Oct. 16, 2005, accessed Jan. 28, 2014.
Genbank Accession No. NM_005931, dated Oct. 16, 2005, accessed Jan. 28, 2014.
Genbank Accession No. NM_080881, dated Oct. 17, 2005, accessed Jan. 28, 2014.
Genbank Accession No. X01394, dated Mar. 21, 1995, accessed Jan. 28, 2014.

* cited by examiner

Polylinker sites

```
p2luci    SalI      ApaI        BglII Eco47III BamHI   SmaI    SacI
         GAA CAA ATG TCG ACG GGG GCC CCT AGG AGA TCT AGC GCT GGA TCC CCC GGG GAG CTC AUG GAA GAC
Rluc      M   S                                                                    M   E   Fluc
```

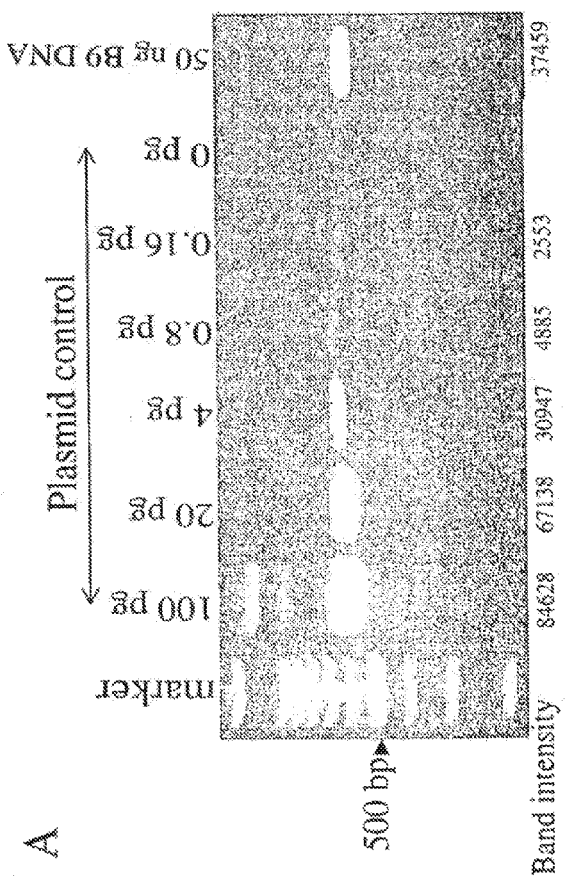
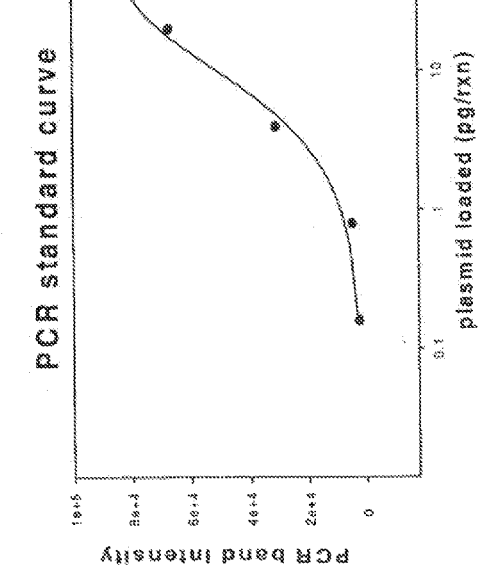
Fig. 6A
Fig. 6B

METHODS FOR IDENTIFYING COMPOUNDS THAT MODULATE UNTRANSLATED REGION-DEPENDENT GENE EXPRESSION AND METHODS OF USING SAME

This application is a continuation of U.S. application Ser. No. 10/543,033, filed Jul. 21, 2005, incorporated herein by reference in its entirety, which is a national stage application of International Application No. PCT/US04/01643, filed Jan. 21, 2004, which claims the benefit of U.S. provisional application No. 60/441,637, filed Jan. 21, 2003, which is incorporated herein by reference in its entirety.

1. INTRODUCTION

The present invention relates to a method for screening and identifying compounds that modulate untranslated region-dependent expression of any gene. In particular, the invention provides reporter gene-based assays for the identification of compounds that modulate untranslated region-dependent expression of a gene. The methods of the present invention provide a simple, sensitive assay for high-throughput screening of libraries of compounds to identify pharmaceutical leads.

2. BACKGROUND OF THE INVENTION

2.1. Gene Expression

Every living organism is a product of expression of its genes in response to a developmental program (encoded in the genome itself) and environmental factors. Gene expression can be defined as the conversion of the nucleotide sequence of a gene into the amino acid sequence of a protein or into the nucleotide sequence of a stable RNA.

In eukaryotes, gene expression begins in the nucleus with the transcription of a gene into a premessenger-RNA, also referred to as a primary transcript. While still in the nucleus, the pre-mRNA is extensively modified. Each primary transcript is capped at the 5' end, associates with hnRNP proteins to form messenger RNA-protein particles ("mRNPs"), acquires a polyadenylic acid tail at the 3' end, and undergoes splicing to remove introns. In addition, the nucleotide sequence of certain pre-mRNAs can be altered post-transcriptionally in a process known as RNA editing. Thus processed, the mature mRNA is exported to the cytoplasm. Upon export, mRNA dissociates from hnRNP proteins and binds a set of cytosol-specific mRNA-binding proteins. Once in the cytoplasm, the mRNA either immediately associates with ribosomes and templates for protein synthesis or is localized to discrete cellular foci to direct compartment-specific protein synthesis. Degradation of mRNA and protein, which occurs both in the nucleus and the cytoplasm, concludes the list of processes that comprise gene expression.

2.2. Post-Transcriptional Gene Expression Regulation

Gene expression is very tightly regulated. To produce the desired phenotype, each gene must be expressed at a defined time and at a defined rate and amount. Extensive experimental evidence indicates that post-transcriptional processes such as mRNA decay, translation, and mRNA localization constitute major control points in gene expression.

An aberration in the expression of one or more genes can be the cause or a downstream effect of a disease or other abnormality. Understanding gene expression regulation mechanisms in the normal/healthy/wild-type cell/body and during pathology will permit rational therapeutic intervention.

Regulation of gene expression both at the mRNA stability and translation levels is important in cellular responses to development or environmental stimuli such as nutrient levels, cytokines, hormones, and temperature shifts, as well as environmental stresses like hypoxia, hypocalcemia, viral infection, and tissue injury (reviewed in Guhaniyogi & Brewer, 2001, Gene 265(1-2):11-23). Furthermore, alterations in mRNA stability have been causally connected to specific disorders, such as neoplasia, thalassemia, and Alzheimer's disease, (reviewed in Guhaniyogi & Brewer, 2001, Gene 265(1-2):11-23 and Translational Control of Gene Expression, Sonenberg, Hershey, and Mathews, eds., 2000, CSHL Press). In contrast, regulation of gene expression at the mRNA localization level is primarily used by the cell to create and maintain polarity (internal gradients of protein concentration) (reviewed in Translational Control of Gene Expression, Sonenberg, Hershey, and Mathews, eds., 2000, CSHL Press).

2.3. mRNA Untranslated Regions in Gene Expression Regulation

A typical mRNA contains a 5' cap, a 5' untranslated region ("5' UTR") upstream of a start codon, an open reading frame, also referred to as coding sequence, that encodes a stable RNA or a functional protein, a 3' untranslated region ("3' UTR") downstream of the termination codon, and a poly(A) tail. Most studied cis-dependent RNA-based gene expression regulation elements map to the 5' or 3' UTRs.

Examples of 5' UTR regulatory elements include the iron response element ("IRE"), internal ribosome entry site ("IRES"), upstream open reading frame ("uORF"), male specific lethal element ("MSL-2"), G-quartet element, and 5'-terminal oligopyrimidine tract ("TOP") (reviewed in Keene & Tenenbaum, 2002, Mol Cell 9:1161 and Translational Control of Gene Expression, Sonenberg, Hershey, and Mathews, eds., 2000, CSHL Press).

Examples of 3' UTR regulatory elements include AU-rich elements ("AREs"), Selenocysteine insertion sequence ("SECIS"), histone stem loop, cytoplasmic polyadenylation elements ("CPEs"), nanos translational control element, amyloid precursor protein element ("APP"), translational regulation element ("TGE")/direct repeat element ("DRE"), bruno element ("BRE"), 15-lipoxygenase differentiation control element (15-LOX-DICE), and G-quartet element (reviewed in Keene & Tenenbaum, 2002, Mol Cell 9:1161).

The internal ribosome entry site ("IRES") is one of the 5' UTR-based cis-acting elements of post-transcriptional gene expression control. IRESes facilitate cap-independent translation initiation by recruiting ribosomes directly to the mRNA start codon. IRESes are commonly located in the 3' region of a 5' UTR and are, as recent work has established, frequently composed of several discrete sequences. IRESes do not share significant primary structure homology, but do form distinct RNA secondary and tertiary structures. Some IRESes contain sequences complementary to 18S RNA and therefore may form stable complexes with the 40S ribosomal subunit and initiate assembly of translationally competent complexes. A classic example of an "RNA-only" IRES is the internal ribosome entry site from Hepatitis C virus. However, most known IRESes require protein cofactors for activity. More than 10 IRES trans-acting factors ("ITAFs") have been identified so far. In addition, all canonical translation initiation factors, with the sole exception of 5' end cap-binding eIF4E, have been shown to participate in IRES-mediated translation initiation (reviewed in Vagner et al., 2001, EMBO reports 2:893 and Translational Control of Gene Expression, Sonenberg, Hershey, and Mathews, eds., 2000, CSHL Press).

AU-rich elements ("AREs") are 3' UTR-based regulatory signals. AREs are the primary determinant of mRNA stability and one of the key determinants of mRNA translation initiation efficiency. A typical ARE is 50 to 150 nucleotides long and contains 3 to 6 copies of $AU_3A$ pentamers embebbed in a generally A/U-enriched RNA region. The $AU_3A$ pentamers can be scattered within the region or can stagger or even overlap (see, e.g., Chen et al., 1995, Trends Biol Sci 20:465). One or several $AU_3A$ pentamers can be replaced by expanded versions such as $AU_4A$ or $AU_5A$ heptamers (see, e.g., Wilkund et al., 2002, J Biol Chem 277:40462 and Tholanikunnel and Malborn, 1997, J Biol Chem 272:11471). Single copies of the $AU_nA$ (where n=3, 4, or 5) elements placed in a random sequence context are inactive. The minimal active ARE has the sequence $U_2AU_nA(U/A)(U/A)$ (where n=3, 4, or 5) (see, e.g. Worthington et al., 2002, J Biol Chem, 277:48558-64). The activity of certain AU-rich elements in promoting mRNA degradation is enhanced in the presence of distal uridine-rich sequences. These U-rich elements do not affect mRNA stability when present alone and thus that have been termed "ARE enhancers" (see, e.g., Chen et al., 1994, Mol. Cell. Biol. 14:416).

Most AREs function in mRNA decay regulation and translation initiation regulation by interacting with specific ARE-binding proteins ("AUBPs"). There are at least 14 known cellular proteins that bind to AU-rich elements. AUBP functional properties determine ARE involvement in one or both pathways. For example, ELAV/HuR binding to c-fox ARE inhibits c-fos mRNA decay (see, e.g., Brennan & Steitz, 2001, Cell Mol Life Sci. 58:266), association of tristetraprolin with TNFα ARE dramatically enhances TNFα mRNA hydrolysis (see, e.g., Carballo et al., 1998, Science 281:1001), whereas interaction of TIA-1 with the TNFα ARE does not alter the TNFα mRNA stability but inhibits TNFα translation (see, e.g., Piecyk et al., 2000, EMBO J. 19:4154). Given its size, it is very likely that one copy of a typical ARE is capable of interacting with several AUBPs molecules. Therefore, it is contended that in the cell the competition of multiple AUBPs for the limited set of AUBP-binding sites in an ARE and the resulting "ARE proteome" determines the ARE regulatory output.

The mechanism of ARE-mediated mRNA decay is poorly understood. It has been established that mammalian mRNA degradation proceeds in 3' to 5' direction and that the first step is deadenylation by poly(A)-specific ribonuclease ("PARN"). Recent work indicates that following deadenylation a stable multi-ribonuclease complex, termed exosome, degrades the body of the message. Exosome alone is capable of initiating and accomplishing mRNA decay. However, the presence of certain AREs upregulates degradation efficiency. Available evidence suggests that AREs alone or bound by AUBPs help recruit exosome to the RNA (see, e.g., Chen et al., 2001, Cell 107:451 and Mukherjee et al., 2002, EMBO J. 21:165).

It has been reported that degradation of some mRNAs depends on ongoing translation. Thus, the translation machinery can also serve as a ribonuclease-recruiting or stabilizing AUBPs-removing entity. Supporting evidence indicates that this mechanism may operate only on a subset of mRNAs under special cell growth conditions (see, e.g., Curatola et al., 1995, Mol. Cell. Biol. 15:6331; Chen et al., 1995, Mol. Cell. Biol. 15:5777; Koeller et al., 1991, Proc. Natl. Acad. Sci. 88:7778; Savant-Bhonsale et al., 1992, Genes Dev. 6:1927; and Aharon & Schneider, 1993, Mol. Cell. Biol. 13:1971).

The mechanism of ARE-dependent translation regulation is understood even less well than that of ARE-mediated mRNA decay. It is not clear how a 3' UTR-localized element can affect translation initiation, a process that takes place in the 5' UTR. One plausible explanation comes from recent work showing that most or all cytoplasmic mRNPs are circularized via eIF4F—poly(A)-binding protein ("PABP") interaction. This interaction can bring AREs in the 3' UTR into close proximity to the translation initiation site (see, e.g., Wells et al., 1998, Mol. Cell. 2:135).

Citation or identification of any reference in Section 2 of this application is not an admission that such reference is available as prior art to the present invention.

3. SUMMARY OF THE INVENTION

The present invention provides methods for identifying a compound that modulates untranslated region-dependent expression of a target gene. In particular, the invention provides methods for identifying compounds that downregulate the translation or the stability of an mRNA of a target gene that is associated with or has been linked to the onset, development, progression or severity of a particular disease or disorder, said compounds functioning, at least in part, by targeting one or more aspects of untranslated region-dependent expression of the target gene. The invention also provides methods for identifying compounds that upregulate the translation or the stability of an mRNA of a target gene whose expression is beneficial to a subject with a particular disease or disorder, said compounds functioning, at least, in part, by targeting one or more aspects of untranslated region-dependent expression of the target gene. The invention encompasses the use of the compounds identified utilizing the methods of the invention for modulating the expression of a target gene in vitro and in vivo. In particular, the invention encompasses the use of the compounds identified utilizing the methods of the invention for the prevention, treatment or amelioration of a disease or disorder or a symptom thereof.

The invention provides reporter gene-based assays for the identification of a compound that modulates untranslated region-dependent expression of a target gene. The reporter gene-based assays may be conducted by contacting a compound with a cell genetically engineered to express a nucleic acid comprising a reporter gene operably linked to one or more untranslated regions of a target gene, and measuring the expression of said reporter gene. Alternatively, the reporter gene-based assays may be conducted by contacting a compound with a cell-free translation mixture and a nucleic acid comprising a reporter gene operably linked to one or more untranslated regions of a target gene, and measuring the expression of said reporter gene. The alteration in reporter gene expression relative to a previously determined reference range or a control in such reporter-gene based assays indicates that a particular compound modulates untranslated region-dependent expression of a target gene. In a specific embodiment, a compound identified utilizing a reporter gene-based assay described herein alters the expression of the reporter gene by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, or at least 1.5 fold, at least 2 fold, at least 2.5 fold, at least 5 fold, at least 7.5 fold or at least 10 fold relative to a control (e.g., PBS), the absence of a control or a previously determined reference range in an assay described herein or well-known in the art. In order to exclude the possibility that a particular compound is functioning solely by modulating the expression of a target gene in an untranslated region-independent manner, one or more mutations (i.e., deletions, insertions, or nucleotide substitutions) may be introduced into the untranslated regions operably linked to a reporter gene and the effect on the expression of the reporter gene in a reporter gene-based assay described herein can be determined.

In one embodiment, the invention provides a method for identifying a compound that modulates untranslated region-dependent expression of a target gene, said method comprising: (a) expressing a nucleic acid comprising a reporter gene operably linked to two, three or more untranslated regions of said target gene in a cell; (b) contacting said cell with a member of a library of compounds; and (c) detecting the expression of said reporter gene, wherein a compound that modulates untranslated region-dependent regulation of expression is identified if the expression of said reporter gene in the presence of a compound is altered as compared to the expression of said reporter gene in the absence of said compound or the presence of a control (e.g., phosphate buffered saline ("PBS")). In an alternative embodiment, the invention provides a method for identifying a compound that modulates untranslated region-dependent expression of a target gene, said method comprising: (a) expressing a nucleic acid comprising a reporter gene operably linked two, three or more untranslated regions of said target gene in a cell; (b) contacting said cell with a member of a library of compounds; and (c) detecting the expression of said reporter gene, wherein a compound that modulates untranslated region-dependent expression is identified if the expression of said reporter gene is altered in the presence of the compound relative to a previously determined reference range.

In another embodiment, the invention provides a method for identifying a compound that modulates untranslated region-dependent expression of a target gene, said method comprising: (a) expressing a nucleic acid consisting of a reporter gene operably linked to one, two, three or more untranslated regions of the target gene in a cell; (b) contacting said cell with a member of a library of compounds; and (c) detecting the expression of said reporter gene, wherein a compound that modulates untranslated region-dependent regulation of expression is identified if the expression of said reporter gene in the presence of a compound is altered as compared to the expression of said reporter gene in the absence of said compound or the presence of a control (e.g., PBS). In an alternative embodiment, the invention provides a method for identifying a compound that modulates untranslated region-dependent expression of a target gene, said method comprising: (a) expressing a nucleic acid consisting of a reporter gene operably linked to one, two, three or more untranslated regions of the target gene in a cell; (b) contacting said cell with a member of a library of compounds; and (c) detecting the expression of said reporter gene, wherein a compound that modulates untranslated region-dependent expression is identified if the expression of said reporter gene in the presence of the compound is altered relative to a previously determined reference range.

In another embodiment, the invention provides a method for identifying a compound that modulates untranslated region-dependent expression of a target gene, said method comprising: (a) contacting a member of a library of compounds with a cell-free translation mixture and a nucleic acid comprising a reporter gene operably linked to one, two, three or more untranslated regions of said target gene; and (b) detecting the expression of said reporter gene, wherein a compound that modulates untranslated region-dependent expression is identified if the expression of said reporter gene in the presence of a compound is altered as compared to the expression of said reporter gene in the absence of said compound or the presence of a control (e.g., PBS). In an alternative embodiment, the invention provides a method for identifying a compound that modulates untranslated region-dependent expression of a target gene, said method comprising: (a) contacting a member of a library of compounds with a cell-free translation mixture and a nucleic acid comprising a reporter gene operably linked to one, two, three or more untranslated regions of said target gene; and (b) detecting the expression of said reporter gene, wherein a compound that modulates untranslated region-dependent expression of a target gene is identified if the expression of said reporter gene in the presence of a compound is altered relative to a previously determined reference range.

In another embodiment, the invention provides a method for identifying a compound that modulates untranslated region-dependent expression of a target gene, said method comprising: (a) contacting a member of a library of compounds with a cell containing a nucleic acid comprising a reporter gene operably linked to one, two, three or more untranslated regions of said target gene; and (b) detecting a reporter protein translated from said reporter gene, wherein a compound that modulates untranslated region-dependent expression is identified if the expression of said reporter gene in the presence of a compound is altered as compared to the expression of said reporter gene in the absence of said compound or the presence of a control (e.g., PBS). In an alternative embodiment, the invention provides a method for identifying a compound that modulates untranslated region-dependent expression of a target gene, said method comprising: (a) contacting a member of a library of compounds with a cell containing a nucleic acid comprising a reporter gene operably linked to one, two, three or more untranslated regions of said target gene; and (b) detecting expression of said reporter gene, wherein a compound that modulates untranslated region-dependent expression is identified if the expression of said reporter gene in the presence of a compound is altered relative to a previously determined reference range.

The invention also provides methods of identifying compounds that upregulate untranslated region-dependent expression of a target gene utilizing the reporter gene-based assays described herein. In a specific embodiment, the invention provides a method of upregulating untranslated region-dependent expression of a target gene, said method comprising (a) contacting a compound with a cell containing a nucleic acid comprising a reporter gene operably linked to one, two, three or more untranslated regions of said target gene; and (b) detecting a reporter gene protein translated from said reporter gene, wherein a compound that upregulates untranslated region dependent expression is identified if the expression of said reporter gene in the presence of a compound is increased relative to the absence of the compound or a previously determined reference range. In another embodiment, the invention provides a method of upregulating untranslated region-dependent expression of a target gene, said method comprising (a) contacting a compound with a cell-free translation mixture and a nucleic acid comprising a reporter gene operably linked to one, two, three or more untranslated regions of said target gene; and (b) detecting a reporter gene protein translated from said reporter gene, wherein a compound that upregulates untranslated region dependent expression is identified if the expression of said reporter gene in the presence of a compound is increased relative to the absence of the compound or a previously determined reference range.

The invention also provides methods of identifying compounds that down-regulate untranslated region-dependent expression of a target gene utlizing the reporter gene-based assays described herein. In a specific embodiment, the invention provides a method of down-regulating untranslated region-dependent expression of a target gene, said method comprising (a) contacting a compound with a cell containing a nucleic acid comprising a reporter gene operably linked to one, two, three or more untranslated regions of said target gene; and (b) detecting a reporter gene protein translated from said reporter gene, wherein a compound that down-regulates untranslated region dependent expression is identified if the expression of said reporter gene in the presence of a compound is decreased relative to the absence of the compound or a previously determined reference range. In another embodiment, the invention provides a method of down-regulating untranslated region-dependent expression of a target gene, said method comprising (a) contacting a compound with a cell-free translation mixture and a nucleic acid comprising a reporter gene operably linked to one, two, three or more untranslated regions of said target gene; and (b) detecting a reporter gene protein translated from said reporter gene, wherein a compound that down-regulates untranslated region dependent expression is identified if the expression of said reporter gene in the presence of a compound is decreased relative to the absence of the compound or a previously determined reference range.

In accordance with the invention, the step of contacting a compound with a cell, or cell-free translation mixture and a nucleic acid in the reporter gene-based assays described herein is preferably conducted in an aqueous solution comprising a buffer and a combination of salts. In a specific embodiment, the aqueous solution approximates or mimics physiologic conditions. In another specific embodiment, the aqueous solution further comprises a detergent or a surfactant.

The present invention provides methods of identifying environmental stimuli (e.g., exposure to different concentrations of $CO_2$ and/or $O_2$, stress, temperature shifts, and different pHs) that modulate untranslated region-dependent expression of a target gene utilizing the reporter gene-based assays described herein. In particular, the invention provides a method of identifying an environmental stimulus, said method comprising (a) contacting a cell containing a nucleic acid comprising a reporter gene operably linked to one, two, three or more untranslated regions of said target gene with an environmental stimulus; and (b) detecting a reporter gene protein translated from said reporter gene, wherein a compound that modulates untranslated region dependent expression is identified if the expression of said reporter gene in the presence of an environmental stimuli is altered relative to the absence of the compound or a previously determined reference range. In a specific embodiment, the environmental stimuli is not hypoxia. In another embodiment, the environmental stimuli does not include a compound.

The reporter gene constructs utilized in the reporter gene-based assays described herein may comprise a 5' untranslated region ("UTR") of a target gene, a 3' UTR of a target gene, or a 5' UTR and a 3' UTR of a target gene operably linked to a reporter gene. In a specific embodiment, a reporter gene construct utilized in the reporter gene-based assays described herein comprises a 5' UTR of a target gene with a stable hairpin secondary structure operably linked to a reporter gene. In a preferred embodiment, a reporter gene construct utilized in the reporter gene-based assays described herein comprises a 5' UTR and a 3' UTR of a target gene. The untranslated regions of a target gene utilized to construct a reporter gene construct may comprise one or more of the following elements: an iron response element ("IRE"), Internal ribosome entry site ("IRES"), upstream open reading frame ("uORF"), male specific lethal element ("MSL-2"), G quartet element, 5'-terminal oligopyrimidine tract ("TOP"), AU-rich element ("ARE"), selenocysteine insertion sequence ("SECIS"), histone stem loop, cytoplasmic polyadenylation element ("CPE"), nanos translational control element, amyloid precursor protein element ("APP"), translational regulation element ("TGE")/direct repeat element ("DRE"), Bruno element ("BRE"), and a 15-lipoxygenase differentiation control element ("15-LOX-DICE").

In addition to untranslated regions, the reporter gene constructs utilized in the reporter gene-based assays described herein may comprise one, two, three or more introns within the open reading frame ("ORF") of the reporter gene. Further, the 3' end of a reporter gene may be polyadenylated and/or the 5' end may be capped. In a specific embodiment, the 5' end of the reporter gene is not capped.

The reporter gene constructs utilized in the reporter gene-based assays described herein may comprise an untranslated region of a gene whose expression is associated with or has been linked to the onset, development, progression or severity of a particular disease or disorder. Alternatively, the reporter gene constructs utilized in the reporter gene-based assays described herein may comprise an untranslated region of a gene whose expression is beneficial to a subject with a particular disease or disorder. Examples of genes from which the untranslated regions may be obtained include, but are not limited, the gene encoding tumor necrosis factor alpha ("TNF-α"), the gene encoding granulocyte-macrophage colony stimulating factor ("GM-CSF"), the gene encoding granulocyte colony stimulating factor ("G-CSF"), the gene encoding interleukin 2 ("IL-2"), the gene encoding interleukin 6 ("IL-6"), the gene encoding vascular endothelial growth factor ("VEGF"), the genome encoding hepatitis C virus ("HCV"), the gene encoding survivin, or the gene encoding Her-2. In a specific embodiment, an untranslated region is obtained or derived from Her-2 and/or VEGF. In another embodiment, an untranslated region is not obtained or derived from the gene encoding Her-2. In another embodiment, an untranslated region is not obtained or derived from the gene encoding VEGF. In another embodiment, an untranslated region is not obtained or derived from the genes encoding VEGF and Her-2.

Any reporter gene well-known to one of skill in the art may be utilized in the reporter gene constructs described herein. Examples of reporter genes include, but are not limited to, the gene encoding firefly luciferase, the gene coding *renilla* luciferase, the genes encoding click beetle luciferase, the gene encoding green fluorescent protein, the gene encoding yellow fluorescent protein, the gene encoding red fluorescent protein, the gene encoding cyan fluorescent protein, the gene encoding blue fluorescent protein, the gene encoding beta-galactosidase, the gene encoding beta-glucoronidase, the gene encoding beta-lactamase, the gene encoding chloramphenicol acetyltransferase, and the gene encoding alkaline phosphatase.

The reporter gene-based assays described herein may be conducted in a cell genetically engineered to express a reporter gene or in vitro utilizing a cell-free translation mixture. Any cell or cell line of any species well-known to one of skill in the art may be utilized in accordance with the methods of the invention. Further, a cell-free translation mixture may be derived from any cell or cell line of any species well-known to one of skill in the art. Examples of cells and cell types include, but are not limited to, human cells (e.g., HeLa cells and 293 cells), yeast, mouse cells (e.g., cultured mouse cells), rat cells (e.g., cultured rat cells), Chinese hamster ovary ("CHO") cells, *Xenopus* oocytes, cancer cells (e.g., undifferentiated cancer cells), primary cells, reticulocytes, wheat germ, rye embryo, or bacterial cells.

The compounds utilized in the reporter gene-based assays described herein may be members of a library of compounds. In specific embodiment, the compound is selected from a combinatorial library of compounds comprising peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small organic molecule libraries. In a preferred embodiment, the small organic molecule libraries are libraries of benzodiazepines, isoprenoids, thiazolidinones, metathiazanones, pyrrolidines, morpholino compounds, or diazepindiones.

Once a compound that modulates untranslated region-dependent expression of a target gene is identified, the structure of the compound may be determined utilizing well-known techniques or by referring to a predetermined code. For example, the structure of the compound may be determined by mass spectroscopy, NMR, vibrational spectroscopy, or X-ray crystallography.

A compound identified in accordance with the methods of the invention may directly bind to an RNA transcribed from a target gene. Alternatively, a compound identified in accordance with the methods of invention may bind to one or more trans-acting factors (such as, but not limited to, proteins) that modulate untranslated region-dependent expression of a target gene. Further, a compound identified in accordance with the methods of invention may disrupt an interaction between the 5' UTR and the 3' UTR.

In a specific embodiment, a compound identified in accordance with the methods of the invention reduces the translation efficiency and/or stability of an mRNA transcribed from a target gene by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, or at least 1.5 fold, at least 2 fold, at least 2.5 fold, at least 5 fold, at least 7.5 fold or at least 10 fold relative to a control (e.g., PBS), the absence of a control or a previously determined reference range in an assay described herein or well-known in the art. In another embodiment, a compound identified in accordance with the methods of the invention reduces the translation efficiency and/or stability of an mRNA transcribed from a target gene by at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, or at least 1.5 fold, at least 2 fold, at least 2.5 fold, at least 5 fold, at least 7.5 fold or at least 10 fold relative to a control (e.g., PBS), the absence of a control or a previously determined reference range in an assay described herein or well-known in the art.

A compound that modulates untranslated region-dependent expression in a reporter gene-based assay described herein may be subsequently tested in in vitro assays (e.g., cell-free assays) or in vivo assays (e.g., cell-based assays) well-known to one of skill in the art or described herein for the effect of said compound on the expression of the target gene from which the untranslated regions of the reporter gene construct were derived. Further, to assess the specificity of a particular compound's effect on untranslated region-dependent expression of a target gene, the effect of said compound on the expression of one or more genes (preferably, a plurality of genes) can be determined utilizing assays well-known to one of skill in the art or described herein. In a preferred embodiment, a compound identified utilizing the reporter gene-based assays described herein has a specific effect on the expression of only one gene or a group of genes within the same signaling pathway.

In a specific embodiment, the specificity of a particular compound for an untranslated region of a target gene is determined by (a) contacting the compound of interest with a cell containing a nucleic acid comprising a reporter gene operably linked to an UTR of a different gene; and (b) detecting a reporter gene protein translated from the reporter gene, wherein the compound is specific for the untranslated region of the target gene if the expression of said reporter gene in the presence of the compound is not altered or is not substantially altered relative to a previously determined reference range, or the expression in the absence of the compound or the presence of a control (e.g., PBS). In another embodiment, the specificity of a particular compound for an untranslated region of a target gene is determined by (a) contacting the compound of interest with a panel of cells, each cell in a different well of a container (e.g., a 48 or 96 well microtiter plate) and each cell containing a nucleic acid comprising a reporter gene operably linked to an UTR of a different gene; and (b) detecting a reporter gene protein translated from the reporter gene, wherein the compound is specific for the untranslated region of the target gene if the expression of said reporter gene in the presence of the compound is not altered or is not substantially altered relative to a previously determined reference range, or the expression in the absence of the compound or the presence of a control (e.g., PBS). In accordance with this embodiment, the panel may comprise 5, 7, 10, 15, 20, 25, 50, 75, 100 or more cells. In another embodiment, the specificity of a particular compound for an untranslated region of a target gene is determined by (a) contacting the compound of interest with a cell-free translation mixture and a nucleic acid comprising a reporter gene operably linked to an UTR of a different gene; and (b) detecting a reporter gene protein translated from the reporter gene, wherein the compound is specific for the untranslated region of the target gene if the expression of said reporter gene in the presence of the compound is not altered or is not substantially altered relative to a previously determined reference range, or the expression in the absence of the compound or the presence of a control (e.g., PBS). As used herein, the term "not substantially altered" means that the compound alters the expression of the reporter gene or target gene by less than 20%, less than 15%, less than 10%, less than 5%, or less than 2% relative to a negative control such as PBS.

The invention provides for methods for treating, preventing or ameliorating one or more symptoms of a disease or disorder associated with the aberrant expression of a target gene, said method comprising administering to a subject in need thereof a therapeutically or prophylactically effective amount of a compound, or a pharmaceutically acceptable salt thereof, identified according to the methods described herein. In one embodiment, the target gene is aberrantly overexpressed. In another embodiment, the target gene is expressed at an aberrantly low level. In particular, the invention provides for a method of treating or preventing a disease or disorder or ameliorating a symptom thereof, said method comprising administering to a subject in need thereof an effective amount of a compound, or a pharmaceutically acceptable salt thereof, identified according to the methods described herein, wherein said effective amount increases the expression of a target gene beneficial in the treatment or prevention of said disease or disorder. The invention also provides for a method of treating or preventing a disease or disorder or ameliorating a symptom thereof, said method comprising administering to a subject in need thereof an effective amount of a compound, or a pharmaceutically acceptable salt thereof, identified according to the methods described herein, wherein said effective amount decreases the expression of a target gene whose expression is associated with or has been linked to the onset, development, progression or severity of said disease or disorder. In a specific embodiment, the disease or disorder is a proliferative disorder, an inflammatory disorder, an infectious disease, a genetic disorder, an autoimmune disorder, a cardiovascular disease, or a central nervous system disorder. In an embodiment wherein the disease or disorder is an infectious disease, the infectious disease can be caused by a fungal infection, a bacterial infection, a viral infection, or an infection caused by another type of pathogen.

The invention provides a method for identifying a compound that inhibits or reduces angiogenesis, said method comprising: (a) contacting a member of a library of compounds with a cell containing a nucleic acid comprising a reporter gene operably linked to one, two, three or more untranslated regions of a target gene; and (b) detecting the expression of said reporter gene, wherein if a compound that reduces the expression of said reporter gene relative to a previously determined reference range, or to the expression of said reporter gene in the absence of said compound or in the presence of a control (e.g., PBS) is detected in (b), then (c) contacting the compound with a tumor cell and detecting the proliferation of said tumor cell, so that if the compound reduces or inhibits the proliferation of the tumor cell, the compound is identified as a compound that inhibits or reduces angiogenesis. The invention provides a method for identifying a compound that inhibits or reduces angiogenesis, said method comprising: (a) contacting a cell-free translation mixture with a member of a library of compounds and a nucleic acid comprising a reporter gene operably linked to one, two, three or more untranslated regions of a target gene; and (b) detecting the expression of said reporter gene, wherein if a compound that reduces the expression of said reporter gene relative to a previously determined reference range, or to the expression of said reporter gene in the absence of said compound or in the presence of a control (e.g., PBS) is detected in (b), then (c) contacting the compound with a tumor cell and detecting the proliferation of said tumor cell, so that if the compound reduces or inhibits the proliferation of the tumor cell, the compound is identified as a compound that inhibits or reduces angiogenesis. In a specific embodiment, the compound is further tested in an animal model for angiogenesis by, e.g., administering said compound to said animal model and verifying that angiogenesis is inhibited by said compound in said animal model. In a preferred embodiment, the target gene is VEGF. In another embodiment, the compound identified in accordance with the methods of the invention inhibits or reduces angiogenesis by at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, or at least 1.5 fold, at least 2 fold, at least 2.5 fold, at least 5 fold, at least 7.5 fold, or at least 10 fold relative to a control (e.g., PBS) in an assay described herein or well-known in the art.

The invention provides for a method for identifying a therapeutic agent for the treatment or prevention of cancer, or amelioration of a symptom thereof, said method comprising: (a) contacting a member of a library of compounds with a cell containing a nucleic acid comprising a reporter gene operably linked to one, two, three or more untranslated regions of a target gene; and (b) detecting the expression of said reporter gene, wherein if a compound that reduces the expression of said reporter gene relative to a previously determined reference range, or the expression of said reporter gene in the absence of said compound or the presence of a control (e.g., PBS) is detected in (b), then (c) contacting the compound with a cancer cell and detecting the proliferation of said cancer cell, so that if the compound reduces or inhibits the proliferation of the cancer cell, the compound is identified as a therapeutic agent for the treatment or prevention of cancer, or amelioration of a symptom thereof. The invention also provides for a method for identifying a therapeutic agent for the treatment or prevention of cancer, or amelioration of a symptom thereof, said method comprising: (a) contacting a cell-free translation mixture with a member of a library of compounds and a nucleic acid comprising a reporter gene operably linked to one, two, three or more untranslated regions of a target gene; and (b) detecting the expression of said reporter gene, wherein if a compound that reduces the expression of said reporter gene relative to a previously determined reference range, or the expression of said reporter gene in the absence of said compound or the presence of a control (e.g., PBS) is detected in (b), then (c) contacting the compound with a cancer cell and detecting the proliferation of said cancer cell, so that if the compound reduces or inhibits the proliferation of the cancer cell, the compound is identified as a therapeutic agent for the treatment or prevention of cancer, or amelioration of a symptom thereof. In a specific embodiment, the compound is further tested in an animal model for cancer by, e.g., administering said compound to said animal model and verifying that the compound is effective in reducing the proliferation or spread of cancer cells in said animal model. In a preferred embodiment, the target gene is survivin.

In a specific embodiment, the invention provides for a method of identifying a therapeutic agent for the treatment or prevention of breast cancer, or amelioration of a symptom thereof, said method comprising: (a) contacting a member of a library of compounds with a cell containing a nucleic acid comprising a reporter gene operably linked to one, two, three or more untranslated regions of a target gene; and (b) detecting the expression of said reporter gene, wherein if a compound that reduces the expression of said reporter gene relative a previously determined reference range, or the expression of said reporter gene in the absence of said compound or the presence of a control is detected in (b), then (c) contacting the compound with a breast cancer cell and detecting the proliferation of said breast cancer cell, so that if the compound reduces or inhibits the proliferation of the breast cancer cell, the compound is identified as a therapeutic agent for the treatment or prevention of breast cancer, or amelioration of a symptom thereof. In another embodiment, the invention provides for a method of identifying a therapeutic agent for the treatment or prevention of breast cancer, or amelioration of a symptom thereof, said method comprising: (a) contacting a cell-free translation mixture with a member of a library of compounds and a nucleic acid comprising a reporter gene operably linked to one, two, three or more untranslated regions of a target gene; and (b) detecting the expression of said reporter gene, wherein if a compound that reduces the expression of said reporter gene relative to a previously determined reference range, or the expression of said reporter gene in the absence of said compound or the presence of a control is detected in (b), then (c) contacting the compound with a breast cancer cell and detecting the proliferation of said breast cancer cell, so that if the compound reduces or inhibits the proliferation of the breast cancer cell, the compound is identified as a therapeutic agent for the treatment or prevention of breast cancer, or amelioration of a symptom thereof. In accordance with these embodiments, the compound may be further tested in an animal model for breast cancer by, e.g., administering said compound to said animal model and verifying that the compound is effective in reducing the proliferation or spread of breast cancer cells in said animal model. In a preferred embodiment, the target gene is Her-2.

The invention also provides methods for upregulating or downregulating the expression of a target gene utilizing a compound identified in accordance with the methods described herein. The upregulation or downregulation of a target gene is particularly useful in vitro when attempting to produce a protein encoded by said target gene for use as a therapeutic or prophylactic agent, or in experiments conducted to, e.g., identify the function or efficacy of said protein. In particular, the invention provides a method of modulating the expression of a target gene, said method comprising contacting a cell with an effective amount of a compound or pharmaceutically acceptable derivative thereof, identified according to the methods described herein. In one embodiment, the cell is a eucaryotic cell. In another embodiment, the cell is a procaryotic cell.

The invention further provides methods for verifying or confirming the ability of a compound to modulate untranslated region-dependent expression of a target gene. The ability of a compound to modulate untranslated region-dependent expression of a target gene can be verified or confirmed utilizing any of the assays described herein to identify such a compound. In a first embodiment, the invention provides a method for verifying the ability of a compound to modulate untranslated region-dependent expression of a target gene, said method comprising: (a) expressing a nucleic acid comprising a reporter gene operably linked to one, two, three or more untranslated regions of said target gene in a cell; (b) contacting said cell with a compound; and (c) detecting the expression of said reporter gene, wherein a compound that modulates untranslated region-dependent expression is verified if the expression of said reporter gene in the presence of a compound is altered as compared to a previously determined reference range or the expression of said reporter gene in the absence of said compound or the presence of a control.

In a second embodiment, the invention provides a method for verifying the ability of a compound to modulate untranslated region-dependent expression of a target gene, said method comprising: (a) contacting a compound with a cell-free translation mixture and a nucleic acid comprising a reporter gene operably linked to one, two, three or more untranslated regions of said target gene; and (b) detecting the expression of said reporter gene, wherein a compound that modulates untranslated region-dependent expression is verified if the expression of said reporter gene in the presence of a compound is altered as compared to a previously determined reference range or the expression of said reporter gene in the absence of said compound or the presence of a control.

In a third embodiment, the invention provides a method for verifying the ability of a compound to modulate untranslated region-dependent expression of a target gene, said method comprising: (a) contacting a compound with a cell containing a nucleic acid comprising a reporter gene operably linked to one, two, three or more untranslated regions of said target gene; and (b) detecting the expression of said reporter gene, wherein a compound that modulates untranslated region-dependent expression is verified if the expression of said reporter gene in the presence of a compound is altered as compared to a previously determined reference range or the expression of said reporter gene in the absence of said compound or the presence of a control.

3.1. Terminology

As used herein, the term "5' cap" refers to a methylated guanine cap, e.g., a 7 methylguanosine (5'-5') RNA triphosphate, that is added to the 5' end of a pre-mRNA.

As used herein, the term "ARE" refers to an adenylate uridylate rich element in the 3' UTR of a mRNA.

As used herein, the term "compound" refers to any agent or complex that is being tested for its ability to modulate untranslated region-dependent expression of a target gene, or any agent or complex identified by the methods described herein. Examples of compounds include, but are not limited to, proteins, polypeptides, peptides, peptide analogs (including peptides comprising non-naturally occurring amino acids, e.g., D-amino acids, phosphorous analogs of amino acids, such as a-amino phosphoric acids and a-amino phosphoric acids, or amino acids having non-peptide linkages), nucleic acids, nucleic acid analogs such as phosphorothioates and PNAs, hormones, antigens, antibodies, lipids, fatty acids, synthetic or naturally occurring drugs, opiates, dopamine, serotonin, catecholamines, thrombin, acetylcholine, prostaglandins, organic molecules, pheromones, adenosine, sucrose, glucose, lactose and galactose.

As used herein, the term "CUG repeat" refers to a repeat of a cytosine-uracil-guanine triplet in the 3' UTR of a mRNA.

As used herein, the term "cytosine rich element" refers to cytosine-rich stability determinant sequences in the 3' UTR of a mRNA.

As used herein, the terms "disorder" and "disease" refer to a condition in a subject.

As used herein, the term "effective amount" refers to the amount of a compound which is sufficient to reduce or ameliorate the severity, duration and/or a disease or disorder or a symptom thereof, prevent the advancement of a disease or disorder, cause regression of a disease or disorder, prevent the recurrence, development, or onset of one or more symptoms associated with a disease or disorder, or enhance or improve the prophylactic or therapeutic effect(s) of another therapy (e.g., prophylactic or therapeutic agent).

As used herein, the term "fragment" refers to a nucleotide sequence comprising an nucleic acid sequence of at least 5 contiguous nucleic acid residues, at least 10 contiguous nucleic acid residues, at least 15 contiguous nucleic acid residues, at least 20 contiguous nucleic acid residues, at least 25 contiguous nucleic acid residues, at least 40 contiguous nucleic acid residues, at least 50 contiguous nucleic acid residues, at least 60 contiguous nucleic acid residues, at least 70 contiguous nucleic acid residues, at least contiguous 80 nucleic acid residues, at least contiguous 90 nucleic acid residues, at least contiguous 100 nucleic acid residues, at least contiguous 125 nucleic acid residues, at least 150 contiguous nucleic acid residues, at least contiguous 175 nucleic acid residues, at least contiguous 200 nucleic acid residues, or at least contiguous 250 nucleic acid residues of the nucleotide sequence of untranslated region of a target gene. In a specific embodiment, a fragment of a untranslated region of a target gene retains at least one element of the untranslated region (e.g., an IRES).

As used herein, the term "target RNA" refers to an RNA of interest, i.e., the RNA transcribed from a target gene or a gene of interest. In a preferred embodiment, the target RNA contains one or more untranslated regions, and more preferably, contains at least one element of the untranslated region (e.g., an IRES).

As used herein, the term "host cell" includes a particular subject cell transformed or transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "in combination" refers to the use of more than one therapies (e.g., prophylactic and/or therapeutic agents). The use of the term "in combination" does not restrict the order in which therapies (e.g., prophylactic and/or therapeutic agents) are administered to a subject with a particular disease or disorder. A first therapy (e.g., a prophylactic or therapeutic agent such as, e.g., a compound identified in accordance with the methods of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as, e.g., a chemotherapeutic agent, an anti-inflammatory agent or a TNF-α antagonist) to a subject with a particular disease or disorder.

As used herein, the term "IRE" refers to an iron response element in the 5' UTR or 3' UTR of a mRNA.

As used herein, the term "IRES" refers to an internal ribosome entry site in the 5' UTR of a mRNA.

As used herein, the term "library" refers to a plurality of compounds. A library can be a combinatorial library, e.g., a collection of compounds synthesized using combinatorial chemistry techniques, or a collection of unique chemicals of low molecular weight (less than 1000 daltons) that each occupy a unique three-dimensional space.

As used herein, the term "ORF" refers to the open reading frame of a mRNA, i.e., the region of the mRNA that is translated into protein.

As used herein, the terms "non-responsive" and "refractory" describe patients treated with a currently available therapy (e.g., a prophylactic or therapeutic agent) for a disease or disorder, which is not clinically adequate to relieve one or more symptoms associated with such disease or disorder. Typically, such patients suffer from severe, persistently active disease and require additional therapy to ameliorate the symptoms associated with their disease or disorder.

As used herein, the phrase "pharmaceutically acceptable salt(s)," includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the term "poly(A) tail" refers to a polyadenylic acid tail that is added to the 3' end of a pre-mRNA.

As used herein, the terms "prophylactic agent" and "prophylactic agents" refer to any agent(s) which can be used in the prevention of a particular disease or disorder. In certain embodiments, the term "prophylactic agent" refers to a compound identified in the screening assays described herein. In certain other embodiments, the term "prophylactic agent" does not refer a compound identified in the screening assays described herein.

As used herein, the phrase "prophylactically effective amount" refers to the amount of a therapy (e.g., a prophylactic agent) which is sufficient to result in the prevention of the development, recurrence or onset of a disease or disorder or one or more symptoms associated thereof.

As used herein, the terms "prevent", "preventing" and "prevention" refer to the prevention of the development, recurrence or onset of a disease or disorder or one or more symptoms thereof resulting from the administration of one or more compounds identified in accordance the methods of the invention or the administration of a combination of such a compound and a known therapy for a particular disease or disorder.

As used herein, the term "previously determined reference range" refers to a reference range for the expression and/or the activity of a reporter gene or a target gene by a particular cell or in a particular cell-free translation mixture. Each laboratory will establish its own reference range for each particular assay, each cell type and each cell-free translation mixture. In a preferred embodiment, at least one positive control and at least one negative control are included in each batch of compounds analyzed.

As used herein, the term "small molecules" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a monkey such as a cynomolgus monkey and a human), and more preferably a human. In one embodiment, the subject is refractory or non-responsive to current therapies for a disease or disorder (e.g., viral infections, fungal infections, bacterial infections, proliferative diseases or inflammatory diseases). In another embodiment, the subject is a farm animal (e.g., a horse, a cow, a pig, etc.) or a household pet (e.g., a dog or a cat). In a preferred embodiment, the subject is a human.

As used herein, the term "synergistic" refers to a combination of a compound identified using one of the methods described herein, and another therapy (preferably, a therapy which has been or is currently being used to prevent or treat a particular disease or disorder) which is more effective than the additive effects of the therapies. A synergistic effect of a combination of therapies (e.g., prophylactic or therapeutic agents) permits the use of lower dosages of one or more of the therapies and/or less frequent administration of said therapies to a subject with a particular disease or disorder. The ability to utilize lower dosages of a therapy (e.g., prophylactic or therapeutic agent) and/or to administer said therapy less frequently reduces the toxicity associated with the administration of said therapy to a subject without reducing the efficacy of said therapies in the prevention or treatment of a particular disease or disorder. In addition, a synergistic effect can result in improved efficacy of therapies in the prevention or treatment of a particular disease or disorder. Finally, a synergistic effect of a combination of therapies (e.g., prophylactic or therapeutic agents) may avoid or reduce adverse or unwanted side effects associated with the use of either therapy alone.

As used herein, the term "target gene" refers to a gene or nucleotide sequence encoding a protein or polypeptide of interest. In a preferred embodiment, the gene or nucleotide sequence comprises an untranslated region.

As used herein, a "target nucleic acid" refers to RNA, DNA, or a chemically modified variant thereof. In a preferred embodiment, the target nucleic acid is RNA. In a preferred embodiment, the target nucleic acid refers to the untranslated region of an mRNA, such as, but not limited to, a 5' UTR and a 3' UTR. In another embodiment, the target nucleic acid refers to an open reading frame of an mRNA. A target nucleic acid also refers to tertiary structures of the nucleic acids, such as, but not limited to loops, bulges, pseudoknots, guanosine quartets and turns. A target nucleic acid also refers to RNA elements such as, but not limited to, the HIV TAR element, internal ribosome entry site, instability elements, and adenylate uridylate-rich elements, which are described in Section 5.1. Non-limiting examples of target nucleic acids are presented in Section 5.1 and Section 6.

As used herein, the terms "therapeutic agent" and "therapeutic agents" refer to any agent(s) which can be used in the prevention, treatment, management or amelioration of one or more symptoms of a particular disease or disorder. In certain embodiments, the term "therapeutic agent" refers to a compound identified in the screening assays described herein. In other embodiments, the term "therapeutic agent" does not refer to a compound identified in the screening assays described herein.

As used herein, the term "therapeutically effective amount" refers to that amount of a therapy (e.g., a therapeutic agent) sufficient to reduce the severity of a disease or disorder, reduce the duration of a disease or disorder, ameliorate of one or more symptoms of a disease or disorder, prevent advancement of a disease or disorder, cause regression of the disease or disorder, or to enhance or improve the therapeutic effect(s) of another therapeutic agent. In a specific embodiment, with respect to the treatment of cancer, a therapeutically effective amount refers to the amount of a therapy (e.g., a therapeutic agent) that inhibits or reduces the proliferation of cancerous cells, inhibits or reduces the spread of tumor cells (metastasis), inhibits or reduces the onset, development or progression of one or more symptoms associated with cancer, or reduces the size of a tumor. Preferably, with respect to the treatment of cancer, a therapeutically effective of a therapy (e.g., a therapeutic agent) reduces the proliferation of cancerous cells or the size of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a control (e.g., PBS) in an assay described herein or well-known in the art.

In another embodiment, with respect to the treatment of a viral infection, a therapeutically effective amount refers to the amount of a therapy (e.g., a therapeutic agent) sufficient to reduce or inhibit the replication of a virus, inhibit or reduce the spread of the virus to other tissues or subjects, or ameliorate one or more symptoms associated with the viral infection. Preferably, with respect to a viral infection, a therapeutically effective amount of a therapy (e.g., a therapeutic agent) reduces the replication or spread of a virus by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a control (e.g., PBS) in an assay described herein or well-known in the art.

In another embodiment, with respect to the treatment of a fungal infection, a therapeutically effective amount refers to the amount of a therapy (e.g., a therapeutic agent) sufficient to inhibit or reduce the replication of the fungus, inhibit or reduce the replication or spread of the fungus to other tissues or subjects, or ameliorate one or more symptoms associated with the fungal infection. Preferably, with respect to a fungal infection, a therapeutically effective amount of a therapy (e.g., a therapeutic agent) reduces the spread of a fungus by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a control (e.g., PBS) in an assay described herein or well-known in the art.

In another embodiment, with respect to the treatment of a bacterial infection, a therapeutically effective amount refers to the amount of a therapy (e.g., a therapeutic agent) sufficient to inhibit or reduce the replication of the bacteria, to inhibit or reduce the replication or spread of the bacteria to other tissues or subjects, or ameliorate one or more symptoms associated with the bacterial infection. Preferably, with respect to a bacterial infection, a therapeutically effective amount of a therapy (e.g., a therapeutic agent) reduces the spread of a bacteria by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a control (e.g., PBS) in an assay described herein or well-known in the art.

In another embodiment, with respect to the treatment of an inflammatory disorder, a therapeutically effective amount refers to the amount of a therapy (e.g., a therapeutic agent) that reduces the inflammation of a joint, organ or tissue. Preferably, with respect to an inflammatory disorder, a therapeutically effective amount of a therapy (e.g., a therapeutic agent) reduces the inflammation of a joint, organ or tissue by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a control (e.g., PBS) in an assay described herein or well-known in the art.

As used herein, the terms "therapies" and "therapy" can refer to any protocol(s), method(s), and/or agent(s) that can be used in the prevention, treatment, management, or amelioration of a disease or disorder or one or more symptoms thereof.

As used herein, the terms "treat", "treatment" and "treating" refer to the reduction or amelioration of the progression, severity and/or duration of a disease or disorder or one or more symptoms thereof resulting from the administration of one or more compounds identified in accordance the methods of the invention, or the administration of a combination of therapies (e.g., a compound identified in accordance with the methods of the invention and another therapeutic agent). In certain embodiments, such terms refer to the inhibition or reduction in the proliferation of cancerous cells, the inhibition or reduction the spread of tumor cells (metastasis), the inhibition or reduction in the onset, development or progression of one or more symptoms associated with cancer, or the reduction in the size of a tumor. In other embodiments, such terms refer to the reduction or inhibition of the replication of a virus, the inhibition or reduction in the spread of a virus to other tissues or subjects, or the amelioration of one or more symptoms associated with a viral infection. In other embodiments, such terms refer to the reduction or inhibition of the replication of a fungus, the reduction or inhibition in the spread of a fungus to other tissues or subjects, or the amelioration of one or more symptoms associated with a fungal infection. In other embodiments, such terms refer to the inhibition or reduction of the replication of a bacteria, the inhibition or reduction in the spread of a bacteria to other tissues or subjects, or the amelioration of one or more symptoms associated with a bacterial infection. In other embodiments, such terms refer to a reduction in the swelling of one or more joints, organs or tissues, or a reduction in the pain associated with an inflammatory disorder.

As used herein, the term "UTR" refers to the untranslated region of a mRNA, i.e., the region of the mRNA that is not translated into protein. In a preferred embodiment, the UTR is a 5' UTR, i.e., upstream of the coding region, or a 3' UTR, i.e., downstream of the coding region. In another embodiment, the term UTR corresponds to a reading frame of the mRNA that is not translated. In another embodiment, a UTR contains a fragment of an untranslated region of a mRNA. In a preferred embodiment, a UTR contains one or more regulatory elements that modulate untranslated region-dependent regulation of gene expression.

As used herein, the term "uORF" refers to an upstream open reading frame that is in the 5' UTR of the main open reading frame, i.e., that encodes a functional protein, of a mRNA.

As used herein, the term "untranslated region-dependent expression" or "UTR-dependent expression" refers to the regulation of gene expression through untranslated regions at the level of mRNA expression, i.e., after transcription of the gene has begun until the protein or the RNA product(s) encoded by the gene has degraded. In a preferred embodiment, the term "untranslated region-dependent expression" or "UTR-dependent expression" refers to the regulation of mRNA stability or translation. In a more preferred embodiment, the term "untranslated region-dependent expression" refers to the regulation of gene expression through regulatory elements present in an untranslated region(s).

4. DESCRIPTION OF DRAWINGS

FIGS. 1A-1C: Schematic representation of the VEGF 5'- and 3'-UTRs generated by PCR. A. VEGF 5'UTR was amplified from human genomic DNA by two separate PCR reactions. 5'UTRI, from position 337 to the 3' end plus first 45 nucleotides of VEGF open reading frame, was generated using primers 3 and 4. 5'UTR2, covered from position 1 to 498, was generated with primers 1 and 2. In the overlap region of 5'UTR1 and 5'UTR2, the unique enzyme site BamH I was used to assemble the full length 5'UTR in the subsequent cloning. B. The full length VEGF 3'UTR was directly amplified from genomic DNA using primers 5 and 6. The two enzyme sites close to 5' end and 3' end of 3'UTR (BgI II and EcoR I) were used for subsequent cloning. C. The following four primers shown were used to amplify VEGF 5'UTR: Primer 1 (SEQ ID NO:69); Primer 2 (SEQ ID NO: 70); Primer 3 (SEQ ID NO:71); and Primer 4 (SEQ ID NO:72). The following two primers shown were used to amplify VEGF 3'UTR: Primer 5 (SEQ ID NO:73) and Primer 6 (SEQ ID NO:74).

Figure 2A:
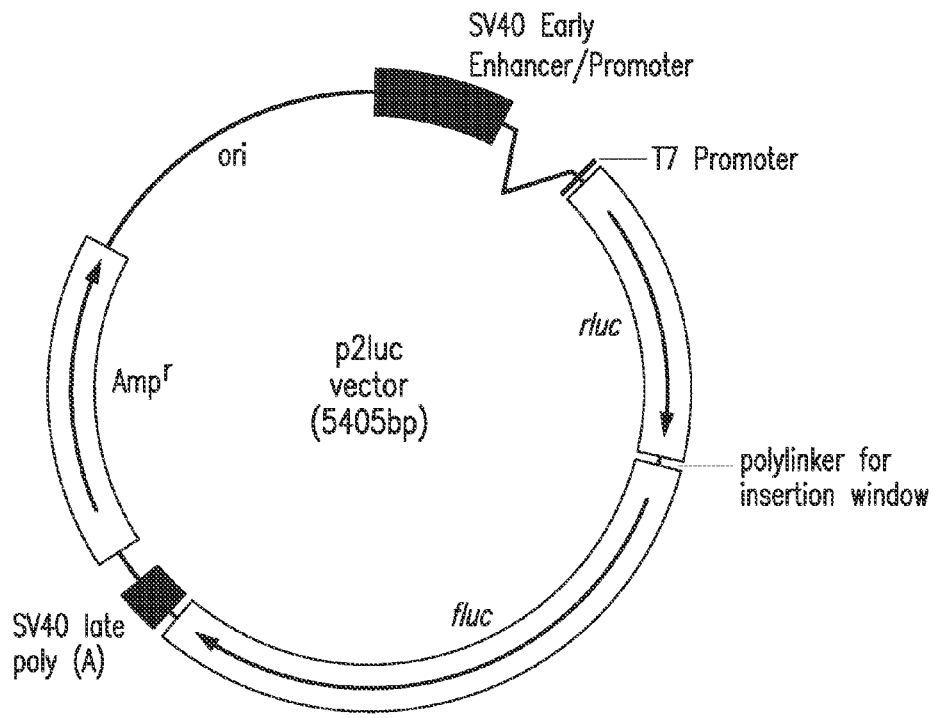
Figure 2B:
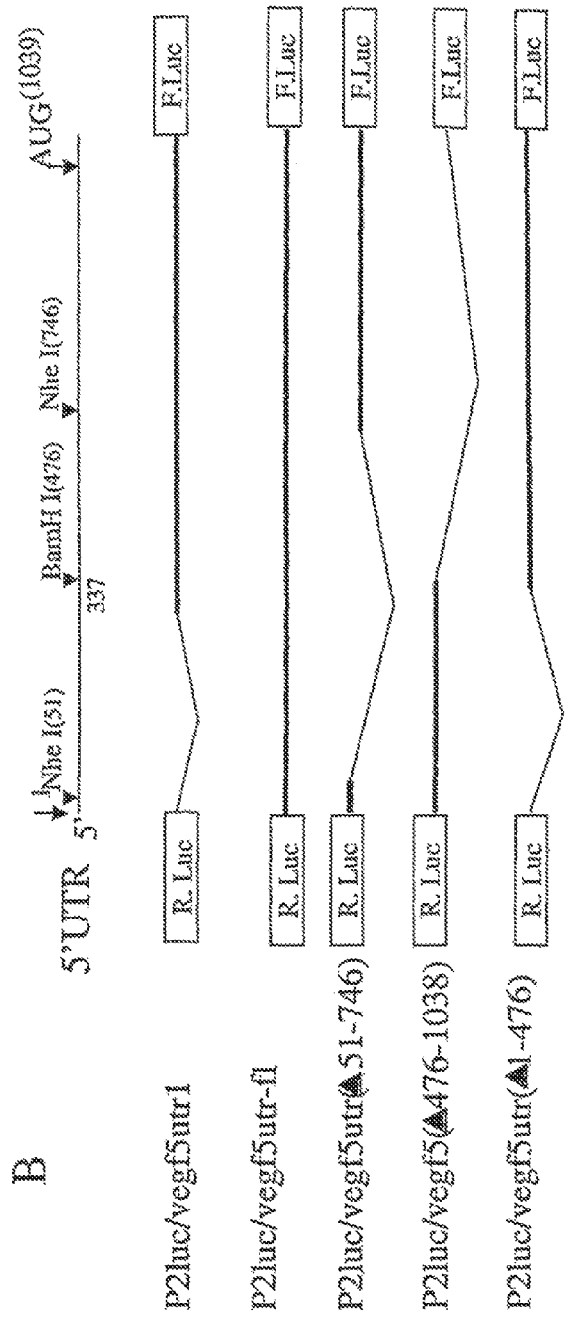
Figure 2C:
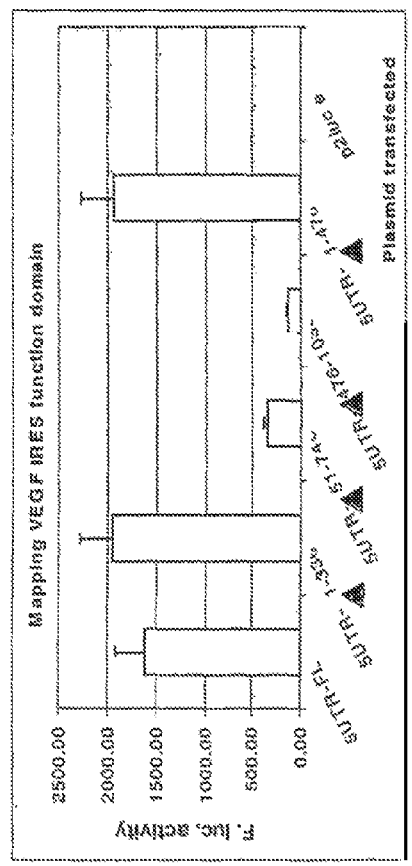

FIGS. 2A-2C: Identification of VEGF IRES domain in the VEGF mRNA 5'UTR. A. Dual luciferase vector used for mapping IRES function (Grentzmann et al., 1998, RNA 4:479-486). The polylinker sites (SEQ ID NO:75) used in mapping IRES function have been identified. B. Schematic representation of the dicistronic plasmids used for transfection experiments. P2luc/vegfSutr1 is the dicistronic plasmid containing the VEGF 5'UTRI, in which nucleotides 337 to 1083 of the VEGF cDNA were fused to the firefly luciferase coding sequence; P2luc/vegf5utr-fl was generated by subcloning VEGF 5'UTR2 into the plasmid p2luc/vegf5utr1 between Sal I and BamH I; plasmid p2Iuc/vegf5'utrdelta51-476 is derived from p2luc/vegf5'utr-fl by removing the Nhe I fragment (nt 51 to 746); plasmid p2Iuc/vegf5utr-delta476-1038 was derived from p2Iuc/vegf5utr-fl by removing the sequence from BamH I site to the 3'end of 5'UTR; plasmid p2luc/vegf5utrdelta1-476 was derived from p2luc/vegf5utr-fl by removing the sequence from BamH I to the 5'end of 5'UTR. P2luc-e used as negative control in this study. C. The constructs depicted in panel A were transfected into 293T cells in the triplicate format and expression was analyzed by monitoring luciferase activity.

Figure 3:
Figure 3:
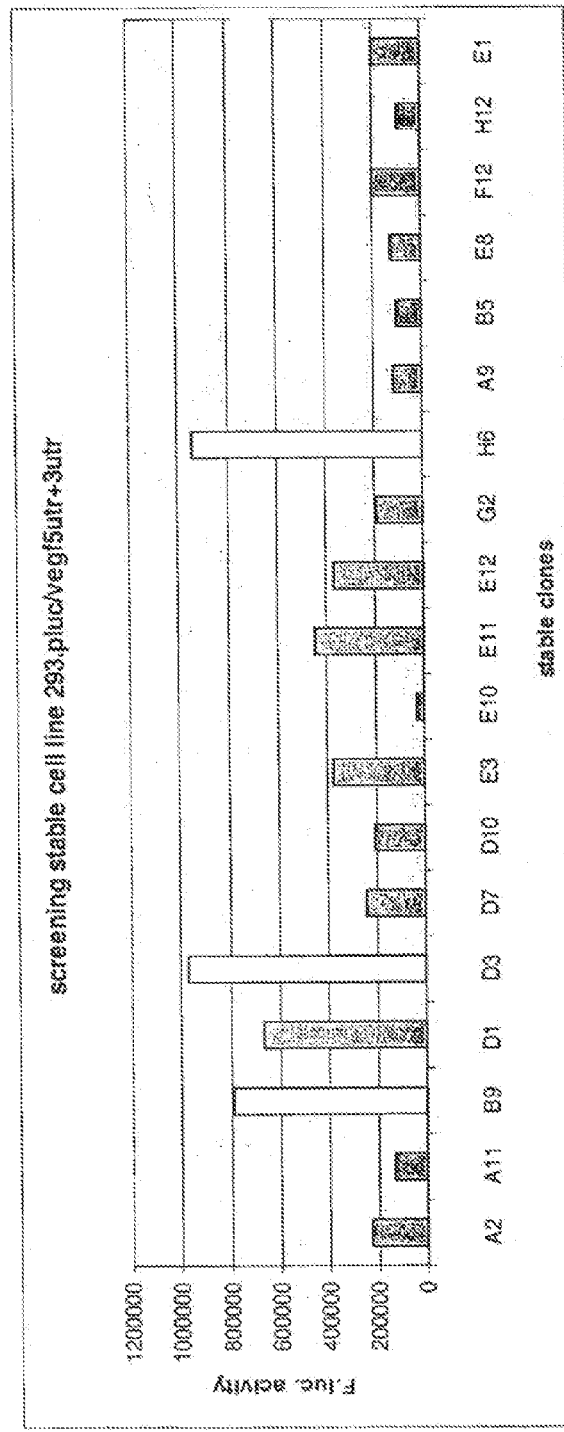

FIGS. 3A-3B: Generation of stable cell lines for cell based high throughput screening ("HTS"). A. Schematic representation of the monocistronic plasmid used in this study for generation of stable cell lines. B. Screening of stable cell lines. The plasmid depicted in panel A was transfected into 293T cells. 48 hours later, the transfected cells were seeded in 96 well plates at 100-500 cells per well and 200 mg/ml hygromycin was added for selection. The culture media plus hygromycin was changed every 3 to 4 days. After 2 weeks of selection, cells were screened under a microscope and single colony wells were expanded for further luciferase assays. The chart in panel shows the luciferase activities for 19 stable clones.

Figure 4:
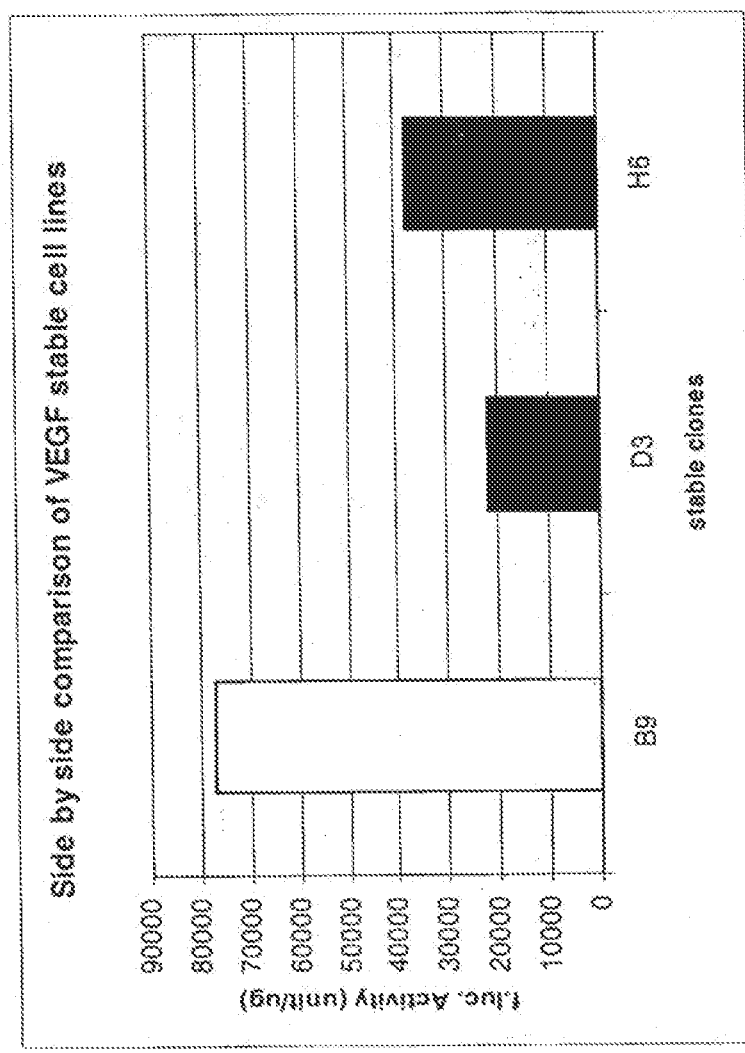

FIG. 4: Side by side comparison of luciferase activities for three stable clones (B9, D3 and H6). For each cell line, $5 \times 10^5$ cells per well were seeded in 24 well plate. 48 hours later, cells were lysed and assayed for luciferase activities. The luciferase activities were normalized against protein concentration.

Figure 5:
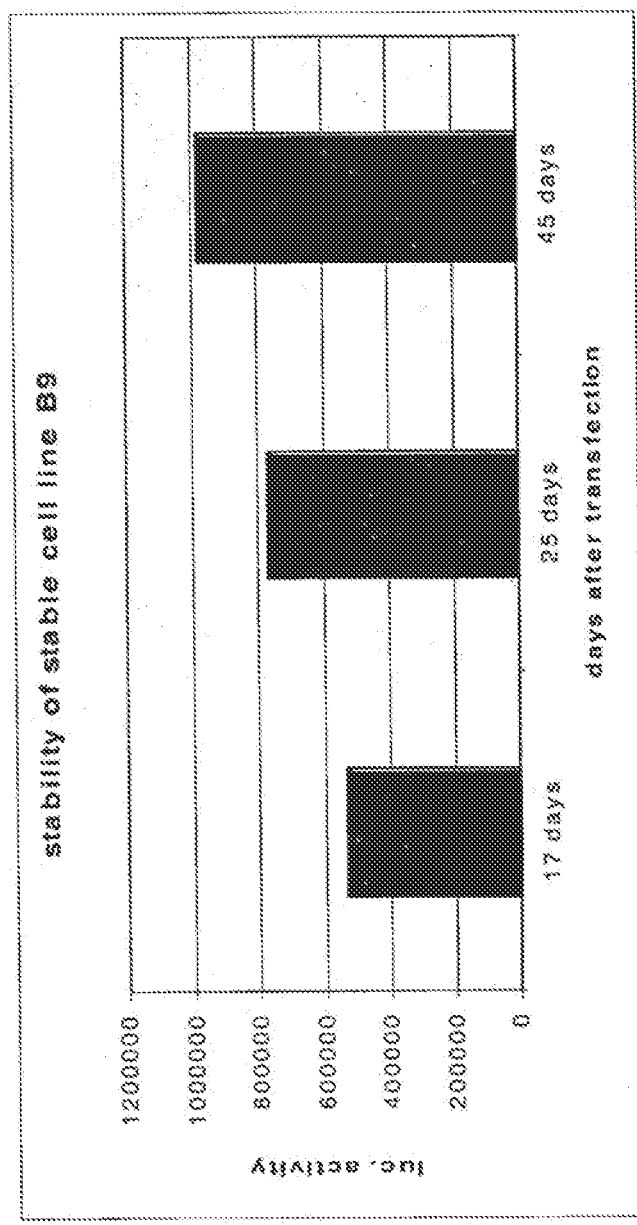

FIG. 5: Sustained high expression of luciferase by B9 cells. B9 cells were continuously cultured in vitro for more than 3 months. At the time points indicated, luciferase activity was tested with Promega's Bright Glow substrate and normalized against the protein concentration.

FIGS. 6A-6B: Reporter gene integration in B9 cells. The integration levels of the reporter gene were determined using semi-quantitative PCR. Series diluted plasmid pluc5'+ 3'vegf-UTR were included as positive control to make sure the reaction for sample (genomic DNA from B9 cells) was in the linear range, i.e., not saturated. Panel A shows the PCR results for sample and positive control. The PCR band intensity for each reaction is at the bottom of the picture. Panel B shows the PCR standard curve, plotted with PCR band intensity against the amount of positive control plasmid loaded for PCR.

Figure 7A:
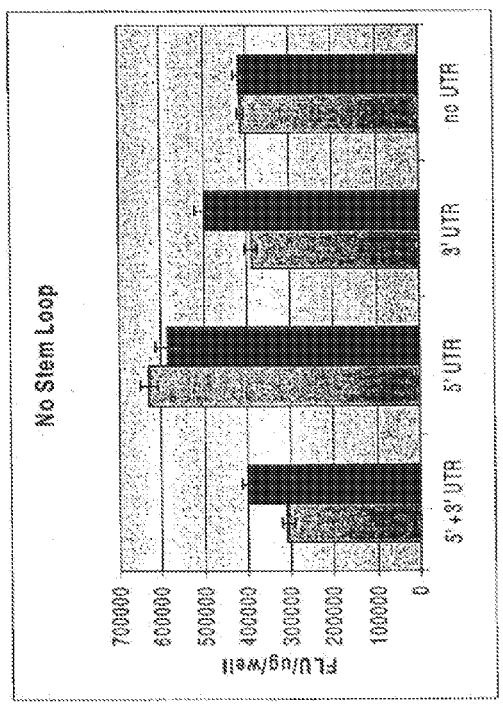
Figure 7B:
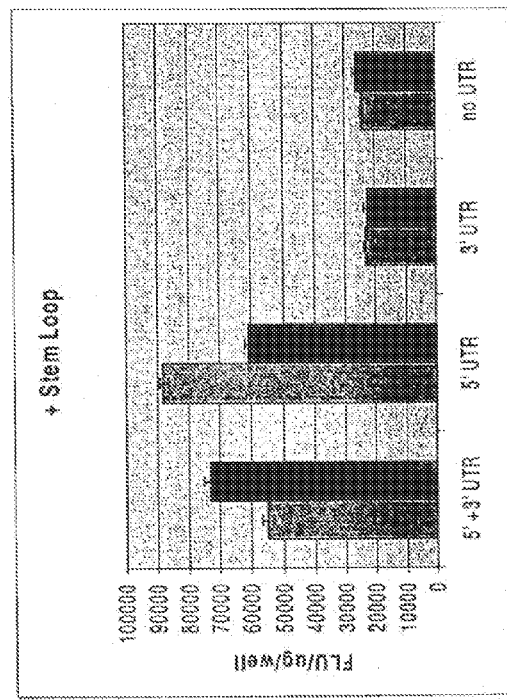

FIGS. 7A-7B: The 5' UTR of survivin can function as an internal ribosome entry site (IRES). A. Firefly luciferase assays on 293T cells transiently transfected with the survivin expression vectors in the absence of a stem-loop secondary structure. "5'+3' UTR" represents the survivin expression vector containing the firefly luciferase reporter gene surrounded by both the 5' and 3' untranslated regions of survivin. "5' UTR" represents the survivin expression vector containing the firefly luciferase reporter gene preceded only by the 5' UTR of survivin. "3' UTR" represents the survivin expression vector containing the firefly luciferase reporter gene followed only by the 3' UTR of survivin. "no UTR" represents the survivin expression vector containing the firefly luciferase reporter gene lacking any surrounding untranslated regions of survivin. The survivin expression vectors were transiently transfected into 293T cells in duplicate (represented by the two bars for each construct in the graph) and firefly luciferase activity (measured in quadruplicate) was normalized to total protein concentration in each of the cell lysates. B. As in FIG. 7A, except that the survivin expression vectors containing the stem-loop secondary structure to separate cap-dependent from cap-independent translation were used.

Figure 8A:
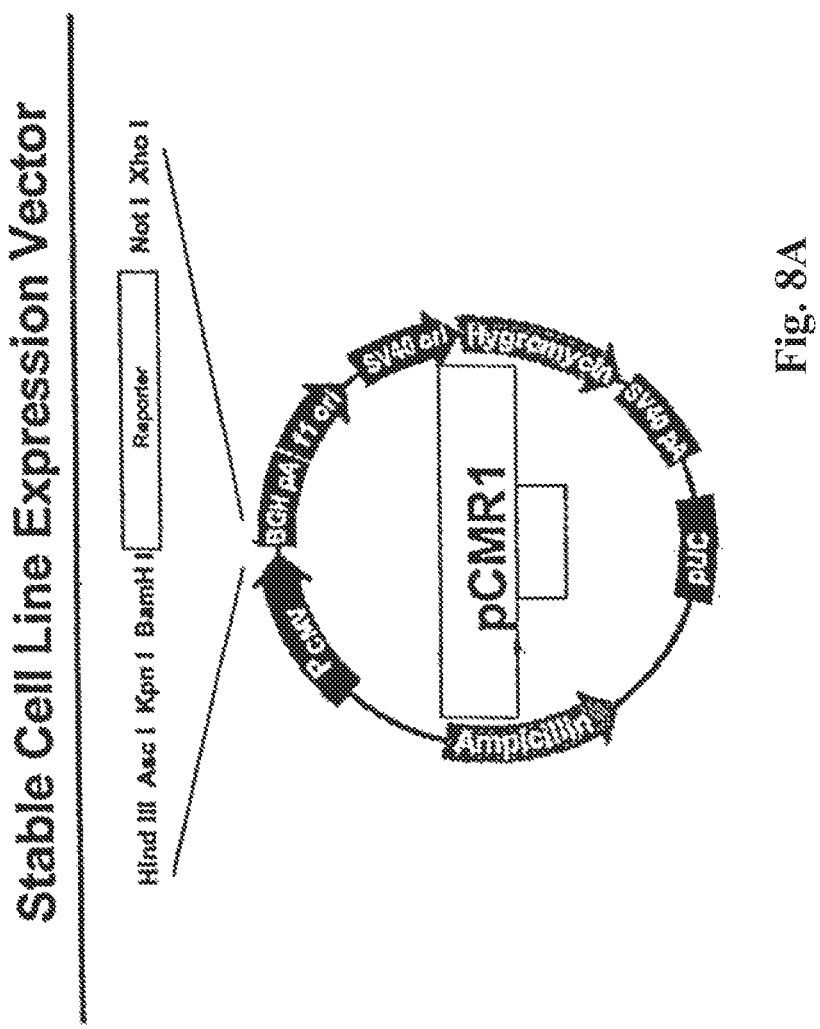
Figure 8B:
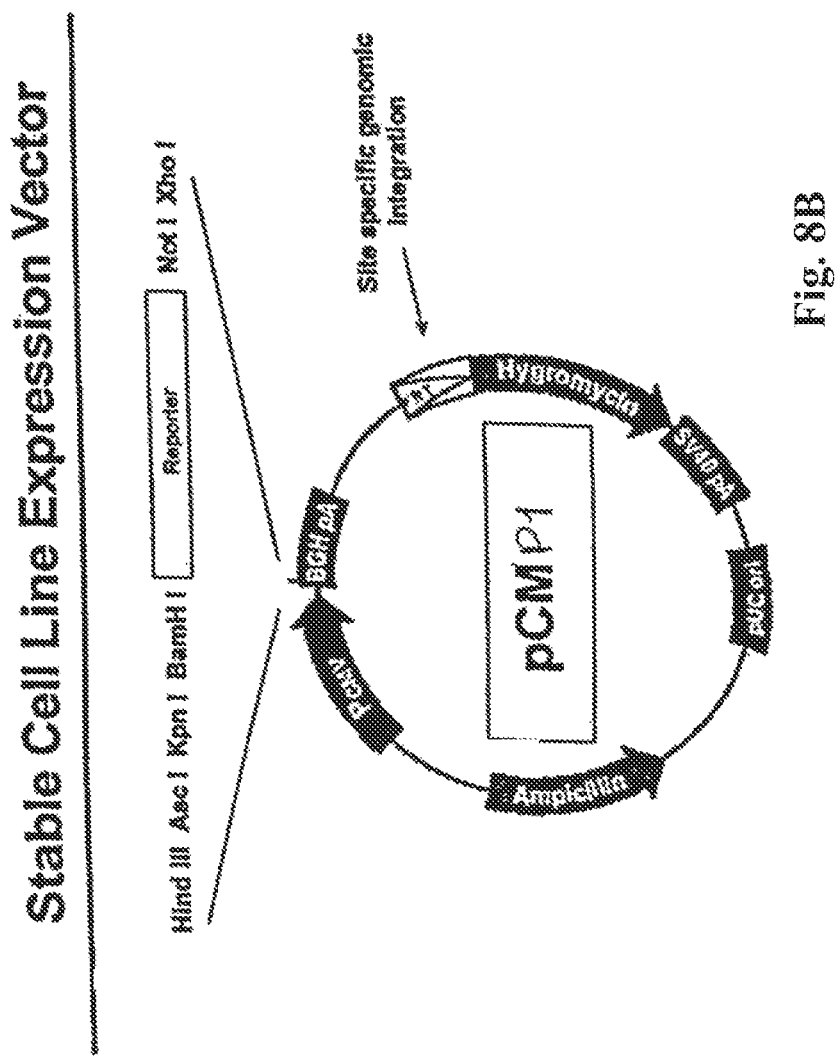
Figure 8C:
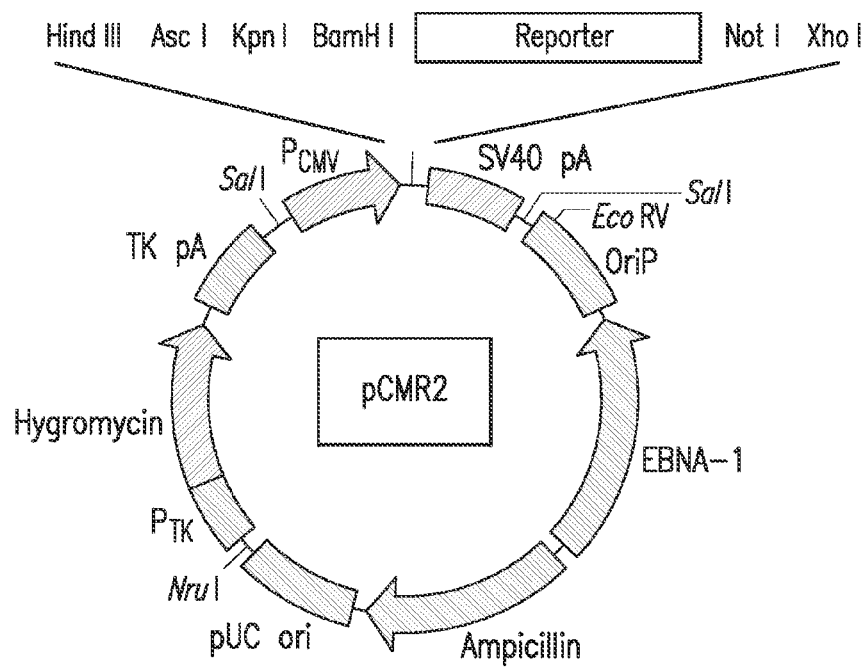

FIGS. 8A-8C: Expression Vectors. A. Schematic representation of pCMR1, a high-level stable and transient mammalian expression vector designed to randomly integrate into the genome. B. Schematic representation of pMCP1, a high level stable and transient mammalian expression vector designed to site-specifically integrate into the genome of cells genetically engineered to contain the FRT site-specific recombination site via the Flp recombinase (see, e.g., Craig, 1988, Ann. Rev. Genet. 22: 77-105; and Sauer, 1994, Curr. Opin. Biotechnol. 5: 521-527). C. Schematic representation of pCMR2, an episomal mammalian expression vector.

5. DETAILED DESCRIPTION OF THE INVENTION

The present invention provides methods for identifying compounds that modulate the untranslated region-dependent expression of any target gene. In particular, the invention provides simple, rapid and sensitive methods for identifying compounds that modulate untranslated region-dependent expression of a target gene utilizing reporter gene-based constructs comprising one or more mRNA untranslated regions ("UTRs") of the target gene. The reporter gene-based assays described herein can be utilized in a high throughput format to screen libraries of compounds to identify those compounds that modulate untranslated region-dependent expression of a target gene.

The reporter gene-based assays of the invention reduce the bias introduced by competitive binding assays which require the identification of use of a host cell factor (presumably essential for modulating RNA function) as a binding partner for the target RNA. The reporter gene-based assays of the invention are designed to detect any compound that modulates untranslated region-dependent expression of a target gene under physiologic conditions.

The reporter gene-based assays may be conducted by contacting a compound with a cell genetically engineered to express a nucleic acid comprising a reporter gene operably linked to one or more untranslated regions (preferably, the 5' and/or 3' UTRs) of a target gene, and measuring the expression of said reporter gene. Alternatively, the reporter gene-based assays may be conducted by contacting a compound with a cell-free translation mixture and a nucleic acid comprising a reporter gene operably linked to one or more untranslated regions of a target gene, and measuring the expression of said reporter gene. The alteration in reporter gene expression relative to a previously determined reference range or a control in such reporter-gene based assays indicates that a particular compound modulates untranslated region-dependent expression of a target gene. In order to exclude the possibility that a particular compound is functioning solely by modulating the expression of a target gene in an untranslated region-independent manner, one or more mutations (i.e., deletions, insertions, or nucleotide substitutions) may be introduced into the untranslated regions operably linked to a reporter gene and the effect on the expression of the reporter gene in a reporter gene-based assay described herein can be determined.

The compounds identified in the reporter gene-based assays described herein that modulate untranslated region-dependent expression may be tested in in vitro assays (e.g., cell-free assays) or in vivo assays (e.g., cell-based assays) well-known to one of skill in the art or described herein for the effect of said compounds on the expression of the target gene from which the untranslated regions of the reporter gene construct were derived. Further, the specificity of a particular compound's effect on untranslated region-dependent expression of one or more other genes (preferably, a plurality of genes) can be determined utilizing assays well-known to one of skill in the art or described herein. In a preferred embodiment, a compound identified utilizing the reporter gene-based assays described herein has a specific effect on the expression of only one gene or a group of genes within the same signaling pathway.

The structure of the compounds identified in the reporter gene-based assays described herein that modulate untranslated region-dependent expression can be determined utilizing assays well-known to one of skill in the art or described herein. The methods used will depend, in part, on the nature of the library screened. For example, assays or microarrays of compounds, each having an address or identifier, may be deconvoluted, e.g., by cross-referencing the positive sample to an original compound list that was applied to the individual test assays. Alternatively, the structure of the compounds identified herein may be determined using mass spectrometry, nuclear magnetic resonance ("NMR"), X ray crystallography, or vibrational spectroscopy.

The invention encompasses the use of the compounds identified in accordance with the methods described herein for the modulation (i.e., upregulation or downregulation) of the expression of a target gene. The upregulation or downregulation of a target gene is particularly useful in vitro when attempting to produce a protein encoded by said target gene for use as a therapeutic or prophylactic agent, or in experiments conducted to, e.g., identify the function or efficacy of said protein. The invention also encompasses the use of the compounds identified in accordance with the methods described herein for the prevention, treatment or amelioration of a disease or disorder or a symptom thereof. Examples of diseases and disorders which may be prevented, treated or ameliorated utilizing a compound identified in accordance with the invention include, but are not limited to, proliferative disorders, disorders associated with aberrant angiogenesis, inflammatory disorders, infectious diseases, genetic disorders, autoimmune disorders, cardiovascular diseases, and central nervous system disorders. In an embodiment wherein the disease or disorder is an infectious disease, the infectious disease can be caused by a fungal infection, a bacterial infection, a viral infection, or an infection caused by another type of pathogen.

5.1. Untranslated Regions

Any untranslated region may be utilized in the reporter gene constructs described herein. An untranslated gene region(s) may be obtained or derived from a gene from any species, including, but not limited to, plants (e.g., soybean, canola, cotton, wheat, corn, rice, potato, and tomato plants), viruses, bacteria, fungus and animals (including, but not limited to, mammals (primates and non-primates), farm animals (e.g., horses, pigs, cows, donkeys, etc.), pets (e.g., guinea pigs, cats, and dogs), and humans). Untranslated regions may be obtained and the nucleotide sequence of the untranslated regions determined by any method well-known to one of skill in the art. The nucleotide sequence of an untranslated region for a target gene can be obtained, e.g., from the literature or a database such as GenBank. Alternatively, the nucleotide sequence of the untranslated regions of a target gene may be generated from nucleic acid from a suitable source. If a clone containing a nucleic acid of an untranslated region of a target gene is not available, but the sequence of the untranslated region is known, a nucleic acid of the untranslated region may be chemically synthesized or obtained from a suitable source (e.g., a cDNA library) by PCR amplification. Once the nucleotide sequence of an untranslated region is determined, the nucleotide sequence of the untranslated region may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate an untranslated region having a different nucleotide sequence.

In one embodiment, an untranslated gene region(s) is obtained or derived from a gene whose expression is associated with or has been linked to the onset, development, progression or severity of a particular disease or disorder. In another embodiment, an untranslated gene region(s) is obtained or derived from a gene whose expression is beneficial to a subject with a particular disease or disorder. Examples of genes from which the untranslated regions may be obtained or derived from include, but are not limited to, cytokines, cytokine receptors, T cell receptors, B cell receptors, co-stimulatory molecules, clotting cascade factors, cyclins, cyclin inhibitors, oncogenes, growth factors, growth factor receptors, tumor suppressors, apoptosis inhibitor proteins, cell adhesion molecules, hormones, GTP-binding proteins, glycoproteins, ion channel receptors, calcium channel pumps, steroid receptors, opioid receptors, sodium channel pumps, heat shock proteins, MHC proteins, and tumor-associated antigens ("TAAs").

Specific examples of genes from which the untranslated regions may be obtained or derived from include, but are not limited, to the gene encoding abl, the gene encoding acetyl CoA carboxylase beta ("ACC2"; see, e.g., OMIM accession number 601557, locus link accession number 32), the gene encoding acetylcholinesterase ("ACHE"; see, e.g., OMIM accession number 100740, locus link accession number 43, GenBank accession number NM 0006 65), the gene encoding actin, alpha cardiac ("ACTC"; see, e.g., OMIM accession number 102540, locus link accession number 70), the gene encoding acyl-CoA dehydrogenase ("ACADVL"; see, e.g., OMIM accession number 201475, locus link accession number 37), the gene encoding adiponectin ("ACRP30"; see, e.g., OMIM accession number 605441, locus link accession number 9370, GenBank accession number NM 0047 97), the gene encoding ADP-ribosylation factor-4 ("ARF4"; see, e.g., OMIM accession number 601177, locus link accession number 378, GenBank accession number NM 0017 ev 25), the gene encoding alpha-glucosidase, the gene encoding Alzheimer's disease amyloid A4 ("APP" or "A4" or "CVAP" or "AD1"; see, e.g., OMIM accession number 104760, locus link accession number 351), the gene encoding angiogenin ("ANG" or "RNASE5"; see, e.g., OMIM accession number 105850, locus link accession number 283, GenBank accession number NM 0011 45), the gene encoding angiopoietin1 ("ANG1"; see, e.g., OMIM accession number 601667, locus link accession number 284), the gene encoding angiopoietin2 ("ANG2"; see, e.g., OMIM accession number 601922, locus link accession number 285), the gene encoding angiostatin, the gene encoding angiotensin 1-converting enzyme ("DCP1"; see, e.g., OMIM accession number 106180, locus link accession number 1636), the gene encoding antigen CD82 ("KAI1"; see, e.g., OMIM accession number 600623, locus link accession number 3732, GenBank accession number NM 0022 31), the gene encoding APC, the gene encoding atrial natriuretic factor, the gene encoding bactericidal/permeability-increasing protein ("BPI"; see, e.g., OMIM accession number 109195, locus link accession number 671, GenBank accession number NM 0017 ev 25), the gene encoding bcl-2, the gene encoding beta-catenin ("CTNNB1"; see, e.g., OMIM accession number 116806, locus link accession number 1499), the gene encoding beta-site APP-cleaving enzyme 2 ("BASE2";

see, e.g., OMIM accession number 605668, locus link accession number 25825, GenBank accession number NM 1389 92), the gene encoding bile salt export pump ("ABCB1 1"; see, e.g., OMIM accession number 603201, locus link accession number 8647), the gene encoding BMP, the gene encoding BNDF, the gene encoding bombesin receptor, the gene encoding brca1, the gene encoding brca2, the gene encoding C1q complement receptor (see, e.g., OMIM accession number 120577, locus link accession number 22918), the gene encoding c-fms, the gene encoding c-myc, the gene encoding calcitonin, the gene encoding calcium-binding protein in macrophages ("MRP14"; see, e.g., OMIM accession number 123886, locus link accession number 6280, GenBank accession number NM 0029 ev 65), the gene encoding calsenilin ("DREAM/CSEN" or "CREAM" or "KCh IP3"; see, e.g., OMIM accession number 604662, locus link accession number 30818, GenBank accession number NM 0134), the gene encoding carnitine o-palmitoyltransferase ("CPT2"; see, e.g., OMIM accession number 600650, locus link accession number 1376), the gene encoding catechol-o-methyltransferase ("COMT"; see, e.g., OMIM accession number 116790, locus link accession number 1312, GenBank accession number NM 000754, NM 007310), the gene encoding cathepsin K, the gene encoding CD40 ligand ("TNFSF5"; see, e.g., OMIM accession number 300386, locus link accession number 959), the gene encoding cdk4 inhibitor, the gene encoding chemokine (C-C) receptor ("IL13R"; see, e.g., OMIM accession number 601268, locus link accession number 1232), the gene encoding chemokine (C-X3-C) receptor 1 ("CX3CR1"; see, e.g., OMIM accession number 601470, locus link accession number 1524), the gene encoding CLCA homolog ("hCLCA2"; see, e.g., OMIM accession number 604003, locus link accession number 9635, GenBank accession number NM 0065 36), the gene encoding complement decay-accelerating factor ("DAF/CD55"; see, e.g., OMIM accession number 125240, locus link accession number 1604), the gene encoding connective tissue growth factor ("CTGF"; see, e.g., OMIM accession number 121009, locus link accession number 1490), the gene encoding corticotrophin releasing factor, the gene encoding CTLA4, the gene encoding cyclin D1, the gene encoding cyclin E, the gene encoding cyclin T1 (see, e.g., OMIM accession number 602506, locus link accession number 904, GenBank accession number NM 0012 40), the gene encoding cyclin-dependent kinase inhibitor 1A ("p21" or "WAFT" or "CDKN1A" or "Cip1"; see, e.g., OMIM accession number 116899, locus link accession number 1026, GenBank accession number NM 0784 67), the gene encoding cyclin-dependent kinase inhibitor 2A ("CDKN2A"; see, e.g., OMIM accession number 600160, locus link accession number 1029), the gene encoding cystic fibrosis transmembrane conductance regulator ("CFTR"), the gene encoding cytochrome P-450, the gene encoding D-1 dopamine receptor ("DRD1"; see, e.g., OMIM accession number 126449, locus link accession number 1812, GenBank accession number NM 00794, X589987), the gene encoding D-amino-acid oxidase ("DAO"; see, e.g., OMIM accession number 124050, locus link accession number 1610, GenBank accession number NM 0019 17), the gene encoding damage specific DNA binding protein ("DDB1"; see, e.g., OMIM accession number 600045, locus link accession number 1642), the gene encoding DCC, the gene encoding desmoglein 1 ("DSG1"; see, e.g., OMIM accession number 125670, locus link accession number 1828), the gene encoding a dihydrofolate reductase ("DHFR"; see, e.g., OMIM accession number 126060, locus link accession number 1719, GenBank accession number NM 0007 91), the gene encoding a disintegrin and metallo proteinase domain 33 ("ADAM 33"; see, e.g., OMIM accession number 607114, locus link accession number 80332), the gene encoding DNA methyltransferase ("DNMT3b"; see, e.g., OMIM accession number 602900, locus link accession number 1789), the gene encoding DPP-IV, the gene encoding drebrin-1 dendritic spine protein ("DBN1"; see, e.g., OMIM accession number 126660, locus link accession number 1627, GenBank accession number NM 004395, NM 080881), the gene encoding E-cadherin, the gene encoding effector cell protease receptor ("EPR1"; see, e.g., OMIM accession number 603411, locus link accession number 8475), the gene encoding EGF, the gene encoding EGFR (see, e.g., OMIM accession number 131550, locus link accession number 1956), the gene encoding an EGFR subunit, the gene encoding EIF4BP (see, e.g., OMIM accession number 602223, locus link accession number 1978, GenBank accession number NM 0040 95), the gene encoding EMMPRIN (see, e.g., OMIM accession number 109480, locus link accession number 682, GenBank accession number NM 0017 28), the gene encoding emotakin ATP-binding cassette, sub-family a, member 1 ("ABCA1"; see, e.g., OMIM accession number 600046, locus link accession number 19), the gene encoding endostatin, the gene encoding eotaxin ("CCL11"; see, e.g., OMIM accession number 601156, locus link accession number 6356, GenBank accession number NM 0029 86), the gene encoding erythropoietin ("EPO"; see, e.g., OMIM accession number 133170, locus link accession number 2056, GenBank accession number NM 0007 99), the gene encoding estrogen receptor, the gene encoding factor IX, the gene encoding factor VIII, the gene encoding farnesyl transferase, the gene encoding FGF, the gene encoding FGF1 (see, e.g., OMIM accession number 131220, locus link accession number 2246, GenBank accession number), the gene encoding FGF2 (see, e.g., OMIM accession number 134920, locus link accession number 2247, GenBank accession number NM 0020 06), the gene encoding FGFR, the gene encoding fibrillin ("FBN1"; see, e.g., OMIM accession number 134797, locus link accession number 2200), the gene encoding FMS-related tyrosine kinase 1 ("FLT1"; see, e.g., OMIM accession number 165070, locus link accession number 2321, GenBank accession number NM 0020 ev 19), the gene encoding forkhead box C2 ("FOXC2"; see, e.g., OMIM accession number 602402, locus link accession number 2303, GenBank accession number NM 0052 51), the gene encoding fos (see, e.g., OMIM accession number 164810, locus link accession number 2353, GenBank accession number NM 0052 52), the gene encoding G-CSF, the gene encoding G-CSF 3 ("CSF3"; see, e.g., OMIM accession number 138970, locus link accession number 1440), the gene encoding a GABA receptor, the gene encoding galanin ("GAL"; see, e.g., OMIM accession number 137035, locus link accession number 2586), the gene encoding gastric inhibitory polypeptide ("GIP"; see, e.g., OMIM accession number 137240, locus link accession number 2695), the gene encoding GDNF, the gene encoding GGF, the gene encoding GGRP, the gene encoding ghrelin ("GHRL"; see, e.g., OMIM accession number 605353, locus link accession number 51738), the gene encoding gip, the gene encoding glucagon, the gene encoding glucagon receptor ("GCGR"; see, e.g., OMIM accession number 138033, locus link accession number 2642), the gene encoding glucagon-like peptide-1 ("GLP1"; see, e.g., OMIM accession number 138030, locus link accession number 2641), the gene encoding glucokinase ("GCK"; see, e.g., OMIM accession number 138079, locus link accession number 2645, GenBank accession number NM 0001 62), the gene encoding glutamic acid decarboxylase 2 (see, e.g., OMIM accession number 138275), the gene encoding glutamic acid decarboxylase 3 (see, e.g., OMIM accession number 138276), the gene encoding glutamic acid decarboxylase, brain, membrane form (see, e.g., OMIM accession number 138277), the gene encoding glycogen synthase kinase-3A ("GSK-3A"; see, e.g., OMIM accession number 606784, locus link accession number 2931), the gene encoding glycogen synthase kinase-3B ("GSK-3B"; see, e.g., OMIM accession number 605004, locus link accession number 2932), the gene encoding GM-CSF (see, e.g., OMIM accession number 138960, locus link accession number 1437), the gene encoding gonadotropin, the gene encoding gonadotropin releasing hormone, the gene encoding GRO2 oncogene or macrophage inflammatory protein-2-alpha precursor ("CXCL2"; see, e.g., OMIM accession number 139110, locus link accession number 2920), the gene encoding growth hormone releasing factor, the gene encoding growth hormone, the gene encoding gsp, the gene encoding H-ras, the gene encoding heat shock protein ("HSP")-70, the gene encoding heparanase ("HPA"; see, e.g., OMIM accession number 604724, locus link accession number 10855), the gene encoding hepatitis A virus cellular receptor ("HAVCR"; see, e.g., OMIM accession number 606518, locus link accession number 26762), the gene encoding hepatitis B virus X interacting protein ("HBXIP"), the gene encoding hepsin ("HPN"; see, e.g., OMIM accession number 142440, locus link accession number 3249, GenBank accession number NM 0021 51), the gene encoding Her-2 ("ERBB2"; see, e.g., OMIM accession number 164870, locus link accession number 2064), the gene encoding HGF, the gene encoding histone acetyltransferase ("HAT1"; see, e.g., OMIM accession number 603053, locus link accession number 8520, GenBank accession number NM 0036 42), the gene encoding histone deacetylase 1 ("HDAC1"; see, e.g., OMIM accession number 601241, locus link accession number 3065), the gene encoding histone deacetylase 3 ("HDAC3"; see, e.g., OMIM accession number 605166, locus link accession number 8841, GenBank accession number NM 0038 ev 83), the gene encoding HIV Tat Specific Factor 1 ("HTATSF1"; see, e.g., OMIM accession number 300346, locus link accession number 27336), the gene encoding HMG CoA synthetase, the gene encoding HSP-90, the gene encoding huntingtin ("HD"; see, e.g., OMIM accession number 143100, locus link accession number 3064, GenBank accession number NM 0021 11), the gene encoding Hu antigen R ("HUR"; see, e.g., OMIM accession number 603466, locus link accession number 1994, GenBank accession number NM 0014 19), the gene encoding 3-hydroxy-3-methylglutaryl-CoA reductase ("HMGCR"; see, e.g., OMIM accession number 142910, locus link accession number 3156), the gene encoding hypoxia-inducible factor 1 ("HIF-1A"; see, e.g., OMIM accession number 603348, locus link accession number 3091), the gene encoding hypoxia-inducible factor 1-alpha inhibitor ("HIF1AN"; see, e.g., OMIM accession number 606615, locus link accession number 55662), the gene encoding iduronate 2-sulfatase ("IDS"; see, e.g., OMIM accession number 309900, locus link accession number 3423), the gene encoding IGF-1 (see, e.g., OMIM accession number 147440, locus link accession number 3486), the gene encoding IGF-1R (see, e.g., OMIM accession number 147370, locus link accession number 3480, GenBank accession number NM 0008 ev 75), the gene encoding IGF-2, the gene encoding IGF binding protein-2 ("IGFBP2"; see, e.g., OMIM accession number 146731, locus link accession number 3485), the gene encoding IkB kinase ("IKBKB"; see, e.g., OMIM accession number 603258, locus link accession number 3551), the gene encoding inositol polyphosphate phosphatase-like 1 ("SHIP-2"; see, e.g., OMIM accession number 600829, locus link accession number 3636, GenBank accession number NM 0015 67), the gene encoding insulin, the gene encoding interferon inducible protein ("CXCL10 (IP10)"; see, e.g., OMIM accession number 147310, locus link accession number 3627, GenBank accession number NM 0015 65), the gene encoding interferon ("IFN")-α, the gene encoding interferon-α 1/13 precursor, the gene encoding interferon-α 5 precursor ("IFNA5"; see, e.g., OMIM accession number 147565, locus link accession number 3442), the gene encoding interferon-α-16 precursor ("IFNA16"; see, e.g., OMIM accession number 147580, locus link accession number 3449), the gene encoding IFN-β, the gene encoding IFN-β 1 ("IFNB1"; see, e.g., OMIM accession number 147640, locus link accession number 3456), the gene encoding IFN-γ (see, e.g., OMIM accession number 147440, locus link accession number 3479), the gene encoding insulin receptor ("INSR"; see, e.g., OMIM accession number 147670, locus link accession number 3643, GenBank accession number NM 0002 08), the gene encoding interleukin-1 b ("IL1B"; see, e.g., OMIM accession number 147720, locus link accession number 3553), the gene encoding interleukin-2 ("IL-2"; see, e.g., OMIM accession number 147680, locus link accession number 3558), the gene encoding interleukin-3 ("IL-3"), the gene encoding interleukin-4 ("IL-4"; see, e.g., OMIM accession number 147780, locus link accession number 3565, GenBank accession number NM 0005 89), the gene encoding interleukin-4 receptor ("IL4R"; see, e.g., OMIM accession number 147781, locus link accession number 3566, GenBank accession number NM 0004 18), the gene encoding interleukin-5 ("IL-5"), the gene encoding interleukin-6 ("IL-6"; see, e.g., OMIM accession number 147620, locus link accession number 3569), the gene encoding interleukin-7 ("IL-7"), the gene encoding interleukin-8 ("IL-8"; see, e.g., OMIM accession number 146930, locus link accession number 3576), the gene encoding interleukin-9 ("IL-9"; see, e.g., OMIM accession number 146931, locus link accession number 3578), the gene encoding interleukin-10 ("IL-10"; see, e.g., OMIM accession number 124092, locus link accession number 3586, GenBank accession number NM 0005 72), the gene encoding interleukin-12 ("IL-12"), the gene encoding interleukin-12 beta chain precursor ("IL12B"; see, e.g., OMIM accession number 161561, locus link accession number 3593), the gene encoding interleukin-13 ("IL-13"; see, e.g., OMIM accession number 147683, locus link accession number 3596, GenBank accession number NM 0021 88), the gene encoding interleukin-15 ("IL-15"), the gene encoding interleukin-17F ("ML1"; see, e.g., OMIM accession number 606496, locus link accession number 11274), the gene encoding interleukin-18 ("IL-18"; see, e.g., OMIM accession number 600953, locus link accession number 3606), the gene encoding INI1/hSNF5 (see, e.g., OMIM accession number 601607, locus link accession number 6598), the gene encoding jun, the gene encoding kallikrein 6 ("KLK6"; see, e.g., OMIM accession number 602652, locus link accession number 5653, GenBank accession number NM 0027 74), the gene encoding KGF, the gene encoding ki-ras, the gene encoding kit ligand, stem cell factor ("KITLG (SCF)"; see, e.g., OMIM accession number 184745, locus link accession number 4254, GenBank accession number NM 0008 99), the gene encoding klotho ("KL"; see, e.g., OMIM accession number 604824, locus link accession number 9365, GenBank accession number NM 0047 95), the gene encoding L-myc, the gene encoding large tumor suppressor ("LATS1"; see, e.g., OMIM accession number 603473, locus link accession number 9113, GenBank accession number NM 0046 ev 90), the gene encoding LDL receptor ("LDLR"; see, e.g., OMIM accession number 606945, locus link accession number 3949, GenBank accession number NM 0005 27), the gene encoding leptin ("LEP"; see, e.g., OMIM accession number 164160, locus link accession number 3952, GenBank accession number NM 0002 30), the gene encoding leptin receptor ("LEPR"; see, e.g., OMIM accession number 601007, locus link accession number 3953), the gene encoding leucine amino peptidase-3 ("LAP3"; see, e.g., OMIM accession number 606832, locus link accession number 51056), the gene encoding leukemia inhibitory factor ("LIF"; see, e.g., OMIM accession number 159540, locus link accession number 3976), the gene encoding leukemia inhibitory factor receptor ("LIFR"; see, e.g., OMIM accession number 151443, locus link accession number 3977), the gene encoding linker for activation of T cells ("LAT"; see, e.g., OMIM accession number 602354, locus link accession number 27040), the gene encoding livin (see, e.g., OMIM accession number 605737, locus link accession number 79444, GenBank accession number NM 1393 ev 17), the gene encoding luteinizing hormone, the gene encoding luteinizing hormone releasing hormone, the gene encoding macrophage migration inhibitory factor ("MIF"; see, e.g., OMIM accession number 153620, locus link accession number 4282, GenBank accession number NM 0024 15), the gene encoding major histocompatibility complex class I chain-related gene A ("MICA"; see, e.g., OMIM accession number 600169, locus link accession number 4276, GenBank accession number NM 0002 47), the gene encoding major histocompatibility complex class I chain-related gene B ("MICB"; see, e.g., OMIM accession number 602436, locus link accession number 4277, GenBank accession number NM 0059 31), the gene encoding matrix metalloproteinase 9 ("MMP9"; see, e.g., OMIM accession number 120361, locus link accession number 4318), the gene encoding matrix metalloproteinase 12 ("MMP12"; see, e.g., OMIM accession number 601046, locus link accession number 4321), the gene encoding max interacting protein 1 ("MXI1"; see, e.g., OMIM accession number 600020, locus link accession number 4601), the gene encoding MCC, the gene encoding MDM2 (see, e.g., OMIM accession number 164785, locus link accession number 4193, GenBank accession number NM 0023 92), the gene encoding METH-1, the gene encoding METH-2, the gene encoding methyl-CpG-binding endonuclease ("MBD4"; see, e.g., OMIM accession number 603574, locus link accession number 8930, GenBank accession number NM 0039 ev 25), the gene encoding monoamine oxidase-A ("MAOA"; see, e.g., OMIM accession number 309850, locus link accession number 4128, GenBank accession number NM 0002 ev 40), the gene encoding monoamine oxidase-B ("MAOB"; see, e.g., OMIM accession number 309860, locus link accession number 4129), the gene encoding monocyte chemotactic protein 1 ("MCP1"; see, e.g., OMIM accession number 158105, locus link accession number 6347), the gene encoding mos, the gene encoding MTS1, the gene encoding myc, the gene encoding myotrophin, the gene encoding N-acetyltransferase, the gene encoding N-cadherin, the gene encoding N-methyl D-aspartate ("NMDA") receptor, the gene encoding NAD(P)-dependent steroid dehydrogenase ("NSDHL"; see, e.g., OMIM accession number 300275, locus link accession number 50814), the gene encoding natural resistance-associated macrophage protein ("NRAM P"; see, e.g., OMIM accession number 600266, locus link accession number 6556), the gene encoding neural cell adhesion molecule 1 ("NCAM1"; see, e.g., OMIM accession number 116930, locus link accession number 4684), the gene encoding neuron growth associated protein 43 ("GAP-43"; see, e.g., OMIM accession number 162060, locus link accession number 2596), the gene encoding NF1, the gene encoding NF2, the gene encoding NGF, the gene encoding a NGFR subunit, the gene encoding nm23, the gene encoding nuclear factor of kappa light polypeptide gene enhancer in B-cells 1 ("NFKB1"; see, e.g., OMIM accession number 164011, locus link accession number 4790), the gene encoding OSM, the gene encoding osteopontin ("OPN"; see, e.g., OMIM accession number 166490, locus link accession number 6696), the gene encoding P-glycoprotein-1 ("PGY1"; see, e.g., OMIM accession number 171050, locus link accession number 5243, GenBank accession number NM 0009 27), the gene encoding p38 MAP kinase ("p38" or "MAPK14"; see, e.g., OMIM accession number 600289, locus link accession number 1432), the gene encoding p53, the gene encoding p300/CBP associated factor ("PCAF"; see, e.g., OMIM accession number 602303, locus link accession number 8850), the gene encoding parathyroid hormone, the gene encoding PDGF, the gene encoding PDGF, beta chain ("PDGF2"; see, e.g., OMIM accession number 190040, locus link accession number 5155), the gene encoding a PDGFR subunit, the gene encoding peroxin-1 ("PEX1"; see, e.g., OMIM accession number 602136, locus link accession number 5189), the gene encoding peroxisome assembly factor-2 ("PEX6"; see, e.g., OMIM accession number 601498, locus link accession number 5190), the gene encoding peroxisome proliferator-activated receptor-gamma ("PPARg"; see, e.g., OMIM accession number 601487, locus link accession number 5468), the gene encoding phenylalanine hydroxylase, the gene encoding phosphodiesterase, the gene encoding human phosphotyrosyl-protein phosphatase ("PTP-1B"; see, e.g., OMIM accession number 176885, locus link accession number 5770, GenBank accession number NM 0028 27), the gene encoding placental growth factor ("PGF"; see, e.g., OMIM accession number 601121, locus link accession number 5228, GenBank accession number NM 0026 ev 32), the gene encoding plasminogen activator inhibitor protein ("PAI1"; see, e.g., OMIM accession number 173360, locus link accession number 5054), the gene encoding pleiotrophin ("PTN"; see, e.g., OMIM accession number 162095, locus link accession number 5764), the gene encoding poly(rC) binding protein 2 ("PCBP2"; see, e.g., OMIM accession number 601210, locus link accession number 5094), the gene encoding progranulin ("PCDGF" or "GRN"; see, e.g., OMIM accession number 138945, locus link accession number 2896), the gene encoding prolactin ("PRL"; see, e.g., OMIM accession number 176760, locus link accession number 5617, GenBank accession number NM 0009 48), the gene encoding proliferating cell nuclear antigen ("PCNA"; see, e.g., OMIM accession number 176740, locus link accession number 5111), the gene encoding protein kinase B/Akt ("AKT1"; see, e.g., OMIM accession number 164730, locus link accession number 207), the gene encoding protein kinase C, gamma ("PKCg"; see, e.g., OMIM accession number 176980, locus link accession number 5582), the gene encoding protein-tyrosine phosphatase, 4A, 3 ("PTP4A3"; see, e.g., OMIM accession number 606449, locus link accession number 11156, GenBank accession number NM 0326 11), the gene encoding psoriasin ("PSOR1"; see, e.g., OMIM accession number 600353, locus link accession number 6278, GenBank accession number NM 0029 63), the gene encoding ras, the gene encoding resistin ("Fizz3"; see, e.g., OMIM accession number 605565, locus link accession number 56729, GenBank accession number NM 0204 15), the gene encoding retinoblastoma ("Rb"; see, e.g., OMIM accession number 180200, locus link accession number 5925, GenBank accession number NM 0003 21), the gene encoding retinoblastoma 1 ("Rb1"), the gene encoding retinoblastoma-binding protein 1-like 1 ("RBBP1L1"; see, e.g., locus link accession number 51742), the gene encoding 5-a reductase, the gene encoding ribonuclease/angiogenin inhibitor ("RNH"; see, e.g., OMIM accession number 173320, locus link accession number 6050), the gene encoding 5100 calcium-binding protein A8 ("MRP8"; see, e.g., OMIM accession number 123885, locus link accession number 6279, GenBank accession number NM 0029 ev 64), the gene encoding signal transducer and activator of transcription 6 ("STAT6"; see, e.g., OMIM accession number 601512, locus link accession number 6778), the gene encoding soluble-type polypeptide FZD4S ("FZD4S"; see, e.g., OMIM accession number 604579, locus link accession number 8322), the gene encoding somatotrophin or somatotropin, the gene encoding src (see, e.g., OMIM accession number 190090, locus link accession number 6714, GenBank accession number NM 0054 ev 17), the gene encoding survivin, the gene encoding T-cell lymphoma invasion and metastasis 1 ("TIAM1"; see, e.g., OMIM accession number 600687, locus link accession number 7074), the gene encoding TEK tyrosine kinase ("TIE2"; see, e.g., OMIM accession number 600221, locus link accession number 7010), the gene encoding telomerase, the gene encoding TGF-β, the gene encoding TGF-β1 (see, e.g., OMIM accession number 190180, locus link accession number 7040), the gene encoding thrombomodulin ("THBD" or "THRM"; see, e.g., OMIM accession number 188040, locus link accession number 7056), the gene encoding thrombopoietin ("THPO" or "TPO"; see, e.g., OMIM accession number 600044, locus link accession number 7066), the gene encoding human trisosephosphate isomerase ("TPI1"; see, e.g., OMIM accession number 109450, locus link accession number 7167), the gene encoding thyroid hormone, the gene encoding thyroid stimulating hormone, the gene encoding tissue factor, the gene encoding tissue inhibitor of metalloprotease 1 ("TIMP1"; see, e.g., OMIM accession number 305370, locus link accession number 7076), the gene encoding tissue inhibitor of metalloprotease 2 ("TIMP2"; see, e.g., OMIM accession number 188825, locus link accession number 7077, GenBank accession number NM 0032 55), the gene encoding tissue inhibitor of metalloprotease 4 ("TIMP4"; see, e.g., OMIM accession number 601915, locus link accession number 7079, GenBank accession number NM 0032 56), the gene encoding TNF-α (see, e.g., OMIM accession number 191160, locus link accession number 7124), the gene encoding troponin T ("TnT"), the gene encoding uncoupling protein 2 ("UCP2"; see, e.g., OMIM accession number 601693, locus link accession number 7351, GenBank accession number NM 0033 55), the gene encoding urokinase plasminogen activator ("uPA"; see, e.g., OMIM accession number 191840, locus link accession number 5328), the gene encoding utrophin ("UTRN"; see, e.g., OMIM accession number 128240, locus link accession number 7402), the gene encoding v-myc myelocytomatosis viral oncogene homolog ("c-MYC"; see, e.g., OMIM accession number 190080, locus link accession number 4609), the gene encoding vanilloid receptor subunit 1 ("VR1"; see, e.g., OMIM accession number 602076, locus link accession number 7442, GenBank accession number NM 0187 ev 27, NM 08 0704, NM 0807 05, NM 0807 06), the gene encoding vascular endothelial growth factor ("VEGF"), the gene encoding virion infectivity factor ("VIF"), and the gene encoding VLA-4.

In a specific embodiment, an untranslated region is obtained or derived from the gene encoding Her-2. In another embodiment, an untranslated region is not obtained or derived from the gene encoding Her-2.

In one embodiment, an untranslated region is obtained or derived from the gene encoding VEGF. In another embodiment, an untranslated region is not obtained or derived from the gene encoding VEGF.

The untranslated regions may be obtained or derived from the genome of any virus utilizing any method well-known to one of skill in the art. The nucleotide sequence of an untranslated region for a genome of a virus can be obtained, e.g., from the literature or a database such as GenBank. Examples of viruses from which the untranslated regions may be obtained or derived from include, but are not limited to, retrovirsues (e.g., human immunodeficiency virus ("HIV") and human T cell leukemia virus ("HTLV"), herpesviruses (e.g., herpes simplex virus, epstein barr virus and varicella zoster virus), reoviruses (e.g., reovirus and rotavirus), picornaviruses (e.g., poliovirus, rhinovirus and hepatitis A virus), togaviruses (e.g., rubella virus), orthomyxovirus (e.g., influenza virus), paramyxoviruses (e.g., measles virus, mumps virus, respiratory syncytical virus and parainfluenza virus), filoviruses (e.g., ebola virus and Marburg virus), rhabdoviruses (e.g., rabies virus), coronaviruses (e.g., coronavirus), rhinoviruses, hepatitis B virus, and hepatitis C virus.

The untranslated regions may be obtained or derived from the genome of any bacteria utilizing any method well-known to one of skill in the art. The nucleotide sequence of an untranslated region for a genome of a bacteria can be obtained, e.g., from the literature or a database such as GenBank. Examples of bacteria from which the untranslated regions may be obtained or derived from include, but are not limited to, the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, *Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, *Helicobacter* family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus fasciae*, and *Streptococcus pneumoniae*), VampirovibrHelicobacter family, and Vampirovibrio family.

The untranslated regions may be obtained or derived from the genome of any fungus utilizing any method well-known to one of skill in the art. The nucleotide sequence of an untranslated region for a genome of a fungus can be obtained, e.g., from the literature or a database such as GenBank. Examples of fungus from which the untranslated regions may be obtained or derived from include, but are not limited to, *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus* niger, and *Aspergillus terreus*), *Basidiobolus ranarum*, *Blastomyces dermatitidis*, *Candida* species (e.g., *Candida albicans*, *Candida glabrata*, *Candida kern*, *Candida krusei*, *Candida parapsilosis*, *Candida pseudotropicalis*, *Candida quillermondii*, *Candida rugosa*, *Candida stellatoidea*, and *Candida tropicalis*), *Coccidioides immitis*, *Conidiobolus* species, *Cryptococcus neoforms*, *Cunninghamella* species, dermatophytes, *Histoplasma capsulatum*, *Microsporum gypseum*, *Mucor pusillus*, *Paracoccidioides brasiliensis*, *Pseudallescheria boydii*, *Rhinosporidium seeberi*, *Pneumocystis carinii*, *Rhizopus* species (e.g., *Rhizopus arrhizus*, *Rhizopus oryzae*, and *Rhizopus microsporus*), *Saccharomyces* species, *Sporothrix schenckii*, zygomycetes, and classes such as Zygomycetes, Ascomycetes, the Basidiomycetes, Deuteromycetes, and Oomycetes.

The untranslated regions may be obtained or derived from the genome of any plant utilizing any method well-known to one of skill in the art. The nucleotide sequence of an untranslated region for a genome of a plant can be obtained, e.g., from the literature or a database such as GenBank, EMBL, DDBJ, rice genome database, cotton.genome database and maize genome database. Examples of plants from which the untranslated regions may be obtained or derived from include, but are not limited to, soybean, canola, cotton, corn, wheat, rice, tomato, and potato. Specific examples of plant genes from which an untranslated region may be obtained or derived from include, but are not limited to, triose phosphate, isomerase, fructose 1,6-bisphosphate adolase, fructose 1,6-bisphosphate, fructose 6-phosphate 2-kinase, phosphoglucoisomerase, pyrophsophate-dependent fructose-6-phosphate phosphotransferase, vacuolar $H^+$ translocating-pyrophosphate, invertase, sucrose synthase, hexokinase, fructokinase, NDP-kinase, glucose-6-phosphate 1-dehydrogenase, phosphoglucomutase, UDP-glucose pyrophosphorylase, glutenin genes, cis-prenyltransferase, lipoxygenase, and soybean vestitone reductase (see, e.g., U.S. Patent Application Publication No. 2003/0135870 A1 and U.S. Pat. No. 6,638,5252, 6,645,747, 6,627,797, and 6,617,493, which are incorporated herein by reference in its entirety).

In particular, a 5' UTR of a target gene, a 3' UTR of a target gene, or a 5' UTR and a 3' UTR of a target gene may be utilized in a reporter construct. In a specific embodiment, a 5' UTR of a target gene with a stable hairpin secondary structure is utilized in a reporter construct. In another specific embodiment, a reporter gene in the reporter construct contains an intron. In a preferred embodiment, a 5' UTR and a 3' UTR of a target gene are utilized in a reporter construct. In another preferred embodiment, a 5' UTR and a 3' UTR of a target gene and an intron-containing reporter gene are utilized in a reporter construct.

5.1.1. Elements of Untranslated Regions

Any element of an untranslated region(s) of a target gene may be utilized in the reporter gene constructs described herein. Elements of an untranslated region(s) may be obtained and the nucleotide sequence of the elements determined by any method well-known to one of skill in the art. The nucleotide sequence of an element of an untranslated region for a target gene can be obtained, e.g., from the literature or a database such as GenBank. Alternatively, the nucleotide sequence of an element of an untranslated region of a target gene may be generated from nucleic acid from a suitable source. If a clone containing a nucleic acid of an element of an untranslated region of a target gene is not available, but the sequence of the element is known, a nucleic acid of the element may be chemically synthesized or obtained from a suitable source (e.g., a cDNA library) by PCR amplification. Once the nucleotide sequence of an element is determined, the nucleotide sequence of the element may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate an element having a different nucleic acid sequence.

In one embodiment, an element(s) of an untranslated region comprises the full-length sequence of a UTR, e.g., the 5' UTR or the 3' UTR. In a specific embodiment, an element(s) of an untranslated region that has been shown or has been suggested to be involved in the regulation of mRNA stability and/or translation is utilized in the reporter constructs described herein. Examples of elements of an untranslated region which may be utilized in the reporter constructs described herein include, but are not limited to, an IRE, IRES, uORF, MSL-2, G quartet element, 5'-terminal oligopyrimidine tract ("TOP"), ARE, SECIS, histone stem loop, CPE, nanos translational control element, APP, TGE/DRE, BRE, and a 15-LOX-DICE.

5.1.1.1. Iron Response Element

The maintenance of cellular iron homeostasis occurs at the level of mRNA stability and translation. Two components of this regulatory system have been defined: a cis-acting mRNA sequence/structure motif called an iron-responsive element ("IRE") and a specific trans-acting cytoplasmic binding protein, referred to herein as IRE-binding protein ("IRE-BP") (reviewed in, e.g., Mikulits et al., 1999, Mutat Res. 437(3):219-30; Harrison & Arosio, 1996, Biochim Biophys Acta. 1275(3):161-203; Kuhn & Hentze, 1992, J Inorg Biochem. 1992, 47(3-4):183-95; and Harford & Klausner, 1990, Enzyme 44(1-4):28-41, the disclosures of which are hereby incorporated by reference in their entireties). Iron scarcity induces binding of IRE-BPs to a single IRE in the 5' UTR of ferritin, eALAS, aconitase, erythroid 5-aminolevulinic acid synthase, and SDHb mRNAs, which specifically suppresses translation initiation. Simultaneous interaction of IRE-BPs with multiple IREs in the 3' UTR of transferrin receptor mRNA selectively causes its stabilization. The pattern is reverted under iron overload: IRE-BP mRNA binding affinity is reduced, which results in efficient protein synthesis of target transcripts harboring IREs in the 5' UTR and rapid degradation of transferrin mRNA. Any gene containing an IRE including, but not limited to, the IREs described in the references cited above, can be used in the present invention to identify compounds that modulate untranslated region-dependent gene expression.

5.1.1.2. Internal Ribosome Entry Site

The internal ribosome entry site ("IRES") is one of the better characterized 5' UTR-based cis-acting elements of post-transcriptional gene expression control. IRESes facilitate cap-independent translation initiation by recruiting ribosomes directly to the 5' UTR of the mRNA. IRESes are commonly located in the 3' region of 5' UTR and are, as recent work has established, frequently composed of several discrete sequences. IRESes do not share significant primary structure homology, but do form distinct RNA tertiary structures. Some IRESes contain sequences complementary to 18S RNA and therefore may form stable complexes with 40S ribosomal subunit and initiate assembly of translationally competent complex. A classic example of an "RNA-only" IRES is the internal ribosome entry site from Hepatitis C virus. However, most known IRESes require protein co-factors for activity. More than 10 IRES trans-acting factors ("ITAFs") have been identified so far. In addition, all canonical translation initiation factors, with the sole exception of 5' end cap-binding eIF4E, have been shown to participate in IRES-mediated translation initiation (reviewed in Vagner et al., 2001, EMBO Reports 2:893 and Translational Control of Gene Expression, Sonenberg, Hershey, and Mathews, eds., 2000, CSHL Press, the disclosures of which are incorporated by reference in their entireties).

IRES were first identified in picornaviruses (see, e.g., Pettetier & Sonenberg, 1988, Nature, 334:320-325). The 5' UTRs of all picornaviruses are long and mediate translational initiation by directly recruiting and binding ribosomes, thereby circumventing the initial cap-binding step. Although IRES elements are frequently found in viral mRNAs, they are rarely found in non-viral mRNAs. The non-viral mRNAs shown to contain functional IRES elements in their respective 5' UTRs include those encoding immunoglobulin heavy chain binding protein ("BiP") (see, e.g., Macejak et al., 1991, Nature, 35390-4); Drosophila Antennapedia (see, e.g., Oh et al., 1992, Genes Dev 6:1643-53) and Ultrabithorax (see, e.g., Ye et al., 1997, Mol. Cell Biol. 17:1714-21); fibroblast growth factor 2 (see, e.g., Vagner et al., 1995, Mol. Cell Biol. 15:35-44); initiation factor eIF4G (see, e.g., Gan et al., 1998, J. Biol. Chem. 273:5006-12); proto-oncogene c-myc (see, e.g., Nanbru et al., 1995, J. Biol. Chem. 272:32061-6 and Stoneley, 1998, Oncogene 16:423-8); vascular endothelial growth factor ("VEGF") (see, e.g., Stein et al., 1998, Mol. Cell Biol. 18:3112-9), and X-linked inhibitor of apoptosis protein ("XIAP") (see, e.g., U.S. Pat. Nos. 6,159,709 and 6,171,821), the disclosures of which are incorporated by reference in their entireties. Any gene containing an IRES including, but not limited to, the IRESes described in the references cited above, can be used in the present invention to identify compounds that modulate untranslated region-dependent gene expression.

5.1.1.3. Male Specific Lethal Element

Male-specific expression of the protein male-specific-lethal 2 ("MSL-2") controls dosage compensation in Drosophila. MSL-2 protein is not produced in females and sequences in both the 5' and 3' UTRs are important for this sex-specific regulation because msl-2 gene expression is inhibited in females by Sex-lethal ("SXL"), an RNA binding protein known to regulate pre-mRNA splicing. An intron present in the 5' untranslated region of msl-2 mRNA contains putative SXL binding sites and is retained in female flies. The msl-2 pre-mRNA is alternatively spliced in a Sex-lethal-dependent fashion (see, e.g., Gebauer et al., 1998, RNA 4(2):142-50 and Bashaw & Baker, 1995, Development 121(10):3245-58, the disclosures of which are hereby incorporated by reference in their entireties). Any gene containing an MSL-2 element including, but not limited to, the MSL-2 elements described in the references cited above, can be used in the present invention to identify compounds that modulate untranslated region-dependent gene expression.

5.1.1.4. G-Quartet Element

A symmetrical structure of two tetrads of guanosine base pairs connected by three loops is commonly referred to as a "G-quartet", "G-quadruplex" or "G-tetraplex" structure (see, e.g., Wang et al., 1993, Biochemistry 32:1899-1904; Macaya et al., 1993, Proc. Natl. Acad. Sci. 90:3745-3749; Schultze et al., 1994, J. Mol. Biol. 235:1532-1547; and Kelly et al., 1996, J. Mol. Biol. 256:417-422, the disclosures of which are incorporated by reference in their entireties). A G-quartet element was first identified as a conserved consensus sequence GGNTGGN$_{2-5}$GGNTGG (SEQ ID NO: 1), which was present in single-stranded DNA aptamers that bind thrombin and inhibited thrombin-catalyzed fibrin-clot formation (see, e.g., Bock et al., 1992, Nature 355:564-566, the disclosure of which is incorporated by reference in its entirety). A similar sequence in which the G-quartet structure is maintained when the length of the oligonucleotide between the G pairs is increased has been identified (see, e.g., Dias et al., 1994, J. Am. Chem. Soc. 116:4479-4480, the disclosure of which is incorporated by reference in its entirety).

A G-quartet element has been identified in mRNAs associated with fragile X mental retardation syndrome (reviewed in, e.g., Bardoni & Mandel, 2002, Curr Opin Genet Dev 12(3):284-93, the disclosure of which is incorporated by reference in its entirety). The fragile X mental retardation syndrome is caused by large methylated expansions of a CGG repeat in the FMR1 gene that lead to the loss of expression of FMRP, an RNA-binding protein. FMRP is proposed to act as a regulator of mRNA transport or translation that plays a role in synaptic maturation and function and has been shown to interact preferentially with mRNAs containing a G quartet structure.

G-quartet oligonucleotides can have the sequence GGN$_x$GGN$_y$GGN$_z$GG (SEQ ID NO: 2), wherein x, y and z indicate a variable number of nucleotides (see, e.g., U.S. Pat. No. 5,691,145, the disclosure of which is incorporated by reference in its entirety). While x, y and z are each typically at least about 2, preferably about 2-10, these segments may be longer if desired The regions of variable sequence (i.e., N$_x$N$_y$N$_z$) are not critical in the present invention and can be varied in length and sequence without disrupting the characteristic G-quartet structure. As a general rule, the variable N sequences should not be self-complementary and should not contain G residues which would result in alternative G-quartet structures within the molecule. Representative G-quartet oligonucleotides are 15-20 nucleotides in length, but G-quartet oligonucleotides of any length which conform to the general formula GGN$_x$GGN$_y$GGN$_z$GG (SEQ ID NO: 3) are also suitable. The G-quartet oligonucleotide is typically about 14-30 nucleotides in length. Any gene containing a G-quartet element including, but not limited to, the G-quartet elements described in the references cited above, can be used in the present invention to identify compounds that modulate untranslated region-dependent gene expression.

5.1.1.5. 5'-Terminal Oligopyrimidine Tract

Translation control can be mediated by a terminal oligopyrimidine element ("TOP") present in the 5' untranslated region of ribosomal protein-encoding mRNAs. TOP elements adopt a specific secondary structure that prevents ribosome-binding and translation-initiation of ribosomal protein-encoding mRNAs. However, binding of cellular nucleic acid binding protein ("CNBP") or La proteins to the TOP hairpin structure abolishes the TOP-mediated transcription block and induces ribosomal protein production (see, e.g., Schlatter & Fussenegger, 2003, Biotechnol Bioeng 81(1):1-12; Zhu et al., 2001, Biochim Biophys Acta 1521(1-3):19-29; and Crosio et al., 2000, Nucleic Acids Res. 28(15):2927-34, the disclosures of which are incorporated by reference in their entireties).

The immunosuppressant rapamycin selectively suppresses the translation of mRNAs containing a TOP tract adjacent to the cap structure. Trans-acting factors, some of which are regulated by rapamycin-responsive signaling pathways, that bind to the 5' untranslated region of TOP mRNAs may be involved in selective translational repression (see, e.g., Kakegawa et al., 2002, Arch Biochem Biophys 402(1):77-83, the disclosure of which is incorporated by reference in its entirety). Any gene containing a TOP element including, but not limited to, the TOP elements described in the references cited above, can be used in the present invention to identify compounds that modulate untranslated region-dependent gene expression.

5.1.1.6. Adenylate Uridylate-Rich Element

AU-rich elements ("AREs") are the most extensively studied 3' UTR-based regulatory signals. AREs are the primary determinant of mRNA stability and one of the key determinants of mRNA translation initiation efficiency.

A typical ARE is 50 to 150 nt long and contains 3 to 6 copies of $AU_3A$ pentamer embedded in a generally A/U-enriched RNA region. The $AU_3A$ pentamers can be scattered within the region or can stagger or even overlap (Chen et al., 1995, Trends Biol. Sciences 20:465, the disclosure of which is incorporated by reference in its entirety). One or several $AU_3A$ pentamers can be replaced by expanded versions such as an $AU_4A$ hexamer or $AU_5A$ heptamer (see, e.g., Wilkund et al., 2002, J. Biol. Chem. 277:40462 and Tholanikunnel & Malbom, 1997, J. Biol. Chem. 272:11471, the disclosures of which are incorporated by reference in their entireties). Single copies of the $AU_nA$ (where n=3, 4, or 5) elements placed in a random sequence context are inactive. The minimal active ARE has been determined to have the sequence $U_2AU_nA(U/A)(U/A)$ (where n=3, 4, or 5) (see, e.g., Worthington et al., 2002, J Biol Chem, 277:48558-64) the disclosure of which is incorporated by reference in its entirety). The activity of certain AU-rich elements in promoting mRNA degradation is enhanced in the presence of distal uridine-rich sequences. These U-rich elements do not affect mRNA stability when present alone and thus that have been termed "ARE enhancers" (see, e.g., Chen et al., 1994, Mol. Cell. Biol. 14:416, the disclosure of which is incorporated by reference in its entirety).

Most AREs function in mRNA decay regulation and translation initiation regulation by interacting with specific ARE-binding proteins ("AUBPs"). There are at least 14 known cellular proteins that bind to AU-rich elements. AUBP functional properties determine ARE involvement in one or both pathways. For example, ELAV/HuR binding to c-fos ARE inhibits c-fos mRNA decay (see, e.g., Brennan & Steitz, 2001, Cell Mol Life Sci. 58:266), association of tristetraprolin with TNFa ARE dramatically enhances TNFa mRNA hydrolysis (see, e.g., Carballo et al., 1998, Science 281:1001), whereas interaction of TIA-1 with the TNFa ARE does not alter the TNFa mRNA stability but inhibits TNFa translation (see, e.g., Piecyk et al., 2000, EMBO J. 19:4154).

Since AREs are clearly important in biological systems, including but not limited to a number of the early response genes that regulate cell proliferation and responses to exogenous agents, the identification of compounds that bind to one or more of the ARE clusters and potentially modulate the stability and translation of the target RNA can potentially be of value as a therapeutic. Any gene containing an ARE including, but not limited to, the AREs described in the references cited above, can be used in the present invention to identify compounds that modulate untranslated region-dependent gene expression.

5.1.1.7. Selenocysteine Insertion Sequence

Selenium is an essential micronutrient that is now known to be incorporated as selenocysteine in a number of selenoproteins, glutathione peroxidase being the prototypical example. Selenocysteine is specifically encoded by the UGA codon, and inserted in peptide chains by a cotranslational mechanism that is able to override the normal function of UGA as a termination codon. In eukaryotes, efficient selenocysteine incorporation at UGA codons requires a cellular protein factor and a cis-acting structural signal usually located in the mRNA 3' untranslated region, consisting of a selenocysteine insertion sequence ("SECIS") in a characteristic stem-loop structure (see, e.g., Peterlin et al., 1993, "Tat Trans-Activator" In Human Retroviruses; Cullen, Ed.; Oxford University Press: New York; pp. 75-100; Le & Maizel, 1989, J. Theor. Biol. 138:495-510; and reviewed in Hubert et al., 1996, Biochimie 78(7):590-6, the disclosures of which are incorporated by reference in their entireties). The required protein factor is presumed to be present in certain cells types that express selenoproteins, such as liver cells, lymphocytes, macrophages, thrombocytes, and other blood cells. In such cell types, the presence of a SECIS element in an mRNA is necessary and sufficient for in-frame UGA codons to be translated as selenocysteine.

A SECIS element is usually UAAAG, although other SECIS elements have been identified or variants have been constructed (see, e.g., U.S. Pat. Nos. 6,303,295, 5,849,520, and 5,700,660, the disclosures of which are incorporated by reference in their entireties). Any gene containing a SECIS element including, but not limited to, the SECIS elements described in the references cited above, can be used in the present invention to identify compounds that modulate untranslated region-dependent gene expression.

5.1.1.8. Histone Stem Loop

Replication-dependent histone mRNAs end with a conserved 26-nucleotide sequence that contains a 16-nucleotide stem-loop, i.e., the histone stem loop, instead of a poly(A) tail. Formation of the 3' end of histone mRNA occurs by endonucleolytic cleavage of pre-mRNA releasing the mature mRNA from the chromatin template. Cleavage requires several trans-acting factors, including a protein, the stem-loop binding protein, which binds the 26-nucleotide sequence, and a small nuclear RNP, U7 snRNP (reviewed in, e.g., Dominski & Marzluff, 1999, Gene 239(1):1-14, the disclosure of which is incorporated by reference in its entirety).

Sequences of histone stem loops have been described in U.S. Pat. Nos. 6,476,208; 6,455,280; 6,399,373; 6,346,381; 6,335,170; 6,331,396; 6,265,546; 6,265,167; 5,990,298; 5,908,779 and 5,843,770, the disclosures of which are incorporated by reference in their entireties. Any gene containing a histone stem loop including, but not limited to, the histone stem loops described in the references cited above, can be used in the present invention to identify compounds that modulate untranslated region-dependent gene expression.

5.1.1.9. Cytoplasmic Polyadenylation Element

Maturation-specific polyadenylation in *Xenopus* oocytes depends on the presence of a U-rich cytoplasmic polyadenylation element ("CPE") close to the 3' end of the RNA. RNAs that lack CPEs appear to be deadenylated by default when meiosis resumes. This default program also applies to maturing mouse oocytes (see, e.g., Paynton & Bachvarova, 1994, Mol Reprod Dev 37(2):172-80, the disclosure of which is incorporated by reference in its entirety). CPEs have been identified in Weel protein tyrosine kinase mRNA (see, e.g., Charlesworth et al., 2000, Dev Biol 227(2):706-19, the disclosure of which is incorporated by reference in its entirety), cyclin B1 mRNA (see, e.g., Tay et al., 2000, Dev Biol 221(1):1-9 and Barkoff et al., 2000, Dev Biol 220(1):97-109, the disclosures of which are incorporated by reference in their entireties), and *Xenopus* Id3 mRNA (see, e.g., Afouda et al., 1999, Mech Dev 88(1):15-31, the disclosure of which is incorporated by reference in its entirety).

A *Xenopus* oocyte CPE binding protein ("CPEB") binds the CPE and stimulates polyadenylation. CPEB is essential for the cytoplasmic polyadenylation of B4 RNA, G10, c-mos, cdk2, cyclins A1, B1 and B2 mRNAs which suggests that this protein is required for polyadenylation of most RNAs during oocyte maturation (see, e.g., Stebbins-Boaz et al., 1996, EMBO J 15(10):2582-92, the disclosure of which is incorporated by reference in its entirety). Any gene containing a CPE including, but not limited to, the CPEs described in the references cited above, can be used in the present invention to identify compounds that modulate untranslated region-dependent gene expression.

5.1.1.10. Nanos Translational Control Element

The nanos translational control element is a discrete translational control element within the nanos 3' untranslated region that acts independently of the localization signal to mediate translational repression of unlocalized nanos RNA (see, e.g., Clark et al., 2002, Development 129(14): 3325-34; Clark et al., 2000, Curr Biol 10(20):1311-4; Crucs et al., 2000, Mol Cell 5(3):457-67; Bergsten & Gavis, 1999, Development 126(4):659-69; Dahanukar & Wharton, 1996, Genes Dev (20):2610-20; and Gavis et al., 1996, Development 122(9):2791-800, the disclosures of which are incorporated by reference in their entireties).

During *Drosophila* embryogenesis, the Smaug protein represses translation of the nanos protein through an interaction with the nanos translational control element (see, e.g., Green et al., 2002, Biochem Biophys Res Commun 297(5): 1085-8, the disclosure of which is incorporated by reference in its entirety). Any gene containing a nanos translational control element including, but not limited to, the nanos translational control elements described in the references cited above, can be used in the present invention to identify compounds that modulate untranslated region-dependent gene expression.

5.1.1.11. Amyloid Precursor Protein Element

In one embodiment, the amyloid precursor protein element ("APP" element) refers to a novel iron-responsive element within the 5' untranslated region of the Alzheimer's amyloid precursor protein ("APP") transcript (+51 to +94 from the 5'-cap site) (see, e.g., Rogers et al., 2002, J Biol Chem 277(47):45518-28). The APP mRNA IRE is located immediately upstream of an interleukin-1 responsive acute box domain (+101 to +146). The APP 5' UTR conferred translation was selectively down-regulated in response to intracellular iron chelation.

In another embodiment, the APP element refers to a 29 base instability element in the 3' UTR of the amyloid precursor protein involved in mRNA stability (see, e.g., Westmark & Malter, 2001, Brain Res Mol Brain Res 90(2): 193-201; Rajagopalan & Malter, 2000, J Neurochem 74(1): 52-9; Amara et al., 1999, Brain Res Mol Brain Res 71(1): 42-9; and Zaidi & Malter, 1995, J Biol Chem 270(29): 17292-8, the disclosures of which are incorporated by reference in their entireties). Any gene containing a APP element including, but not limited to, the APP elements described in the references cited above, can be used in the present invention to identify compounds that modulate untranslated region-dependent gene expression.

5.1.1.12. Translation Regulation Element

Negative translational control elements in 3' UTRs regulate pattern formation, cell fate, and sex determination in a variety of organisms. tra-2 mRNA in *Caenorhabditis elegans* is required for female development but must be repressed to permit spermatogenesis in hermaphrodites. Translational repression of tra-2 mRNA in *C. elegans* is mediated by tandemly repeated elements in its 3' UTR; these elements are called TGEs (for tra-2 and GLI element) (see, e.g., Thompson et al., 2000, Mol Cell Biol 20(6):2129-37; Haag & Kimble, 2000, Genetics 155(1):105-16; and Jan et al., 1997, EMBO J 16(20):6301-13, the disclosures of which are incorporated by reference in their entireties). Any gene containing a TGE including, but not limited to, the TGEs described in the references cited above, can be used in the present invention to identify compounds that modulate untranslated region-dependent gene expression.

5.1.1.13. Direct Repeat Element

The direct repeat element ("DRE") is one control element in the 3' UTR of the tra-2 mRNA that causes repression of tra-2, i.e., inhibits translation of tra-2 mRNA, which is responsible for the onset of hermaphrodite spermatogenesis in *C. elegans* (see, e.g., Goodwin et al., 1993, Cell 75:329-339, the disclosure of which is incorporated by reference in its entirety). Three germline-specific regulators have been identified that mediate DRE regulation by the tra-2 3' UTR. These include DRFQ2/GLD-1, a protein that specifically binds the DRE (see, e.g., Goodwin et al., 1993, Cell 75:329-339) and controls tra-2 translation (see, e.g., Jan et al. 1999, EMBO J. 18:258-269); FOG-2, a protein that binds GLD-1 and is required for the onset of hermaphrodite spermatogenesis (see, e.g., Schedl & Kimble, 1988, Genetics 119:43-61); and laf-1, a gene that has not yet been identified at the molecular level (see, e.g., Goodwin et al., 1997, Development 124:749-758), the disclosures of which are incorporated by reference in their entireties. Any gene containing a DRE including, but not limited to, the DREs described in the references cited above, can be used in the present invention to identify compounds that modulate untranslated region-dependent gene expression.

5.1.1.14. Bruno Response Element

The Bruno Response Element ("BRE"), is located in the 3' untranslated region (UTR) of oskar mRNA (see, e.g., Castagnetti et al., 2000, Development 127(5):1063-8, the disclosure of which is incorporated by reference in its entirety). The coupled regulation of oskar mRNA localization and translation in time and space is critical for correct anteroposterior patterning of the *Drosophila* embryo. Localization-dependent translation of oskar mRNA, a mechanism whereby oskar RNA localized at the posterior of the oocyte is selectively translated and the unlocalized RNA remains in a translationally repressed state, ensures that Oskar activity is present exclusively at the posterior pole. Genetic experiments indicate that translational repression involves the binding of Bruno protein to multiple sites, the BREs, in the 3' untranslated region of oskar mRNA. Any gene containing a BRE including, but not limited to, the BREs described in the references cited above, can be used in the present invention to identify compounds that modulate untranslated region-dependent gene expression.

5.1.1.15. 15-Lipoxygenase Differentiation Control Element

The translation of 15-lipoxygenase ("LOX") mRNA in erythroid precursor cells and of the L2 mRNA of human papilloma virus type 16 (HPV-16) in squamous epithelial cells is silenced when either of these cells is immature and is activated in maturing cells by unknown mechanisms. It has been shown that hnRNP K and the c-Src kinase specifically interact with each other, leading to c-Src activation and tyrosine phosphorylation of hnRNP K in vivo and in vitro. c-Src-mediated phosphorylation reversibly inhibits the binding of hnRNP K to the differentiation control element ("DICE") of the LOX mRNA 3' untranslated region in vitro and specifically derepresses the translation of DICE-bearing mRNAs in vivo (see, e.g., Ostareck-Lederer et al., 2002, Mol Cell Biol 22(13):4535-43, the disclosure of which is incorporated by reference in its entirety).

Cytidine-rich 15-lipoxygenase differentiation control element ("15-LOX-DICE") is a multifunctional cis-acting element found in the 3' untranslated region of numerous eukaryotic mRNAs. It binds KH domain proteins of the type hnRNP E and K, thus mediating mRNA stabilization and translational control. Translational silencing is caused by formation of a simple binary complex between DICE and recombinant hnRNP E1. Electromobility shift assays and sucrose gradient centrifugation demonstrate that rabbit 15-LOX-DICE, which is composed of ten subunits of the sequence (CCCCPuCCCUCUUCCCCAAG, SEQ ID NO: 4), is able to bind up to ten molecules of hnRNP E1 (see, e.g., Reimann et al., 2002, J Mol Biol 315(5):965-74 and Thiele et al., 1999, Adv Exp Med Biol 447:45-61, the disclosures of which are incorporated by reference in their entireties). Any gene containing a 15-LOX-DICE including, but not limited to, the 15-LOX-DICEs described in the references cited above, can be used in the present invention to identify compounds that modulate untranslated region-dependent gene expression.

5.2. Reporter Gene Constructs, Transfected Cells, and Cell-Free Extracts

The invention provides for specific vectors containing a reporter gene flanked by one or more UTRs of a target gene and host cells transfected with the vectors. The invention also provides for the in vitro translation of a reporter gene flanked by one or more UTRs of a target gene. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

5.2.1. Reporter Genes

Any reporter gene well-known to one of skill in the art may be used in reporter gene constructs to ascertain the effect of a compound on untranslated region-dependent expression of a target gene. Reporter genes refer to a nucleotide sequence encoding a protein that is readily detectable either by its presence or activity. Reporter genes may be obtained and the nucleotide sequence of the reporter gene determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

Examples of reporter genes include, but are not limited to, luciferase (e.g., firefly luciferase, *renilla* luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("b-gal"), beta-glucoronidase, beta-lactamase, chloramphenicol acetyltransferase ("CAT"), and alkaline phosphatase ("AP"). In a preferred embodiment, a reporter gene utilized in the reporter constructs is easily assayed and has an activity which is not normally found in the cell or organism of interest.

5.2.1.1. Luciferase

Luciferases are enzymes that emit light in the presence of oxygen and a substrate (luciferin) and which have been used for real-time, low-light imaging of gene expression in cell cultures, individual cells, whole organisms, and transgenic organisms (reviewed by Greer & Szalay, 2002, Luminescence 17(1):43-74).

As used herein, the term "luciferase" is intended to embrace all luciferases, or recombinant enzymes derived from luciferases which have luciferase activity. The luciferase genes from fireflies have been well characterized, for example, from the *Photinus* and *Luciola* species (see, e.g., International Patent Publication No. WO 95/25798 for *Photinus pyralis*, European Patent Application No. EP 0 524 448 for *Luciola cruciata* and *Luciola lateralis*, and Devine et al., 1993, Biochim. Biophys. Acta 1173(2):121-132 for *Luciola mingrelica*). Other eukaryotic luciferase genes include, but are not limited to, the click beetle (*Photinus plagiophthalamus*, see, e.g., Wood et al., 1989, Science 244:700-702), the sea panzy (*Renilla reniformis*, see, e.g., Lorenz et al., 1991, Proc Natl Acad Sci USA 88(10):4438-4442), and the glow worm (*Lampyris noctiluca*, see e.g., Sula-Newby et al., 1996, Biochem J. 313:761-767). The click beetle is unusual in that different members of the species emit bioluminescence of different colors, which emit light at 546 nm (green), 560 nm (yellow-green), 578 nm (yellow) and 593 nm (orange) (see, e.g, U.S. Pat. Nos. 6,475,719; 6,342,379; and 6,217,847, the disclosures of which are incorporated by reference in their entireties). Bacterial luciferin-luciferase systems include, but are not limited to, the bacterial lux genes of terrestrial *Photorhabdus luminescens* (see, e.g., Manukhov et al., 2000, Genetika 36(3):322-30) and marine bacteria *Vibrio fischeri* and *Vibrio harveyi* (see, e.g., Miyamoto et al., 1988, J Biol Chem. 263(26):13393-9, and Cohn et al., 1983, Proc Natl Acad Sci USA., 80(1):120-3, respectively). The luciferases encompassed by the present invention also includes the mutant luciferases described in U.S. Pat. No. 6,265,177 to Squirrell et al., which is hereby incorporated by reference in its entirety.

In a preferred embodiment, the luciferase is a firefly luciferase, a *renilla* luciferase, or a click beetle luciferase, as described in any one of the references listed supra, the disclosures of which are incorporated by reference in their entireties.

5.2.1.2. Green Fluorescent Protein

Green fluorescent protein ("GFP") is a 238 amino acid protein with amino acid residues 65 to 67 involved in the formation of the chromophore which does not require additional substrates or cofactors to fluoresce (see, e.g., Prasher et al., 1992, Gene 111:229-233; Yang et al., 1996, Nature Biotechnol. 14:1252-1256; and Cody et al., 1993, Biochemistry 32:1212-1218).

As used herein, the term "green fluorescent protein" or "GFP" is intended to embrace all GFPs (including the various forms of GFPs which exhibit colors other than green), or recombinant enzymes derived from GFPs which have GFP activity. In a preferred embodiment, GFP includes green fluorescent protein, yellow fluorescent protein, red fluorescent protein, cyan fluorescent protein, and blue fluorescent protein. The native gene for GFP was cloned from the bioluminescent jellyfish *Aequorea victoria* (see, e.g., Morin et al., 1972, J. Cell Physiol. 77:313-318). Wild type GFP has a major excitation peak at 395 nm and a minor excitation peak at 470 nm. The absorption peak at 470 nm allows the monitoring of GFP levels using standard fluorescein isothiocyanate (FITC) filter sets. Mutants of the GFP gene have been found useful to enhance expression and to modify excitation and fluorescence. For example, mutant GFPs with alanine, glycine, isoleucine, or threonine substituted for serine at position 65 result in mutant GFPs with shifts in excitation maxima and greater fluorescence than wild type protein when excited at 488 nm (see, e.g., Heim et al., 1995, Nature 373:663-664; U.S. Pat. No. 5,625,048; Delagrave et al., 1995, Biotechnology 13:151-154; Cormack et al., 1996, Gene 173:33-38; and Cramer et al., 1996, Nature Biotechnol. 14:315-319). The ability to excite GFP at 488 nm permits the use of GFP with standard fluorescence activated cell sorting ("FACS") equipment. In another embodiment, GFPs are isolated from organisms other than the jellyfish, such as, but not limited to, the sea pansy, *Renilla reriformis*.

Techniques for labeling cells with GFP in general are described in U.S. Pat. Nos. 5,491,084 and 5,804,387, which are incorporated by reference in their entireties; Chalfie et al., 1994, Science 263:802-805; Heim et al., 1994, Proc. Natl. Acad. Sci. USA 91:12501-12504; Morise et al., 1974, Biochemistry 13:2656-2662; Ward et al., 1980, Photochem. Photobiol. 31:611-615; Rizzuto et al., 1995, Curr. Biology 5:635-642; and Kaether & Gerdes, 1995, FEBS Lett 369:267-271. The expression of GFPs in *E. coli* and *C. elegans* are described in U.S. Pat. No. 6,251,384 to Tan et al., which is incorporated by reference in its entirety. The expression of GFP in plant cells is discussed in Hu & Cheng, 1995, FEBS Lett 369:331-33, and GFP expression in *Drosophila* is described in Davis et al., 1995, Dev. Biology 170:726-729.

5.2.1.3. Beta-Galactosidase

Beta galactosidase ("b-gal") is an enzyme that catalyzes the hydrolysis of b-galactosides, including lactose, and the galactoside analogs o-nitrophenyl-b-D-galactopyranoside ("ONPG") and chlorophenol red-b-D-galactopyranoside ("CPRG") (see, e.g., Nielsen et al., 1983 Proc Natl Acad Sci USA 80(17):5198-5202; Eustice et al., 1991, Biotechniques 11:739-742; and Henderson et al., 1986, Clin. Chem. 32:1637-1641). The b-gal gene functions well as a reporter gene because the protein product is extremely stable, resistant to proteolytic degradation in cellular lysates, and easily assayed. When ONPG is used as the substrate, b-gal activity can be quantitated with a spectrophotometer or microplate reader.

As used herein, the term "beta galactosidase" or "b-gal" is intended to embrace all b-gals, including lacZ gene products, or recombinant enzymes derived from b-gals which have b-gal activity. The b-gal gene functions well as a reporter gene because the protein product is extremely stable, resistant to proteolytic degradation in cellular lysates, and easily assayed. In an embodiment where ONPG is the substrate, b-gal activity can be quantitated with a spectrophotometer or microplate reader to determine the amount of ONPG converted at 420 nm. In an embodiment when CPRG is the substrate, b-gal activity can be quantitated with a spectrophotometer or microplate reader to determine the amount of CPRG converted at 570 to 595 nm. In yet another embodiment, the b-gal activity can be visually ascertained by plating bacterial cells transformed with a b-gal construct onto plates containing Xgal and IPTG. Bacterial colonies that are dark blue indicate the presence of high b-gal activity and colonies that are varying shades of blue indicate varying levels of b-gal activity.

5.2.1.4. Beta-Glucoronidase

Beta-glucuronidase ("GUS") catalyzes the hydrolysis of a very wide variety of b-glucuronides, and, with much lower efficiency, hydrolyzes some b-galacturonides. GUS is very stable, will tolerate many detergents and widely varying ionic conditions, has no cofactors, nor any ionic requirements, can be assayed at any physiological pH, with an optimum between 5.0 and 7.8, and is reasonably resistant to thermal inactivation (see, e.g., U.S. Pat. No. 5,268,463, which is incorporated by reference in its entirety).

In one embodiment, the GUS is derived from the *Esherichia coli* b-glucuronidase gene. In alternate embodiments of the invention, the b-glucuronidase encoding nucleic acid is homologous to the *E. coli* b-glucuronidase gene and/or may be derived from another organism or species.

GUS activity can be assayed either by fluorescence or spectrometry, or any other method described in U.S. Pat. No. 5,268,463, the disclosure of which is incorporated by reference in its entirety. For a fluorescent assay, 4-trifluoromethylumbelliferyl b-D-glucuronide is a very sensitive substrate for GUS. The fluorescence maximum is close to 500 nm—bluish green, where very few plant compounds fluoresce or absorb. 4-trifluoromethylumbelliferyl b-D-glucuronide also fluoresces much more strongly near neutral pH, allowing continuous assays to be performed more readily than with MUG. 4-trifluoromethylumbelliferyl b-D-glucuronide can be used as a fluorescent indicator in vivo. The spectrophotometric assay is very straightforward and moderately sensitive (Jefferson et al., 1986, Proc. Natl. Acad. Sci. USA 86:8447-8451). A preferred substrate for spectrophotometric measurement is p-nitrophenyl b-D-glucuronide, which when cleaved by GUS releases the chromophore p-nitrophenol. At a pH greater than its plc (around 7.15) the ionized chromophore absorbs light at 400-420 nm, giving a yellow color.

5.2.1.5. Beta-Lactamase

Beta-lactamases are nearly optimal enzymes in respect to their almost diffusion-controlled catalysis of b-lactam hydrolysis, making them suited to the task of an intracellular reporter enzyme (see, e.g., Christensen et al., 1990, Biochem. J. 266: 853-861). They cleave the b-lactam ring of b-lactam antibiotics, such as penicillins and cephalosporins, generating new charged moieties in the process (see, e.g., O'Callaghan et al., 1968, Antimicrob. Agents. Chemother. 8: 57-63 and Stratton, 1988, J. Antimicrob. Chemother. 22, Suppl. A: 23-35). A large number of b-lactamases have been isolated and characterized, all of which would be suitable for use in accordance with the present invention (see, e.g., Richmond & Sykes, 1978, Adv. Microb. Physiol. 9:31-88 and Ambler, 1980, Phil. Trans. R. Soc. Lond. [Ser.B.] 289: 321-331, the disclosures of which are incorporated by reference in their entireties).

The coding region of an exemplary b-lactamase employed has been described in U.S. Pat. No. 6,472,205, Kadonaga et al., 1984, J. Biol. Chem. 259: 2149-2154, and Sutcliffe, 1978, Proc. Natl. Acad. Sci. USA 75: 3737-3741, the disclosures of which are incorporated by reference in their entireties. As would be readily apparent to those skilled in the field, this and other comparable sequences for peptides having b-lactamase activity would be equally suitable for use in accordance with the present invention. The combination of a fluorogenic substrate described in U.S. Pat. Nos. 6,472,205, 5,955,604, and 5,741,657, the disclosures of which are incorporated by reference in their entireties, and a suitable b-lactamase can be employed in a wide variety of different assay systems, such as are described in U.S. Pat. No. 4,740,459, which is hereby incorporated by reference in its entirety.

5.2.1.6. Chloramphenicol Acetyltransferase

Chloramphenicol acetyl transferase ("CAT") is commonly used as a reporter gene in mammalian cell systems because mammalian cells do not have detectable levels of CAT activity. The assay for CAT involves incubating cellular extracts with radiolabeled chloramphenicol and appropriate co-factors, separating the starting materials from the product by, for example, thin layer chromatography ("TLC"), followed by scintillation counting (see, e.g., U.S. Pat. No. 5,726,041, which is hereby incorporated by reference in its entirety).

As used herein, the term "chloramphenicol acetyltransferase" or "CAT" is intended to embrace all CATs, or recombinant enzymes derived from CAT which have CAT activity. While it is preferable that a reporter system which does not require cell processing, radioisotopes, and chromatographic separations would be more amenable to high through-put screening, CAT as a reporter gene may be preferable in situations when stability of the reporter gene is important. For example, the CAT reporter protein has an in vivo half life of about 50 hours, which is advantageous when an accumulative versus a dynamic change type of result is desired.

5.2.1.7. Secreted Alkaline Phosphatase

The secreted alkaline phosphatase ("SEAP") enzyme is a truncated form of alkaline phosphatase, in which the cleavage of the transmembrane domain of the protein allows it to be secreted from the cells into the surrounding media. In a preferred embodiment, the alkaline phosphatase is isolated from human placenta.

As used herein, the term "secreted alkaline phosphatase" or "SEAP" is intended to embrace all SEAP or recombinant enzymes derived from SEAP which have alkaline phosphatase activity. SEAP activity can be detected by a variety of methods including, but not limited to, measurement of catalysis of a fluorescent substrate, immunoprecipitation, HPLC, and radiometric detection. The luminescent method is preferred due to its increased sensitivity over calorimetric detection methods. The advantages of using SEAP is that a cell lysis step is not required since the SEAP protein is secreted out of the cell, which facilitates the automation of sampling and assay procedures. A cell-based assay using SEAP for use in cell-based assessment of inhibitors of the Hepatitis C virus protease is described in U.S. Pat. No. 6,280,940 to Potts et al. which is hereby incorporated by reference in its entirety.

5.2.2. Reporter Gene Constructs

The invention provides reporter gene constructs for use in the reporter gene-based assays described herein for the identification of compounds that modulate untranslated region-dependent expression of a target gene. The reporter gene constructs of the invention comprise one or more reporter genes fused to one or more untranslated regions. For example, specific RNA sequences, RNA structural motifs, and/or RNA structural elements that are known or suspected to modulate untranslated region-dependent expression of a target gene may be fused to the reporter gene.

The present invention provides for a reporter gene flanked by one or more untranslated regions (e.g., the 5' UTR, 3' UTR, or both the 5' UTR and 3' UTR of the target gene). The present invention also provides for a reporter gene flanked by one or more UTRs of a target gene, said UTRs containing one or more mutations (e.g., one or more substitutions, deletions and/or additions). In a preferred embodiment, the reporter gene is flanked by both 5' and 3' UTRs so that compounds that interfere with an interaction between the 5' and 3' UTRs can be identified. In another preferred embodiment, a stable hairpin secondary structure is inserted into the UTR, preferably the 5' UTR of the target gene. For example, in cases where the 5' UTR possesses IRES activity, the addition of a stable hairpin secondary structure in the 5' UTR can be used to separate cap-dependent from cap-independent translation (see, e.g., Muhlrad et al., 1995, Mol. Cell. Biol. 15(4):2145-56, the disclosure of which is incorporated by reference in its entirety). In another embodiment, an intron is inserted into a UTR (preferably, the 5' UTR) or at the 5' end of an ORF of a target gene. For example, but not by limitation, in cases where an RNA possesses instability elements, an intron, e.g., the human elongation factor one alpha (EF-1 alpha) first intron, can be cloned into a UTR (preferably, the 5' UTR) or a 5' end of the ORF to increase expression (see, e.g., Kim et al., 2002, J Biotechnol 93(2): 183-7, the disclosure of which is incorporated by reference in its entirety). In a preferred embodiment, both a stable hairpin secondary structure and an intron are added to the reporter gene construct. In a more preferred embodiment, the stable hairpin secondary structure is cloned into the 5' UTR and the intron is added at the 5' end of the ORF of the reporter gene.

The reporter gene can be positioned such that the translation of that reporter gene is dependent upon the mode of translation initiation, such as, but not limited to, cap-dependent translation or cap-independent translation (i.e., translation via an internal ribosome entry site). Alternatively, where the UTR contains an upstream open reading frame, the reporter gene can be positioned such that the reporter protein is translated only in the presence of a compound that shifts the reading frame of the UTR so that the formerly untranslated open reading frame is then translated.

The reporter gene constructs can be monocistronic or multicistronic. A multicistronic reporter gene construct may encode 2, 3, 4, 5, 6, 7, 8, 9, 10 or more, or in the range of 2-5, 5-10 or 10-20 reporter genes. For example, a dicistronic reporter gene construct comprising in the following order a promoter, a first reporter gene, a 5' UTR of a target gene, a second reporter gene and optionally, a 3' UTR of a target gene. In such a reporter construct, the transcription of both reporter genes is driven by the promoter, whereas the translation of the mRNA from the first reporter gene is by a cap-dependent scanning mechanism and the translation of the mRNA from the second reporter gene is by a cap-independent mechanism by an IRES. The IRES-dependent translation of the mRNA of the second reporter gene can be normalized against cap-dependent translation.

5.2.3. Expression of Reporter Gene Constructs in Cells
5.2.3.1. Vectors

The nucleotide sequence coding for a reporter gene can be inserted into an appropriate expression vector, i.e., a vector which contains the necessary elements for the transcription and translation of the inserted protein-coding sequence. The necessary transcriptional and translational signals can also be supplied by the target gene or the reporter gene. A variety of host-vector systems may be utilized to express the reporter gene. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. The expression elements of vectors vary in their strengths and specificities. Depending on the host-vector system utilized, any one of a number of suitable transcription and translation elements may be used. In specific embodiments, the reporter gene is expressed, or a fusion protein comprising the reporter gene and ORF of a fragment thereof, of the target gene is expressed.

Any of the methods previously described for the insertion of DNA fragments into a vector may be used to construct expression vectors containing a chimeric nucleic acid consisting of appropriate transcriptional/translational control signals and the protein coding sequences. These methods may include in vitro recombinant DNA and synthetic techniques and in vivo recombinants (genetic recombination). Expression of the reporter gene construct may be regulated by a second nucleic acid sequence so that the reporter gene is expressed in a host transformed with the recombinant DNA molecule. For example, expression of a reporter gene construct may be controlled by any promoter/enhancer element known in the art, such as a constitutive promoter, a tissue-specific promoter, or an inducible promoter. Specific examples of promoters which may be used to control gene expression include, but are not limited to, the SV40 early promoter region (Bernoist & Chambon, 1981, Nature 290: 304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a reporter gene flanked by one or more UTRs of a target gene, origins of replication from one or more species, and, optionally, one or more selectable markers (e.g., an antibiotic resistance gene). In a preferred embodiment, the vectors are CMV vectors, T7 vectors, lac vectors, pCEP4 vectors, or 5.0/FRT vectors.

In a specific embodiment, an expression construct is made by amplifying the 5' and/or 3' UTRs of a target gene and ligating the UTRs to a reporter gene such as luciferase, and subcloning them into a pT-Adv vector (Clontech Laboratories, Palo Alto, Calif.). It is understood by one of skill in the art that the construction of the reporter plasmid may require the construction of intermediate plasmids if several ligations are involved.

Expression vectors containing the reporter gene construct of the present invention can be identified by four general approaches: (a) nucleic acid sequencing, (b) nucleic acid hybridization, (c) presence or absence of "marker" nucleic acid functions, and (d) expression of inserted sequences. In the first approach, the presence of the UTRs and/or the reporter gene inserted in an expression vector can be detected by sequencing. In the second approach, the presence of the UTRs and/or the reporter gene inserted in an expression vector can be detected by nucleic acid hybridization using probes comprising sequences that are homologous to the inserted UTRs and/or reporter gene. In the third approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the reporter gene construct, in the vector. For example, if the nucleic acid of interest is inserted within the marker nucleic acid sequence of the vector, recombinants containing the insert can be identified by the absence of the marker nucleic acid function. In the fourth approach, recombinant expression vectors can be identified by assaying the reporter gene product expressed by the recombinant. Such assays can be based, for example, on the physical or functional properties of the particular reporter gene.

In a preferred embodiment, the reporter gene constructs are cloned into stable cell line expression vectors. In a preferred embodiment, the stable cell line expression vector contains a site specific genomic integration site, such as but not limited to, pCMP1 (see, e.g., FIG. 8C in Example 10). In another preferred embodiment, the reporter gene construct is cloned into an episomal mammalian expression vector, such as, but not limited to, pCMR2 (see, e.g., FIG. 8B in Example 10).

5.2.3.2. Transfection

Once a vector encoding the appropriate gene has been synthesized, a host cell is transformed or transfected with the vector of interest. The use of stable transformants is preferred. In a preferred embodiment, the host cell is a mammalian cell. In a more preferred embodiment, the host cell is a human cell. In another embodiment, the host cells are primary cells isolated from a tissue or other biological sample of interest. Host cells that can be used in the methods of the present invention include, but are not limited to, hybridomas, pre-B cells, 293 cells, 293T cells, HeLa cells, HepG2 cells, K562 cells, 3T3 cells, MCF7 cells, SkBr3 cells, or BT474 cells. In another preferred embodiment, the host cells are derived from tissue specific to the target gene. In yet another preferred embodiment, the host cells are immortalized cell lines derived from a source, e.g., a tissue, specific to the target gene. Other host cells that can be used in the present invention include, but are not limited to, bacterial cells, yeast cells, virally-infected cells, or plant cells.

Transformation may be by any known method for introducing polynucleotides into a host cell, for example by packaging the polynucleotide in a virus and transducing a host cell with the virus, and by direct uptake of the polynucleotide. The transformation procedure used depends upon the host to be transformed. Bacterial transformation by direct uptake generally employs treatment with calcium or rubidium chloride (see, e.g., Cohen, 1972, Proc. Nat. Acad. Sci. USA 69:2110 and Maniatis et al., 1982, "Molecular Cloning; A Laboratory Manual" (Cold Spring Harbor Press, Cold Spring Harbor, N.Y.). Yeast transformation by direct uptake may be carried out using the method of Schiestl & Gietz, 1989, Current Genetics 16:339-346 or Hinnen et al., 1978, Proc. Nat. Acad. Sci. USA 75:1929. Mammalian transformations (i.e., transfections) by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well-known to one of skill in the art.

In a preferred embodiment, stable cell lines containing the constructs of interest are generated for high throughput screening. Such stable cells lines may be generated by introducing a reporter gene construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (see, e.g., Wigler et al., 1977, Cell 11:223), hypoxanthine-guanine phosphoribosyltransferase (see, e.g., Szybalska & Szybalski, 1962, Proc. Natl. Acad. Sci. USA 48:2026), and adenine phosphoribosyltransferase (see, e.g., Lowy et al., 1980, Cell 22:817) genes can be employed in tk-, hgprt- or aprt-cells, respectively. Also, anti-metabolite resistance can be used as the basis of selection for dhfr, which confers resistance to methotrexate (see, e.g., Wigler et al., 1980, Natl. Acad. Sci. USA 77:3567 and O'Hare et al., 1981, Proc. Natl. Acad. Sci. USA 78:1527); gpt, which confers resistance to mycophenolic acid (see, e.g., Mulligan & Berg, 1981, Proc. Natl. Acad. Sci. USA 78:2072); neo, which confers resistance to the aminoglycoside G-418 gene (see, e.g., Colberre-Garapin et al., 1981, J. Mol. Biol. 150:1); and hygro, which confers resistance to hygromycin genes (see, e.g., Santerre et al., 1984, Gene 30:147).

5.2.4. Cell-Free Extracts

The invention provides for the translation of the reporter gene constructs in a cell-free system. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); and Transcription and Translation (Hames & Higgins, Eds. 1984).

Any technique well-known to one of skill in the art may be used to generate cell-free extracts for translation in vitro (otherwise referred to herein as cell-free translation mixtures). For example, the cell-free extracts for in vitro translation reactions can be generated by centrifuging cells and clarifying the supernatant. The cell extracts for the present invention is about a S1 (i.e., the supernatant from a 1,000×g spin) to about a S500 extract (i.e., the supernatant from a 500,000×g spin), preferably about a S10 (i.e., the supernatant from a 10,000×g spin) to S250 (i.e., the supernatant from a 250,000×g spin) extract. In some embodiments, about a S50 (i.e., the supernatant from a 50,000×g spin) to S100 (i.e., the supernatant from a 100,000×g spin) extract is preferred.

The cell-free translation extract may be isolated from cells of any species origin. For example, the cell-free translation extract may be isolated from human cells (e.g., HeLA cells), 293 cells, Vero cells, yeast, mouse cells (e.g., cultured mouse cells), rat cells (e.g., cultured rat cells), Chinese hamster ovary (CHO) cells, *Xenopus* oocytes, rabbit reticulocytes, primary cells, cancer cells (e.g., undifferentiated cancer cells), cell lines, wheat germ, rye embryo, or bacterial cell extract (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). It is preferred that the cells from which the cell-free extract is obtained do not endogenously express a target gene of interest. In a preferred embodiment, the cell-free extract is an extract isolated from human cells. In a more preferred embodiment, the human cells are HeLa cells.

5.3. Libraries of Compounds

Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (preferably small organic molecules). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as a-amino phosphoric acids and a-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a preferred embodiment, the combinatorial libraries are small organic molecule libraries including, but not limited to, benzodiazepines, isoprenoids, beta carbalines, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides, vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., ComGenex, Princeton, N.J.; Asinex, Moscow, Ru, Tripos, Inc., St. Louis, Mo.; ChemStar, Ltd, Moscow, Russia; 3D Pharmaceuticals, Exton, Pa.; Martek Biosciences, Columbia, Md.; etc.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multistep solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264:399; and Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see e.g., Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472).

As used herein, the term "solid support" is not limited to a specific type of solid support. Rather a large number of supports are available and are known to one skilled in the art. Solid supports include silica gels, resins, derivatized plastic films, glass beads, cotton, plastic beads, polystyrene beads, alumina gels, and polysaccharides. A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden).

In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the solid support prior to high throughput screening of the compounds.

5.4. Reporter Gene-Based Screening Assays 5.4.1. Cell-Based Assays

After a vector containing the reporter gene construct is transformed or transfected into a host cell and a compound library is synthesized or purchased or both, the cells are used to screen the library to identify compounds that modulate untranslated region-dependent expression of a target gene. In a preferred embodiment, the cells are stably transfected with the reporter gene construct. The reporter gene-based assays may be conducted by contacting a compound or a member of a library of compounds with a cell genetically engineered to express a nucleic acid comprising a reporter gene operably linked to one or more untranslated regions of a target gene, and measuring the expression of said reporter gene. The alteration in reporter gene expression relative to a previously determined reference range, the absence of the compound or a control in such reporter-gene based assays indicates that a particular compound modulates untranslated region-dependent expression of a target gene. In a preferred embodiment, a negative control (e.g., PBS or another agent that is known to have no effect on the expression of the reporter gene) and a positive control (e.g., an agent that is known to have an effect on the expression of the reporter gene, preferably an agent that effects untranslated region-dependent expression) are included in the cell-based assays described herein.

The step of contacting a compound or a member of a library of compounds with a cell genetically engineered to express a reporter gene operably linked to one or more untranslated regions may be conducted under physiologic conditions. In specific embodiment, a compound or a member of a library of compounds is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cells and compounds used and can be determined using routine experimentation.

The invention provides for contacting a compound or a member of a library of compounds with a cell genetically engineering to express a reporter gene operably linked to one or more untranslated regions for a specific period of time. For example, the contacting can take place for about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In a preferred embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In one embodiment, the invention provides a method for identifying a compound that modulates untranslated region-dependent expression of a target gene, said method comprising: (a) expressing a nucleic acid comprising a reporter gene operably linked to one or more untranslated regions of said target gene in a cell; (b) contacting said cell with a member of a library of compounds; and (c) detecting the expression of said reporter gene, wherein a compound that modulates untranslated region-dependent regulation of expression is identified if the expression of said reporter gene in the presence of a compound is altered relative to a previously determined reference range or the expression of said reporter gene in the absence of said compound or the presence of a control (e.g., phosphate buffered saline ("PBS")). In another embodiment, the invention provides a method for identifying a compound that modulates untranslated region-dependent expression of a target gene, said method comprising: (a) contacting a member of a library of compounds with a cell containing a nucleic acid comprising a reporter gene operably linked to one or more untranslated regions of said target gene; and (b) detecting a reporter protein translated from said reporter gene, wherein detecting the expression of said reporter gene, wherein a compound that modulates untranslated region-dependent expression is identified if the expression of said reporter gene in the presence of a compound is altered relative to a previously determined reference range or the expression of said reporter gene in the absence of said compound or the presence of a control (e.g., PBS).

The invention also provides methods of identifying compounds that upregulate or down-regulate untranslated region-dependent expression of a target gene utlitizing the cell-based reporter gene assays described herein. In a specific embodiment, the invention provides a method of upregulating untranslated region-dependent expression of a target gene, said method comprising (a) contacting a compound with a cell containing a nucleic acid comprising a reporter gene operably linked to one, two, three or more untranslated regions of said target gene; and (b) detecting a reporter gene protein translated from said reporter gene, wherein a compound that upregulates untranslated region dependent expression is identified if the expression of said reporter gene in the presence of a compound is increased relative a previously determined reference range, or the expression in the absence of the compound or the presence of a control (e.g., PBS). In another embodiment, the invention provides a method of down-regulating untranslated region-dependent expression of a target gene, said method comprising (a) contacting a compound with a cell containing a nucleic acid comprising a reporter gene operably linked to one, two, three or more untranslated regions of said target gene; and (b) detecting a reporter gene protein translated from said reporter gene, wherein a compound that down-regulates untranslated region dependent expression is identified if the expression of said reporter gene in the presence of a compound is decreased relative a previously determined reference range, or the expression in the absence of the compound or the presence of a control (e.g., PBS).

The present invention provides methods of identifying environmental stimuli (e.g., exposure to different concentrations of $CO_2$ and/or $O_2$, stress and different pHs) that modulate untranslated region-dependent expression of a target gene utilizing the cell-based reporter gene assays described herein. In particular, the invention provides a method of identifying an environmental stimulus, said method comprising (a) contacting a cell containing a nucleic acid comprising a reporter gene operably linked to one, two, three or more untranslated regions of said target gene with an environmental stimulus; and (b) detecting a reporter gene protein translated from said reporter gene, wherein a compound that modulates untranslated region dependent expression is identified if the expression of said reporter gene in the presence of an environmental stimuli is altered relative to a previously determined reference range, or the expression in the absence of the compound or the presence of a control (e.g., PBS). In a specific embodiment, the environmental stimuli is not hypoxia. In another embodiment, the environmental stimuli does not include a compound.

The expression of a reporter gene in the cell-based reporter-gene assays may be detected by any technique well-known to one of skill in the art. Methods for detecting the expression of a reporter gene will vary with the reporter gene used. Assays for the various reporter genes are well-known to one of skill in the art. For example, as described in Section 5.2.1., luciferase, beta-galactosidase ("b-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("b-gal"), and alkaline phosphatase ("AP") are assayed by changes in light imaging (e.g., luciferase), spectrophotometric absorbance (e.g., b-gal), or fluorescence (e.g., AP). Assays for changes in light output, absorbance, and/or fluorescence are easily adapted for high throughput screening. For example, b-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

Alterations in the expression of a reporter gene may be determined by comparing the level of expression of the reporter gene to a negative control (e.g., PBS or another agent that is known to have no effect on the expression of the reporter gene) and optionally, a positive control (e.g., an agent that is known to have an effect on the expression of the reporter gene, preferably an agent that effects untranslated region-dependent expression). Alternatively, alterations in the expression of a reporter gene may be determined by comparing the level of expression of the reporter gene to a previously determined reference range.

5.4.2. Cell-Free Assays

After a vector containing the reporter gene construct is produced, a cell-free translation extract is generated or purchased, and a compound library is synthesized or purchased or both, the cell-free translation extract and nucleic acid are used to screen the library to identify compounds that modulate untranslated region-dependent expression of a target gene. The reporter gene-based assays may be conducted in a cell-free manner by contacting a compound or a member of a library of compounds with a cell-free translation mixture and a nucleic acid comprising a reporter gene operably linked to one or more untranslated regions of a target gene, and measuring the expression of said reporter gene. The alteration in reporter gene expression relative to a previously determined reference range, the absence of a compound or a control in such reporter-gene based assays indicates that a particular compound modulates untranslated region-dependent expression of a target gene. In a preferred embodiment, a negative control (e.g., PBS or another agent that is known to have no effect on the expression of the reporter gene) and a positive control (e.g., an agent that is known to have an effect on the expression of the reporter gene, preferably an agent that effects untranslated region-dependent expression) are included in the cell-free assays described herein.

The step of contacting a compound or a member of a library of compounds with a cell-free translation mixture containing a nucleic acid comprising a reporter gene operably linked to one or more untranslated regions may be conducted under conditions approximating or mimicking physiologic conditions. In specific embodiment, a compound or a member of a library of compounds is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cells and compounds used and can be determined using routine experimentation.

The invention provides for contacting a compound or a member of a library of compounds with a cell genetically engineering to express a reporter gene operably linked to one or more untranslated regions for a specific period of time. For example, the contacting can take place for about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In a preferred embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In a specific embodiment, the invention provides a method for identifying a compound that modulates untranslated region-dependent expression of a target gene, said method comprising: (a) contacting a member of a library of compounds with a cell-free translation mixture and a nucleic acid comprising a reporter gene operably linked to one or more untranslated regions of said target gene; and (b) detecting the expression of said reporter gene, wherein a compound that modulates untranslated region-dependent expression is identified if the expression of said reporter gene in the presence of a compound is altered relative to a previously determined reference range or the expression of said reporter gene in the absence of said compound or the presence of a control (e.g., PBS).

The invention also provides methods of identifying compounds that upregulate or down-regulate untranslated region-dependent expression of a target gene utlitizing the cell-free reporter gene assays described herein. In a specific embodiment, the invention provides a method of upregulating untranslated region-dependent expression of a target gene, said method comprising (a) contacting a compound with a cell-free translation mixture and a nucleic acid comprising a reporter gene operably linked to one, two, three or more untranslated regions of said target gene; and (b) detecting a reporter gene protein translated from said reporter gene, wherein a compound that upregulates untranslated region dependent expression is identified if the expression of said reporter gene in the presence of a compound is increased relative a previously determined reference range, or the expression in the absence of the compound or the presence of a control (e.g., PBS). In another embodiment, the invention provides a method of down-regulating untranslated region-dependent expression of a target gene, said method comprising (a) contacting a compound with a cell-free translation mixture and a nucleic acid comprising a reporter gene operably linked to one, two, three or more untranslated regions of said target gene; and (b) detecting a reporter gene protein translated from said reporter gene, wherein a compound that down-regulates untranslated region dependent expression is identified if the expression of said reporter gene in the presence of a compound is decreased relative to a previously determined reference range, or the expression in the absence of the compound or the presence of a control (e.g., PBS).

The activity of a compound in the in vitro translation mixture can be determined by assaying the activity of a reporter protein encoded by a reporter gene, or alternatively, by quantifying the expression of the reporter gene by, for example, labeling the in vitro translated protein (e.g., with $^{35}$S-labeled methionine), northern blot analysis, RT-PCR or by immunological methods, such as western blot analysis or immunoprecipitation. Such methods are well-known to one of skill in the art.

5.4.3. Direct Binding Assays

Compounds that modulate untranslated region-dependent expression of a target gene can be identified by direct binding assays. In this embodiment, the target RNA comprises one or more untranslated regions, and preferably contains at least one element of an untranslated region. Such assays are described in International Patent Publication Nos. WO 02/083837 and WO 02/083953, the disclosures of which are hereby incorporated by reference in their entireties. Briefly, direct binding assays may be conducted by attaching a library of compounds to solid supports, e.g., polymer beads, with each solid support having substantially one type of compound attached to its surface. The plurality of solid supports of the library is exposed in aqueous solution to target RNA having a detectable label, forming a dye-labeled target RNA:support-attached compound complex. Binding of a target RNA molecule to a particular compound labels the solid support, e.g., bead, comprising the compound, which can be physically separated from other, unlabeled solid supports. Once labeled solid supports are identified, the chemical structures of the compounds thereon can be determined by, e.g., by reading a code on the solid support that correlates with the structure of the attached compound.

Alternatively, direct binding assays may be conducted by contacting a target RNA having a detectable label with a member of a library of compounds free in solution, in labeled tubes or microtiter wells, or a microarray. Compounds in the library that bind to the labeled target RNA will form a detectably labeled complex that can be identified and removed from the uncomplexed, unlabeled compounds in the library, and from uncomplexed, labeled target RNA, by a variety of methods including, but not limited to, methods that differentiate changes in the electrophoretic, chromatographic, or thermostable properties of the complexed target RNA.

5.4.3.1. Electrophoresis

Methods for separation of the complex of a target RNA bound to a compound from the unbound RNA comprises any method of electrophoretic separation, including but not limited to, denaturing and non-denaturing polyacrylamide gel electrophoresis, urea gel electrophoresis, gel filtration, pulsed field gel electrophoresis, two dimensional gel electrophoresis, continuous flow electrophoresis, zone electrophoresis, agarose gel electrophoresis, and capillary electrophoresis.

In a preferred embodiment, an automated electrophoretic system comprising a capillary cartridge having a plurality of capillary tubes is used for high-throughput screening of compounds bound to target RNA. Such an apparatus for performing automated capillary gel electrophoresis is disclosed in U.S. Pat. Nos. 5,885,430; 5,916,428; 6,027,627; and 6,063,251, the disclosures of which are incorporated by reference in their entireties.

The device disclosed in U.S. Pat. No. 5,885,430, which is incorporated by reference in its entirety, allows one to simultaneously introduce samples into a plurality of capillary tubes directly from microtiter trays having a standard size. U.S. Pat. No. 5,885,430 discloses a disposable capillary cartridge which can be cleaned between electrophoresis runs, the cartridge having a plurality of capillary tubes. A first end of each capillary tube is retained in a mounting plate, the first ends collectively forming an array in the mounting plate. The spacing between the first ends corresponds to the spacing between the centers of the wells of a microtiter tray having a standard size. Thus, the first ends of the capillary tubes can simultaneously be dipped into the samples present in the tray's wells. The cartridge is provided with a second mounting plate in which the second ends of the capillary tubes are retained. The second ends of the capillary tubes are arranged in an array which corresponds to the wells in the microtiter tray, which allows for each capillary tube to be isolated from its neighbors and therefore free from cross-contamination, as each end is dipped into an individual well.

Plate holes may be provided in each mounting plate and the capillary tubes inserted through these plate holes. In such a case, the plate holes are sealed airtight so that the side of the mounting plate having the exposed capillary ends can be pressurized. Application of a positive pressure in the vicinity of the capillary openings in this mounting plate allows for the introduction of air and fluids during electrophoretic operations and also can be used to force out gel and other materials from the capillary tubes during reconditioning. The capillary tubes may be protected from damage using a needle comprising a cannula and/or plastic tubes, and the like when they are placed in these plate holes. When metallic cannula or the like are used, they can serve as electrical contacts for current flow during electrophoresis. In the presence of a second mounting plate, the second mounting plate is provided with plate holes through which the second ends of the capillary tubes project. In this instance, the second mounting plate serves as a pressure containment member of a pressure cell and the second ends of the capillary tubes communicate with an internal cavity of the pressure cell. The pressure cell is also formed with an inlet and an outlet. Gels, buffer solutions, cleaning agents, and the like may be introduced into the internal cavity through the inlet, and each of these can simultaneously enter the second ends of the capillaries.

In another preferred embodiment, the automated electrophoretic system can comprise a chip system consisting of complex designs of interconnected channels that perform and analyze enzyme reactions using part of a channel design as a tiny, continuously operating electrophoresis material, where reactions with one sample are going on in one area of the chip while electrophoretic separation of the products of another sample is taking place in a different part of the chip. Such a system is disclosed in U.S. Pat. Nos. 5,699,157; 5,842,787; 5,869,004; 5,876,675; 5,942,443; 5,948,227; 6,042,709; 6,042,710; 6,046,056; 6,048,498; 6,086,740; 6,132,685; 6,150,119; 6,150,180; 6,153,073; 6,167,910; 6,171,850; and 6,186,660, the disclosures of which are incorporated by reference in their entireties.

The system disclosed in U.S. Pat. No. 5,699,157, which is hereby incorporated by reference in its entirety, provides for a microfluidic system for high-speed electrophoretic analysis of subject materials for applications in the fields of chemistry, biochemistry, biotechnology, molecular biology and numerous other areas. The system has a channel in a substrate, a light source and a photoreceptor. The channel holds subject materials in solution in an electric field so that the materials move through the channel and separate into bands according to species. The light source excites fluorescent light in the species bands and the photoreceptor is arranged to receive the fluorescent light from the bands. The system further has a means for masking the channel so that the photoreceptor can receive the fluorescent light only at periodically spaced regions along the channel. The system also has an unit connected to analyze the modulation frequencies of light intensity received by the photoreceptor so that velocities of the bands along the channel are determined, which allows the materials to be analyzed.

The system disclosed in U.S. Pat. No. 5,699,157 also provides for a method of performing high-speed electrophoretic analysis of subject materials, which comprises the steps of holding the subject materials in solution in a channel of a microfluidic system; subjecting the materials to an electric field so that the subject materials move through the channel and separate into species bands; directing light toward the channel; receiving light from periodically spaced regions along the channel simultaneously; and analyzing the frequencies of light intensity of the received light so that velocities of the bands along the channel can be determined for analysis of said materials. The determination of the velocity of a species band determines the electrophoretic mobility of the species and its identification.

U.S. Pat. No. 5,842,787, which is hereby incorporated by reference in its entirety, is generally directed to devices and systems employ channels having, at least in part, depths that are varied over those which have been previously described (such as the device disclosed in U.S. Pat. No. 5,699,157), wherein said channel depths provide numerous beneficial and unexpected results such as but not limited to, a reduction in sample perturbation, reduced non-specific sample mixture by diffusion, and increased resolution.

In another embodiment, the electrophoretic method of separation comprises polyacrylamide gel electrophoresis. In a preferred embodiment, the polyacrylamide gel electrophoresis is non-denaturing, so as to differentiate the mobilities of the target RNA bound to a compound from free target RNA. If the polyacrylamide gel electrophoresis is denaturing, then the target RNA:compound complex must be crosslinked prior to electrophoresis to prevent the disassociation of the target RNA from the compound during electrophoresis. Such techniques are well known to one of skill in the art.

In one embodiment of the method, the binding of compounds to target nucleic acid can be detected, preferably in an automated fashion, by gel electrophoretic analysis of interference footprinting. RNA can be degraded at specific base sites by enzymatic methods such as ribonucleases A, $U_2$, $CL_3$, $T_1$, Phy M, and B. cereus or chemical methods such as diethylpyrocarbonate, sodium hydroxide, hydrazine, piperidine formate, dimethyl sulfate, [2,12-dimethyl-3,7,11,17-tetraazacyclo[11.3.1]heptadeca-1(17),2,11,13,15-pentaenato] nickel(II) (NiCR), cobalt(II)chloride, or iron(II) ethylenediaminetetraacetate (Fe-EDTA) as described for example in Zheng et al., 1999, Biochem. 37:2207-2214; Latham & Cech, 1989, Science 245:276-282; and Sambrook et al., 2001, in Molecular Cloning: A Laboratory Manual, pp 12.61-12.73, Cold Spring Harbor Laboratory Press, and the references cited therein, which are hereby incorporated by reference in their entireties. The specific pattern of cleavage sites is determined by the accessibility of particular bases to the reagent employed to initiate cleavage and, as such, is therefore is determined by the three-dimensional structure of the RNA.

The interaction of small molecules with a target nucleic acid can change the accessibility of bases to these cleavage reagents both by causing conformational changes in the target nucleic acid or by covering a base at the binding interface. When a compound binds to the nucleic acid and changes the accessibility of bases to cleavage reagents, the observed cleavage pattern will change. This method can be used to identify and characterize the binding of small molecules to RNA as described, for example, by Prudent et al., 1995, J. Am. Chem. Soc. 117:10145-10146 and Mei et al., 1998, Biochem. 37:14204-14212.

In the preferred embodiment of this technique, the detectably labeled target nucleic acid is incubated with an individual compound and then subjected to treatment with a cleavage reagent, either enzymatic or chemical. The reaction mixture can be preferably be examined directly, or treated further to isolate and concentrate the nucleic acid. The fragments produced are separated by electrophoresis and the pattern of cleavage can be compared to a cleavage reaction performed in the absence of compound. A change in the cleavage pattern directly indicates that the compound binds to the target nucleic acid. Multiple compounds can be examined both in parallel and serially.

Other embodiments of electrophoretic separation include, but are not limited to urea gel electrophoresis, gel filtration, pulsed field gel electrophoresis, two dimensional gel electrophoresis, continuous flow electrophoresis, zone electrophoresis, and agarose gel electrophoresis.

5.4.3.2. Size Exclusion Chromatography

In another embodiment of the present invention, size-exclusion chromatography is used to purify compounds that are bound to a target nucleic acid from a complex mixture of compounds. Size-exclusion chromatography separates molecules based on their size and uses gel-based media comprised of beads with specific size distributions. When applied to a column, this media settles into a tightly packed matrix and forms a complex array of pores. Separation is accomplished by the inclusion or exclusion of molecules by these pores based on molecular size. Small molecules are included into the pores and, consequently, their migration through the matrix is retarded due to the added distance they must travel before elution. Large molecules are excluded from the pores and migrate with the void volume when applied to the matrix. In the present invention, a target nucleic acid is incubated with a mixture of compounds while free in solution and allowed to reach equilibrium. When applied to a size exclusion column, compounds free in solution are retained by the column, and compounds bound to the target nucleic acid are passed through the column. In a preferred embodiment, spin columns commonly used for gel filtration of nucleic acids will be employed to separate bound from unbound compounds (e.g., Bio-Spin columns manufactured by BIO-RAD). In another embodiment, the size exclusion matrix is packed into multiwell plates to allow high throughput separation of mixtures (e.g., PLASMID 96-well SEC plates manufactured by Millipore).

5.4.3.3. Affinity Chromatography

In one embodiment of the present invention, affinity capture is used to purify compounds that are bound to a target nucleic acid labeled with an affinity tag from a complex mixture of compounds. To accomplish this, a target nucleic acid labeled with an affinity tag is incubated with a mixture of compounds while free in solution and then captured to a solid support once equilibrium has been established; alternatively, target nucleic acids labeled with an affinity tag can be captured to a solid support first and then allowed to reach equilibrium with a mixture of compounds.

The solid support is typically comprised of, but not limited to, cross-linked agarose beads that are coupled with a ligand for the affinity tag. Alternatively, the solid support may be a glass, silicon, metal, or carbon, plastic (polystyrene, polypropylene) surface with or without a self-assembled monolayer (SAM) either with a covalently attached ligand for the affinity tag, or with inherent affinity for the tag on the target nucleic acid.

Once the complex between the target nucleic acid and compound has reached equilibrium and has been captured, one skilled in the art will appreciate that the retention of bound compounds and removal of unbound compounds is facilitated by washing the solid support with large excesses of binding reaction buffer. Furthermore, retention of high affinity compounds and removal of low affinity compounds can be accomplished by a number of means that increase the stringency of washing; these means include, but are not limited to, increasing the number and duration of washes, raising the salt concentration of the wash buffer, addition of detergent or surfactant to the wash buffer, and addition of non-specific competitor to the wash buffer.

In one embodiment, the compounds themselves are detectably labeled with fluorescent dyes, radioactive isotopes, or nanoparticles. When the compounds are applied to the captured target nucleic acid in a spatially addressed fashion (e.g., in separate wells of a 96-well microplate), binding between the compounds and the target nucleic acid can be determined by the presence of the detectable label on the compound using fluorescence.

Following the removal of unbound compounds, bound compounds with high affinity for the target nucleic acid can be eluted from the immobilized target nucleic acids and analyzed. The elution of compounds can be accomplished by any means that break the non-covalent interactions between the target nucleic acid and compound. Means for elution include, but are not limited to, changing the pH, changing the salt concentration, the application of organic solvents, and the application of molecules that compete with the bound ligand. In a preferred embodiment, the means employed for elution will release the compound from the target RNA, but will not effect the interaction between the affinity tag and the solid support, thereby achieving selective elution of compound. Moreover, a preferred embodiment will employ an elution buffer that is volatile to allow for subsequent concentration by lyophilization of the eluted compound (e.g., 0 M to 5 M ammonium acetate).

5.5. Methods for Confirming that a Compound Modulates Untranslated Region-Dependent Expression In order to exclude the possibility that a particular compound is functioning solely by modulating the expression of a target gene in an untranslated region-independent manner, one or more mutations may be introduced into the untranslated regions operably linked to a reporter gene and the effect on the expression of the reporter gene in a reporter gene-based assay described herein can be determined. For example, a reporter gene construct comprising the 5' UTR of a target gene may be mutated by deleting a fragment of the 5' UTR of the target gene or substituting a fragment of the 5' UTR of the target gene with a fragment of the 5' UTR of another gene and measuring the expression of the reporter gene in the presence and absence of a compound that has been identified in a screening assays described supra (See Section 5.4). If the deletion of a fragment of the 5' UTR of the target gene or the substitution of a fragment of the 5' UTR of the target gene with a fragment of the 5' UTR of another gene affects the ability of the compound to modulate the expression of the reporter gene, then the fragment of the 5' UTR deleted or substituted plays a role in the regulation of the reporter gene expression and the regulation, at least in part, in an untranslated region-dependent manner.

The possibility that a particular compound is functioning solely by modulating the expression of a target gene in an untranslated region-independent manner may be also determined by changing the vector utilized as a reporter construct. The untranslated regions flanked by a reporter gene from the first reporter construct in which an effect on reporter gene expression was detected following exposure to a compound may be inserted into a new reporter construct that has, e.g., different transcriptional regulation elements (e.g., a different promoter) and a different selectable marker. The level of reporter gene expression in the presence of the compound can be compared to the level of reporter gene expression in the absence of the compound or in the presence of a control (e.g., PBS). If there is no change in the level of expression of the reporter gene in the presence of the compound relative to the absence of the compound or in the presence of a control, then the compound probably is functioning in an untranslated region-independent manner.

The specificity of a particular compound's effect on untranslated region-dependent expression of a target gene can also be determined. In particular, the effect of a particular compound on the expression of one or more genes (preferably, a plurality of genes) can be determined utilizing assays well-known to one of skill in the art or described herein. In a specific embodiment, the specificity of a particular compound for an untranslated region of a target gene is determined by (a) contacting the compound of interest with a cell containing a nucleic acid comprising a reporter gene operably linked to an UTR of a different gene (i.e., a gene different from the target gene which has a UTR different from the target gene); and (b) detecting a reporter gene protein translated from the reporter gene, wherein the compound is specific for the untranslated region of the target gene if the expression of said reporter gene in the presence of the compound is not altered or is not substantially altered relative to a previously determined reference range, or the expression in the absence of the compound or the presence of a control (e.g., PBS). In another embodiment, the specificity of a particular compound for an untranslated region of a target gene is determined by (a) contacting the compound of interest with a panel of cells, each cell in a different well of a container (e.g., a 48 or 96 well microtiter plate) and each cell containing a nucleic acid comprising a reporter gene operably linked to an UTR of a different gene; and (b) detecting a reporter gene protein translated from the reporter gene, wherein the compound is specific for the untranslated region of the target gene if the expression of said reporter gene in the presence of the compound is not altered or is not substantially altered relative to a previously determined reference range, or the expression in the absence of the compound or the presence of a control (e.g., PBS). In accordance with this embodiment, the panel may comprise 5, 7, 10, 15, 20, 25, 50, 75, 100 or more cells. In another embodiment, the specificity of a particular compound for an untranslated region of a target gene is determined by (a) contacting the compound of interest with a cell-free translation mixture and a nucleic acid comprising a reporter gene operably linked to an UTR of a different gene; and (b) detecting a reporter gene protein translated from the reporter gene, wherein the compound is specific for the untranslated region of the target gene if the expression of said reporter gene in the presence of the compound is not altered or is not substantially altered relative to a previously determined reference range, or the expression in the absence of the compound or the presence of a control (e.g., PBS). As used herein, the term "not substantially altered" means that the compound alters the expression of the reporter gene or target gene by less than 20%, less than 15%, less than 10%, less than 5%, or less than 2% relative to a negative control such as PBS.

The compounds identified in the assays described supra that modulate untranslated region-dependent expression of a target gene (for convenience referred to herein as a "lead" compound) can be further tested for untranslated region-dependent binding to the target RNA (which contains at least one untranslated region, and preferably at least one element of an untranslated region). Furthermore, by assessing the effect of a compound on target gene expression, cis-acting elements, i.e., specific nucleotide sequences, that are involved in untranslated region-dependent expression may be identified.

5.5.1. RNA Binding Assays

The compounds that modulate untranslated region-dependent expression of a target gene can be tested for binding to the target RNA (which contains at least one untranslated region, and preferably at least one element of an untranslated region) by any method known in the art. See Section 5.4.3 supra.

5.5.1. Subtraction Assay

The element(s) of an untranslated region(s) that is necessary for a compound identified in accordance with the methods of the invention to modulate untranslated region-dependent expression of a target gene can be determined utilizing standard mutagenesis techniques well-known to one of skill in the art. One or more mutations (e.g., deletions, additions and/or substitutions) may be introduced into the untranslated regions operably linked to a reporter gene and the effect on the expression of the reporter gene in a reporter gene-based assay described herein can be determined. For example, a reporter gene construct comprising the 5' UTR of a target gene may be mutated by deleting a fragment or all of the 5' UTR of the target gene or substituting a fragment of the 5' UTR of the target gene with a fragment of the 5' UTR of another gene and measuring the expression of the reporter gene in the presence and absence of a compound that has been identified in a screening assays described supra (See Section 5.4). If the deletion of a fragment of the 5' UTR of the target gene or the substitution of a fragment of the 5' UTR of the target gene with a fragment of the 5' UTR of another gene affects the ability of the compound to modulate the expression of the reporter gene, then the fragment of the 5' UTR deleted or substituted plays a role in the regulation of the reporter gene expression.

Standard techniques known to those of skill in the art can be used to introduce mutations in the nucleotide sequence of an untranslated region of a target gene, including, for example, site-directed mutagenesis and PCR-mediated mutagenesis. In a specific embodiment, less than 75 nucleic acid residue substitutions, less than 50 nucleic acid residue substitutions, less than 45 nucleic acid residue substitutions, less than 40 nucleic acid residue substitutions, less than 35 nucleic acid residue substitutions, less than 30 nucleic acid residue substitutions, less than 25 nucleic acid residue substitutions, less than 20 nucleic acid residue substitutions, less than 15 nucleic acid residue substitutions, less than 10 nucleic acid residue substitutions, or less than 5 nucleic acid residue substitutions are introduced into the nucleotide sequence of an untranslated region of a target gene. In another embodiment, less than 10 elements of an untranslated region of a target gene, less than 9 of an untranslated region of a target gene, less than 8 elements of an untranslated region of a target gene, less than 7 elements of an untranslated region of a target gene, less than 6 elements of an untranslated region of a target gene, less than 5 elements of an untranslated region of a target gene, less than 4 elements of an untranslated region of a target gene, less than 3 elements of an untranslated region of a target gene, or less than 2 elements of an untranslated region of a target gene are mutated at one time.

5.5.3. Expressed Protein Concentration and Activity Assays

The compounds identified in the reporter gene-based assays described herein that modulate untranslated region-dependent expression may be tested in in vitro assays (e.g., cell-free assays) or in vivo assays (e.g., cell-based assays) well-known to one of skill in the art or described herein for the effect of said compounds on the expression of the target gene from which the untranslated regions of the reporter gene construct were derived. The specificity of a particular compound's effect on untranslated region-dependent expression of one or more other genes (preferably, a plurality of genes) can also be determined utilizing assays well-known to one of skill in the art or described herein. In a preferred embodiment, a compound identified utilizing the reporter gene-based assays described herein has a specific effect on the expression of only one gene or a group of genes within the same signaling pathway.

The expression of a gene can be readily detected, e.g., by quantifying the protein and/or RNA encoded by said gene. Many methods standard in the art can be thus employed, including, but not limited to, immunoassays to detect and/or visualize gene expression (e.g., western blot, immunoprecipitation followed by sodium dodecyl sulfate polyacrylamide gel electrophoresis (SDS-PAGE), immunocytochemistry, etc.) and/or hybridization assays to detect gene expression by detecting and/or visualizing respectively mRNA encoding a gene (e.g., northern assays, dot blots, in situ hybridization, etc.). Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Another antibody based separation that can be used to detect the protein of interest is the use of flow cytometry such as by a florescence activated cell sorter ("FACS"). Typically, separation by flow cytometry is performed as follows. The suspended mixture of cells are centrifuged and resuspended in media. Antibodies which are conjugated to fluorochrome are added to allow the binding of the antibodies to specific proteins. In another embodiment, the secondary antibodies that are conjugated to fluorochromes can be used to detect primary antibodies specific to the protein of interest. The cell mixture is then washed by one or more centrifugation and resuspension steps. The mixture is run through a FACS which separates the cells based on different fluorescence characteristics. FACS systems are available in varying levels of performance and ability, including multi-color analysis. The facilitating cell can be identified by a characteristic profile of forward and side scatter which is influenced by size and granularity, as well as by positive and/or negative expression of certain cell surface markers.

In addition to measuring the effect of a compound identified in the reporter gene-based assays described herein on the expression of the target gene from which the untranslated regions of the reporter gene construct were derived, the activity of the protein encoded by the target gene can be assessed utilizing techniques well-known to one of skill in the art. For example, the activity of a protein encoded by a target gene can be determined by detecting induction of a cellular second messenger (e.g., intracellular $Ca^{2+}$, diacylglycerol, $IP_3$, etc.), detecting the phosphorylation of a protein, detecting the activation of a transcription factor, or detecting a cellular response, for example, cellular differentiation, or cell proliferation. The induction of a cellular second messenger or phosporylation of a protein can be determined by, e.g., immunoassays well-known to one of skill in the art and described herein. The activation of a transcription factor can be detected by, e.g., electromobility shift assays, and a cellular response such as cellular proliferation can be detected by, e.g., trypan blue cell counts, $^3H$-thymidine incorporation, and flow cytometry.

5.6. Methods for Characterizing the Compounds that Modulate Untranslated Region-Dependent Expression of a Target Gene If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds bound to the target RNA. Examples of such techniques include, but are not limited to, mass spectrometry, NMR spectroscopy, X-ray crystallography and vibrational spectroscopy.

5.6.1. Mass Spectrometry

Mass spectrometry (e.g., electrospray ionization ("ESI"), matrix-assisted laser desorption-ionization ("MALDI"), and Fourier-transform ion cyclotron resonance ("FT-ICR") can be used for elucidating the structure of a compound.

MALDI uses a pulsed laser for desorption of the ions and a time-of-flight analyzer, and has been used for the detection of noncovalent tRNA:amino-acyl-tRNA synthetase complexes (Gruic-Sovulj et al., 1997, J. Biol. Chem. 272:32084-32091). However, covalent cross-linking between the target nucleic acid and the compound is required for detection, since a non-covalently bound complex may dissociate during the MALDI process.

ESI mass spectrometry ("ESI-MS") has been of greater utility for studying non-covalent molecular interactions because, unlike the MALDI process, ESI-MS generates molecular ions with little to no fragmentation (Xavier et al., 2000, Trends Biotechnol. 18(8):349-356). ESI-MS has been used to study the complexes formed by HIV Tat peptide and protein with the TAR RNA (Sannes-Lowery et al., 1997, Anal. Chem. 69:5130-5135).

Fourier-transform ion cyclotron resonance ("FT-ICR") mass spectrometry provides high-resolution spectra, isotope-resolved precursor ion selection, and accurate mass assignments (Xavier et al., 2000, Trends Biotechnol. 18(8): 349-356). FT-ICR has been used to study the interaction of aminoglycoside antibiotics with cognate and non-cognate RNAs (Hofstadler et al., 1999, Anal. Chem. 71:3436-3440; and Griffey et al., 1999, Proc. Natl. Acad. Sci. USA 96:10129-10133). As true for all of the mass spectrometry methods discussed herein, FT-ICR does not require labeling of the target RNA or a compound.

An advantage of mass spectroscopy is not only the elucidation of the structure of the compound, but also the determination of the structure of the compound bound to a target RNA. Such information can enable the discovery of a consensus structure of a compound that specifically binds to a target RNA.

5.6.2. NMR Spectroscopy

NMR spectroscopy is a valuable technique for identifying complexed target nucleic acids by qualitatively determining changes in chemical shift, specifically from distances measured using relaxation effects, and NMR-based approaches have been used in the identification of small molecule binders of protein drug targets (Xavier et al., 2000, Trends Biotechnol. 18(8):349-356). The determination of structure-activity relationships ("SAR") by NMR is the first method for NMR described in which small molecules that bind adjacent subsites are identified by two-dimentional $^1$H-$^{15}$N spectra of the target protein (Shuker et al., 1996, Science 274:1531-1534). The signal from the bound molecule is monitored by employing line broadening, transferred NOEs and pulsed field gradient diffusion measurements (Moore, 1999, Curr. Opin. Biotechnol. 10:54-58). A strategy for lead generation by NMR using a library of small molecules has been recently described (Fejzo et al., 1999, Chem. Biol. 6:755-769).

In one embodiment of the present invention, the target nucleic acid complexed to a compound can be determined by SAR by NMR. Furthermore, SAR by NMR can also be used to elucidate the structure of a compound.

As described above, NMR spectroscopy is a technique for identifying binding sites in target nucleic acids by qualitatively determining changes in chemical shift, specifically from distances measured using relaxation effects. Examples of NMR that can be used for the invention include, but are not limited to, one-dimentional NMR, two-dimentional NMR, correlation spectroscopy ("COSY"), and nuclear Overhauser effect ("NOE") spectroscopy. Such methods of structure determination of compounds are well-known to one of skill in the art.

Similar to mass spectroscopy, an advantage of NMR is the not only the elucidation of the structure of the compound, but also the determination of the structure of the compound bound to the target RNA. Such information can enable the discovery of a consensus structure of a compound that specifically binds to a target RNA.

5.6.3. X Ray Crystallography

X-ray crystallography can be used to elucidate the structure of a compound. For a review of x-ray crystallography see, e.g., Blundell et al., 2002, Nat Rev Drug Discov 1(1):45-54. The first step in x-ray crystallography is the formation of crystals. The formation of crystals begins with the preparation of highly purified and soluble samples. The conditions for crystallization are then determined by optimizing several solution variables known to induce nucleation, such as pH, ionic strength, temperature, and specific concentrations of organic additives, salts and detergent. Techniques for automating the crystallization process have been developed for the production of high-quality protein crystals. Once crystals have been formed, the crystals are harvested and prepared for data collection. The crystals are then analyzed by diffraction (such as multi-circle diffractometers, high-speed CCD detectors, and detector off-set). Generally, multiple crystals must be screened for structure determinations.

5.6.4. Vibrational Spectroscopy

Vibrational spectroscopy (e.g. infrared (IR) spectroscopy or Raman spectroscopy) can be used for elucidating the structure of a compound.

Infrared spectroscopy measures the frequencies of infrared light (wavelengths from 100 to 10,000 nm) absorbed by the compound as a result of excitation of vibrational modes according to quantum mechanical selection rules which require that absorption of light cause a change in the electric dipole moment of the molecule. The infrared spectrum of any molecule is a unique pattern of absorption wavelengths of varying intensity that can be considered as a molecular fingerprint to identify any compound.

Infrared spectra can be measured in a scanning mode by measuring the absorption of individual frequencies of light, produced by a grating which separates frequencies from a mixed-frequency infrared light source, by the compound relative to a standard intensity (double-beam instrument) or pre-measured (blank') intensity (single-beam instrument). In a preferred embodiment, infrared spectra are measured in a pulsed mode ("FT-IR") where a mixed beam, produced by an interferometer, of all infrared light frequencies is passed through or reflected off the compound. The resulting interferogram, which may or may not be added with the resulting interferograms from subsequent pulses to increase the signal strength while averaging random noise in the electronic signal, is mathematically transformed into a spectrum using Fourier Transform or Fast Fourier Transform algorithms.

Raman spectroscopy measures the difference in frequency due to absorption of infrared frequencies of scattered visible or ultraviolet light relative to the incident beam. The incident monochromatic light beam, usually a single laser frequency, is not truly absorbed by the compound but interacts with the electric field transiently. Most of the light scattered off the sample will be unchanged (Rayleigh scattering) but a portion of the scatter light will have frequencies that are the sum or difference of the incident and molecular vibrational frequencies. The selection rules for Raman (inelastic) scattering require a change in polarizability of the molecule. While some vibrational transitions are observable in both infrared and Raman spectrometry, must are observable only with one or the other technique. The Raman spectrum of any molecule is a unique pattern of absorption wavelengths of varying intensity that can be considered as a molecular fingerprint to identify any compound.

Raman spectra are measured by submitting monochromatic light to the sample, either passed through or preferably reflected off, filtering the Rayleigh scattered light, and detecting the frequency of the Raman scattered light. An improved Raman spectrometer is described in U.S. Pat. No. 5,786,893 to Fink et al., which is hereby incorporated by reference.

Vibrational microscopy can be measured in a spatially resolved fashion to address single beads by integration of a visible microscope and spectrometer. A microscopic infrared spectrometer is described in U.S. Pat. No. 5,581,085 to Reffner et al., which is hereby incorporated by reference in its entirety. An instrument that simultaneously performs a microscopic infrared and microscopic Raman analysis on a sample is described in U.S. Pat. No. 5,841,139 to Sostek et al., which is hereby incorporated by reference in its entirety.

In one embodiment of the method, compounds are synthesized on polystyrene beads doped with chemically modified styrene monomers such that each resulting bead has a characteristic pattern of absorption lines in the vibrational (IR or Raman) spectrum, by methods including but not limited to those described by Fenniri et al., 2000, J. Am. Chem. Soc. 123:8151-8152. Using methods of split-pool synthesis familiar to one of skill in the art, the library of compounds is prepared so that the spectroscopic pattern of the bead identifies one of the components of the compound on the bead. Beads that have been separated according to their ability to bind target RNA can be identified by their vibrational spectrum. In one embodiment of the method, appropriate sorting and binning of the beads during synthesis then allows identification of one or more further components of the compound on any one bead. In another embodiment of the method, partial identification of the compound on a bead is possible through use of the spectroscopic pattern of the bead with or without the aid of further sorting during synthesis, followed by partial resynthesis of the possible compounds aided by doped beads and appropriate sorting during synthesis.

In another embodiment, the IR or Raman spectra of compounds are examined while the compound is still on a bead, preferably, or after cleavage from bead, using methods including but not limited to photochemical, acid, or heat treatment. The compound can be identified by comparison of the IR or Raman spectral pattern to spectra previously acquired for each compound in the combinatorial library.

5.7. Secondary Screens of Compounds

Once a compound has been identified to modulate untranslated region-dependent expression of a target gene and preferably, the structure of the compound has been identified by the methods described in Section 5.6, the compounds are tested for biological activity in further assays and/or animal models (see, e.g., Sections 5.7.1 and 5.7.2). Further, a lead compound may be used to design congeners or analogs (see, e.g., Section 5.7.3).

5.7.1. Cell-Based Screens

The compounds identified in the assays described supra (for convenience referred to herein as a "lead" compound) can be tested for biological activity using host cells containing or engineered to contain the target RNA element involved in untranslated region-dependent gene expression coupled to a functional readout system. For example, a phenotypic or physiological readout can be used to assess untranslated region-dependent activity of the target RNA in the presence and absence of the lead compound.

In one embodiment, a phenotypic or physiological readout can be used to assess untranslated region-dependent activity of the target RNA in the presence and absence of the lead compound. For example, the target RNA may be overexpressed in a cell in which the target RNA is endogenously expressed. Where the target RNA controls untranslated region-dependent expression of a gene product involved in cell growth or viability, the in vivo effect of the lead compound can be assayed by measuring the cell growth or viability of the target cell. Such assays can be carried out with representative cells of cell types involved in a particular disease or disorder (e.g., leukocytes such as T cells, B cells, natural killer cells, macrophages, neutrophils and eosinophils). A lower level of proliferation or survival of the contacted cells indicates that the lead compound is effective to treat a condition in the patient characterized by uncontrolled cell growth. Alternatively, instead of culturing cells from a patient, a lead compound may be screened using cells of a tumor or malignant cell line or an endothelial cell line.

Specific examples of cell culture models include, but are not limited to, for lung cancer, primary rat lung tumor cells (see, e.g., Swafford et al., 1997, Mol. Cell. Biol., 17:1366-1374) and large-cell undifferentiated cancer cell lines (see, e.g., Mabry et al., 1991, Cancer Cells, 3:53-58); colorectal cell lines for colon cancer (see, e.g., Park & Gazdar, 1996, J. Cell Biochem. Suppl. 24:131-141); multiple established cell lines for breast cancer (see, e.g., Hambly et al., 1997, Breast Cancer Res. Treat. 43:247-258; Gierthy et al., 1997, Chemosphere 34:1495-1505; and Prasad & Church, 1997, Biochem. Biophys. Res. Commun. 232:14-19); a number of well-characterized cell models for prostate cancer (see, e.g., Webber et al., 1996, Prostate, Part 1, 29:386-394; Part 2, 30:58-64; and Part 3, 30:136-142 and Boulikas, 1997, Anticancer Res. 17:1471-1505); for genitourinary cancers, continuous human bladder cancer cell lines (see, e.g., Ribeiro et al., 1997, Int. J. Radiat. Biol. 72:11-20); organ cultures of transitional cell carcinomas (see, e.g., Booth et al., 1997, Lab Invest. 76:843-857) and rat progression models (see, e.g., Vet et al., 1997, Biochim. Biophys Acta 1360:39-44); and established cell lines for leukemias and lymphomas (see, e.g., Drexler, 1994, Leuk. Res. 18:919-927 and Tohyama, 1997, Int. J. Hematol. 65:309-317).

Many assays well-known in the art can be used to assess the survival and/or growth of a patient cell or cell line following exposure to a lead compound; for example, cell proliferation can be assayed by measuring bromodeoxyuridine (BrdU) incorporation (see, e.g., Hoshino et al., 1986, Int. J. Cancer 38:369 and Campana et al., 1988, J. Immunol. Meth. 107:79) or ($^3$H)-thymidine incorporation (see, e.g., Chen, 1996, Oncogene 13:1395-403 and Jeoung, 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc.). The levels of such protein and mRNA and activity can be determined by any method well known in the art. For example, protein can be quantitated by known immunodiagnostic methods such as western blotting or immunoprecipitation using commercially available antibodies. mRNA can be quantitated using methods that are well known and routine in the art, for example, using northern analysis, RNase protection, the polymerase chain reaction in connection with reverse transcription ("RT-PCR"). Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

The lead compound can also be assessed for its ability to inhibit cell transformation (or progression to malignant phenotype) in vitro. In this embodiment, cells with a transformed cell phenotype are contacted with a lead compound, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see, e.g., Luria et al., 1978, General Virology, 3d Ed., John Wiley & Sons, New York, pp. 436-446).

Loss of invasiveness or decreased adhesion can also be assessed to demonstrate the anti-cancer effects of a lead compound. For example, an aspect of the formation of a metastatic cancer is the ability of a precancerous or cancerous cell to detach from primary site of disease and establish a novel colony of growth at a secondary site. The ability of a cell to invade peripheral sites reflects its potential for a cancerous state. Loss of invasiveness can be measured by a variety of techniques known in the art including, for example, induction of E-cadherin-mediated cell-cell adhesion. Such E-cadherin-mediated adhesion can result in phenotypic reversion and loss of invasiveness (see, e.g., Hordijk et al., 1997, Science 278:1464-66).

Loss of invasiveness can further be examined by inhibition of cell migration. A variety of 2-dimensional and 3-dimensional cellular matrices are commercially available (Calbiochem-Novabiochem Corp. San Diego, Calif.). Cell migration across or into a matrix can be examined using microscopy, time-lapsed photography or videography, or by any method in the art allowing measurement of cellular migration. In a related embodiment, loss of invasiveness is examined by response to hepatocyte growth factor ("HGF"). HGF-induced cell scattering is correlated with invasiveness of cells such as Madin-Darby canine kidney ("MDCK") cells. This assay identifies a cell population that has lost cell scattering activity in response to HGF (see, e.g., Hordijk et al., 1997, Science 278:1464-66).

Alternatively, loss of invasiveness can be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated can then be correlated with invasiveness (see e.g., Ohnishi, 1993, Biochem. Biophys. Res. Commun. 193:518-25).

The effect of a compound of the invention on cell adhesion can be measured using HUVECS. HUVECs are seeded on 24 well culture plates and incubated for 2 days to allow formation of a confluent monolayer. Cancerous cells or a cancer cell line such as LS-180 human colon adenocarcinoma cells are labeled with 5 μM Calcein-AM for 30 min. Calcein-AM labeled LS180 cells are added into each well of the HUVEC culture; and incubated for 10 min at 37° C. TNF-α (80 ng/ml) is then added and the culture incubated for is an additional 110 min. Non-adherent cells are removed by washing with PBS. The fluorescence intensity of adherent LS-180 cell in each individual well is measured by a fluorescent plate reader set at excitation 485/20 nm and emission at 530/25 nm.

The effect of a compound of the invention on cell migration and invasion can also be determined using an assay based on the BD BioCoast Angiogenesis System (BD Biosciences, Bedford, Mass.). The fluorescence blocking membrane of the insert is a 3 micron pore size PET filter which has been coated either with BD Matrigel basement matrix (for invasion assay) or without Matrigel matrix (for migration assay). HUVECs (250 μl/well) in culture medium without serum are added to the top chamber; a compound added to bottom wells containing medium (750 μl/well) with VEGF as a chemo-attractant. Cells are then incubated for 22 h at 37° C. After incubation, cells are stained with Calcein AM for measurement of fluorescence.

Further, a lead compound can be assessed for its ability to alter viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art. A lead compound can also be assessed for its ability to alter bacterial replication (as determined, e.g., by measuring bacterial growth rates) or the production of bacterial proteins (as determined, e.g., by western blot analysis) or bacterial RNAs (as determined, e.g., by RT-PCR or northern blot analysis) in cultured cells in vitro using methods which are well known in the art. Finally, a lead compound can be assessed for its ability to alter fungal replication (as determined, e.g., by fungal growth rates, such as macrodilution methods and/or microdilution methods using protocols known to those skilled in the art (see, e.g., Clancy et al., 1997, Journal of Clinical Microbiology, 35(11): 2878-82; Ryder et al., 1998, Antimicrobial Agents and Chemotherapy, 42(5): 1057-61; or U.S. Pat. No. 5,521,153; U.S. Pat. No. 5,883,120, U.S. Pat. No. 5,521,169)) or the production of fungal proteins (as determined, e.g., by western blot analysis) or fungal RNAs (as determined, e.g., by RT-PCR or northern blot analysis) in cultured cells in vitro using methods which are well known in the art.

5.7.2. Animal Model-Based Screens

The lead compounds identified in the reporter gene-based assay described herein can be tested for biological activity using animal models for a disease, disorder, condition, or syndrome of interest. These include animals engineered to contain a target gene coupled to a functional readout system, such as a transgenic mouse. Such animal model systems include, but are not limited to, rats, mice, chicken, cows, monkeys, pigs, dogs, rabbits, etc. In a specific embodiment of the invention, a compound identified in accordance with the methods of the invention is tested in a mouse model system. Such model systems are widely used and well-known to the skilled artisan such as the SCID mouse model or transgenic mice.

The anti-angiogenic activity of a compound identified in accordance with the invention can be determined by using various experimental animal models of vascularized tumors. The anti-tumor activity of a compound identified in accordance with the invention can be determined by administering the compound to an animal model and verifying that the compound is effective in reducing the proliferation or spread of cancer cells in said animal model. An example of an animal model for human cancer in general includes, but is not limited to, spontaneously occurring tumors of companion animals (see, e.g., Vail & MacEwen, 2000, Cancer Invest 18(8):781-92).

Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

The anti-inflammatory activity of a compound identified in accordance with the invention can be determined by using various experimental animal models of inflammatory arthritis known in the art and described in Crofford & Wilder, "Arthritis and Autoimmunity in Animals", in Arthritis and Allied Conditions: A Textbook of Rheumatology, McCarty et al. (eds.), Chapter 30 (Lee & Febiger, 1993). Experimental and spontaneous animal models of inflammatory arthritis and autoimmune rheumatic diseases can also be used to assess the anti-inflammatory activity of a compound identified in accordance with the invention. The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford & Wilder, "Arthritis and Autoimmunity in Animals", in Arthritis and Allied Conditions: A Textbook of Rheumatology, McCarty et al. (eds.), Chapter 30 (Lee & Febiger, 1993), incorporated herein by reference in its entirety.

The anti-inflammatory activity of a compound identified in accordance with the invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra et al., 2000, Inflammation, 24(2): 141-155. Also commonly used are zymosan-induced inflammation animal models as known and described in the art.

The anti-inflammatory activity of a compound identified in accordance with the invention can also be assessed by measuring the inhibition of carrageenan-induced paw edema in the rat, using a modification of the method described in Winter et al., 1962, Proc. Soc. Exp. Biol Med. 111, 544-547. This assay has been used as a primary in vivo screen for the anti-inflammatory activity of most NSAIDs, and is considered predictive of human efficacy. The anti-inflammatory activity of a compound identified in accordance with the invention is expressed as the percent inhibition of the increase in hind paw weight of the test group relative to the vehicle dosed control group.

In a specific embodiment of the invention where the experimental animal model used is adjuvant-induced arthritis rat model, body weight can be measured relative to a control group to determine the anti-inflammatory activity of a compound identified in accordance with the invention. Alternatively, the efficacy of a compound identified in accordance with the invention can be assessed using assays that determine bone loss. Animal models such as ovariectomy-induced bone resorption mice, rat and rabbit models are known in the art for obtaining dynamic parameters for bone formation. Using methods such as those described by Yositake et al. or Yamamoto et al., bone volume is measured in vivo by microcomputed tomography analysis and bone histomorphometry analysis (see, e.g., Yoshitake et al., 1999, Proc. Natl. Acad. Sci. 96:8156-8160 and Yamamoto et al., 1998, Endocrinology 139(3):1411-1419, both incorporated herein by reference in their entireties).

Additionally, animal models for inflammatory bowel disease can also be used to assess the efficacy of a compound identified in accordance with the invention (see, e.g., Kim et al., 1992, Scand. J. Gastroentrol. 27:529-537 and Strober, 1985, Dig. Dis. Sci. 30(12 Suppl):3S-10S). Ulcerative cholitis and Crohn's disease are human inflammatory bowel diseases that can be induced in animals. Sulfated polysaccharides including, but not limited to, amylopectin, carrageen, amylopectin sulfate, and dextran sulfate or chemical irritants including, but not limited to, trinitrobenzenesulphonic acid (TNBS) and acetic acid can be administered to animals orally to induce inflammatory bowel diseases.

Animal models for asthma can also be used to assess the efficacy of a compound identified in accordance with the invention. An example of one such model is the murine adoptive transfer model in which aeroallergen provocation of TH1 or TH2 recipient mice results in TH effector cell migration to the airways and is associated with an intense neutrophilic (TH1) and eosinophilic (TH2) lung mucosal inflammatory response (see, e.g., Cohn et al., 1997, J. Exp. Med. 1861737-1747).

Animal models for autoimmune disorders can also be used to assess the efficacy of a compound identified in accordance with the invention. Animal models for autoimmune disorders such as type 1 diabetes, thyroid autoimmunity, sytemic lupus eruthematosus, and glomerulonephritis have been developed (see, e.g., Flanders et al., 1999, Autoimmunity 29:235-246; Krogh et al., 1999, Biochimie 81:511-515; and Foster, 1999, Semin. Nephrol. 19:12-24).

Animal models for viral infections can also be used to assess the efficacy of a compound identified in accordance with the invention. Animal models for viral infections such as EBV-associated diseases, gammaherpesviruses, infectious mononucleosis, simian immunodeficiency virus ("SIV"), Borna disease virus infection, hepatitis, varicella virus infection, viral pneumonitis, Epstein-Barr virus pathogenesis, feline immunodeficiency virus ("FIV"), HTLV type 1 infection, human rotaviruses, and genital herpes have been developed (see, e.g., Hayashi et al., 2002, Histol Histopathol 17(4):1293-310; Arico et al., 2002, J Interferon Cytokine Res 22(11):1081-8; Flano et al., 2002, Immunol Res 25(3): 201-17; Sauermann, 2001, Curr Mol Med 1(4):515-22; Pletnikov et al., 2002, Front Biosci 7:d593-607; Engler et al., 2001, Mol Immunol 38(6):457-65; White et al., 2001, Brain Pathol 11(4):475-9; Davis & Matalon, 2001, News Physiol Sci 16:185-90; Wang, 2001, Curr Top Microbiol Immunol. 258:201-19; Phillips et al., 2000, J Psychopharmacol. 14(3):244-50; Kazanji, 2000, AIDS Res Hum Retroviruses. 16(16):1741-6; Saif et al., 1996, Arch Virol Suppl. 12:153-61; and Hsiung et al., 1984, Rev Infect Dis. 6(1): 33-50).

Animal models for bacterial infections can also be used to assess the efficacy of a compound identified in accordance with the invention. Animal models for bacterial infections such as *H. pylori*-infection, genital mycoplasmosis, primary sclerosing cholangitis, cholera, chronic lung infection with *Pseudomonas aeruginosa*, Legionnaires' disease, gastroduodenal ulcer disease, bacterial meningitis, gastric *Helicobacter* infection, pneumococcal otitis media, experimental allergic neuritis, leprous neuropathy, mycobacterial infection, endocarditis, *Aeromonas*-associated enteritis, *Bacteroides fragilis* infection, syphilis, streptococcal endocarditis, acute hematogenous osteomyelitis, human scrub typhus, toxic shock syndrome, anaerobic infections, *Escherichia*

*coli* infections, and *Mycoplasma pneumoniae* infections have been developed (see, e.g., Sugiyama et al., 2002, J Gastroenterol. 37 Suppl 13:6-9; Brown et al., 2001, Am J Reprod Immunol. 46(3):232-41; Vierling, 2001, Best Pract Res Clin Gastroenterol. 15(4):591-610; Klose, 2000, Trends Microbiol. 8(4):189-91; Stotland et al., 2000, Pediatr Pulmonol. 30(5):413-24; Brieland et al., 2000, Immunopharmacology 48(3):249-52; Lee, 2000, Baillieres Best Pract Res Clin Gastroenterol. 14(1):75-96; Koedel & Pfister, 1999, Infect Dis Clin North Am. 13(3):549-77; Nedrud, 1999, FEMS Immunol Med Microbiol. 24(2):243-50; Prellner et al., 1999, Microb Drug Resist. 5(1):73-82; Vriesendorp, 1997, J Infect Dis. 176 Suppl 2:S164-8; Shetty & Antia, 1996, Indian J Lepr. 68(1):95-104; Balasubramanian et al., 1994, Immunobiology 191(4-5):395-401; Carbon et al., 1994, Int J Biomed Comput. 36(1-2):59-67; Haberberger et al., 1991, Experientia. 47(5):426-9; Onderdonk et al., 1990, Rev Infect Dis. 12 Suppl 2:S169-77; Wicher & Wicher, 1989, Crit Rev Microbiol. 16(3):181-234; Scheld, 1987, J Antimicrob Chemother. 20 Suppl A:71-85; Emslie & Nade, 1986, Rev Infect Dis. 8(6):841-9; Ridgway et al., 1986, Lab Anim Sci. 36(5):481-5; Quimby & Nguyen, 1985, Crit Rev Microbiol. 12(1):1-44; Onderdonk et al., 1979, Rev Infect Dis. 1(2):291-301; Smith, 1976, Ciba Found Symp. (42): 45-72, and Taylor-Robinson, 1976, Infection. 4(1 Suppl):4-8).

Animal models for fungal infections can also be used to assess the efficacy of a compound identified in accordance with the invention. Animal models for fungal infections such as *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic *keratitis, Cryptococcus neoformans* infection, fungal peritonitis, *Curvularia geniculata* infection, staphylococcal endophthalmitis, sporotrichosis, and dermatophytosis have been developed (see, e.g., Arendrup et al., 2002, Infection 30(5):286-91; Kamei, 2001, Mycopathologia 152 (1):5-13; Guhad et al., 2000, FEMS Microbiol Lett. 192(1): 27-31; Yamagata et al., 2000, J Clin Microbiol. 38(9):32606; Andrutis et al., 2000, J Clin Microbiol. 38(6):2317-23; Cock et al., 2000, Rev Inst Med Trop Sao Paulo 42(2):59-66; Shibuya et al., 1999, Microb Pathog. 27(3):123-31; Beers et al., 1999, J Lab Clin Med. 133(5):423-33; Najvar et al., 1999, Antimicrob Agents Chemother. 43(2):413-4; Williams et al., 1988, J Infect Dis. 178(4):1217-21; Yoshida, 1988, Kansenshogaku Zasshi. 1998 June; 72(6):621-30; Alexandrakis et al., 1998, Br J Ophthalmol. 82(3):306-11; Chakrabarti et al., 1997, J Med Vet Mycol. 35(4):295-7; Martin et al., 1997, Antimicrob Agents Chemother. 41(1): 13-6; Chu et al., 1996, Avian Dis. 40(3):715-9; Fidel et al., 1996, J Infect Dis. 173(2):425-31; Cole et al., 1995, FEMS Microbiol Lett. 15; 126(2):177-80; Pollock et al., 1995, Nat Genet. 9(2):202-9; Uchida et al., 1994, Jpn J Antibiot. 47(10):1407-12; Maebashi et al., 1994, J Med Vet Mycol. 32(5):349-59; Jensen & Schonheyder, 1993, J Exp Anim Sci. 35(4):155-60; Gokaslan & Anaissie, 1992, Infect Immun. 60(8):3339-44; Kurup et al., 1992, J Immunol. 148(12):3783-8; Singh et al., 1990, Mycopathologia. 112 (3):127-37; Salkowski & Balish, 1990, Infect Immun. 58(10):3300-6; Ahmad et al., 1986, Am J Kidney Dis. 7(2):153-6; Alture-Werber E, Edberg S C, 1985, Mycopathologia. 89(2):69-73; Kane et al., 1981, Antimicrob Agents Chemother. 20(5):595-9; Barbee et al., 1977, Am J Pathol. 86(1):281-4; and Maestrone et al., 1973, Am J Vet Res. 34(6):833-6).

The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

5.7.3. Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical *Fennica* 97:159-166; Ripka, 1998, New Scientist 54-57; McKinaly & Rossmann, 1989, Annu Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to the target RNA using the above-described secondary screens for biologic activity. Alternatively, lead compounds with little or no biologic activity, as ascertained in the secondary screen, can also be used to design analogs and congeners of the compound that have biologic activity.

5.8. Use of Identified Compounds that Modulate Untranslated Region-Dependent Gene Expression to Treat/Prevent Disease Biologically active compounds identified using the methods of the invention or a pharmaceutically acceptable salt thereof can be administered to a patient, preferably a mammal, more preferably a human, suffering from a disease or disorder whose onset, progression, development and/or severity is associated with the expression of a target gene. Alternatively, biologically active compounds identified using the methods of the invention or a pharmaceutically acceptable salt thereof that are beneficial for the treatment of a disease or disorder can be administered to a patient, preferably a mammal, more preferably a human, suffering from such a disease or disorder. In a specific embodiment, a compound or a pharmaceutically acceptable salt thereof is administered to a patient, preferably a mammal, more preferably a human, as a preventative measure against a disease or disorder associated with an RNA:host cell factor interaction in vivo.

When administered to a patient, the compound or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the compound or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides.

In another embodiment, the compound and pharmaceutically acceptable salts thereof can be delivered in a vesicle, in particular a liposome (see Langer, 1990, Science 249: 1527-1533; Treat et al., 1989, in Liposomes in the Therapy of Infectious Disease and Cancer, Lopez-Berestein and Fidler (eds.), Liss, New York, pp. 353-365; and Lopez-Berestein, ibid., pp. 317-327; see generally ibid.).

In yet another embodiment, the compound and pharmaceutically acceptable salts thereof can be delivered in a controlled release system (see, e.g., Goodson, 1984, in Medical Applications of Controlled Release, supra, vol. 2, pp. 115-138). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), 1974, CRC Pres., Boca Raton, Fla.; Controlled Drug Bioavailability, Drug Product Design and Performance, Smolen and Ball (eds.), 1984, Wiley, New York; Ranger & Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

Compositions comprising the compound or a pharmaceutically acceptable salt thereof ("compound compositions") can additionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Compound compositions, if desired, can also contain minor amounts of wetting or emulsifying agents, or pH buffering agents.

Compound compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro, ed., Mack Publishing Co. Easton, Pa., 19th ed., 1995, pp. 1447 to 1676, incorporated herein by reference.

In a preferred embodiment, the compound or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade. Typically, compositions for intravenous administration comprise sterile isotonic aqueous buffer. Where necessary, the compositions may also include a solubilizing agent.

In another embodiment, the compound or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the compound or a pharmaceutically acceptable salt thereof is to be administered by infusion, it can be dispensed, for example, with an infusion bottle containing sterile pharmaceutical grade water or saline. Where the compound or a pharmaceutically acceptable salt thereof is administered by injection, an ampoule of sterile water for injection or saline can be provided so that the ingredients may be mixed prior to administration.

The amount of a compound or a pharmaceutically acceptable salt thereof that will be effective in the treatment of a particular disease will depend on the nature of the disease, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral administration are generally about 0.001 milligram to about 500 milligrams of a compound or a pharmaceutically acceptable salt thereof per kilogram body weight per day. In specific preferred embodiments of the invention, the oral dose is about 0.01 milligram to about 500 milligrams per kilogram body weight per day, about 0.01 milligram to about 250 milligram per kilogram body weight per day, about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound is administered, or if a compound is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The compound and pharmaceutically acceptable salts thereof are preferably assayed in vitro and in vivo, for the desired therapeutic or prophylactic activity, prior to use in humans. For example, in vitro assays can be used to determine whether it is preferable to administer the compound, a pharmaceutically acceptable salt thereof, and/or another therapeutic agent. Animal model systems can be used to demonstrate safety and efficacy.

5.9. Target Diseases or Disorders

The present invention provides methods for preventing, treating or ameliorating a disease or disorder or one or more symptoms thereof, said methods comprising administering to a subject in need thereof one or more compounds identified in accordance with the methods of the invention. In one embodiment, the invention provides a method of preventing, treating or ameliorating a disease or disorder or one or more symptoms thereof, said method comprising administering to a subject in need thereof a dose of a prophylactically or therapeutically effective amount of one or more compounds identified in accordance with the methods of the invention. In another embodiment, the invention provides a method of preventing, treating or ameliorating a disease or disorder or one or more symptoms thereof, said method comprising administering to a subject in need thereof a dose of a prophylactically or therapeutically effective amount of one or more compounds identified in the assays described herein, said compounds increasing untranslated region-dependent expression of a target gene whose expression useful in the prevention or treatment of said disease or disorder. In another embodiment, the invention provides a method of preventing, treating or ameliorating a disease or disorder or one or more symptoms thereof, said method comprising administering to a subject in need thereof a dose of a prophylactically or therapeutically effective amount of one or more compounds identified in the assays described, said compounds decreasing untranslated region-dependent expression of a target gene whose expression is associated with the onset, progression, development and/or severity of said disease or disorder. In a specific embodiment, a compound identified in accordance with the methods of the invention is not administered to prevent, treat, or ameliorate a disease or disorder or one or more symptoms thereof, if such compound has been used previously to prevent, treat or ameliorate said disease or disorder.

The invention also provides methods of preventing, treating or ameliorating a disease or disorder or one or more symptoms thereof, said methods comprising administering to a subject in need thereof one or more of the compounds identified utilizing the screening methods described herein, and one or more other therapies (e.g., prophylactic or therapeutic agents). Preferably, such therapies (e.g., prophylactic or therapeutic agents) are currently being used, have been used or are known to be useful in the prevention, treatment or amelioration of one or more symptoms associated with said disease or disorder. The therapies (e.g., prophylactic or therapeutic agents) of the combination therapies of the invention can be administered sequentially or concurrently. In a specific embodiment, the combination therapies of the invention comprise a compound of the invention and at least one other therapy (e.g., prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In a specific embodiment, a pharmaceutical composition comprising one or more compounds identified in a screening assay described herein is administered to a subject, preferably a human, to prevent, treat or ameliorate a disease or disorder or a symptom thereof. In accordance with the invention, pharmaceutical compositions of the invention may also comprise one or more prophylactic or therapeutic agents which are currently being used, have been used or are known to be useful in the prevention, treatment or amelioration of one or more symptoms associated with a disease or disorder.

5.9.1. Proliferative Disorders

A compound identified in accordance with the methods of the invention may be administered to a subject in need thereof to prevent, treat or ameliorate a cancer or one or more symptoms thereof. A compound identified in accordance with the methods of the invention may also be administered in combination with one or more other therapies (e.g., prophylactic or therapeutic agents) to a subject in need thereof to prevent, treat or ameliorate a cancer or one or more symptoms thereof. Preferably, such therapies are useful for the prevention or treatment of cancer. Examples of such therapies include, but are not limited to chemotherapeutic agents (e.g., acivicin, anthramycin, bleomycin sulfate, carbetimer, carboplatin, cisplatin, cyclophosphamide, daunorubicin hydrochloride, docetaxel, doxorubicin, doxorubicin hydrochloride, epipropidine, etoposide, etoposide phosphate, etoprine fluorouracil, gemcitabine, gemcitabine hydrochloride, hydroxyurea, idarubicin hydrochloride, ifosfamide, ilmofosine, methotrexate, methotrexate sodium, paclitaxel, trimetrexate, trimetrexate glucuronate, vinblastine sulfate, vincristine sulfate, vindesine, vindesine sulfate, and vinepidine sulfate) and anti-angiogenic agents (e.g., angiostatin (plasminogen fragment), antiangiogenic antithrombin III, angiozyme, combretastatin A-4, endostatin (collagen XVIII fragment), and fibronectin fragment). In a specific embodiment, the invention provides a method of preventing, treating or ameliorating cancer or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating cancer or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

A compound identified in accordance with the methods of the invention may be used as a first, second, third or fourth line of therapy for the treatment of cancer. The invention provides methods for treating or ameliorating cancer or a symptom thereof in a subject refractory to conventional therapies for such a cancer, said methods comprising administering to said subject a dose of a prophylactically or therapeutically effective amount of a compound identified in accordance with the methods of the invention. A cancer may be determined to be refractory to a therapy means when at least some significant portion of the cancer cells are not killed or their cell division arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

The invention provides methods for treating or ameliorating cancer or a symptom thereof in a subject refractory to existing single agent therapies for such a cancer, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating cancer by administering a compound identified in accordance with the methods of the invention in combination with any other therapy (e.g., radiation therapy, chemotherapy or surgery) to patients who have proven refractory to other therapies but are no longer on these therapies. The invention also provides methods for the treatment of a patient having cancer and immunosuppressed by reason of having previously undergone other cancer therapies. The invention also provides alternative methods for the treatment of cancer where chemotherapy, radiation therapy, hormonal therapy, and/or biological therapy/immunotherapy has proven or may prove too toxic, i.e., results in unacceptable or unbearable side effects, for the subject being treated. Further, the invention provides methods for preventing the recurrence of cancer in patients that have been treated and have no disease activity by administering a compound identified in accordance with the methods of the invention.

In this embodiment, target genes encoding proteins include, but are not limited to, angiogenin; angiopoietin1; angiopoietin2; antigen CD82; aryl hydrocarbon receptor nuclear translocator; B cell lymphoma 2; beta-catenin; cadherin-1; CLCA homolog; connective tissue growth factor, cysteine-rich 61; cyclin D1; cyclin-dependent kinase inhibitor 2A, CDKN2 CDK4 inhibitor multiple tumor suppressor 1, SOR 1, MTS1TP16 p16(INK4) p16(INK4A) p14(ARF); cyclin-dependent kinase inhibitor 1A (p21, Cip1); dihydrofolate reductase; DNA methyltransferase; effector cell protease receptor; EMMPRIN; epithelial growth factor receptor; fibroblast growth factor 2; fibroblast growth factor 1; FMS-related tyrosine kinase 1; heparanase; hepsin; Her-2; histone acetyltransferase; histone deacetylase3; histone deacetylase 1; Hu Antigen R, a member of the Elav (embryonic lethal abnormal vision) family of RNA-binding proteins; hypoxia-inducible factor 1-alpha inhibitor; hypoxia-inducible factor 1; insulin like growth factor 1 receptor, IGF-1R; insulin-like growth factor 1; insulin-like growth factor binding protein-2; interleukin 2; interleukin-8 precursor (i1-8) (monocyte-derived neutrophilchemotactic factor) (mdnsf) (T-cell chemotactic factor) (neutrophil-activating protein 1) (nap-1) (lymphocyte-derived neutrophil-activating factor) (lynap) (protein 3-10c) (neutrophil-activating factor) (naf) (granulocyte chemotactic protein 1) (gsp-1); kit ligand, stem cell factor; large tumor suppressor; leucine amino peptidase-3; livin; major histocompatibility complex class I chain-related gene B; major histocompatibility complex class I chain-related gene A; matrix metalloproteinase 9; matrix metalloproteinase 12; max interacting protein 1 (mxi 1 protein); methyl-CpG-binding endonuclease; NF-Kappa-B; oncoprotein MDM2; oncoprotein fos; P-glycoprotein-1 (PGY1); placental growth factor; plasminogen activator inhibitor protein; platelet derived growth factor, beta chain; pleiotrophin; progranulin; proliferating cell nuclear antigen; protein kinase B/Akt (PBK), v-akt murine thymoma viral oncogene homolog 1, oncogene akt1 protein kinase b, pkb rac serine/threonine protein kinase; protein-tyrosine phosphatase, 4A, 3, PTP4A3; ras; retinoblastoma-binding protein 1-like 1; ribonuclease/angiogenin inhibitor; soluble-type polypeptide FZD4S; src, oncogen src protooncogene src src oncogene avian sarcoma; TEK tyrosine kinase; thrombopoietin (TPO); TIAM1: T-cell lymphoma invasion and metastasis 1; tissue inhibitor of metalloprotease 1; tissue inhibitor of metalloprotease 2; tissue inhibitor of metalloprotease 4; transforming growth factor, beta-1; tumor necrosis factor receptor superfamily, member 5, TNFRSF5; urokinase plasminogen activator; and v-myc myelocytomatosis viral oncogene homolog.

In a specific embodiment, a compound identified in the assays described herein to down-regulate untranslated region-dependent VEGF expression may be used to prevent, treat or ameliorate a vascularized tumor or one or more symptoms thereof. In another embodiment, a compound not previously known to affect VEGF expression which was identified in the assays described herein to down-regulate untranslated region-dependent VEGF may be used to prevent, treat or ameliorate a vascularized tumor or one or more symptoms thereof.

In another embodiment, a compound identified in the assays described herein to down-regulate untranslated region-dependent survivin expression may be used to prevent, treat or ameliorate cancer (in particular, cancer in which survivin is highly expressed) or one or more symptoms thereof. In another embodiment, a compound not previously known to affect survivin expression which was identified in the assays described herein to down-regulate untranslated region-dependent survivin may be used to prevent, treat or ameliorate cancer or one or more symptoms thereof.

In another embodiment, a compound identified in the assays described herein to down-regulate untranslated region-dependent Her-2 expression in breast cancer cells may be used to prevent, treat or ameliorate breast cancer (in particular, Her-2 positive breast cancer) or one or more symptoms thereof. In another embodiment, a compound not previously known to affect Her-2 expression which was identified in the assays described herein to down-regulate untranslated region-dependent Her-2 expression may be used to prevent, treat or ameliorate breast cancers or one or more symptoms thereof.

Cancers that can be treated by the methods encompassed by the invention include, but are not limited to, neoplasms, tumors, metastases, or any disease or disorder characterized by uncontrolled cell growth. The cancer may be a primary or metastatic cancer. Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

Anti-cancer therapies and their dosages, routes of administration and recommended usage are known in the art and have been described in such literature as the *Physician's Desk Reference* ($56^{th}$ ed., 2002).

5.9.2. Inflammatory Disorders

A compound identified in accordance with the methods of the invention may be administered to a subject in need thereof to prevent, treat or ameliorate an inflammatory disorder or one or more symptoms thereof. A compound identified in accordance with the methods of the invention may also be administered in combination with one or more other therapies (e.g., prophylactic or therapeutic agents) to a subject in need thereof to prevent, treat or ameliorate an inflammatory disorder or one or more symptoms thereof. Preferably, such therapies are useful for the prevention or treatment of an inflammatory disorder. Examples of such therapies include, but are not limited to, immunomodulatory agents (e.g., methothrexate, leflunomide, cyclophosphamide, cytoxan, Immuran, cyclosporine A, minocycline, azathioprine, and antibiotics (e.g., FK506 (tacrolimus)), anti-angiogenic agents (e.g., endostatin, angiostatin, apomigren, anti-angiogenic antithrombin III, the 29 kDa N-terminal and a 40 kDa C-terminal proteolytic fragments of fibronectin, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, acid fibroblast growth factor ("aFGF") antagonists, basic fibroblast growth factor ("bFGF") antagonists, vascular endothelial growth factor ("VEGF") antagonists, and VEGF receptor ("VEGFR") antagonists (e.g., anti-VEGFR antibodies), TNF-α antagonists (e.g., infliximab (REMICADE™; Centacor), D2E7 (Abbott Laboratories/Knoll Pharmaceuticals Co., Mt. Olive, N.J.), CDP571 which is also known as HUMICADE™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379), non-steroidal anti-inflammatory drugs (NSAIDs) (e.g., aspirin, ibuprofen, celecoxib (CELEBREX™), diclofenac (VOLTAREN™), etodolac (LODINE™), fenoprofen (NALFON™), indomethacin (INDOCIN™), ketoralac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™)), steroidal anti-inflammatory drugs (e.g., glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes), beta-agonists, anticholingeric agents, and methyl xanthines. In a specific embodiment, the invention provides a method of preventing, treating or ameliorating an inflammatory disorder or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating an inflammatory disorder or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

The invention provides methods for treating or ameliorating an inflammatory disorder or a syptom thereof in a subject refractory to conventional therapies (e.g., methotrexate and a TNF-α antagonist (e.g., REMICADE™ or ENBREL™)) for such an inflammatory disorder, said methods comprising administering to said subject a dose of a prophylactically or therapeutically effective amount of a compound identified in accordance with the methods of the invention. The invention also provides methods for treating or ameliorating an inflammatory disorder or a symptom thereof in a subject refractory to existing single agent therapies for such an inflammatory disorder, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating an inflammatory disorder by administering a compound identified in accordance with the methods of the invention in combination with any other therapy to patients who have proven refractory to other therapies but are no longer on these therapies. The invention also provides alternative methods for the treatment of an inflammatory disorder where another therapy has proven or may prove too toxic, i.e., results in unacceptable or unbearable side effects, for the subject being treated. Further, the invention provides methods for preventing the recurrence of an inflammatory disorder in patients that have been treated and have no disease activity by administering a compound identified in accordance with the methods of the invention.

In this embodiment, target genes encoding proteins include, but are not limited to, a disintegrin and metallo proteinase domain 33; angiopoietin1; angiopoietin2; beta-catenin; chemokine (C-C) receptor; eotaxin; fibroblast growth factor 1; fibroblast growth factor 2; FMS-related tyrosine kinase 1; granulocyte—macrophage colony-stimulating factor precursor (GM-CSF) (colony-stimulating factor) (CSF) (sargramostim); GRO2 oncogene; macrophage inflammatory protein-2-alpha precursor (mip2-alpha) (growth regulated protein beta) (gro-beta); Hu antigen R; a member of the Elav (Embryonic lethal abnormal vision) family of RNA-binding proteins; insulin-like growth factor 1; interferon inducible protein; interferon 1 beta; interferon-alpha; interleukin 17F; interleukin 1-beta; interleukin 6; interleukin 10; interleukin 18; interleukin 13; interleukin 4; interleukin-9; leukemia Inhibitory factor Receptor; leukemia inhibitory factor; linker for Activation of T cells; macrophage migration inhibitory factor; monocyte chemotactic protein 1; NF-Kappa-B; nuclear factor of kappa light polypeptide gene enhancer in B-cells 1 (p105, NF-kappaB); osteopontin; p38 MAP Kinase; placental growth factor; platelet derived growth factor, beta chain; pleiotrophin; prolactin; receptor for interleukin-4; signal transducer and activator of transcription 6; TEK tyrosine kinase; and tumor necrosis factor alpha.

Inflammatory disorders that can be treated by the methods encompassed by the invention include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. Some autoimmune disorders are associated with an inflammatory condition, and thus, can be characterized as either or both an autoimmune disorder and/or an inflammatory disorder.

Anti-inflammatory therapies and their dosages, routes of administration and recommended usage are known in the art and have been described in such literature as the *Physician's Desk Reference* (56$^{th}$ ed., 2002).

5.9.3. Autoimmune Disorders

A compound identified in accordance with the methods of the invention may be administered to a subject in need thereof to prevent, treat or ameliorate an autoimmune disorder or one or more symptoms thereof. A compound identified in accordance with the methods of the invention may also be administered in combination with one or more other therapies (e.g., prophylactic or therapeutic agents) to a subject in need thereof to prevent, treat or ameliorate an autoimmune disorder or one or more symptoms thereof. Preferably, such therapies are useful for the prevention or treatment of an autoimmune disorder. In a specific embodiment, the invention provides a method of preventing, treating or ameliorating an autoimmune disorder or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating an autoimmune disorder or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

The invention provides methods for treating or ameliorating an autoimmune disorder or a symptom thereof in a subject refractory to conventional therapies for such an autoimmune disorder, said methods comprising administering to said subject a dose of a prophylactically or therapeutically effective amount of a compound identified in accordance with the methods of the invention. The invention also provides methods for treating or ameliorating an autoimmune disorder or a symptom thereof in a subject refractory to existing single agent therapies for such an autoimmune disorder, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating an autoimmune disorder by administering a compound identified in accordance with the methods of the invention in combination with any other therapy to patients who have proven refractory to other therapies but are no longer on these therapies. The invention also provides alternative methods for the treatment of an autoimmune disorder where another therapy has proven or may prove too toxic, i.e., results in unacceptable or unbearable side effects, for the subject being treated. Further, the invention provides methods for preventing the recurrence of an autoimmune disorder in patients that have been treated and have no disease activity by administering a compound identified in accordance with the methods of the invention.

In this embodiment, target genes encoding proteins include, but are not limited to, adiponectin; alpha-glucosidase; forkhead box C2; G-CSF, colony stimulating factor 3 (granulocyte); galanin; gastric inhibitory polypeptide; ghrelin; glucagon receptor; glucagon-like peptide-1, GLP-1; glucokinase; glycogen synthase kinase-3B; glycogen synthase kinase-3A; human phosphotryosyl-protein phosphatase (PTP-1B); IkB kinase; inositol pholyphosphate phosphatase-like 1; insulin receptor; interleukin 10; leptin; neural cell adhesion molecule 1; neuron growth associated protein 43; peroxisome proliferator-activated receptor-gamma; phas; EIF4BP; protein kinase C, gamma; resistin; and uncoupling protein 2.

In autoimmune disorders, the immune system triggers an immune response when there are no foreign substances to fight and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders that can be prevented, treated or ameliorated by the methods of the invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis.

Autoimmune therapies and their dosages, routes of administration and recommended usage are known in the art and have been described in such literature as the Physician's Desk Reference (56$^{th}$ ed., 2002).

5.9.4. Genetic Disorders

A compound identified in accordance with the methods of the invention may be administered to a subject in need thereof to prevent, treat or ameliorate a genetic disorder or one or more symptoms thereof. A compound identified in accordance with the methods of may also be administered in combination with one or more other therapies (e.g., prophylactic or therapeutic agents) to a subject in need thereof to prevent, treat or ameliorate a genetic disorder or one or more symptoms thereof. Preferably, such therapies are useful for the prevention or treatment of a genetic disorder. In a specific embodiment, the invention provides a method of preventing, treating or ameliorating a genetic disorder or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating a genetic disorder or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

In this embodiment, target genes encoding proteins include, but are not limited to, NAD(P)-dependent steroid dehydrogenase (EC 1.1.1.-h105e3 protein); peroxisome biogenesis factor 1 (peroxin-1) (peroxisome biogenesis disorder protein 1); and utrophin.

Examples of genetic disorders which can be prevented or treated in accordance with the invention include, but are not limited to, alopecia areata, alpha-1-antitrypsin deficiency, ataxia, Fragile X Syndrome, Gaucher disease, Hemophilia, Huntington disease, Niemann-Pick disease, Retinitis Pigmentosa, SCID (Severe Combined Immunodeficiency), Thalassemia, and Xeroderma Pigmentosum.

5.9.5. Viral Infections

A compound identified in accordance with the methods of the invention may be administered to a subject in need thereof to prevent, treat or ameliorate a viral infection or one or more conditions or symptoms associated therewith. A compound identified in accordance with the methods of the invention may also be administered in combination with one or more other therapies (e.g., prophylactic or therapeutic agents) to a subject in need thereof to prevent, treat or ameliorate a viral infection or one or more conditions or symptoms associated therewith. Preferably, such therapies are useful for the prevention or treatment of a viral infection. Examples of such therapies include, but are not limited to, amantadine, ribavirin, rimantadine, acyclovir, famciclovir, foscarnet, ganciclovir, trifluridine, vidarabine, didanosine, stavudine, zalciltabine, zidovudine, interferon, an antibiotic, amantadine, ribavirin, rimantadine, acyclovir, famciclovir, foscarnet, ganciclovir, trifluridine, vidarabine, didanosine, stavudine, zalciltabine, zidovudine, interferon, an antibiotic, PRO542 (Progenics) which is a CD4 fusion antibody useful for the treatment of HIV infection, Ostavir (Protein Design Labs, Inc., CA) which is a human antibody useful for the treatment of hepatitis B virus, and Protovir (Protein Design Labs, Inc., CA) which is a humanized IgG1 antibody useful for the treatment of cytomegalovirus (CMV). In a specific embodiment, the invention provides a method of preventing, treating or ameliorating a viral infection or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating a viral infection or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

The invention provides methods for treating or ameliorating a viral infection or a symptom thereof in a subject refractory to conventional therapies for such a viral infection, said methods comprising administering to said subject a dose of a prophylactically or therapeutically effective amount of a compound identified in accordance with the methods of the invention. The invention also provides methods for treating or ameliorating a viral infection or a symptom thereof in a subject refractory to existing single agent therapies for such a viral infection, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating a viral infection by administering a compound identified in accordance with the methods of the invention in combination with any other therapy to patients who have proven refractory to other therapiess but are no longer on these therapies. The invention also provides alternative methods for the treatment of a viral infection where another therapy has proven or may prove too toxic, i.e., results in unacceptable or unbearable side effects, for the subject being treated. Further, the invention provides methods for preventing the recurrence of a viral infection in patients that have been treated and have no disease activity by administering a compound identified in accordance with the methods of the invention.

In this embodiment, target genes encoding proteins include, but are not limited to, C1q complement receptor-gC1qR; chemokine (C-X3-C) receptor 1; complement decay-accelerating factor [Precursor] Synonym CD55 antigen; cyclinT1; desmoglein 1; hepatitis A virus cellular receptor 1-havcr-1; hepatitis B virus X interacting protein-XIP; HIV Tat Specific Factor 1; human interferon gamma; human damage specific DNA binding protein-DDB1; INI1/hSNF5; interferon alpha-16 precursor (interferon alpha-wa); interferon alpha-5 precursor (interferon alpha-g) (leif g) (interferon alpha-61). human leukocyte (alpha) interferon; interferon alpha-1/13 precursor (interferon alpha-d) (leif d); interferon-beta 1; interleukin 8 precursor (il-8) (monocyte-derived neutrophilchemotactic factor) (mdnsf) (T-cell chemotactic factor) (Neutrophil-activating protein 1) (nap-1) (lymphocyte-derived neutrophil-activating factor) (lynap) (protein 3-10c) (neutrophil-activating factor) (naf) (granulocyte chemotactic protein 1) (gsp-1)-activating factor) (naf) (granulocyte chemotactic protein 1) (gsp-1); interleukin 2; interleukin-12 beta chain precursor (i1-12b) (cytotoxic lymphocyte maturation factor 40 kda subunit) (clmf p40) (nk cell stimulatory factor chain 2) (nksf2); natural resistance-associated macrophage protein 1 (nramp 1); p300/CBP associated factor (PCAF); poly(rC) binding protein 2; and virion infectivity factor.

Any type of viral infection can be prevented, treated or ameliorated in accordance with the methods of invention. Examples of viruses which cause viral infections include, but not limited to, retroviruses (e.g., human T-cell lymphotrophic virus (HTLV) types I and II and human immunodeficiency virus (HIV)), herpes viruses (e.g., herpes simplex virus (HSV) types I and II, Epstein-Barr virus, HHV6-HHV8, and cytomegalovirus), arenavirues (e.g., lassa fever virus), paramyxoviruses (e.g., morbillivirus virus, human respiratory syncytial virus, mumps, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., influenza viruses A, B and C), papovaviruses (e.g., papillomavirues), picornaviruses (e.g., rhinoviruses, enteroviruses and hepatitis A viruses), poxviruses, reoviruses (e.g., rotavirues), togaviruses (e.g., rubella virus), rhabdoviruses (e.g., rabies virus).

Viral infection therapies and their dosages, routes of administration and recommended usage are known in the art and have been described in such literature as the Physician's Desk Reference ($56^{th}$ ed., 2002).

5.9.6. Fungal Infections

A compound identified in accordance with the methods of the invention may be administered to a subject in need thereof to prevent, treat or ameliorate a fungal infection or one or more conditions or symptoms associated therewith. A compound identified in accordance with the methods of the invention may also be administered in combination with one or more other therapies (e.g., prophylactic or therapeutic agents) to a subject in need thereof to prevent, treat or ameliorate a fungal infection or one or more conditions or symptoms associated therewith. Preferably, such therapies are useful for the prevention or treatment of a fungal infection. Examples of such therapies include, but are not limited to, amphotericin B or analogs or derivatives thereof (including 14(s)-hydroxyamphotericin B methyl ester, the hydrazide of amphotericin B with 1-amino-4-methylpiperazine, and other derivatives) or other polyene macrolide antibiotics (including, e.g., nystatin, candicidin, pimaricin and natamycin), flucytosine; flucytosine; griseofulvin; echinocandins or aureobasidins, including naturally occurring and semi-synthetic analogs; dihydrobenzo[a]napthacenequinones; nucleoside peptide antifungals including the polyoxins and nikkomycins; allylamines such as naftifine and other squalene epoxidease inhibitors; azoles, imidazoles and triazoles such as, e.g., clotrimazole, miconazole, ketoconazole, econazole, butoconazole, oxiconazole, terconazole, itraconazole or fluconazole and the like; rapamycin and rapalogs (non-immunosuppressive derivatives of rapamycin); cyclosporin A; FK506; terbinafine; and natural compounds found in goldenseal root powder, ipe roxo powder, poke root powder, lavender oil, and tea tree oil. In a specific embodiment, the invention provides a method of preventing, treating or ameliorating a fungal infection or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating a fungal infection or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

The invention provides methods for treating or ameliorating a fungal infection or a symptom thereof in a subject refractory to conventional therapies for such a fungal infection, said methods comprising administering to said subject a dose of a prophylactically or therapeutically effective amount of a compound identified in accordance with the methods of the invention. The invention also provides methods for treating or ameliorating a fungal infection or a symptom thereof in a subject refractory to existing single agent therapies for such a fungal infection, said methods comprising administering to said subject a dose of a prophylactically or therapeutically effective amount of a compound identified in accordance with the methods of the invention and a dose of a prophylactically or therapeutically effective amount of one or more therapies (e.g., prophylactic or therapeutic agents). The invention also provides methods for treating a fungal infection by administering a compound identified in accordance with the methods of the invention in combination with any other therapy to patients who have proven refractory to other therapies but are no longer on these therapies. The invention also provides alternative methods for the treatment of a fungal infection where another therapy has proven or may prove too toxic, i.e., results in unacceptable or unbearable side effects, for the subject being treated. Further, the invention provides methods for preventing the recurrence of a fungal infection in patients that have been treated and have no disease activity by administering a compound identified in accordance with the methods of the invention.

In this embodiment, target genes encoding proteins include, but are not limited to, complement decay-accelerating factor [precursor] synonym CD55 antigen; desmoglein 1; human interferon gamma; interferon alpha-16 precursor (interferon alpha-wa); interferon alpha-1/13 precursor (interferon alpha-d) (leif d); interferon alpha-5 precursor (interferon alpha-g) (leif g) (interferon alpha-61). human leukocyte (alpha) interferon; interferon-beta 1; interleukin 2; interleukin-12 beta chain precursor (i1-12b) (cytotoxic lymphocyte maturation factor 40 kda subunit) (clmf p40) (nk cell stimulatory factor chain 2) (nksf2); interleukin-8 precursor (i1-8) (monocyte-derived neutrophilchemotactic factor) (mdnsf) (T-cell chemotactic factor) (neutrophil-activating protein 1) (nap-1) (lymphocyte-derived neutrophil-activating factor) (lynap) (protein 3-10c) (neutrophil-activating factor) (naf) (granulocyte chemotactic protein 1) (gsp-1); and natural resistance-associated macrophage protein 1 (nramp 1).

Any type of fungal infection can be prevented, treated or ameliorated in accordance with the methods of invention. Examples of fungi which cause fungal infections include, but not limited to, *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger,* and *Aspergillus terreus*), *Basidiobolus ranarum, Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea,* and *Candida tropicalis*), *Coccidioides immitis, Conidiobolus* species, *Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae,* and *Rhizopus microsporus*), *Saccharomyces* species, *Sporothrix schenckii*, zygomycetes, and classes such as Zygomycetes, Ascomycetes, the Basidiomycetes, Deuteromycetes, and Oomycetes.

Fungal infection therapies and their dosages, routes of administration and recommended usage are known in the art and have been described in such literature as the Physician's Desk Reference (56$^{th}$ ed., 2002).

5.9.7. Bacterial Infections

A compound identified in accordance with the methods of the invention may be administered to a subject in need thereof to prevent, treat or ameliorate a bacterial infection or one or more conditions or symptoms thereof. A compound identified in accordance with the methods of the invention may also be administered in combination with one or more other therapies (e.g., prophylactic or therapeutic agents) to a subject in need thereof to prevent, treat or ameliorate a bacterial infection or one or more conditions or symptoms thereof. Preferably, such therapies are useful for the prevention or treatment of a bacterial infection. Examples of such therapies include, but are not limited to, amoxycillin, bacteriophages, chloramphenicol, chlorhexidine, co-trimoxazole, fluoroquinolones (e.g., ciprofloxacin and ofloxacin), isoniazid, macrolides, oxazolidinones, penicillin, quinolones, rifampicin, rifamycins, streptomycin, sulfonamides, and tetracyclines. In a specific embodiment, the invention provides a method of preventing, treating or ameliorating a bacterial infection or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating a bacterial infection or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

The invention provides methods for treating or ameliorating a bacterial infection or a symptom thereof in a subject refractory to conventional therapies for such a bacterial infection, said methods comprising administering to said subject a dose of a prophylactically or therapeutically effective amount of a compound identified in accordance with the methods of the invention. The invention also provides methods for treating or ameliorating a bacterial infection or a symptom thereof in a subject refractory to existing single agent therapies for such a bacterial infection, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating a bacterial infection by administering a compound identified in accordance with the methods of the invention in combination with any other therapy to patients who have proven refractory to other therapies but are no longer on these therapies. The invention also provides alternative methods for the treatment of a bacterial infection where another therapy has proven or may prove too toxic, i.e., results in unacceptable or unbearable side effects, for the subject being treated. Further, the invention provides methods for preventing the recurrence of a bacterial infection in patients that have been treated and have no disease activity by administering a compound identified in accordance with the methods of the invention.

In this embodiment, target genes encoding proteins include, but are not limited to, ADP-ribosylation factor-4; bactericidal/permeability-increasing protein; complement decay-accelerating factor [precursor] synonym CD55 antigen; desmoglein 1; human interferon gamma; interferon alpha-16 precursor (interferon alpha-wa); interferon alpha-1/13 precursor (interferon alpha-d) (leif d); interferon alpha-5 precursor (interferon alpha-g) (leif g) (interferon alpha-61). human leukocyte (alpha) interferon; interferon-beta 1; interleukin 2; interleukin-12 beta chain precursor (il-12b) (cytotoxic lymphocyte maturation factor 40 kda subunit) (clmf p40) (nk cell stimulatory factor chain 2) (nksf2); interleukin-8 precursor (il-8) (monocyte-derived neutrophilchemotactic factor) (mdnsf) (T-cell chemotactic factor) (neutrophil-activating protein 1) (nap-1) (lymphocyte-derived neutrophil-activating factor) (lynap) (protein 3-10c) (neutrophil-activating factor) (naf) (granulocyte chemotactic protein 1) (gsp-1); and natural resistance-associated macrophage protein 1 (nramp 1).

Any type of bacterial infection can be prevented, treated or ameliorated in accordance with the methods of invention. Examples of bacteria which cause bacterial infections include, but not limited to, the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, *Edwardsiella, Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, *Helicobacter* family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus fasciae*, and *Streptococcus pneumoniae*) VampirovibrHelicobacter family, and Vampirovibrio family.

Bacterial infection therapies and their dosages, routes of administration and recommended usage are known in the art and have been described in such literature as the Physician's Desk Reference (56$^{th}$ ed., 2002).

5.9.8. Cardiovascular Diseases

A compound identified in accordance with the methods of the invention may be administered to a subject in need thereof to prevent, treat or ameliorate a cardiovascular disease or one or more symptoms thereof. A compound identified in accordance with the methods of the invention may also be administered in combination with one or more other therapies (e.g., prophylactic or therapeutic agents) to a subject in need thereof to prevent, treat or ameliorate a cardiovascular disease or one or more symptoms thereof. Preferably, such therapies are useful for the prevention or treatment of a cardiovascular disease. Examples of such therapies include, but are not limited to, peripheral anti-adrenergic drugs, centrally acting antihypertensive drugs (e.g., methyldopa and methyldopa HCl), antihypertensive direct vasodilators (e.g., diazoxide and hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, and sulmazole), antidysrhythmic drugs, calcium entry blockers, ranitine, bosentan, and rezulin. In a specific embodiment, the invention provides a method of preventing, treating or ameliorating a cardiovascular disease or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating a cardiovascular disease or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

The invention provides methods for treating or ameliorating one or more symptoms of a cardiovascular disease in a subject refractory to conventional therapies for such a cardiovascular disease, said methods comprising administering to said subject a dose of a prophylactically or therapeutically effective amount of a compound identified in accordance with the methods of the invention. The invention also provides methods for treating or ameliorating one or more symptoms of a cardiovascular disease in a subject refractory to existing single agent therapies for such a cardiovascular disease, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating a cardiovascular disease by administering a compound identified in accordance with the methods of the invention in combination with any other therapy to patients who have proven refractory to other therapies but are no longer on these therapies. The invention also provides alternative methods for the treatment of a cardiovascular disease where another therapy has proven or may prove too toxic, i.e., results in unacceptable or unbearable side effects, for the subject being treated. Further, the invention provides methods for preventing the recurrence of a cardiovascular disease in patients that have been treated and have no disease activity by administering a compound identified in accordance with the methods of the invention.

In this embodiment, target genes encoding proteins include, but are not limited to, 3-hydroxy-3-methylglutaryl-CoA reductase; actin, alpha cardiac; acyl-coa dehydrogenase; angiotensin 1-converting enzyme; bile salt export pump (atp-binding cassette, sub-family b, member 11); cardiac muscle troponin T; carnitine o-palmitoyltransferase; emotakin ATP-binding cassette, sub-family a, member 1 (atp-binding cassette transporter 1) (atp-binding cassette 1) (abc-1) (cholesterol efflux regulatory protein); erythropoietin; fibrillin; human trisosephosphate isomerase; iduronate 2-sulfatase; klotho; and thrombomodulin.

Any cardiovascular disease can be prevented, treated or ameliorated in accordance with the methods of the invention. Examples of cardiovascular diseases include, but not limited to, athlerosclerosis, stroke, cerebral infarction, endothelium dysfunctions (in particular, those dysfunctions affecting blood vessel elasticity) ischemic heart disease (e.g., angina pectoris, myocardial infarction, and chronic ischemic heart disease), hypertensive heart disease, pulmonary heart disease, coronary heart disease, valvular heart disease (e.g., rheumatic fever and rheumatic heart disease, endocarditis, mitral valve prolapse, restenosis and aortic valve stenosis), congenital heart disease (e.g., valvular and vascular obstructive lesions, atrial or ventricular septal defect, and patent ductus arteriosus), and myocardial disease (e.g., myocarditis, congestive cardiomyopathy, and hypertrophic cariomyopathy).

Cardiovascular disease therapies and their dosages, routes of administration and recommended usage are known in the art and have been described in such literature as the *Physician's Desk Reference* (56$^{th}$ ed., 2002).

5.9.9. Central Nervous System Disorders

A compound identified in accordance with the methods of the invention may be administered to a subject in need thereof to prevent, treat or ameliorate a central nervous system ("CNS") disorder or one or more symptoms thereof. A compound identified in accordance with the methods of the invention may also be administered in combination with one or more other therapies (e.g., prophylactic or therapeutic agents) to a subject in need thereof to prevent, treat or ameliorate a CNS disorder or one or more symptoms thereof. Preferably, such therapies are useful for the prevention or treatment of a CNS disorder. Examples of such therapies include, but are not limited to, levodopa, Parlodel (bromocriptine), Permax (pergolide), Eldepryl (selegiline hydrochloride), donepezil (Aricept®), tacrine (Cognex®), acyclovir, antibiotics, chemotherapeutics, and radiation therapy. In a specific embodiment, the invention provides a method of preventing, treating or ameliorating a CNS disorder or one or more symptoms thereof, said method comprising administering to a subject in need thereof a dose of a prophylactically or therapeutically effective amount of a compound identified in accordance with the methods of the invention. In another embodiment, the invention provides a method of preventing, treating or ameliorating a CNS disorder or one or more symptoms thereof, said method comprising administering to a subject in need thereof a dose of a prophylactically or therapeutically effective amount of a compound identified in accordance with the methods of the invention and a dose of a prophylactically or therapeutically effective amount of one or more other therapies (e.g., prophylactic or therapeutic agents).

The invention provides methods for treating or ameliorating one or more symptoms of a CNS disorder in a subject refractory to conventional therapies for such a cardiovascular disease, said methods comprising administering to said subject a dose of a prophylactically or therapeutically effective amount of a compound identified in accordance with the methods of the invention. The invention also provides methods for treating or ameliorating one or more symptoms of a CNS disorder in a subject refractory to existing single agent therapies for such a CNS disorder, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating a CNS disorder by administering a compound identified in accordance with the methods of the invention in combination with any other therapy to patients who have proven refractory to other therapies but are no longer on these therapies. The invention also provides alternative methods for the treatment of a CNS disorder where another therapy has proven or may prove too toxic, i.e., results in unacceptable or unbearable side effects, for the subject being treated. Further, the invention provides methods for preventing the recurrence of a cardiovascular disease in patients that have been treated and have no disease activity by administering a compound identified in accordance with the methods of the invention.

In this embodiment, target genes encoding proteins include, but are not limited to, acetylcholinesterase; Alzheimer's disease amyloid A4 [precursor], synonyms: protease nexin-II PN-II APPI; beta-site APP-cleaving enzyme 2; catechol-O-methyltransferase; CREAM/calsenilin/KCh IP3; D-amino-acid oxidase; drebrin-1 dendritic spine protein; glutamic acid decarboxylase 2; glutamic acid decarboxylase, brain, membrane form; glutamic acid decarboxylase 3; human D-1 dopamine receptor; huntingtin; kallikrein 6; monoamine oxidase-A; monoamine oxidase-B; N-methylD-aspartate (NMDA) receptor; peroxisome assembly factor-2 (paf-2) (peroxisomal-type atpase 1) (peroxin-6); and vanilloid receptor subunit 1 (capsaicin receptor).

Any CNS disorder can be treated in accordance with the methods of the invention. Examples of CNS disorders include, but are not limited to, bacterial and viral meningitis, Alzheimers Disease, cerebral toxoplasmosis, Parkinson's disease, multiple sclerosis, brain cancers (e.g., metastatic carcinoma of the brain, glioblastoma, astrocytoma, and acoustic neuroma), hydrocephalus, and encephalitis.

CNS disorder therapies and their dosages, routes of administration and recommended usage are known in the art and have been described in such literature as the *Physician's Desk Reference* (56$^{th}$ ed., 2002).

5.10. Classification of UTRs, Compound, and Disease State

The names of the compounds identified in accordance with the methods described herein and the names of the genes whose expression are modulated in response to said compounds can be maintained in a database. By performing an assay for modulators of untranslated region-dependent gene expression using the same assay format for a group of untranslated regions of target genes (i.e., an assay format in which the only variable between each individual assay is the nucleotide sequence of untranslated regions operably linked to a reporter gene) and by storing all relevant data in a database, cluster analysis can be performed on the data and functional associations between and/or within relevant data sets (e.g., (a) compounds, (b) nucleotide sequences of untranslated regions of genes, and (c) pathological conditions associated with genes) can be determined.

For example, if a common set of compounds modulates the expression of a reporter gene when the latter is operably linked to a set of untranslated regions from all untranslated regions analyzed, it can be concluded that the untranslated regions in the set are involved in a common process or processes in post-transcriptional control of gene expression. If functional involvement in post-transcriptional control of gene expression has been reported for any of the untranslated regions in the set, the untranslated regions without known roles in gene expression regulation can be assigned a function. By performing further analysis and looking for sets of compounds that modulate sets of untranslated regions common to a particular pathological condition, the following can be identified: (a) members of biochemical reaction pathways involved in the disease, (b) targets for multiple drug intervention and/or regulation, and (c) multiple pathological conditions that can be treated with a single compound or set of compounds.

6. EXAMPLE

Therapeutic Untranslated Region Targets

The therapeutic targets presented herein are by way of example, and the present invention is not to be limited by the targets described herein. The therapeutic targets presented herein as DNA sequences are understood by one of skill in the art that the sequences can be converted to RNA sequences.

6.1. Tumor Necrosis Factor Alpha

See, e.g., GenBank Accession # X01394.

```
General Target Regions:
(1) 5' Untranslated Region - nts 1 - 152 of
GenBank Accession # X01394:
                                        (SEQ ID NO: 5)
gcagaggacc agctaagagg gagagaagca actacagacc cccctgaaa acaaccctca gacgccacat cccctgacaa gctgccaggc aggttctctt cctctcacat actgacccac ggctccaccc tctctcccct ggaaaggaca cc (2) 3' Untranslated Region - nts 852 - 1643 of
GenBank Accession # X01394:
                                        (SEQ ID NO: 6)
tgaggagga cgaacatcca accttcccaa acgcctcccc tgccccaatc cctttattac cccctccttc agacaccctc aacctcttct ggctcaaaaa gagaattggg ggcttagggt cggaacccaa gcttagaact ttaagcaaca agaccaccac ttcgaaacct gggattcagg aatgtgtggc ctgcacagtg aattgctggc aaccactaag aattcaaact ggggcctcca gaactcactg gggcctacag cttttgatccc tgacatctgg aatctggaga ccagggagcc tttggttctg gccagaatgc tgcaggactt gagaagacct cacctagaaa ttgacacaag tggaccttag gccttcctct ctccagatgt ttccagactt ccttgagaca cggagcccag ccctccccat ggagccagct ccctctattt atgtttgcac ttgtgattat ttattattta tttattattt atttatttac agatgaatgt atttatttgg gagaccgggg tatcctgggg gacccaatgt aggagctgcc ttggctcaga catgttttcc gtgaaaacgg agctgaacaa taggctgttc ccatgtagcc ccctggcctc tgtgccttct tttgattatg ttttttaaaa tatttatctg attaagttgt ctaaacaatg ctgatttggt gaccaactgt cactcattgc tgagcctctg ctccccaggg gagttgtgtc tgtaatcgcc ctactattca gtggcgagaa ataaagtttg ctt
```

```
Initial Specific Target Motif:
(3) Group I AU-Rich Element (ARE) Cluster in 3'
untranslated region:
                                        (SEQ ID NO: 7)
5' AUUUAUUUAUUUAUUUAUUUA 3'
```

6.2. Granulocyte-Macrophage Colony Stimulating Factor

See, e.g., GenBank Accession # NM_000758 or # XM_003751.

```
General Target Regions:
(1) 5' Untranslated Region - nts 1 - 32 of GenBank
Accession #NM_000758:
                                        (SEQ ID NO: 8)
g/tctggaggat gtggctgcag agcctgctgc tcttgggcac (2) 3' Untranslated Region - nts 468 - 789 of
GenBank Accession #NM_000758:
                                        (SEQ ID NO: 9)
gcc ggggagctgc tctctcatga aacaagagct agaaactcag gatggtcatc ttggagggac caaggggtgg gccacagcca tggtgggagt ggcctggacc tgccctgggc cacactgacc ctgatacagg catggcagaa gaatgggaat attttatact gacagaaatc agtaatattt atatatttat atttttaaaa tatttattta tttatttatt taagttcata ttccatattt attcaagatg ttttaccgta ataattatta ttaaaaatat gcttct Initial Specific Target Motif:
Group I AU-Rich Element (ARE) Cluster in 3'
untranslated region:
                                        (SEQ ID NO: 10)
5' AUUUAUUUAUUUAUUUAUUUA 3'
```

6.3. Interleukin 2

See, e.g., GenBank Accession # U25676.

```
General Target Regions:
(1) 5' Untranslated Region - nts 1 - 47 of GenBank
Accession # U25676:
                                        (SEQ ID NO: 11)
atcactctct ttaatcacta ctcacattaa cctcaactcc tgccaca (2) 3' Untranslated Region - nts 519- 825 of
GenBank Accession # U25676:
                                        (SEQ ID NO: 12)
ta attaagtgct tcccacttaa aacatatcag gccttctatt tatttattta aatatttaaa ttttatattt attgttgaat gtatggttgc tacctattgt aactattatt cttaatctta aaactataaa tatggatctt ttatgattct ttttgtaagc cctaggggct ctaaaatggt ttaccttatt tatcccaaaa atatttatta ttatgttgaa tgttaaatat agtatctatg tagattggtt agtaaaacta tttaataaat ttgataaata taaaaaaaaa aaacaaaaaa aaaaa Initial Specific Target Motifs:
Group III AU-Rich Element (ARE) Cluster in 3'
untranslated region:
                                        (SEQ ID NO: 13)
5' NAUUUAUUUAUUUAN 3'
```

6.4. Interleukin 6
See, e.g., GenBank Accession # NM_000600.

```
General Target Regions:
(1) 5' Untranslated Region - nts 1 - 62 of GenBank
Accession #NM_000600:
                                    (SEQ ID NO: 14)
ttctgccctc gagcccaccg ggaacgaaag agaagctcta tctcgcctcc aggagcccag ct (2) 3' Untranslated Region - nts 699 - 1125 of
GenBank Accession #NM_000600:
                                    (SEQ ID NO: 15)
ta gcatgggcac ctcagattgt tgttgttaat gggcattcct tcttctggtc agaaacctgt ccactgggca cagaacttat gttgttctct atggagaact aaaagtatga gcgttaggac actattttaa ttatttttaa tttattaata tttaaatatg tgaagctgag ttaatttatg taagtcatat ttatattttt aagaagtacc acttgaaaca ttttatgtat tagttttgaa ataataatgg aaagtggcta tgcagtttga atatcctttg tttcagagcc agatcatttc ttggaaagtg taggcttacc tcaaataaat ggctaactta tacatatttt taaagaaata tttatattgt atttatataa tgtataaatg gttttatac caataaatgg cattttaaaa aattc Initial Specific Target Motifs:
Group III AU-Rich Element (ARE) Cluster in 3'
untranslated region:
                                    (SEQ ID NO: 16)
5' NAUUUAUUUAUUUAN 3'
```

6.5. Vascular Endothelial Growth Factor
See, e.g., GenBank Accession # AF022375.

```
General Target Regions:
(1) 5' Untranslated Region - nts 1 - 701 of
GenBank Accession # AF022375:
                                    (SEQ ID NO: 17)
aagagctcca gagagaagtc gaggaagaga gagacgggt cagagagagc gcgcgggcgt gcgagcagcg aaagcgacag gggcaaagtg agtgacctgc ttttggggt gaccgccgga gcgcggcgtg agccctcccc cttgggatcc cgcagctgac cagtcgcgct gacggacaga cagacagaca ccgcccccag ccccagttac cacctcctcc ccggccgcg gcggacagtg gacgcggcgg cgagccgcgg gcaggggccg gagcccgccc ccggaggcgg ggtggagggg gtcggagctc gcggcgtcgc actgaaactt ttcgtccaac ttctgggctg ttctcgcttc ggaggagccg tggtccgcgc gggggaagcc gagccgagcg gagccgcgag aagtgctagc tcgggccggg aggagccgca gccgaggag ggggaggagg aagaagagaa ggaagaggag agggggccgc agtggcgact cggcgctcgg aagccgggct catgacgggg tgaggcggcg gtgtgcgcag acagtgctcc agcgcgcgcg ctccccagcc ctggccggc ctcgggccgg gaggaagagt agctcgccga ggcgccgagg agagcgggcc gccccacagc ccgagccgga gagggacgcg agccgcgcgc cccggtcggg cctccgaaac c (2) 3' Untranslated Region - nts 1275 - 3166 of
GenBank Accession # AF022375:
                                    (SEQ ID NO: 18)
tgagcc gggcaggagg aaggagcctc cctcagggtt tcgggaacca gatctctctc caggaaagac tgatacagaa cgatcgatac agaaaccacg ctgccgccac cacaccatca ccatcgacag aacagtcctt aatccagaaa cctgaaatga aggaagagga gactctgcgc agagcacttt gggtccggag ggcgagactc cggcggaagc attcccggc gggtgaccca gcacggtccc tcttggaatt ggattcgcca ttttatttt cttgctgcta aatcaccgag cccggaagat tagagagttt tatttctggg attcctgtag acacacccac ccacatacat acatttatat atatatatat tatatatata taaaaataaa tatctctatt ttatatatat aaaatatata tattctttt ttaaattaac agtgctaatg ttattggtgt cttcactgga tgtatttgac tgctgtggac ttgagttggg aggggaatgt tcccactcag atcctgacag ggaagaggag gagatgagag actctggcat gatcttttt ttgtcccact tggtggggcc agggtcctct cccctgccca agaatgtgca aggccagggc atgggggcaa atatgaccca gttttgggaa caccgacaaa cccagccctg gcgctgagcc tctctacccc aggtcagacg gacagaaaga caaatcacag gttccgggat gaggacaccg gctctgacca ggagtttggg gagcttcagg acattgctgt gctttgggga ttccctccac atgctgcacg cgcatctcgc cccagggc actgcctgga agattcagga gcctgggcgg ccttcgctta ctctcacctg cttctgagtt gcccaggagg ccactggcag atgtccggc gaagagaaga gacacattgt tggaagaagc agcccatgac agcgccctt cctgggactc gccctcatcc tcttcctgct cccttcctg gggtgcagcc taaaaggacc tatgtcctca caccattgaa accactagtt ctgtcccccc aggaaacctg gttgtgtgtg tgtgagtggt tgaccttcct ccatccctg gtccttccct tcccttcccg aggcacagag agacagggca ggatccacgt gcccattgtg gaggcagaga aaagagaaag tgttttatat acggtactta tttaatatcc ctttttaatt agaaattaga acagttaatt taattaaaga gtagggtttt ttttcagtat tcttggttaa tatttaattt caactatta tgagatgtat ctttgctct ctcttgctct cttatttgta ccggttttg tatataaaat tcatgtttcc aatctctctc tccctgatcg gtgacagtca ctagcttatc
```

-continued ttgaacagat atttaatttt gctaacactc agctctgccc tccccgatcc cctggctccc cagcacacat tcctttgaaa gagggtttca atatacatct acatactata tatatattgg gcaacttgta tttgtgtgta tatatatata tatatgttta tgtatatatg tgatcctgaa aaaataaaca tcgctattct gttttttata tgttcaaacc aaacaagaaa aatagagaa ttctacatac taaatctctc tccttttta attttaatat ttgttatcat ttatttattg gtgctactgt ttatccgtaa taattgtggg gsaangatat taacatcacg tctttgtctc tagtgcagtt tttcgagata ttccgtagta catatttatt tttaaacaac gacaaagaaa tacagatata tcttaaaaaa aaaaaa Initial Specific Target Motifs:
(1) Internal Ribosome Entry Site (IRES) in 5' untranslated region nts 513 - 704:
(SEQ ID NO: 19)
5'CCGGGCUCAUGGACGGGUGAGGCGGCGGUGUGCGCAGACAGUGCUCCA

GCGCGCGCGCUCCCCAGCCCUGGCCCGGCCUCGGGCCGGGAGGAAGAGUA

GCUCGCCGAGGCGCCGAGGAGAGCGGGCCGCCCCACAGCCCGAGCCGGAG

AGGGACGCGAGCCGCGCGCCCCGGUCGGGCCUCCGAAACCAUGAACUUUC

UGCUGUCUUGGGUGCAUUGGAGCCUUGCCUUGCUGCUCUACCUCCACCAU

G 3'

(2) Group III AU-Rich Element (ARE) Cluster in 3' untranslated region:
(SEQ ID NO: 20)
5' NAUUUAUUUAUUUAN 3'

6.6. Survivin
See, e.g., GenBank Accession # NM_001168.

General Target Regions:
(1) 5' Untranslated Region - nts 1 - 49 of GenBank Accession #NM_001168:
(SEQ ID NO: 21)
ccgccagatt tgaatcgcgg gacccgttgg cagaggtggc ggcggcggc (2) 3' Untranslated Region - nts 479 - 1619 of GenBank Accession #NM_001168:
(SEQ ID NO: 22)
gg cctctggccg gagctgcctg gtcccagagt ggctgcacca cttccagggt ttattccctg gtgccaccag ccttcctgtg ggccccttag caatgtctta ggaaaggaga tcaacatttt caaattgat gtttcaactg tgctcctgtt ttgtcttgaa agtggcacca gaggtgcttc tgcctgtgca gcgggtgctg ctggtaacag tggctgcttc tctctctctc tctctttttt gggggctcat ttttgctgtt ttgattcccg ggcttaccag gtgagaagtg agggaggaag aaggcagtgt cccttttgct agagctgaca gctttgttcg cgtgggcaga gccttccaca gtgaatgtgt ctggacctca tgttgttgag gctgtcacag tcctgagtgt ggacttggca ggtgcctgtt gaatctgagc tgcaggttcc ttatctgtca cacctgtgcc tcctcagagg acagtttttt tgttgttgtg ttttttttgtt ttttttttt ggtagatgca tgacttgtgt gtgatgagag aatggagaca gagtccctgg ctcctctact gtttaacaac atggctttct tattttgttt gaattgttaa ttcacagaat agcacaaact acaattaaaa ctaagcacaa agccattcta agtcattggg gaaacggggt gaacttcagg tggatgagga gacagaatag agtgatagga agcgtctggc agatactcct tttgccactg ctgtgtgatt agacaggccc agtgagccgc ggggcacatg ctggccgctc ctccctcaga aaaaggcagt ggcctaaatc cttttaaat gacttggctc gatgctgtgg gggactggct gggctgctgc aggccgtgtg tctgtcagcc caaccttcac atctgtcacg ttctccacac gggggagaga cgcagtccgc ccaggtcccc gctttctttg gaggcagcag ctcccgcagg gctgaagtct ggcgtaagat gatggatttg attcgccctc ctccctgtca tagagctgca gggtggattg ttacagcttc gctggaaacc tctggaggtc atctcggctg ttcctgagaa ataaaaagcc tgtcatttc

6.7. Epidermal Growth Factor Receptor
See, e.g., GenBank Accession # XOO588.1.

General Target Regions:
(1) 5' Untranslated Region (247 nt) (GenBank Accession No. Hu EST gi|6302071|gb|AW163038.1|AW163038):
(SEQ ID NO: 23)
ccccggcgcagcgcggccgcagcagcctccgccccccgcacggtgtgagc gcccgacgcggccgaggcggccggagtcccgagctagcccggcggccgc cgccgcccagaccggacgacaggccacctcgtcggcgtccgcccgagtcc ccgcctcgccgccaacgccacaaccaccgcgcacggccccctgactccgt ccagtattgatcgggagagccggagcgagctcttcggggagcagcag (2) 3' Untranslated Region (1.7 kb, 58% AT-density):
(SEQ ID NO: 24)
tgaccacggaggatagtatgagccctaaaaatccagactctttcgatacc caggaccaagccacagcaggtcctccatcccaacagccatgcccgcatta gacttagacccacagactggattgcaacgtttacaccgactagccaggaa gtacttccacctcgggcacattttgggaagttgcattcctttgtcttcaa actgtgaagcatttacagaaacgcatccagcaagaatattgtccctttga gcagaaatttatctttcaaagaggtatatttgaaaaaaaaaaaaaagta tatgtgaggattttttattgattggggatcttggagttttttcattgtcgct attgattttttacttcaatgggctatccaacaaggaagaagatgctggtag cacttgctaccctgagttcatccaggcccaactgtgagcaaggagcacaa gccacaagtattccagaggatgatgattccagtggttctgcttcaaggct tccactgcaaaacactaaagatccaagaaggccttcatggccccagcagg -continued
```
ccggatcggtactgtatcaagtcatggcaggtacagtaggataagccact
ctgtcccttcctgggcaaagaagaaacggaggggatgaattcttccttag
acttacttttgtaaaaatgtccccacggtacttactccccactgatggac
cagtggtttccagtcatgagcgttagactgacttgtttgtatccattcca
ttgttttgaaactcagtatgccgcccctgtatgagtcatgaaatcagcaa
gagaggatgacacatcaaataatctcggattccagcccacattggatt
catcagcatttggaccaatagcccacagctgagaatgtggaatacctaag
gataacaccgcttttgttctcgcaaaaacgtatctcctaatttgaggctc
agatgaaatgcatcaggtcctttggggcatagatcagaagactacaaaaa
tgaagctgctctgaaatacctttagccatcacccaaccacccaaaatta
gtttgtgttacttatggaagatagttttctccttttacttcacttcaaaa
gcttttactcaaagagtatatgttccctccaggtcagctgcccccaaac
cccatcattacgatttgtcacacaaaaagtgtctctgccttgagtcatct
attcaagcacttacagctctggccacaacagggcattttacaggtgcgaa
tgacagtagcattatgagtagtgtgaattcaggtagtaaatatgaaacta
gggtttgaaattgataatgctttcacaacatttgcagatgattagaagga
aaaaagttccttcctaaaataatttactacaattggaagattggaagatt
cagctagttaggagcccattattcctaatagtgtgtgccctgtaacctga
ctggttaacagcagtcctttgtaaacagtgttttaaactctcctagtcaa
tatccaccccatccaatttatcaaggaagaaatggttcagaaaatatttt
cagcctacagttatgttcagtcacacacacatacaaaatgttccttttgc
ttttaaagtaattttttgactcccagatcagtcagagcccctacagcattg
ttaagaaagtatttgattttttgtctcaatgaaaataaaactatattcatt
tcc
```

6.8. CCAAT/Enhancer Binding Protein
See, e.g., GenBank Accession # NM_004364.

General Target Regions:
(1) CEBP-αa, uORF (5'UTR, 160 nt):
(SEQ ID NO: 25)
```
Tataaaagctgggccggcgcgggccgggccattcgcgacccggaggtgcg
cgggcgcgggcgagcagggtctccgggtgggcggcgcgacgccccgcgca
ggctggaggccgccgaggctcgccatgccgggagaactctaactcccca
tggagtcggc
```

(2) CEBP-α, uORF (3'UTR, 1306 nt):
(SEQ ID NO: 26)
```
tgaggcgcgcggctgtgggaccgccctgggccagcctccggcggggaccc
agggagtggtttggggtcgccggatctcgaggcttgcccagaccgtgcga
gccaggactaggagattccggtgcctcctgaaagcctggcctgctccgcg
tgtcccaccttcctctgcgccggacttggtgcgtctaagatgagggggc
caggcggtggcttaccctgcgaggaggggagaattcttggggctgagatg
ggagcccggcaactctagtatttaggataacttgtgccttggaaatgcaa
actcaccgctccaatgcctactgagtaggggagcaaatcgtgccttgtc
attttatttggaggtttcctgcctccttcccgaggctacagcagacccc
atgagagaaggagggggagcaggcccgtggaggagggggggctcagggagag
agatcccgacaagcccgccagcccagccgctcctccacgcctgtccttta
gaaaggggtggaaacatagggacttgggcttggaacctaaggttgttcc
ctagttctacatgaaggtggaggtctctagttccacgcctctcccacctc
cctccgcacacaccccacccagcctgctataggctggctttcccttgggg
ctggaactcactgcgatggggtcaccaggtgaccagtggagcccccaccc
cgagtcagaccagaaagctaggtcgtgggtcagctctgaggatgtatacc
cctggtgggagagggagacctagagatctggctgtggggcgggcatgggg
ggtgaagggccactgggaccctcagccttgtttgtactgtatgccttcag
cattgcctaggaacacgaagcacgatcagtccatccagagggaccggagt
tatgacaagcttcccaaatattttgctttatcagccgatatcaacacttg
tatctggcctctgtgcccagcagtgccttgtgcaatgtgaatgtaccgtc
tctgctaaaccaccatttatttggttttgttttgtttggttttctcgga
tacttgccaaaatgagactctccgtcggcagctgggggaagggtctgaga
ctctcttccttttggttttgggattacttttgatcctgggggaccaatg
aggtgagggggtctcctttgccctcagctttcccagccctccggcctg
ggctgcccacaaggcttctcccccagaggccctggctcctggtcgggaag
ggaggtgcaccgccaacgcatcactggggctgggagcagggaagggaat
tc
```

6.9. Cysteine-Rich, Angiogenic Inducer, 61
See, e.g., Gen Bank Accession # XM_001831.

General Target Regions:
(1) 5' Untranslated Region (GenBank Accession No.
gi|19200928|gb|BM844529.1|BM844529):
(SEQ ID NO: 27)
```
agcgagagcgcccccgagcagcgcccgcgccaccgcgccttctccgccgg
gacctcgagcgaaagacgcccgcccgccgccagccctcgcctccctgcc
caccgggcacaccgcgccgccaccccgacccccgctgcgcacggcctgtcc
gctgcacaccagcttgttggcgtcttcgtcgccgcgctcgccccgggcta
ctcctgcgcgccaca
```

(2) 3' Untranslated Region (687 nt) (GenBank
Accession No. 12898379|emb|AL556057.1|AL556057):
(SEQ ID NO: 28)
```
taaatgctacctgggtttccagggcacacctagacaaacargggagaaga
gtgtcagaatcagaatcatggagaaaatgggcgggggtggtgtgggtgat
gggactcattgtagaaaggaagccttgctcattatgaggagcattaaggt
attcgaaactgccaagggtgctggtgcggatggacactaatgcagccac
gattggagaatactttgcttcatagtattggagcacatgttactgcttca
ttttggagcttgtggagttgatgactttctgttttctgtttgtaaattat
ttgctaagcatattttctctaggcttttttccttttggggttctacagtc
gtaaaagagataataagattagttggacagtttaaagatttattcgtcct
ttgacaaaagtaaatgggagggcattccatcccttcctgaaggggacac
tccatgagtgtctgtgagaggcagctatctgcactctaaactgcaaacag
```

6.10. Basis Fibroblast Growth Factor

See, e.g., GenBank Accession No. NM_002006.

```
General Target Regions:
(1) 5' Untranslated Region:
                                         (SEQ ID NO: 29)
cggccccagaaaacccgagcgagtaggggcggcgcgcaggaggggaggag aactgggggcgcgggaggctggtgggtgtcggggtggagatgtagaaga tgtgacgccgcggcccggcgggtgccagattagcggacggctgcccgcgg ttgcaacgggatcccgggcgctgcagcttggggaggcggctctccccaggc ggcgtccgcggagacacccatccgtgaaccccaggtcccgggccgccggc tcgccgcgcaccaggggcggcggacagaagagcggccgagcggctcgag gctggggac (2) 3' Untranslated Region (5.8 kb):
                                         (SEQ ID NO: 30)
ctgctaagagctgatttaatggccacatctaatctcatttcacatgaaa gaagaagtatattttagaaatttgttaatgagagtaaaagaaaataaatg tgtatagctcagtttggataattggtcaaacaattttttatccagtagta aaatatgtaaccattgtcccagtaaagaaaaataacaaaagttgtaaaat gtatattctcccttttatattgcatctgctgttacccagtgaagcttacc tagagcaatgatcttttttcacgcatttgctttattcgaaaagaggctttt aaaatgtgcatgtttagaaacaaaattttcttcatggaaatcatatacatt agaaaatcacagtcagatgtttaatcaatccaaaatgtccactatttctt atgtcattcgttagtctacatgtttctaaacatataaatgtgaatttaat caattcattcatagattataattctctggcagttccttatgatagagttt ataaaacagtcctgtgtaaactgctggaagttcttccacagtcaggtcaa ttttgtcaaaccottctctgtacccatacagcagcagcctagcaactctg ctggtgatgggagttgtattttcagtcttcgccaggtcattgagatccat ccactcacatcttaagcattcttcctggcaaaaatttatggtgaatgaat atggctttaggcggcagatgatatacatatctgacttcccaaaagctcca ggatttgtgtgctgttgccgaatactcaggacggacctgaattctgattt tataccagtctcttcaaaaacttctcgaaccgctgtgtctcctacgtcaa aaaagagatgtacaaatcaataataattacacttttagaaactgtatcat caaagattttcagttaaagtagcattatgtaaaggctcaaaacattaccc taacaaagtaaagttttcaatacaaattctttgccttgtggatatcaaga aatcccaaaatattttcttaccactgtaaattcaagaagcttttgaaatg ctgaatatttctttggctgctacttggaggcttatctacctgtacattt tggggtcagctcttttttaacttcttgctgctcttttttcccaaaaggtaaa aatatagattgaaaagttaaaacattttgcatggctgcagttcctttgtt tcttgagataagattccaaagaacttagattcatttcttcaacaccgaaa tgctggaggtgtttgatcagttttcaagaaacttggaatataaataatt tataattcaacaaaggttttcacattttataaggttgattttttcaattaa atgcaaatttgtgtggcaggattttttattgccattaacatatttttgtgg ctgcttttctacacatccagatggtccctctaactgggctttctctaat tttgtgatgttctgtcattgtctcccaaagtatttaggagaagcccttta aaaagctgccttcctctaccactttgctggaaagcttcacaattgtcaca gacaaagattttgttccaatactcgttttgcctctattttcttgtttg tcaaatagtaaatgatatttgcccttgcagtaattctactggtgaaaaac atgcaaagaagaggaagtcacagaaacatgtctcaattcccatgtgctgt gactgtagactgtcttaccatagactgtcttacccatcccctggatatgc tcttgtttttttccctctaatagctatggaaagatgcatagaaagagtata atgttttaaaacataaggcattcatctgccatttttcaattacatgctga cttcccttacaattgagatttgcccataggttaaacatggttagaaacaa ctgaaagcataaaagaaaaatctaggccgggtgcagtggctcatgcctat attccctgcactttgggaggccaaagcaggaggatcgcttgagcccagga gttcaagaccaacctggtgaaaccccgtctctacaaaaaaacacaaaaaa tagccaggcatggtggcgtgtacatgtggtctcagatacttgggaggctg aggtgggagggttgatcacttgaggctgagaggtcaaggttgcagtgagc cataatcgtgccactgcagtccagcctaggcaacagagtgagactttgct caaaaaaagagaaattttccttaataagaaaagtaatttttactctgatg tgcaatacatttgttattaaatttattatttaagatggtagcactagtct taaattgtataaaatatccctaacatgtttaaatgtccatttttattca ttatgctttgaaaataattatggggaaatacatgtttgttattaaattt attattaaagatagtagcactagtcttaaatttgatataacatctcctaa cttgtttaaatgtccattttttattctttatgcttgaaaatataatgtattggg gatcctatttagctcttagtaccactaatcaaaagttcggcatgtagctc atgatctatgctgtttctatgtcgtggaagcaccggatgggggtagtgag caaatctgccctgctcagcagtcaccatagcagctgactgaaaatcagca ctgcctgagtagtatgatcagttaacttgaatcactaactgactgaaaat tgaatgggcaaataagtgcttttgtctccagagtatgcgggagaccctc cacctcaagatggatatttcttccccaaggatttcaagatgaattgaaat ttttaatcaagatagtgtgctttattctgttgtatttttttattattttaa tatactgtaagccaaactgaaataacatttgctgttttataggtttgaag aacataggaaaactaagaggttttgtttttatttttgctgatgaagaga tatgtttaaatatgttgtattgttttgtttagttacaggacaataatgaa atggagtttatatttgttatttctattttgttatatttaataatagaatt agattgaaataaaatataatgggaaataatctgcagaatgtgggtttcct ggtgtttcctctgactctagtgcactgatgatctctgataaggctcagct gcttatagttctctggctaatgcagcagatactcttcctgccagtggta atacgatttttttaagaaggcagtttgtcaattttaatcttgtggatacct
```

```
ttatactcttagggtattattttatacaaaagccttgaggattgcattct attttctatatgaccctcttgatatttaaaaaacactatggataacaatt cttcatttacctagtattatgaagaatgaaggagttcaaacaaatgtgt ttcccagttaactagggtttactgtttgagccaatataaatgtttaactg tttgtgatggcagtattcctaaagtacattgcatgttttcctaaatacag agtttaaataatttcagtaattcttagatgattcagcttcatcattaaga atatcttttgttttatgttgagttagaaatgccttcatatagacatagtc tttcagacctctactgtcagttttcatttctagctgcttttcagggtttta tgaattttcaggcaaagctttaatttatactaagcttaggaagtatggct aatgccaacggcagttttttttcttcttaattccacatgactgaggcatat atgatctctgggtaggtgagttgttgtgacaaccacaagcactttttttt ttttaaagaaaaaaaggtagtgaattttttaatcatctggactttaagaa ggattctggagtatacttaggcctgaaattatatatatttggcttggaaa tgtgttttttcttcaattacatctacaagtaagtacagctgaaattcagag gacccataagagttcacatgaaaaaaatcaattcatttgaaaaggcaaga tgcaggagagaggaagccttgcaaacctgcagactgcttttttgcccaata tagattgggtaaggctgcaaaacataagcttaattagctcacatgctctg ctctcacgtggcaccagtggatagtgtgagagaattaggctgtagaacaa atggccttctctttcagcattcacaccactacaaaatcatctttttatatc aacagaagaataagcataaactaagcaaaaggtcaataagtacctgaaac caagattggctagagatatatcttaatgcaatccattttctgatggattg ttacgagttggctatataatgtatgtatggtatttttgatttgtgtaaaag ttttaaaaatcaagctttaagtacatggacattttttaaataaaatattta aagacaatttagaaaattgccttaatatcattgttggctaaatagaatag gggacatgcatattaaggaaaaggtcatggagaaataatattggtatcaa acaaatacattgatttgtcatgatacacattgaatttgatccaatagttt aaggaataggtaggaaaatttggtttctattttttcgatttcagtaaatca gtgacataaataattcttagcttattttatatttccttgtcttaaatact gagctcagtaagttgtgttaggggattattctcagttgagactttctta tatgacattttactatgttttgacttcctgactattaaaaataaatagta gaaacaattttcataaagtgaagaattatataatcactgctttataactg actttattatatttatttcaaagttcatttaaaggctactattcatcctc tgtgatggaatggtcaggaatttgttttctcatagtttaattccaacaac aatattagtcgtatccaaaataacctttaatgctaaactttactgatgta tatccaaagcttctccttttcagacagattaatccagaagcagtcataaa cagaagaataggtggtatgttcctaatgatattatttctactaatggaat aaactgtaatattagaaattatgctgctaattatatcagctctgaggtaa tttctgaaatgttcagactcagtcggaacaaattggaaaatttaaatttt tattcttagctataaagcaagaaagtaaacacattaatttcctcaacatt tttaagccaattaaaaatataaaagatacacaccaatatcttcttcaggc tctgacaggcctcctggaaacttccacatattttttcaactgcagtataaa gtcagaaaataaagttaacataacttttcactaacacacacatatgtagat ttcacaaaatccacctataattggtcaaagtggttgagaatatattttt agtaattgcatgcaaaattttttctagcttccatcctttctccctcgtttc ttctttttttgggggagctggtaactgatgaaatcttttcccaccttttc tcttcaggaaatataagtggttttgtttggttaacgtgatacattctgta tgaatgaaacattggagggaaacatctactgaatttctgtaatttaaaat attttgctgctagttaactatgaacagatagaagaatcttacagatgctg ctataaatagtagaaaatataaatttcatcactaaaatatgctattta aaatctatttcctatattgtatttctaatcagatgtattactcttattat ttctattgtatgtgttaatgatttatgtaaaaatgtaattgcttttcat gagtagtatgaataaaattgattagtttgtgttttcttgtctcccgaaaa aaaaaaaaaaaaaaaaaaaaaaaaaa
```

6.11. Cyclin D1
See, e.g., GenBank Accession No. NM_053056.

```
General Target Regions:
(1) 5' Untranslated Region:
                                     (SEQ ID NO: 31)
cggccccagaaaacccgagcgagtagggggcggcgcgcaggagggaggag aactggggggcgcgggaggctggtgggtgtcggggtggagatgtagaaga tgtgacgccgcggcccggcgggtgccagattagcggacggctgcccgcgg ttgcaacgggatcccgggcgctgcagcttggggaggcggactccccaggcg gcgtccgcggagacacccatccgtgsaccccaggtcccgggccgccggct cgccgcgcaccaggggccggcggacagaagagcggccgagcggctcgagg ctggggac (2) 3' Untranslated Region (3.2 kb):
                                     (SEQ ID NO: 32)
tgagggcgccaggcaggcgggcgccaccgccacccgcagcgagggcggag ccggccccaggtgctcccctgacagtccctcctctccggagcatttgat accagaagggaaagcttcattctccttgttgttggttgtttttcctttg ctctttccccccttccatctctgacttaagcaaaagaaaaagattacccaa aaactgtctttaaaagagagagagagaaaaaaaaaatagtatttgcataa ccctgagcggtgggggaggagggttgtgctacagatgatagaggattta tacccccaataatcaactcgttttatattaatgtacttgtttctctgttg taagaataggcattaacacaaaggaggcgtctcgggagaggattaggttc catcctttacgtgtttaaaaaaagcataaaaacattttaaaaacataga aaaattcagcaaaccattttttaaagtagaagagggttttaggtagaaaaa catattcttgtgcttttcctgataaagcacagctgtagtgggttctagg catctctgtactttgcttgctcatatgcatgtagtcactttataagtcat tgtatgttattatattccgtaggtagatgtgtaacctcttcaccttattc atggctgaagtcacctcttggttacagtagcgtagcgtggccgtgtgcat gtcctttgcgcctgtgaccaccacccccaacaaaccatccagtgacaaacc atccagtggaggtttgtcgggcaccagccagcgtagcagggtcgggaaag
```

```
gccacctgtcccactcctacgatacgctactataaagagaagacgaaata gtgacataatatattctattttttatactcttcctattttttgtagtgacct gtttatgagatgctggttttctacccaacggccctgcagccagctcacgt ccaggttcaacccacagctacttggtttgtgttcttcttcatattctaaa accattccatttccaagcactttcagtccaataggtgtaggaaatagcgc tgttttttgttgtgtgtgcagggagggcagttttctaatggaatggtttgg gaatatccatgtacttgtttgcaagcaggactttgaggcaagtgtgggcc actgtggtggcagtggaggtgggtgtttggaggctgcgtgccagtcaa gaagaaaaaggtttgcattctcacattgccaggatgataagttcctttcc ttttattaaagaagttgaagtttaggaatcattggtgccaactggtgttt gaaagtagggacctcagaggtttacctagagaacaggtggtgttaaggt tatcttagatgtttcacaccggaaggttttttaaacactaaaatatataat ttatagttaaggctaaaaagtatatttagtgcagaggatgttcataaggc cagtatgatttataaatgcaatctccccttgatttaaacacacagataca cacacacacacacacacacacaaaccttctgcctttgatgttacagat ttaatacagtttattttttaaagatagatccttttataggtgagaaaaaaa caatctggaagaaaaaaaccacacaaagacattgattcagcctgtttggc gtttcccagagtcatctgattggacaggcatgggtgcaaggaaaattagg gtactcaacctaagttcggttccgatgaattcttatcccctgcccttcc tttaaaaaacttagtgacaaaatagacaatttgcacatcttggctatgta attcttgtaattttttattaggaagtgttgaagggaggtggcaagagtgt ggaggctgacgtgtgagggaggacaggcgggaggaggtgtgaggaggagg ctcccgaggggaaggggcggtgcccacaccggggacaggccgcagaccat tttatattgcgctgctaccgttgacttccaggcacggtttggaaatattc acatcgcttctgtgtatctcttcacattgtttgctgctattggaggatc agttttttgttttacaatgtcatatactgccatgtactagttttagtttt ctcttagaacattgtattacagatgcctttttgtagtttttttttttttt tatgtgatcaattttgacttaatgtgattactgctctattccaaaaggt tgctgtttcacaatacctcatgcttcacttagccatggtggacccagcgg gcaggttctgcctgctttggcgggcagacacgcgggcgcgatcccacaca ggctggcggggccggccccgaggccgcgtgcgtgagaaccgcgccggtg tccccagagaccaggctgtgtccctatctcttccagcgcctgtgatgctg ggcacttcatctgatcgggggcgtagcatcatagtagtttttacagctgt gttattctttgcgtgtagctatggaagttgcataattattattattatta ttataacagtgtgtcttacgtgccaccacggcgttgtacctgtaggact ctcattcgggatgattggaatagctctggaatttgttcaagtttgggt atgtttaatctgttatgtactagtgttctgtttgttattgttttgttaat tacaccataatgctaatttaaagagactccaaatctcaatgaagccagct cacagtgctgtgtgccccggtcacctagcaagagccgaaccaaaagaatt tgcaccccgctgcgggcccacgtggttggggccctgccctggcagggtca
```

```
tcctgtgacggaggccatacgggcacaggcccaccccgccccaccccctcc agaacacggctcacgcttacctcaaccatcctggctgcggcgtagtagaa ccactcgggggccttgagggacgctttgtctgtcgtgatggggcaagggc acaagtcctggatgttgtgtgtatcgagaggccaaaggctggtggcaagt gcacggggcacagcggagtctgtcctgtgacgcgcaagtctgagggtctg ggcggcgggcggctgggtctgtgcatttctggttgcaccgcggcgcttcc cagcaccaacatgtaaccggcatgtttccagcagaagacaaaaagacaaa catgaaagtctagaaataaaactggtaaaacccccaaaaaaaaaaaaaaa
```

6.12. Murine Double Minute 2
See, e.g., GenBank Accession No. NM_002392.

```
General Target Regions:
(1) 5'End/Intron 1/p53 BS for s-mdm-2: U39736:
                                      (SEQ ID NO: 33)
gcaccgcggcgagcttggctgcttctggggcctgtgtggccctgtgtgtc ggaaagatggagcaagaagccgagcccgaggggcggccgcgacccctctg accgagatcctgctgctttcgcagccaggagcaccgtccctccccggatt agtgcgtacgagcgcccagtgccctggcccggagagtggaatgatccccg aggcccagggcgtcgtgcttccgcgcgccccgtgaaggaaactggggagt cttgagggaccccgactccaagcgcgaaaaccccggatggtgaggagca ggtactggcccggcagcgagcggtcacttttgggtctgggctctgacggt gtcccctctatcgctggttcccagcctctgcccgttcgcagcctttgtgc ggttcgtgnctgggggctcggggcgcggggcgcggggcatgggncacgtg gctttgcggaggttttgttggactggggctagacagtccccgccagggag gagggcgggatttcggacggctctcgcggcggtgggggtgggggtggttc ggaggtctccgcgggagttcagggtaaaggtcacggggccggggctgcgg gccgcttcggcgcgggaggtccggatgatcgcagtgcctgtcgggtcact agtgtgaacgctgcgcgtagtctgggcgggattgggccggttcagtgggc aggttgactcagcttttcctcttgagctggtcaagttcagacacgttccg aaactgcagtaaaaggagttaagtcctgacttgtctccagctggggctat ttaaaccatgcattttcccagctgtgttCAGTGGCGATTGGAGGGTAGAC CTGTGGGCACGGACGCACGCCACTTTTTCTCTGCTGATCCAGgtaagcac cgacttgcttgtagctttagttttaactgttgtttatgttcttatatat gatgtattttccacagatgtttcatgatttccagttttcatcgtgtcttt ttttcttgtaggcaaatgtgcaataccaacatgtctgtacc (2) 3'UTR (GenBank Accession No. gi|9150029|gb|
BE275079.1|BE275079):
                                      (SEQ ID NO: 34)
tagttgacctgtctataagagaattatatatttctaactatataaccta ggaatttagacaacctgaaatttattcacatatatcaaagtgagaaaatg cctcaattcacatagatttcttctattagtataattgacctactttggta gtggaatagtgaatacttactataatttgacttgaatatgtagctcatca ttacaccaactcctaatttttaaataatttctactctgtcttaaatgagaa gtacttggtttttttttttcttaaatatgtatatgacatttaaatgtaact
```

```
tattatttatttgagaccgagtatgctctgttacccaggctggagtgcag tgggtgatcttggctcactgcaagctctgccctcccgggttcgaccat tctcctgcctcagcctcccaattagcttggcctacagtcatctgccacca cacctggctaatttttgtacattagtagagacagggtttcaccgtgtta gccaggatggtctcgatctcctgacctcgtgatccgccaactcggcctc ccaaagtgagggattacaggcatgagccaccgtgctctccagcctaggca acagagtgagactctgtctccaaaaaaaaaaaaaaaaaaggggactata acaccccagggaaagggacaggtgggacattcttattcttaatttaaat aaattgacagggaaagttgggccactcttgagcttgtgggtgctcacca ggttgacccaaaaaagaagcatccacaaaacattaatttattcccta atataccgcctctgtgagttaagggataatgcatcaggactatgcaacc agacaaaattatttaaaaacgccacttgggggggaggcgggtccctcctg gggattcgcctttgtgggagagaaactgcacagacttgggcaaataatg tttttgtcaccccaaaacgtattcgcgagacatttcattagaacgaagc tttaccctaatattgaactccccatttaaacagtttccacacacacttag ggagattttccctctgtgagttccgcagaacaatagttggacgggaata gaaccctgaaacactttagttcaccacgaactattatagggcggg
```

6.13. Protein Tyrosine Phosphatase Type IVA, Member 3
See, e.g., GenBank Accession No. NM_032611.

```
General Target Regions:
(1) 5' Untranslated Region:
                                (SEQ ID NO: 35)
tgactatccagactgagagacgggagtttggagttgcccgctttactttg gttgggttgggggggcggcggctcgttttgttccttttcttattaagag ttgggtatcttttttaattatccaaacagtgggcagatcctcccccacac ccaagtatttgcacaatatttgtgcggggtatgggggtgggtttttaaat ctcgtttctcttggacaagcacagggatctcgttctcctcattttttggg ggtgtgtgggacttctcaggtcgtgtccccagccttctctgcagtccct tctgccctgccgggccgtcggagggcgcc (2) 3' Untranslated Region:
                                (SEQ ID NO: 36)
tagctcaggaccttggctgggcctggtcgtcatgtaggtcaggaccttgg ctggacctggaggccctgcccagccctgctctgcccagcccagcagggc tccaggccttggctggcccacatcgccttttcctccccgacacctccgt gcacttgtgtccgaggagcgaggagcccctcgggccctggtggcctctg ggccctttctcagtctccgccactccctctggcggcgctggccgtggctc tgtctctctgaggtgggtcgggcgccctctgcccgcccctcccacacca gccaggctggtctcctctagcctgtttgttgtggggtgggggtatattt gtaaccactgggcccccagcccctcttttgcgacccttgtcctgacctg ttctcggcacccttaaattattagacccgggcagtcaggtgctccggac acccgaaggcaataaaacaggagccgtgaaaaaaaaaaaaaaaaaaaa aaaaaaaaaaaaaaaaaaaaaaaaaaaaaaaaaaaaaaa
```

6.14. Tissue Inhibitor of Metalloproteinase
See, e.g., GenBank Accession No. XM_003061 for TIMP-4.

```
General Target Regions:
(1) 5' Untranslated Region (GenBank Accession No.
gi|11293824|gb|BF346229.1|BF346229):
                                (SEQ ID NO: 37)
gctcagcaaggggtccgtccttctctgtcactgtctcttttgcctgttgt aattctgtctgcctctctgggactctgcctgtctcactctttctgtctgt gcctctcctcactcttgttctttctgcctgaatcacagccctcagttttt ctgtcctcatgcatttgtattgtggctctttccgtctttctgcccttgac accatccctctcccagtgatccctctgcttccagatcgcttcatgact taggcagggaaacagaggtcagggcctccttccaggatccctctgcatct tactgagtatgcaggtcggaagagcctcgggtcctgcctccgcgggtggc ctagagccaaaggaaggcggagcccgtcggggcgggattggcccttaggg ccacctcataaagcctgggcgaggggcacaacggccttgggaaggagcc ctgctggggccgtccagtcccccagacctcacaggctcagtcgcggatct gcagtgtc (2) 3' Untranslated Region:
                                (SEQ ID NO: 38)
tagtagggaccagtgaccatcacatcccttcaagagtcctgaagatcaag ccagttctccttccctgcagagctttggccattaccacctgacctcttgc tgccagctaataagaagtgccaagtggacagtatggccactgtcaaggca gggaagggccatgacttttctgccctgccctcagcctgttgccctgcct cccaaacccccattagtctagccttgtagctgttactgcaagtgtttcttc tggcttagtctgttttctaaagccaggactattcccttttcctccccagga atatgtgtatcctttgtcttaatcgatcttggtaggggagaaatggcgaat gtcatacacatgagatggtatatccttgcgatgtacagaatcagaaggtg gtttgacagcatcataaacaggctgactggcaggaatgaaaaaaaaaaaa aaaaaaa
```

See, e.g., GenBank Accession No. S48568 for TIMP-2.

```
General Target Regions:
(1)5' Untranslated Region (84% GC-rich):
                                (SEQ ID NO: 39)
ggggccgccgagagccgcagcgccgctcgcccgccgcccccacccgc cgccccgcccggcgaattgcgccccgcgccctcccctcgcgcccccgag acaaagaggagagaaagtttgcgcggccgagcgggcaggtgaggagggt gagccgcgcggaggggcccgcctcggccccggctcagccccgcccgcg ccccagcccgccgcgcgagcagcgcccggaccccccagcggcggccc cgcccgcccagcccccggccgcc (2) 3' Untranslated Region (GenBank Accession No.
18505971|gb|BM456931.1|BM456931):
                                (SEQ ID NO: 40)
taagcaggcctccaacgccctgtggccaactgcaaaaaagcctccaa gggtttcgactggtccagctctgacatccttcctggaaacagcatgaa taaaacactcatcccatgggtccaaattaatatgattctgctccccct
```

-continued
tctccttttagacatggttgtgggtctggagggagacgtgggtccaagg tcctcatcccatcctccctctgccaggcactatgtgtctggggcttcga tccttgggtgcaggcagggctgggacacgcggcttccctcccagtccct gccttggcaccgtcacagatgccaagcaggcagcacttagggatctccc agctgggttagggcagggcctggaaatgtgcattttgcagaaacttttg agggtcgttgcaagactgtgtagcaggcctaccaggtcccttcatctt gagagggacatggcccttgttttctgcagcttccacgcctctgcactc cctgccctggcaagtgctcccatcgcccccggtgcccaccatgnagct ccccgcacctgactcccccacatccaagggcagccctggaaccagtgg gctagttccttgaaggaagccccactcattcctattaatccctcagaat tcccgggggagccttccctcctgaaccttggtaaaaaatggggaacga gaaaaaccccgcttggagctgtgcgtttccagccctacttgagagnc ttttttttgggggccg

6.15. Peroxisome Proliferative Activated Receptor-g
See, e.g., GenBank Accession No. NM_138712.

```
General Target Regions:
(1) 5' Untranslated Region (GenBank Accession No.
12786927|emb|AL523434.1|(AL523434):
                                            (SEQ ID NO: 41)
```
cgcgccgggcccggctcggcccgacccggctccgcgcgggcaggcggggc ccagcgcactcggagcccgagcccgagccgcagccgccgcctgggcgct tgggtcggcctcgaggacaccggagaggggcgccacgccgccgtggccgc agatttgaaagaagccgacactaaaccaccaatatacaacaaggccattt tgtcaaacgagagtcagcctttaacgaaa

```
(2) 3' Untranslated Region:
                                            (SEQ ID NO: 42)
```
tagcagagagtcctgagccactgccaacatttcccttcttccagttgcac tattctgagggaaaatctgacacctaagaaatttactgtgaaaaagcatt ttaaaaagaaaaggttttagaatatgatctatttttatgcatattgtttat aaagacacatttacaatttacttttaatattaaaaattaccatattatga aaaaaaaaaaaaaaaaaaaaaaaaaaaaaa

6.16. PC-Cell Derived Growth Factor/Epithelin/Granulin Precursor
See, e.g., GenBank Accession No. NM_002087.

```
General Target Regions:
(1) 5' Untranslated Region:
                                            (SEQ ID NO: 43)
```
ggcacgaggggcgagaggaagcagggaggagagtgatttgagtagaaaag aaacacagcattccaggaggcccacctctatattgataagtagccaatg ggagcgggtagccctgatccctggccaatggaaactgaggtaggcgggtc atcgcgctggggtctgtagtctgagcgctacccggttgctgctgcccaag gaccgcggagtcggacgcaggcagaccatgtggaccctggtgagctgggt ggccttaacagcagggctggtggctggaacgcggtgcccagatggtcagt tctgccctgtggcctgctgcctggaccccggaggagccagctacagct -continued
```
(2) 3' Untranslated Region:
                                            (SEQ ID NO: 44)
```
tgagggacagtactgaagactctgcagccctcgggaccccactcggaggg tgccctctgctcaggcctccctagcacctcccctaaccaaattctccag gaccccattctgagctccccatcaccatgggaggtggggcctcaatctaa ggccttccctgtcagaagggggttgtggcaaaagccacattacaagctgc catcccctcccgtttcagtggaccctgtggccaggtgatttccctatcc acagggtgtttgtgtgtgtgcgcgtgtgcgtttcaataaagtttgtaca ctttcaaaaaaaaaaaaaaaaaaaaaaaaaaaa

6.17. Angiogenin
See, e.g., GenBank Accession No. M11567.

```
General Target Regions:
(1) 5' Untranslated Region:
                                            (SEQ ID NO: 45)
```
tgtttgcattaagttcatagattataatttgtaatggaatcaacaccaaa tgcaaattagaaagagagcccactttgctcacccagtcacgtcttcccat gtaaccatagaacgttggggtcagtgtctttctagatccacagtcttgct ctcagaacaggctagccacaccacaggcctagtgccaggacccatggcct tttttttaagctcagactcccttctgtgaacagcaatatccccacaacttg tacaacattggtgcttcctgcaagggctacagaactatttgatacgaaaa tgttcattgacttacacacaagagaagcacaaaataaaaaattaataatt aatttaatgtctttgaaaatgtaccatttattttttacatttggggtcata agaattgtattacacttaagaatgcaatacaatttgaagatcagatttt ctccctttgtgagaatttctcagtatgtgtgatgactaccaagaaatcat agccagtcataaattcagtgagttactcataaacgaacaagaaccaccta cttcttggggaggtaggtctgcttcccttcaactcaggatacaactgctt tcaactgctttcttcacattagctgactaattagctagaagcctgtcgta aacaatttatggttgactccttccctgggctcagggttccctagaacag agaggtccccaaatcccggtagtggcctgtccgcctaagctctgcctcct gccagatcagcaggcagcattagattctcataggagctggacgcctattg tgaactgcgcatgtgcgggatccagattgtgcactctttatgagaatcta actaatgcttgatgatctatctgaaccagaacaatttcatcctgaaacca tcccccaccaatccatagaaatactccttccacaaaaatgatccctggtg ccaaaaatgttagagaccactcccctaaaactctcttcttagctctcacc tcctgtattactatctcatctcagtacattgaagcccccatctttccc atggatgcctcatttcctattagggaggcattttttatttttttgttttt atttttttccgagacggagtctcgctctgtcgccaaggctggagtgcagt ggcgcgatctcggctcactgcaagctccgcctcccgggttcacgccattc tcctgcctcagcctcccaagtagctgggactacaggcgcccgcactacgc ccggctaattttttgtatttttagtagagacggggtttcaccgtggtagc caggatggtctcgatctcctgacctcgtgatccgcccgccttggcctccc aaagtgctgggattacaggcgtgagaccgcgcccggccgtcatttggtat gtcttaatgtgcctcaggacctagcacagtccctggtacccagtagagac (2) 3' Untranslated Region:

(SEQ ID NO: 46)
taaccagcgggcccctggtcaagtgctggctctgctgtccttgccttcca tttcccctctgcacccagaacagtggtggcaacattcattgccaagggcc caaagaaagagctacctggaccttttgttttctgtttgacaacatgttta ataaataaaaatgtcttgatatcagtaagaatcagagtcttctcactgat tctgggcatattgatctttcccccattttctctacttggctgctccctga gaggactgcataggatagaaatgccttttctttctttttcgttttttt ttttttttttttgagatggagtctcactctgtcgcccaggcttaagtgc aatggcacaatctcggctcactgcaacctctctctcctgggttcaagtga ttctcctgcctcagcctcccaaatagctgagattacaggcatgcaccacc acacctggctaattttttgtgttttttagtagagacagggtttcaccgttttt ggccaggttggtcttgaactcctgacctcgggagatccgcccaccttggc ctctctttgtgctgggattacaggcatgagccactgagccgggccactttt ttccttatcagtcagttttttacaagtcattagggaggtagacttacctc tctgtgaaggaaagtatggtatgttgatctacagagagagatggaaaaat tccagggctcgtagctactaagcagaattccaagataggcaaattgttt tttctgtcaaataataagctaatattacttctacaaatatgagaccttgg agagaagtttccaaggaccaagtaccaacataccaacagattattatagt ttctctcactcttacacacacacacacatatacacatatgtaatccag catgaataccaaaattcattcagggtagccacatttgtcttaatcgagag ataattttgatgtttgaatggaatgctcccaggatattctcttgtcatgg ttattttatataaaattcaaaaaccaattacattattttcctctgtaatat ttactttatcaactaatgtctggcaagtgtgatgttttggggaagttata gaagattccggccaggcgcttatctcacgcttgtaatccagcactttggg aagctgaggcggacagatcacgaggtcaagagatcaagaccatcctggac aacatggtgaaccttgtctctactaaaaatgtgaaaattagagggcgtg gtggcacacacctatagtcccagctactcgggaggctgaggcaggagaat cgcttgaacctaggaggcggaggttgcactgagccgagatcacgccactg cactccagcctgggcgacagagcgagactccatctcaaaaaaaaaaaaaa aagaaagatcccagtttatccccagtttatcccttattcttcctcaattct caagatttgtttttaagttaacataacttaggttaacacactattgtaaa atacactgttcaatctacagactcagtggttagcttcctgttaactaatt tctgttgacaggtacttggatatttattagaaagtggttgccaataaa ttagttataagtcgccagtttcactgccttgtgaacacataattattgtg gtctcagtattccctatggtggcttacctgctcctggtattgccctgaaa tgggccaaaagccgtggctccccaatgctcaggttatagaacattgtcca ggtaccacctaggagagcccagcctcactgaaagtattcaaatttaggaa tgggtttgagaagtaggtagctggtatgtgatagcacaagaatctctctt ccttgggttagtctgtttcaaaactgaaaacactgtcattccttaagaaa ataggaaaaagtattccaaacctctgtcactagaaaatttgccatattac caaatctcaaaaacctctcaggaaatgagaaagtcccagtttctggtaaa ctatttgggccatttctcaagttctccttccagtgctatttccttgaggt gaggcaaagttactcaagatcatcgctgccactcaaggccttgatagggc aagtgaaaggcatggaccattattatattgatcacagcataagctgtgaa aacccacatcttctccaaacatctgcttggagcattatcatcgcatagtt tgctctggtgttcagggaaatcgctgtttcataggaaatcacatggcagt gggatgggagtgttcctgacctgccgatggtactggcacctgagcaagc attcctagtccttttggtctgggcctcttgttctatcacaaccacaagc tgtttaaaataaaaacgtcaagtcacaggcaggtcattttatcctgcgtg aatcaattgaag 6.18. Hypoxia-Inducible Factor-a See, e.g., GenBank Accession No. U22431.

General Target Regions:
(1) 5' Untranslated Region:

(SEQ ID NO: 47)
tcctcagtgcacagtgctgcctcgtctgaggggacaggaggatcaccctc ttcgtcgcttcggccagtgtgtcgggctgggccctgacaagccacctgag gagaggctcggagccgggcccggaccccggcgattgccgcccgcttctct ctagtctcacgaggggtttcccgcctcgcaccccccacctctggacttgcc tttccttctcttctccgcgtgtgggaggagccagcgcttaggccggagcg agcctgggggccgcccgccgtgaagacatcgcggggaccgattcacc (2) 3' Untranslated Region (GenBank Accession No. gi|19116743|gb|BM799920.1|BM799920):

(SEQ ID NO: 48)
tgagcttttcttaatttcattcctttttttggacactggtggctcacta cctaaagcagtctatttatattttctacatctaattttagaagcctggct acaatactgcacaaacttggttagttcaattttttgatccccttttctactt aatttacattaatgctcttttttagtatgttctttaatgctggatcacag acagctcattttctcagttttttggtatttaaaccattgcattgcagtag catcattttaaaaaatgcacctttttatttatttattttttggctagggag tttatcccttttttcgaattattttttaagaagatgccaatataatttttgt aagaaggcagtaacctttcatcatgatcataggcagttgaaaaattttta caccttttttttcacattttacataaataataatgctttgccagcagtac gtggtagccacaattgcacaatatattttcttaaaaaataccagcagtta ctcatggaatatattctgcgtttataaaactagttttttaagaagaaattt ttttttggcctatgaaattgttaaacctggaacatgacattgttaatcata taataatgattcttaaatgctgtatggtttattatttaaatgggtaaagc catttacataatatagaaagatatgcatatatctagaaggtatgtggcat ttattttggataaaattctcaattcagagaaatcatctgatgtttctatag -continued tcactttgccagctcaaaagaaaacaataccctatgtagttgtggaagtt tatgctaatattgtgtaactgatattaaacctaaatgttctgcctaccct gttggtataaagatattttgagcagactgtaaacaagaaaaaaaaatca tgcattcttagcaaaattgcctagtatgttaatttgctcaaaatacaatg tttgattttatgcactttgtcgctattaacatcctttttttcatgtagat ttcaataattgagtaattttagaagcattattttaggaatatatagttgt cacagtaaatatcttgttttttctatgtacattgtacaaattttcattc cttttgctctttgtggttggatctaacactaactgtattgttttgttaca tcaaataaacatcttctgtggaccaggaaaaaaaaaaaaaa 6.19. Large Tumor Suppressor, Homolog 1
See, e.g., GenBank Accession No. XM_015547.

```
General Target Regions:
(1) 5' Untranslated Region (GenBank Accession No.
gi|19008744|gb|BM695486.1|BM695486):
                            (SEQ ID NO: 49)
```
agacagccttaacccacgggcgcgggcgagtcgtatgggcaggggcaggc gggagcgacgtggggcgacgctcacgaacgatcagagctgcgggcgacgc aacgaagcccggaggccgcaggctgcgcgctccctcgcagcagccgggcg ggcaaaagcccccagtcctcggcccccgcgcaagcgacgccgggaaa

```
(2) 3' Untranslated Region (GenBank Accession No.
gi|12274655|gb|BF884528.1|BF884528):
                            (SEQ ID NO: 50)
```
taattatttatattgtaaagaattttaacagtcctggggacttccttgaa ggatcattttcacttttgctcagaagaaagactggatctatcaaataaag aagtccttcgtgtgggctacatatatagatgatcatgaagaggagtgaaa agccagaaggatatagacaaatgaggcctaagacctttcctgccagtaac tatactgtcagtagccggcaaatgttacaagaaattcgggaatccatagg aatttatctaaaccatctgatgctgctaaggctgagcataacatgagtaa aaatgtcaaccgaagatcctcgacaagtcagaaatccacccaaatttggg acgcatcataaagccttgcaggaaattcgaaactctctgcttccatttgc aaatgaaacaaattcttctcggagtacttcagaagttaatccacaaatgc ttcaagacttgcaagctgctggatttgatgaggatatggttatacaagct cttcagaaaactaacaacagaagtatagaagcagcaattgaattcattag taaaatgagttaccaagatcctcgacgagagcagatggctgcagcagctg ccagacctattaatgccagcatgaaaccagggaatgtgcagcaatcagtt aaccgcaaacagagctggaaaggttctaaagaatccttagttcctcagag gcatggcccgccactaggagaaagtgtggcctatcattctgagagtccca actcacagacagatgtaggaagacctttgtctggatctggtatatcagca tttgttcaagctcaccctagcaacggacagagagtgaaccccccaccacc acctcaagtaaggagtgttactcctccaccacctccaagaggccagactc cccctccaagaggtacaactccacctcccccttcatgggaaccaaactct caaacaaagcgctattctggaaacatggaatacgtaatctcccgaatact cctgtcccacctggggcatggcaagagggctatcctccaccacctctcaa cacttcccccatgaatcctcctaatcaaggacagagaggcattagttctg ttcctgttggcagacaaccaatcatcatgcagagttctagcaaatttaac tttccatcagggagacctggaatgcagaatggtactggacaaactgattt catgatacaccaaaatgttgtccctgctggcactgtgaatcggcagccac cacctccatatcctctgacagcagctaatggacaaagcccttctgcttta caaacaggggatctgctgctccttcgtcatatacaaatggaagtattcc tcagtctatgatggtgccaaacagaaatagtcataacatggaactatata acattagtgtacctggactgcaaacaaattggcctcagtcatcttctgct ccagcccagtcatccccgagcagtgggcatgaaatccctacatggcaacc taacataccagtgaggtcaaattcttttaataacccattaggaaatagag caagtcactctgctaattctcagccttctgctacaacagtcactgcaatt acaccagctcctattcaacagcctgtgaaaagtatgcgtgtattaaaacc agagctacagactgctttagcacctacacaccccttcttggataccacagc caattcaaactgttcaacccagtccttttcctgagggaaccgcttcaaat gtgactgtgatgccacctgttgctgaagctccaaactatcaaggaccacc accaccctacccaaaacatctgctgcaccaaaacccatctgttcctccat acgagtcaatcagtaagcctagcaaagaggatcagccaagcttgcccaag gaagatgagagtgaaaagagttatgaaaatgttgatagtggggataaaga aaagaaacagattacaacttcacctattactgttaggaaaaacaagaaag atgaagagcgaagggaatctcgtattcaaagttattctcctcaagcatttc aaattctttatggagcaacatgtagaaaatgtactcaaatctcatcagca gcgtctacatcgtaaaaaacaattagagaatgaaatgatgcgggttggat tatctcaagatgcccaggatcaaatgagaaagatgctttgccaaaaagaa tctaattacatccgtcttaaaagggctaaaatggacaagtctatgtttgt gaagataaagacactaggaataggagcatttggtgaagtctgtctagcaa gaaaagtagatactaaggctttgtatgcaacaaaaactcttcgaaagaaa gatgttcttcttcgaaatcaagtcgctcatgttaaggctgagagagatat cctggctgaagctgacaatgaatgggtagttcgtctatattattcattcc aagataaggacaatttatactttgtaatggactacattcctgggggtgat atgatgagcctattaattagaatgggcatctttccagaaagtctggcacg attctacatagcagaacttacctgtgcagttgaaagtgttcataaaatgg gttttattcatagagatattaaacctgataatattttgattgatcgtgat ggtcatattaaattgactgactttggcctctgcactggcttcagatggac acacgattctaagtactatcagagtggtgaccatccacggcaagatagca tggatttcagtaatgaatgggggatccctcaagctgtcgatgtggagac agactgaagccattagagcggagagctgcacgccagcaccagcgatgtct agcacattctttggttgggactcccaattatattgcacctgaagtgttgc tacgaacaggatacacacagttgtgtgattggtggagtgttggtgctatt catttgaaatgttggtgggacaacctcctttcttggcacaaacaccatta gaaacacaaatgaaggtcacctgctgctatatacatcattggctcgagaa gaaactactgaacaccctgcgagagagaagcctagaaaagaaagaaaggg ccaaaaggttttgaactcttcatccctaatttgctacactgatcaaaacc aagtaagggctcctgaagtccatgagtctatcatcaatcagcacaaatgc tatactagtttgtaactgcggggtcagttgtgaaggggaaggacagcagt cttatccatattccaggaagccacagtaaactgctcga

6.20. P-Glycoprotein

See, e.g., GenBank Accession No. M14758.

General Target Sequences:
(1) 5' Untranslated Region:
(SEQ ID NO: 51)
cctactctattcagatattctccagattcctaaagattagagatcatttc tcattctcctaggagtactcacttcaggaagcaaccagataaaagagagg tgcaacggaagccagaacattcctcctggaaattcaacctgtttcgcagt ttctcgaggaatcagcattcagtcaatccgggccgggagcagtcatctgt ggtgaggctgattggagggcaggaacagcgccggggcgtgggctgagcac agcgcttcgctctctttgccacaggaagcctgagctcattcgagtagcgg ctcttccaagctcaaagaagcagaggccgctgttcgtttcctttaggtct ttccactaaagtcggagtatcttcttccaagatttcacgtcttggtggcc gttccaaggagcgcgaggtcggg (2) 3' Untranslated Region (GenBank Accession No.:
gi|13334786|gb|BG428280.1|BG428280):
(SEQ ID NO: 52)
tgaactctgactgtatgagatgttaaatacttttaatatttgtttagat atgacatttattcaaagttaaaagcaaacacttacagaattatgaagagg tatctgtttaacatttcctcagtcaagttcagagtcttcagagacttcgt aattaaaggaacagagtgagagacatcatcaagtggagagaaatcatagt ttaaactgcattataaattttataacagaattaaagtagattttaaaaga taaaatgtgtaattttgttatattttcccatttggactgtaactgactg ccttgctaaaagattatagaagtagcaaaaagtattgaaatgtttgcata aagtgtctataataaaactaaacttttcatgtgactggagtcatcttgtcc aaactgcctgtgaatatatcttctctcaattggaatattgtagataactt ctgctttaaaaaagttttctttaaatatacctactcattttttgtgggaat ggttaagcagtttaaataattcctgtgtatatgtctatcacatagggtc taacagaacaatctggattcattatttctaggacttgatcctgctgatgc tgaatttgcacattaaggtgtgttaacaaccaaaacacagatcgatataa gaagtaaggaggtggggagaggcaaattatgatgtgctatgagttagatg tatagt

6.21. CD82 Antigen

See, e.g., GenBank Accession No. NM_002231

General Target Regions:
(1) 5' Untranslated Region (GenBank Accession No.
gi|19088880|gb|BM759265.1|BM759265):
(SEQ ID NO: 53)
agtccgcggcgttccccggctgcagccgggaggggccgaggagtgactg agccccgggctgtgcagtccgacgccgactgaggcacgagcgggtgacgc tgggcctgcagcgcggagcagaaagcagaacccgcagagtcctccctgag agtgtggacgacacgtgggcacaggcagaagtgggccctgtgaccagctg cactggtttcgtggaaggaagctccaggactggcggg (2) 3' Untranslated Region:
(SEQ ID NO: 54)
tgaggcagctgctatcccc atacccctgcctggccccaacctcagggctcccaggggtctccctggctc cctcctccaggcctgcctcccacttcactgcgaagaccctcttgcccacc ctgactgaaagtagggggctttctggggcctagcgatctctcctggccta tccgctgccagccttgagccctggctgttctgtggttcctctgctcaccg cccatcagggttctcttatcaactcagagaaaaatgctccccacagcgtc cctggcgcaggtgggctggacttctacctgccctcaagggtgtgtatatt gtatagggcaactgtatgaaaaattggggaggagggggccgggcgcggt gctcacgcctgtaatcccagcactttgggaggccgagcgggtggatcac gaggtcaggagatcgagaccatcctggctaacatggtgaaaccccgtctc tactaaaaatacaaaaaaaatttagccgggcgcggtggcgggcacctgta gtcccagctacttgggaggctgaggcaggagaatggtgtgaacccgggag cggaggttgcagtgagctgagatcgtgctactgcactccagcctgggga cagaaagagactccgtctcaa

6.22. 6.22. Bcl-2

See, e.g., GenBank Accession No. M14745

General Target Regions:
(1) 5' Untranslated Region (GenBank Accession No.
gi|19887364|gb|BQ061909.1|BQ061909):
(SEQ ID NO: 55)
tttctgtgaagcagaagtctgggaatcgatctggaaatcctcctaatttt tactccctctccccccgactcctgattcattgggaagtttcaaatcagct ataactggagagagctgaagattgatgggatcgttgccttatgcctttgt tttggttttacaaaaaggaaacttgacagaggatcatgctatacttaaaa aatacaacatcgcagaggaagtagactcatattaaaaatacttactaata ataacgtgcctcatgaagtaaagatccgaaaggaattggaataaaactttt cctgcatctcaagccaaggggaaacaccagaatcaaggttccgcgtgat tgaagacacccctcgtccaagaatgcaaagcacatccaataaaagagct ggattataactcctcttctttactgggggccgtggggtgggagctgggc gagaggtgccgttggcccccgttgcttttcctctgggaggg (2) 3' Untranslated Region:
(SEQ ID NO: 56)
tgaagtcaacatgcctgccccaaacaaatatgcaaaaggttcactaaagc agtagaaataatatgcattgtcagtgatgttccatgaaacaaagctgcag gctgtttaagaaaaaataacacacatataaacatcacacacacagacaga cacacacacacaacaattaacagtcttcaggcaaaacgtcgaatcagc tatttactgccaaagggaaatatcatttattttttacattattaagaaaa aaagatttatttatttaagacagtcccatcaaaactcctgtctttggaaa tccgaccactaattgccaagcaccgcttcgtgtggctccacctggatgtt -continued

```
ctgtgcctgtaaacatagattcgctttccatgttgttggccggatcacca
tctgaagagcagacggatggaaaaaggacctgatcattggggaagctggc
tttctggctgctggaggctggggagaaggtgttcattcacttgcatttct
ttgccctgggggctgtgatattaacgagggagggttcctgtgggggaa
gtccatgcctccctggcctgaagaagagactctttgcatatgactcacat
gatgcatacctggtgggaggaaaagagttgggaacttcagatggacctag
tacccactgagatttccacgccgaaggacagcgatgggaaaaatgccctt
aaatcataggaaagtattttttttaagctaccaattgtgccgagaaaagca
ttttagcaatttatacaatatcatccagtaccttaagccctgattgtgta
tattcatatattttggatacgcaccccccaactcccaatactggctctgt
ctgagtaagaaacagaatcctctggaacttgaggaagtgaacatttcggt
gacttccgcatcaggaaggctagagttacccagagcatcaggccgccaca
agtgcctgcttttaggagaccgaagtccgcagaacctgcctgtgtcccag
cttggaggcctggtcctggaactgagccggggccctcactggcctcctcc
agggatgatcaacagggcagtgtggtctccgaatgtctggaagctgatgg
agctcagaattccactgtcaagaaagagcagtagaggggtgtggctgggc
ctgtcaccctggggccctccaggtaggcccgttttcacgtggagcatggg
agccacgaccttcttaagacatgtatcactgtagagggaaggaacagag
gccctgggccctcctatcagaaggacatggtgaaggctgggaacgtgag
gagaggcaatggccacggcccattttggctgtagcacatggcacgttggc
tgtgtggccttggcccacctgtgagtttaaagcaaggcttaaatgactt
tggagagggtcacaaatcctaaaagaagcattgaagtgaggtgtcatgga
ttaattgaccctgtctatggaattacatgtaaaacattatcttgtcact
gtagtttggttttatttgaaaacctgacaaaaaaaagttccaggtgtgg
aatatgggggttatctgtacatcctggggcattaaaaaaaaaatcaatgg
tggggaactataaagaagtaacaaaagaagtgacatcttcagcaaataaa
ctaggaaattttttttttcttccagtttagaatcagccttgaaacattgat
ggaataactctgtggcattattgcattatataccatttatctgtattaac
tttggaatgtactctgttcaatgtttaatgctgtggttgatatttcgaaa
gctgctttaaaaaatacatgcatctcagcgtttttgttttaattgt
atttagttatgcctatacactattgtgagcaaaggtgatcgttttctg
tttgagattttatctcttgattcttcaaaagcattctgagaaggtgaga
taagccctgagtctcagctacctaagaaaacctggatgtcactggccac
tgaggagctttgtttcaaccaagtcatgtgcatttccacgtcaacagaat
tgtttattgtgacagttatatctgttgtccctttgaccttgttttcttgaa
ggtttcctcgtccctgggcaattccgcatttaattcatggtattcaggat
tacatgcatgtttggttaaacccatgagattcattcagttaaaaatccag
atggcaaatgaccagcagattcaaatctatggtggtttgacctttagaga
gttgctttacgtggcctgtttcaacacagacccacccagagccacctgcc
accttccgcgggggattctcatggctgtccttcagggtatcctgaaatgc
agtggtgcttacgctccaccaagaaagcaggaaacctgtggtatgaagcc
```

-continued

```
agacctccccggcgggcctcagggaacagaatgatcagacattgaatgat
tctaattttaagcaaaatattattttatgaaaggtttacattgtcaaag
tgatgaatatggaatatccaatcagtgctgctatcctgccaaaatcattt
taatggagtcagtttgcagtatgctccacgtggtaagatcctccaagctg
ctttagaagtaacaatgaagaacgtggacgcttttaatatatagcctgtt
ttgtcttctgttgttgttcaaacgggattcacagagtatttgaaaaatgt
atatatattaagaggtcacgggggctaattgctggctggctgccttttgc
tgtggggttttgttacctggttttaataacagtaaatgtgcccagcctct
tggccccagaactgtacagtattgtggctgcacttgctctaagagtagtt
gatgttgcattttccttattgttaaaaacatgttagaagcaatgaatgta
tataaaagcctcaactagtcattttttttctcctcttctttttttttatcat
tatatctaattattttgcagttgggcaacagagaaccatccctatttgt
attgaagagggattcacatagcatcttaactgctattatgaatgaaaaaa
cagtcctctgtatgtactcctctttacactggccagggtcagagttcaat
agagtatatgcactttccaaattggggacaagggctctaaaaaaagcccc
aaaaggagaagaacatctgagaacctcctcggccctcccagtccctcgct
gcacaaatactccgcaagagaggccagaatgacagctgacgggtctatg
gccatcgggtcgtctccgaagatttggcaggggcagcaaactctggcagg
cttaagatttggaataaagtcacagaatcaaggaagcacctcaatttagt
tcaaacaagacgccaacattctctccacagctcacttacctctctgtgtt
cagatgtggccttccatttatatgtgatctttgttttattagtaaatgct
tatcatctaaagatgtagctctgsgcccagtgggaaaaattaggaagtgat
tataaatcgagaggagttataataatcaagattaaatgtaaataatcagg
gcaatcccaacacatgtctagctttcacctccaggatctattgagtgaac
agaattgcaaatagtctctatttgtaattgaacttatcctaaaacaaata
gtttataaatgtgaacttaaactctaattaattccaactgtacttttaag
gcagtggctgatttagactttcttatcacttatagttagtaatgtacacc
tactctatcagagaaaaacaggaaaggctcgaaatacaagccattctaag
gaaattagggagtcagttgaaattctattctgatcttattctgtggtgtc
ttttgcagcccagacaaatgtggttacacacttttttaagaaatacaattc
tacattgtcaagcttatgaaggttccaatcagatctttattgttattcaa
tttggatctttcagggatttttttttttaaattattatgggacaaaggaca
tttgttggaggggtggagggaggaacaattttttaaatataaaacattcc
caagtttggatcagggagttggaagttttcagaataaccagaactaaggg
tatgaaggacctgtattgggtcgatgtgatgcctctgcgaagaaccttg
tgtgacaaatgagaaacattttgaagtttgtggtacgacattagattcca
gagacatcagcatggctcacagtgcagctccgtttggcagtgcaatggta
taaatttcaagaggatatgtctaatgggtatttaaacaatcaatgtgcag
ttttaactaacaggatatttaatgacaaccttctggttggtagggacatc
tgtttctaaatgttttattatgtacaatacagaaaaaaatttttataaaatt
```

-continued aagcaatgtgaaactgaattggagagtgataatacaagtcctttagtctt acccagtgaatcattctgttccatgtctttggacaaccatgaccttggac aatcatgaaatatgcatctcactggatgcaaagaaaatcagatggagcat gaatggtactgtaccggttcatctggactgccccagaaaaataacttcaa gcaaacatcctatcaacaacaaggttgttctgcataccaagctgagcaca gaagatgggaacactggtggaggatggaaaggctcgctcaatcaagaaaa ttctgagactattaataaataagactgtagtgtagatactgagtaaatcc atgcacctaaaccttttggaaaatctgccgtgggccctccagatagctca tttcattaagttttccctccaaggtagaatttgcaagagtgacagtgga ttgcatttcttttggggaagctttcttttggtggttttgtttattatacc ttcttaagttttcaaccaaggtttgcttttgtttgagttactgggtta ttttgttttaaataaaaataagtgtacaataagtgttttgtattgaaa gcttttgttatcaagatttttcatacttttaccttccatggctcttttaa gattgatacttttaagaggtggctgatattctgcaacactgtacacataa aaaatacggtaaggatactttacatggttaaggtaaagtaagtctccagt tggccaccattagctataatggcactttgtttgtgttgttggaaaaagtc acattgccattaaactttccttgtctgtctagttaatattgtgaagaaaa ataaagtacagtgtgagatactg

6.23. Insulin-Like Growth Factor Binding Protein-2
See, e.g., GenBank Accession No. X16302.

General Target Regions:
(1) 5' Untranslated Region:
(SEQ ID NO: 57)
attcggggcgagggaggaggaagaagcggaggaggcggctcccgctcgca gggccgtgcacctgcccgcccgcccgctcgctcgctcgcccgccgcgccg cgctgccgaccgccagc (2) 3' Untranslated Region:
(SEQ ID NO: 58)
tgatccaggagcccccaccatccggggggacccgagtgtcatctcttc tacaatgagcagcaggaggcttgcggggtgcacacccagcggatgcagta gaccgcagccagccggtgcctggcgccctgccccccgcccctctccaaa caccggcagaaaacggagagtgcttgggtggtgggtgctggaggatttc cagttctgacacacgtatttatatttggaaagagaccagcaccgagctcg gcacctccccggcctctctcttcccagctgcagatgccacacctgctcct tcttgctttccccggggaggaaggggggttgtggtcggggagctggggta caggtttggggaggggaagagaaatttttattttttgaaccctgtgtcc cttttgcataagattaaaggaaggaaaagt

6.24. K-Ras Oncogene Protein
See, e.g., GenBank Accession No. M54968.

General Target Regions:
(1) 5' Untranslated Region:
(SEQ ID NO: 59)
tcctaggcggcggccgcggcggcggaggcagcagcggcggcggcagtggc ggcggcgaaggtggcggcggctcggccagtactcccggccccgccattt cggactgggagcgagcgcggcgcaggcactgaaggcggcggcggggccag aggctcagcggctcccaggtgcgggagagaggcctgctgaaa (2) 3' Untranslated Region:
(SEQ ID NO: 60)
taaatacaatttgtacttattcttaaggcatactagtacaagtggtaatt tttgtacattacactaaattattagcatttgttttagcattacctaattt ttttcctgctccatgcagactgttagcttttaccttaaatgcttatttta aaatgacagtggaagttttttttcctcgaagtgccagtattcccagagt tttggttttgaactagcaatgcctgtgaaaaagaaactgaatacctaag atttctgtcttggggtttttggtgcatgcagttgattacttcttattttt cttaccaagtgtgaatgttggtgtgaaacaaattaatgaagcttttgaat catccctattctgtgttttatctagtcacataaatggattaattactaat ttcagttgagaccttctaattggttttactgaaacattgagggacacaa atttatgggcttcctgatgatgattcttctaggcatcatgtcctatagtt tgtcatccctgatgaatgtaaagttacactgttcacaaaggttttgtctc cttccactgctattagtcatggtcactctccccaaaatattatattttt tctataaaagaaaaaatggaaaaaaattacaaggcaatggaaactatt ataaggccatttccttttcacattagataaattactataaagactcctaa tagcttttcctgttaaggcagacccagtatgaatgggattattatagca accattttggggctatatttacatgctactaaatttttataataattgaa aagattttaacaagtataaaaaaattctcataggaattaaatgtagtctc cctgtgtcagactgctattcatagtataactttaaatcttttatcaactt gagtctttgaagatagttttaattctgatgtgacattaaaagattatttg ggccagttatagcttattaggtgttgaagagaccaaggttgcaagccagg ccctgtgtgaaccttgagctttcatagagagtttcacagcatggactgtg tgccccacggtcatccgagtggttgtacgatgcattggttagtcaaaaat ggggagggactagggcagtttggatagctcaacaagatacaatctcacta gtggtggtcctgctgacaaatcaagagcattgatttgtttataagaaaac aaactcttttttaaaaattacttttaaatattaactcaaaagttgagatt ttggggtggtggtgtgccaagacattaatttttttttaaacaatgaagt gaaaaagttttacaatctctaggtttggctagttctcttaacactggtta aattaacattgcataaacacttttcaagtctgatccatatttaataatgc tttaaaataaaaataaaaacaatccttttgataaatttaaaatgttactt attttaaaataaatgaagtgagatggcatggtgaggtgaaagtatcactg gactaggttgttggtgacttaggttctagataggtgtcttttaggactct gattttgaggacatcacttactatccatttcttcatgttaaagaagtca tctcaaactcttagttttttttttttacactatgtgatttatattccatt tacataaggatacacttatttgtcaagctcagcacaatctgtaaatttt aacctatgttacaccatcttcagtgccagtcttgggcaaaattgtgcaag aggtgaagtttatatttgaatatccattctcgttttaggactcttcttcc atattagtgtcatcttgcctccctaccttccacatgccccatgacttgat -continued
```
gcagttttaatacttgtaattcccctaaccataagatttactgctgctgt ggatatctccatgaagttttcccactgagtcacatcagaaatgccctaca tcttattttcctcagggctcaagagaatctgacagataccataaagggat ttgacctaatcactaattttcaggtggtggctgatgctttgaacatctat tgctgcccaatccattagcgacagtaggattatcaaccctggtatgaata gacagaaccctatccagtggaaggagaatttaataaagatagtgcagaaa gaattccttaggtaatctataactaggactactcctggtaacagtaatac attccattgttttagtaaccagaaatcttcatgcaatgaaaaatacttta attcatgaagcttactttttttttttggtgtcagagtctcgctcttgtc acccaggctggaatgcagtggcgccatctcagctcactgcaaccttccat cttcccaggttcaagcgattctcgtgcctcggcctcctgagtagctggga ttacaggcgtgtgcactacactcaactaattttgtattttaggagaga cggggtttcacctgttggccaggctggtctcgaactcctgacctcaagtg attcacccaccttggcctcataaacctgttttgcagaactcatttattca gcaaatatttattgagtgcctaccagatgccagtcaccgcacaaggcact gggtatatggtatccccaaacaagagacataatcccggtccttaggtact gctagtgtggtctgtaatatcttactaaggcctttggtatacgaccaga gataacacgatgcgtattttagttttgcaaagaagggtttggtctctgt gccagctctataattgtttgctacgattccactgaaactcttcgatcaa gctactttatgtaaatcacttcattgttttaaaggaataaacttgattat attgtttttttatttggcataactgtgattcttttaggacaattactgta cacattaaggtgtatgtcagatattcatattgacccaaatgtgtaatatt ccagttttctctgcataagtaattaaaatatacttaaaaattaatagttt tatctgggtacaaataaacagtgcctgaactagttcacagacaagggaaa cttctatgtaaaaatcactatgatttctgaattgctatgtgaaactacag atctttggaacactgtttaggtagggtgttaagacttgacacagtacctc gtttctacacagagaaagaaatggccatacttcaggaactgcagtgctta tgagggatatttaggcctcttgaatttttgatgtagatgggcatttttt taaggtagtggttaattaccttttatgtgaactttgaatggtttaacaaaa gatttgttttgtagagatttaaaggggagaattctagaaataaatgt tacctaattattacagcctaaagacaaaaatccttgttgaagtttttt aaaaaaagactaaattacatagacttaggcattaacatgtttgtggaaga atatagcagacgtatattgtatcatttgagtgaatgttcccaagtaggca ttctaggctctatttaactgagtcacactgcataggaatttagaacctaa cttttataggttatcaaaactgttgtcaccattgcacaattttgtcctaa tatatacatagaaactttgtggggcatgttaagttacagtttgcacaagt tcatctcatttgtattccattgatttttttttttcttctaaacattttttt cttcaaaacagtatatataactttttttaggggatttatttagacagcaa aaaactatctgaagatttccatttgtcaaaaagtaatgatttcttgataa ttgtgtagtgaatgttttttagaacccagcagttaccttgaaagctgaat ttatatttagtaactctgtgttaatactggatagcatgaattctgcatt
```

-continued
```
gagaaactgaatagctgtcataaaatgctttctttcctaaagaaagatac tcacatgagttcttgaagaatagtcataactagattaagatctgtgtttt agtttaatagtttgaagtgcctgtttgggataatgataggtaatttagat gaatttaggggaaaaaaaagttatctgcagttatgttgagggcccatctc tcccccacaccccacagagctaactgggttacagtgttttatccgaaa gtttccaattcc
```

6.25. Target of Antiproliferative Antibody

See, e.g., GenBank Accession No. M33680 and Trifillis et al., 1999, RNA 5:1071-1082.

```
General Target Regions:
(1) 5' Untranslated Region:
                                       (SEQ ID NO: 61)
ccattgtgct ggaaaggcgc gcaacggcgg cgacggcggc gacccaccg cgcatcctgc caggcctccg cgcccagccg cccacgcgcc cccgcgcccc gcgccccgac cctttcttcg cgcccccgcc cctcggcccg ccaggccccc ttgccggcca cccgccaggc cccgcgccgg cccgcccgcc gcccaggacc ggcccgcgcc ccgcaggccg cccgccgccc gcgccgcc (2) 3' Untranslated Region:
                                       (SEQ ID NO: 62)
g gccccgcagc tctggccaca gggacctctg cagtgccccc taagtgaccc ggacacttcc gagggggcca tcaccgcctg tgtatataac gtttccggta ttactctgct acacgtagcc tttttacttt tggggttttg ttttgttct gaactttcct gttacctttt cagggctgat gtcacatgta ggtggcgtgt atgagtggag acgggcctgg gtcttgggga ctggagggca ggggtccttc tgcccctggg gtcccaggt gctctgcctg ctcagccagg cctctcctgg gagccactcg cccagagact cagcttggcc aacttggggg gctgtgtcca cccagcccgc ccgtcctgtg ggctgcacag ctcaccttgt tccctcctgc cccggttcga gagccgagtc tgtgggcact ctctgccttc atgcacctgt cctttctaac acgtcgcctt caactgtaat cacaacatcc tgactccgtc atttaataaa gaaggaacat caggcatgct aaaaaaaaaa aaaaaa
```

6.26. Downstream Regulatory Element-Antagonist Modulator

See, e.g., GenBank Accession No. AJ131730.

```
General Target Regions:
(1) 5' Untranslated Region:
                                       (SEQ ID NO: 63)
gaattccggc aaacatgagg cagctgccag ccggcctggg cagtcttgtc tgcctcggct gtgaagtggg gaggctggca acagttttct tcagcgccca gg
```

-continued
(2) 3' Untranslated Region:
(SEQ ID NO: 64)
gacacgt ccaaaggagt gcatggccac agccacctcc accccccaaga aacctccatc ctgccaggag cagcctccaa gaaacttta aaaaatagat ttgcaaaaag tgaacagatt gctacacaca cacacacaca cacacacaca cacacacaca gccattcatc tgggctggca gaggggacag agttcaggga ggggctgagt ctggctaggg gccgagtcca gaggccccag ccagcccttc ccaggccagc gaggcgaggc tgcctctggg tgagtggctg acagagcagg tctgcaggcc accagctgct ggatgtcacc aagaaggggc tcgagtgccc tgcaggaggg tccaatcctc cggtcccacc tcgtcccgtt catccattct gctttcttgc cacacagtgc ccggcccagg ctcccctggt ctcctccccg tagccactct ctgcccacta cctatgcttc tagaaagccc ctcacctcag gaccccagag gaccagctgg ggggcagggg ggagaggggg taatggaggc caagcctgca gctttctgga aattcttccc tgggggtccc agtatcccct gctactccac tgacctgaa gagctgggta ccaggccacc cactgtgggg caagcctgag tggtgagggg ccactggcat cattctccct ccatggcagg aaggcggggg atttcaagtt tagggattgg gtcgtggtgg agaatctgag ggcactctgc cagctccaca ggtggatgag cctctccttg ccccagtcct ggttcagtgg gaatgcagtg ggtggggctg tacacaccct ccagcacaga ctgttccctc caaggtcctc ttaggtcccg gggaggaacg tggttcagag actggcagcc agggagcccg gggcagagct cagaggagtc tgggaagggg cgtgtccctc ctcttcctgt agtgcccctc ccatggccca gcagcttggc tgagccctc tcctgaagca gctgtgcgcc gtccctctgc cttgcacaaa aagcacaaga cattccttag cagctcagcg cagccctagt gggagcccag cacactgctt tcggaggcc aggccctcct gctggctgag cttgggcccg gtggccccaa tatggtggcc ctggggaaga ggccttgggg gtctgctctg tgcctgggat cagtggggcc ccaaagccca gcccggctga ccaacattca aaagcacaaa ccctgggac tctgcttggc tgtcccctcc atctggggat ggagaatgca gcccaaagct ggagccaatg gtgagggctg agagggctgt ggctgggtgg tcagcagaaa ccccaggagg agagagatgc tgctcccgcc tgattggggc ctcacccaga aggaacccgg tcccagccgc atggcccctc caggaacatt cccacataat acattccatc acagccagcc cagctccact cagggctggc ccgggggagtc cccgtgtgcc ccaagaggct agccccaggg tgagcagggc cctcagagga aaggcagtat ggcggaggcc atggggcccc -continued
ctcggcattc acacacagcc tggcctcccc tgcggagctg catggacgcc tggctccagg ctccaggctg actggggcct ctgcctccag gagggcatca gctttccctg gctcagggat cttctccctc ccctcacccg ctgccagcc ctcccagctg atgtcactct gcctctaagc caaggcctca ggagagcatc accaccacac cctgcggcct tgccttgggg ccagactggc tgcacagccc aaccaggagg ggtctgcctc ccacgctggg acacagaccg gccgcatgtc tgcatggcag aagcgtctcc cttgccacgg cctgggaggg tggttcctgt tctcagcatc cactaatatt cagtcctgta tattttaata aaataaactt gacaaaggaa aaaaaaaccg 6.27. 6.27. Cox2
See, e.g., GenBank Accession No. M90100.

General Target Regions:
(1) 5' Untranslated Region:
(SEQ ID NO: 65)
gtccaggaac tcctcagcag cgcctccttc agctccacag ccagacgccc tcagacagca aagcctaccc ccgcgccgcg ccctgcccgc cgctgcg (2) 3' Untranslated Region:
(SEQ ID NO: 66)
aagtctaa tgatcatatt tatttattta tatgaaccat gtctattaat ttaattattt aataatattt atattaaact ccttatgtta cttaacatct tctgtaacag aagtcagtac tcctgttgcg gagaaaggag tcatacttgt gaagactttt atgtcactac tctaaagatt ttgctgttgc tgttaagttt ggaaaacagt ttttattctg ttttataaac cagagagaaa tgagttttga cgtcttttta cttgaatttc aacttatatt ataaggacga aagtaaagat gtttgaatac ttaaacacta tcacaagatg ccaaaatgct gaaagttttt acactgtcga tgtttccaat gcatcttcca tgatgcatta gaagtaacta atgtttgaaa ttttaaagta cttttgggta tttttctgtc atcaaacaaa acaggtatca gtgcattatt aaatgaatat ttaaattaga cattaccagt aatttcatgt ctactttta aaatcagcaa tgaaacaata atttgaaatt tctaaattca tagggtagaa tcacctgtaa aagcttgttt gatttcttaa agttattaaa cttgtacata taccaaaaag aagctgtctt ggatttaaat ctgtaaaatc agatgaaatt ttactacaat tgcttgttaa aatatttat aagtgatgtt cctttttcac caagagtata aaccttttta gtgtgactgt taaaacttcc ttttaaatca aaatgccaaa tttattaagg tggtggagcc actgcagtgt tatctcaaaa taagaatatc ctgttgagat

```
                         -continued
attccagaat ctgtttatat ggctggtaac atgtaaaaac cccataaccc cgccaaaagg ggtcctaccc ttgaacataa agcaataacc aaaggagaaa agcccaaatt attggttcca aatttagggt ttaaactttt tgaagcaaac ttttttttag ccttgtgcac tgcagacctg gtactcagat tttgctatga ggttaatgaa gtaccaagct gtgcttgaat aacgtatatgt tttctcagat tttctgttgt acagtttaat ttagcagtcc atatcacatt gcaaaagtag caatgacctc ataaaatacc tcttcaaaat gcttaaattc atttcacaca ttaattttat ctcagtcttg aagccaattc agtaggtgca ttggaatcaa gcctggctac ctgcatgctg ttccttttct tttcttcttt tagccatttt gctaagagac acagtcttct caaacacttc gtttctccta ttttgtttta ctagttttaa gatcagagtt cactttcttt ggactctgcc tatattttct tacctgaact tttgcaagtt ttcaggtaaa cctcagctca ggactgctat ttagctcctc ttaagaagat taaaaaaaaa aaaaaa
```

6.28. Her-2

```
General Target Regions:
(1) 5' Untranslated Region:
                                    (SEQ ID NO: 67)
gcgcccggccccaccccctcgcagcaccccgcgccccgcgccctcccagc cgggtccagccggagccatggggccggagccgcagtgagcaccatggag (2) 3' Untranslated Region:
                                    (SEQ ID NO: 68)
tgaaccagaaggccaagtccgcagaagccctgatgtgtcctcagggagca gggaaggcctgacttctgctggcatcaagaggtgggagggccatccgacc acttccaggggaacctgccatgccaggaacctgtcctaaggaaccttcat cctgcttgagttcccagatggctggaaggggtccagcctcgttggaagag gaacagcactggggagtctttgtggattctgaggccctgcccaatgagac tctagggtccagtggatgccacagcccagcttggccattcatccagatcc tgggtactgaaagccttagggaagctggcctgagaggggaagcggcccta agggagtgtctaagaacaaaagcgacccattcagagactgtccctgaaac ctagtactgccccccatgaggaaggaacagcaatggtgtcagtatccagg ctttgtacagagtgatttctgtttagtttttactttctttgattgtattt taaagacgaaataaagacccaggggagaatgggtgttgtatggggaggca agtgtgggggtccttaccacacccactttgtccatttgcaaatatatta ggaaaac
```

7. EXAMPLE

Vascular Endothelial Growth Factor 7.1. Introduction

Vascular endothelial growth factor (VEGF) plays a key role in tumor angiogenesis. Considerable evidence demonstrates that VEGF is a viable target for tumor therapy (Carmeliet & Jain, 2000, Nature 407:249-257; Sepp-Lorenzino & Pan, 2000, Angiogenesis—Research frontiers. A basic science conference of the New York Academy of Medicine. Exp. Opin. Invest. Drugs 9:1-7; and Hichlin et al., 2001, DDT 6: 517-528). There are several ongoing clinical trials (phase I-phase III) indicating that either VEGF neutralizing antibodies or VEGFR2-mediated signal transduction inhibitors are effective for tumor therapy (Carmeliet & Jain, 2000, Nature 407:249-257 and Matter, 2001, Drug Discovery Today 6:1005-1024).

VEGF protein expression is tightly regulated at both the transcriptional and post-transcriptional levels. Under hypoxic conditions, tumor cells express high levels of VEGF that can promote angiogenesis and thus support the growth of tumor cells. Increase of VEGF protein is due to both increased transcription and enhanced mRNA stability. Hypoxia-inducible factor 1 (HIF-1) is responsible for the transcriptional activation of the VEGF gene in hypoxic cells by binding to a hypoxia response element (HRE) located 1 kb upstream of the transcription initiation site. In addition, the abundance of VEGF mRNA is increased due to stabilization of the mRNA by binding of HuR to the 3' UTR (untranslated region). Under hypoxic conditions, cap-dependent translation is replaced by cap-independent translation of the VEGF mRNA which is mediated by an internal ribosome entry site (IRES) within the VEGF 5'UTR.

This Example demonstrates the generation of stable cell lines, harboring VEGF 5' and 3'UTR sequences, which can be used to identify small molecular weight compounds that inhibit VEGF IRES-dependent translation or modulate VEGF mRNA stability.

7.2. Materials and Methods 7.2.1. Generation of VEGF 5' and 3'UTRs

The VEGF 5'UTR was generated using PCR from human genomic DNA. The full-length 5'UTR was prepared by the ligation of two separate PCR products (FIG. 1A). The first half of the 5'UTR (designated VEGF 5'UTR2, encompassing nucleotides 1 to 498) was amplified with primer 1 (5'-AAA GTC GAC GTA ATC GCG GAG GCT TGG GCA GCC GG-3', SEQ ID NO: 69, and primer 2 (5' TTT GCG ACT GGT CAG CTG CGG GAT CCC AAG 3', SEQ ID NO: 70). The second half of the VEGF 5'UTR (designated VEGF 5'UTR1, from nucleotide 337 to 1038, plus the first 45 bp of the VEGF open reading frame) was amplified using primer 3 (5'-AA GTC GAC GTA AGA GCT CCA GAG AGA AGT CGA G-3, SEQ ID NO: 71 and primer 4 (5'-AAA CCC GGG CAG CAA GGC AAG GCT CCA ATG CAC-3', SEQ ID NO: 72). Each PCR product was digested with BamH I, and ligated together to produce the full length 5'UTR. To facilitate downstream cloning into dicistronic plasmid p2luc-i, primers 1 and 3 were designed to include a Sal I site and a stop code (TAA), immediately after the Sal I site at the 5' end, and primer 4 for VEGF 5'UTR1 includes a Xma I site at the 5' end (FIG. 1C).

The entire VEGF 3' UTR (shown in FIG. 1B) was amplified by genomic PCR using primer 5 (5'-GCC GGG CAG GAG GAA GGA GCC TCC CTC AGG GTT TGG GGA 3', SEQ ID NO: 73) and primer 6 (5'-CTG CAC TAG AGA CAA AGA CG T GAT GTT AAT-3', SEQ ID NO: 74. The BgI II and EcoR I restriction sites were used for subsequent cloning.

7.2.2. Plasmid Construction

Each PCR fragment (VEGF 5'UTR1, VEGF 5'UTR2 and VEGF 3'UTR) was cloned into pT-Adv vector for confirmation by DNA sequencing using the Clontech advantage cloning kit. A SalI-XmaI VEGF 5'UTR1 fragment was subcloned into the p2luc-i dicistronic plasmid (FIG. 2A, Grentzmann et al., 1998, RNA 4:479-486). The sequence of the polylinker site is GAA CAA ATG TCG ACG GGG GCC CCT AGG AGA TCT AGC GCT GGA TCC CCC GGG GAG CTC AUG GAA GAC (SEQ ID NO: 75, FIG. 2A). The resulting plasmid (designated p2luc/VEGF5UTR1, see FIG. 2B) contains VEGF 5'UTR1 between the two reporter genes (*renilla* luciferase and firefly luciferase) with a stop code (TAA) immediately after the Sal I site and a fusion translation junction between the first 15 AA of VEGF and firefly luciferase open reading frame. To construct the dicistronic plasmid containing the full length VEGF 5'UTR, VEGF 5'UTR2 was then subcloned into p2luc/VEGF5UTR1 between SalI and BamHI (designated p2luc/VEGF5UTR-fl; FIG. 2B). This plasmid also has a stop code (TAA) immediately after the Sal I site to prevent read-through from the first reporter to the second.

To map the region of the IRES essential for activity, dicistronic plasmids containing various deletions within the VEGF 5'UTR were prepared (FIG. 2B). Plasmid p2luc/vegf5'utr-delta51-476 is derived from p2luc/vegf5'utr-fl by removing the Nhe I fragment (nt51 to 746); plasmid p2luc/vegf5utr-delta476-1038 was derived from p2luc/vegf5utr-fl by removing the sequence from BamH I site to the 3'end of 5'UTR; plasmid p2luc/vegf5utr-delta1-476 was derived from p2luc/vegf5utr-fl by removing the sequence from BamH I to the 5'end of 5'UTR.

To generate stable cell lines for high throughput screening, a monocistronic reporter plasmid (pluc/VEGF5'+3'UTR) containing the VEGF 5' and 3'UTRs and firefly luciferase gene (FIG. 3A) was constructed. Briefly, a Sal I-Not I fragment, containing the full length VEGF 5'UTR and firefly reporter gene, from p2luc/VEGF5'UTR-fl was subcloned into pCDNA5/TO between EcoR V and Not I, and then the VEGF 3'UTR was subcloned into the intermediate plasmid at the Not I site by blunt-end ligation.

7.2.3. DNA Transfection and Generation of Stable Cell Lines 293T cells were transfected with pluc/VEGF5'+3'UTR using the Fugene 6 transfection reagent (Roche) according to manufacture's instruction. 48 hours after transfection, the cells were lysed and plasmid function was monitored by measuring luciferase activity using Promega's luciferase kit according to manufacture's instruction.

To generate stable cell lines, plasmid pluc/VEGF5'+3'UTR was transfected into 293T cells as described. 48 hours after transfection, the cells were trypsinized, resuspended in culture media plus 200 mg/ml hygromycin B, then seeded in 96 well plates at 100 to 500 cells per well for selection. The media containing hygromycin B was changed every 3 to 4 days. After 10 to 14 days of selection, hygromycin resistant clones were screened under a microscope and wells harboring a single colony were expanded under hygromycin selection for further experiments.

7.2.4. Luciferase Assay

F. luciferase and R. luciferase activities were measured using the Luciferase reporter assay system (Promega) according to manufacturer's instruction.

7.2.5. Semi-Quantitative PCR

DNA and RNA were isolated from B9 cells using TRIzol reagent (GIBCO BRL) according to the manufacturer's instructions. cDNA was synthesized using Promega's reverse transcription system. Semi-quantitative PCR was performed with gene specific primers for firefly luciferase or glyceraldehyde phosphodehydrogenase (GAPDH) as an internal control. The primer pairs for firefly luciferase amplification were as follows: 5'-CGG TGT TGG GCG CGT TAT TTA TCG GAG TTG-3' (SEQ ID NO: 76) and 5'-TTG GCG AAG AAT GAA AAT AGG GTT GGT ACT-3' (SEQ ID NO: 77); the primer pairs for GAPDH were as follows: 5'-GGT GAA GGT CGG AGT CAA CGG A-3' (SEQ ID NO: 78) and 5'-GAG GGA TCT CGC TCC TGG AAG A-3' (SEQ ID NO: 79). The PCR products were separated on 1% agarose gel, stained with ethidium bromide and quantified on UVP with Labworks software.

7.2.6. High Throughput Screening

High throughput screening ("HTS") for compounds that inhibit untranslated region-dependent expression of vascular endothelial growth factor ("VEGF") is accomplished using stable cell lines described in Section 7.2.3. The 293T cell line contained stably integrated copies of the firefly luciferase gene flanked by both the 5' and 3' UTRs of VEGF. Cell lines exhibiting consistently high levels of firefly luciferase expression are further expanded and optimized for HTS.

Screening of compounds is done using one hundred 384-well plates per day. Each 384-well plate contains a standard puromycin titration curve that is used as a reference to calculate % inhibition and the statistical significance of the data points generated in the assay. This curve occurs in wells from column 3 and 4 of the 384-well plate. The concentration of puromycin is 20 mM serially diluted 2-fold to 0.078 mM plated in quadruplicate. Columns 1 and 2 contain 16 standards each of a positive control 0.5% DMSO and a negative control consisting of the puromycin at 20 mM. The difference between the two controls is used as the window to calculate the percentage of inhibition of luciferase expression in the presence of a compound. Columns 5 through 24 contain compounds from a library of small molecules.

Two confluent T175 flasks of the VEGF stable cell line described above (B9) are split into twenty T175 flasks three days prior to screening. On each day of the HTS assay, the cells are dislodged from the flask with 3 ml of 0.25% trypsin-EDTA (Gibco, cat no. 25200-056) and diluted to 10 ml with non-selective media. This is repeated for all twenty flasks and the cells are combined, counted and diluted to a concentration of 263.15 cells/ml. 38 to 39 ml are then added to each well containing 1 to 2 ml of compound from a small molecule library to a final compound concentration of 7.5 mM (3.75 mg/ml) in 0.5% DMSO. The puromycin standard curve also contains 0.5% DMSO. The stable cell line is incubated in the presence of compound overnight (approximately 16 hours) at 37 C in 5% $CO_2$. To monitor firefly luciferase activity, LucLite Plus (Packard cat no. 6016969) is prepared according to manufactures' instructions and 20 ml is added to each well. Following a brief incubation at room temperature (minimum 2 min.), firefly luciferase activity in each well is detected with the ViewLux 1430 ultraHTS Microplate Imager (Perkin Elmer). All data obtained is uploaded into Activity Base for % inhibition calculations and statistical analyses.

7.3. Results

The ability of VEGF 5'UTR sequences to modulate internal translation initiation was tested using the plasmid vector that encodes a dicistronic mRNA (FIG. 2A). The *renilla* luciferase is translated from the first cistron by a cap-dependent scanning mechanism, while the firefly luciferase in the second cistron is translated only if preceded by an internal ribosome entry site. In this study, five discistronic plasmids containing various deletions of the VEGF 5'UTR (FIG. 2B) were generated and transiently transfected into 293T cells to monitor IRES-dependent translation of firefly luciferase. 48 hours after transfection, extracts were prepared and assayed for *renilla* and firefly luciferase activities using the dual luciferase kit from Promega. As shown in FIG. 2C, deletion of either the first 336 or the first 476 nucleotides has no significant effect on firefly luciferase activity compared to full length VEGF5'UTR directed luciferase levels. However, deletion between nucleotides 51 and 746 decreased firefly luciferase activity more than 75% (33.68+/−4.91 vs 161+/−30.49). Deletion of nucleotides 476 to the 3' end of the VEGF 5'UTR decreased firefly luciferase activity more than 90% (12.15+/−1.2 v.s. 161+/−30.49). Taken together, these results confirm that the VEGF 5'UTR harbors IRES activity, and also indicates that the region of the VEGF IRES essential for function is located within nucleotide 476 to the 3' end of VEGF 5'UTR.

To generate stable cell lines for High Throughput Screening ("HTS"), a monocistronic reporter plasmid under the transcriptional control of the CMV promoter (pluc/vegf5'+3'UTR; FIG. 3A) was constructed. This plasmid contains both the VEGF 5'- and 3'-UTRs separated by the firefly luciferase gene. After confirmation of luciferase production by transient transfection (data not shown), transfected 293-T cells were seeded in 96 well plates at a concentration of 100-500 cells per well, and then cultured under hygomycin B selection. After two weeks of selection, 19 clones were screened for luciferase activity, three of which demonstrated high levels of luciferase activities (clones B9, D3, H6; FIG. 3B). To determine which cell line demonstrated the highest level of expression, the luciferase activities of clones B9, D3, H6 were compared and normalized against the protein concentrations extracted from each cell line. The results shown in FIG. 4 demonstrate that the luciferase activity from B9 cells was two fold greater than H6 cells, and more than three fold higher than D3 cells.

To determine if the B9 cells are stable, these cells were maintained under hygromycin selection for more than three months, with intermittent monitoring of luciferase activity. The results indicate that this cell line is stable and sustains a high level of luciferase expression when continuously cultured in vitro for more than three months (FIG. 5). Sustained expression of luciferase by B9 cells indicated that the monocistronic plasmid integrated into the genomic DNA. Semi-quantitative PCR was performed to determine the number of copies of the reporter plasmid integrated per B9 cell. As FIG. 6A shows, series diluted plasmid pluc5'+3'vegf-UTR were included as positive control to make sure the reaction for sample (genomic DNA from B9 cells) was within the linear range, i.e., not saturated. The PCR standard curve was plotted with the PCR product intensity against the amount of positive plasmid control loaded for PCR (FIG. 6B). Sigma plot regression indicated that PCR product intensity for B9 genomic DNA (50 ng) is about the same level of 6.4 pg plasmid control. As 1 mg of 8 kb plasmid roughly contains $10^{11}$ copies and $10^6$ cells have 10 mg genomic DNA, the results here indicated that approximately 100 copies of the plasmid were integrated per cell.

High throughput screening ("HTS") for compounds that inhibit untranslated region-dependent expression of vascular endothelial growth factor ("VEGF") is accomplished with the generated stable cell lines.

8. EXAMPLE

Survivin

8.1. Introduction

Survivin, a member of IAP (inhibitor of apoptosis proteins) gene family, is critically required for suppression of apoptosis and ensuring cell division through the G2/M phase of the cell cycle. It is absent in normal adult tissues, but highly expressed in all of the most common cancers in a cell cycle-regulated manner. Disruption of survivin expression/function by antisense or dominant-negative mutation resulted in deregulation of mitotic progression and spontaneous apoptosis. It has been demonstrated that survivin targeting in vivo increased apoptosis and reduced proliferation of tumor cells, but did not affect cell viability of proliferating normal cells. It has also been showed that survivin targeting induces apoptosis and sensitizes tumor cells to chemical agents. Therefore, inhibition of survivin may be of great benefit for refractory cancer therapy when combined with standard chemotherapy. Another benefit for this project will be low toxicity because survivin expression is absent in normal adult tissues. Taken together, these indicated survivin is valid target for cancer therapy.

Translation of survivin might be cap-independent/IRES dependent since it is maximally expressed in metaphase. In G2/M phase, the eIF4E-binding proteins (4E-BPs) become hypophosphorylated. 4E-BPs compete with eIF4G for eIF4E binding, thus preventing eIF4F formation and cap-dependent translation initiation. In addition, survivin mRNA has a long 3'UTR featuring a poly(U) sequence and multiple CU repeats.

This Example demonstrates the generation of stable cell lines, harboring survivin 5' and 3'UTR sequences, to identify small molecular weight compounds that inhibit survivin IRES-dependent translation or modulate survivin mRNA stability.

8.2. Materials and Methods

8.2.1. Generation of Survivin 5' and 3' UTRs

The 5' UTR of survivin was generated by filling-in partially overlapping oligonucleotides with Taq polymerase. A 5' UTR forward oligonucleotide (5' AAAGTCGACGTAACCGCCAGATTTGAATCGCGGGACCCGTTGGCAGAGGTGGC GG 3', SEQ ID NO: 80) encompassing nucleotides 1 to 42 of the 5' UTR of survivin and a 5' UTR reverse oligonucleotide (5' AAAGGATCCGGGCAACGTCGGGGCACCCATGCCGCCGCCGCCACCTCTGCCAA C 3', SEQ ID NO: 81) encompassing nucleotides 26 to 49 of the 5' UTR of survivin as well as the first 21 nucleotides of the open reading frame of survivin were annealed at 45 C and extended at 72 C with Taq polymerase. The Sal I and BamH I restriction sites (underlined) were used for subsequent cloning.

The 3' UTR of survivin was amplified from human genomic DNA using the 3' UTR forward oligonucleotide (5' AAAGCGGCCGCGGCCTCTGCCGGAGCTGCCTGGTCCCAGA 3', SEQ ID NO: 82) and the 3' UTR reverse oligonucleotide (5' AAATCTAGACTCAGGAACAGCCGAGATGACCTCCAGA 3', SEQ ID NO: 83). The Not I and Xba I restriction sites were used for subsequent cloning.

8.2.2. Plasmid Construction

The survivin 3' UTR PCR product generated in Section 8.2.1 was cloned into the pT-Adv for sequence verification. A positive clone was subsequently digested with Not I and Xba I and the resulting 1.1 kb survivin 3' UTR PCR fragment was subcloned into pcDNA3.1/Hygro (Invitrogen cat. no. V87020) to generate the intermediate plasmid Surv3'UTR/pcDNA3.1/Hygro.

The survivin 5' UTR DNA fragment generated in Section 8.2.1 was digested with Sal I and BamH I and was subcloned into p2luci (see, e.g., Grentzmann et al., 1998, RNA 4:479-486) to generate the intermediate plasmid, Surv5'UTR/p2luci, which contains the 5' UTR of survivin between the open reading frames of the *renilla* and firefly luciferase reporter genes. Surv5'UTR/p2luci was then digested with either Sal I and Not I or BamH I and Not I to isolate and gel purify the 1.75 kb survivin 5' UTR-firefly luciferase or the 1.7 kb firefly luciferase DNA fragments. The Sal I 5' overhang of the 1.75 kb survivin 5' UTR-firefly luciferase fragment was filled-in with T4 DNA polymerase and was subcloned into both Surv3'UTR/pcDNA3.1/Hygro and pcDNA3.1/Hygro digested with EcoR V and Not I to generate the plasmids, Surv5'UTR-Fluc-Surv3'UTR/pcDNA3.1/Hygro and Surv5'UTR-Fluc/pcDNA3.1/Hygro. The former plasmid contains the firefly luciferase reporter gene surrounded by both the 5' and 3' untranslated regions of survivin while the latter plasmid contains the firefly luciferase reporter gene preceded only by the 5' UTR of survivin and will be used as a "5' UTR-only" control plasmid in future experiments. The 1.7 kb BamH I-Not I firefly luciferase fragment was subcloned into both Surv3'UTR/pcDNA3.1/Hygro and pcDNA3.1/Hygro to generate the plasmids, Fluc-Surv3'UTR/pcDNA3.1/Hygro and Fluc/pcDNA3.1/Hygro. The former plasmid contains the firefly luciferase reporter gene followed only by the 3' UTR of survivin and will be used as a "3' UTR-only" control plasmid in future experiments. The latter plasmid contains only the firefly luciferase reporter gene lacking any surrounding untranslated regions of survivin and will be used in subsequent studies as a "no UTR" control plasmid.

Since the 5' UTR of survivin is small (49 nucleotides), it is likely that cap-dependent and cap-independent firefly luciferase expression in the survivin expression plasmids described above cannot be distinguished. One method of separating cap-dependent from cap-independent translation is through the introduction of a stable hairpin or secondary structure upstream or near the 5' end of the 5' UTR of the expression vector (see, e.g., Muhlrad et al., 1995 Mol. Cell. Biol. 15:2145-2156). Therefore, two complementary oligonucleotides, SL top (5' CTAGAAGCTTAGGGCCGCGGATCCGCGCGCGGTTCGCCGCGCGCGGATCCGCG GTAGCAAGTTAGTC 3', SEQ ID NO: 84) and SL bottom (5' GACTAAGCTTGCTACCGCGGATCCGCGCGCGGC-GAACCGCGCGCGGATCCGCG GCCCTAAGCTTCTAG 3', SEQ ID NO: 85) were synthesized, digested with Hind III, annealed and subcloned into the survivin expression vectors described above. A stable stem-loop structure with an 18 base-pair stem and a UUCG loop sequence will form and effectively block cap-dependent translation (see, e.g., Beelman & Parker, 1994 J. Biol. Chem. 269:9687-9692 and Muhlrad et al., 1995 Mol. Cell. Biol. 15:2145-2156).

8.2.3. DNA Transfection and Stable Cell Line Generation 293T cells were transiently transfected with equal amounts of each of the survivin expression vectors described in Section 8.2.2 (both with and without each of the 5' and 3' UTRs of survivin and in the presence and absence of the stem-loop secondary structure) using the Fugene 6 transfection reagent (Roche) according to manufacture's instruction. Untranslated region-dependent firefly luciferase activity was monitored forty-eight hours post-transient transfection according to manufacture's instruction (see, e.g., Section 8.2.4.).

To generate stable cell lines, 293T cells were transiently transfected as above. Instead of lysing the transiently transfected 293T cells to monitor firefly luciferase activity, the cells were trypsinized, counted and seeded (10 ml) in 10 cm petri dishes at a concentration of 5000 cells/ml. The following day, hygromycin B was added in culture media to a final concentration of 200 mg/ml to select for cells in which the transiently transfected plasmid has stably integrated into the genome. Following ten to fourteen days of hygromycin B selection, individual hygromycin-resistant clones were expanded by transferring the cells from the petri dish to a single well in a six or twenty-four well plate using trypsin-soaked filter discs according to manufacture's instructions. Individual cell lines are then selected for further studies based on firefly luciferase expression levels.

8.2.4. Luciferase Assays

Firefly luciferase activity was measured with the luciferase reporter assay system (Promega) according to manufacture's instructions.

8.2.5. High Throuphput Screening

High throughput screening ("HTS") for compounds that inhibit untranslated region-dependent expression of survivin is accomplished with stable cell lines described in Section 8.2.3. The 293T cell line contained stably integrated copies of the firefly luciferase gene flanked by both the 5' and 3' UTRs of survivin. Cell lines exhibiting consistently high levels of firefly luciferase expression are further expanded and optimized for HTS.

Screening of compounds is done using one hundred 384-well plates per day. Each 384-well plate contains a standard puromycin titration curve that is used as a reference to calculate % inhibition and the statistical significance of the data points generated in the assay. This curve occurs in wells from column 3 and 4 of the 384-well plate. The concentration of puromycin is 20 mM serially diluted 2-fold to 0.078 mM plated in quadruplicate. Columns 1 and 2 contain 16 standards each of a positive control 0.5% DMSO and a negative control consisting of the puromycin at 20 mM. The difference between the two controls is used as the window to calculate the percentage of inhibition of luciferase expression in the presence of a compound. Columns 5 through 24 contain compounds from a library of small molecules.

Two confluent T175 flasks of the survivin stable cell line described above are split into twenty T175 flasks three days prior to screening. On each day of the HTS assay, the cells are dislodged from the flask with 3 ml of 0.25% trypsin-EDTA (Gibco, cat no. 25200-056) and diluted to 10 ml with non-selective media. This is repeated for all twenty flasks and the cells are combined, counted and diluted to a concentration of 263.15 cells/ml. 38 ml are then added to each well containing 2 ml of compound from a small molecule library to a final compound concentration of 7.5 mM (3.75 mg/ml) in 0.5% DMSO. The puromycin standard curve also contains 0.5% DMSO. The stable cell line is incubated in the presence of compound overnight (approximately 16 hours) at 37 C in 5% $CO_2$. To monitor firefly luciferase activity, LucLite Plus (Packard cat no. 6016969) is prepared according to manufactures' instructions and 20 ml is added to each well. Following a brief incubation at room temperature (minimum 2 min.), firefly luciferase activity in each well is detected with the ViewLux 1430 ultraHTS Microplate Imager (Perkin Elmer). All data obtained is uploaded into Activity Base for % inhibition calculations and statistical analyses.

8.3. Results

To determine the effect of the survivin untranslated regions on post-transcriptional control of gene expression, transient transfections of the survivin expression vectors described in Section 8.1.2., containing both, one or none of the 5' and 3' UTRs of survivin both in the absence or presence of the stem-loop secondary structure were performed. In the absence of the stem-loop secondary structure, cap-dependent and cap-independent translation are equally favored and no significant difference in firefly luciferase expression could be detected when either or both of the 5' and 3' UTRs are present or absent (FIG. 7A). This results confirms the earlier notion that, in the survivin expression vectors without the stem-loop secondary structure, the 5' UTR of survivin is unable to block cap-dependent translation. In the presence of the stem-loop secondary structure, a 3-fold increase in firefly luciferase expression can be detected only in the survivin expression vectors that contain the 5' UTR of survivin (FIG. 7B). This result strongly suggests that the 5' UTR of survivin can function as an internal ribosome entry site and promote cap-independent translation and helps explain the increase in the endogenous levels of survivin in the G2/M phase of the cell cycle when overall translation is dramatically reduced.

High throughput screening ("HTS") for compounds that inhibit untranslated region-dependent expression of survivin is accomplished with the generated stable cell lines.

9. EXAMPLE

HER-2

This Example demonstrates the generation of stable cell lines, harboring Her-2 5' and 3'UTR sequences, to identify small molecular weight compounds that inhibit Her-2 5' UTR-dependent translation or modulate Her-2 mRNA stability.

9.1. Her-2 Constructs 9.1.1. Generation of her-2 In Vitro Expression Constructs

The 99 nucleotide 5' UTR of Her-2 was PCR-amplified from a human genomic DNA (Promega) using the following primers: Sense/HindIII: CAAGAAGCTTgcgcccggc-cccccacccctcg (SEQ ID NO: 86) and Antisense/NcoI: AGC-CCATGGtgctcactgcggctccggcccc (SEQ ID NO: 87). The Advantage-GC2-PCR kit was used according to the manufacturer's instructions (Clontech) with the following conditions: PCR cycle conditions were 94 C, 3 minutes, followed by 35 cycles of 94 C, 30 seconds, and 68 C, 30 seconds. The PCR-amplified product was cloned using the pT Adv kit (Clontech) according to the manufacturer's instructions. All clones were confirmed by sequencing. The resulting clone was digested with HindIII/NcoI and the fragment was cloned into pT7Luc, upstream of the luciferase gene, to generate pT7Luc/5'UTR.

The 615 nucleotide 3'UTR was PCR-amplified from human genomic DNA (Promega) using the following primers: sense/BglII: agactctgaaccagaaggccaa (SEQ ID NO: 88) and antisense/KpnI: ctcggtaccagttttccaaaatatatttgcaaatgg (SEQ ID NO: 89). The Titanium Taq kit (Clontech) was used according to the manufacturer's instructions with the following amplification conditions: 94 C, 1 minute, followed by 35 cycles at 94 C, 30 seconds to denature, 60 C 30 seconds to anneal, 72 C 1 minute to extend. The product was gel purified and cloned using pT Adv (Clontech) according to the manufacturer's instructions. All clones were sequenced. The resulting clone was digested with BglII/KpnI and cloned into a BglII/KpnI digested pT7Luc and pT7Luc/5'UTR to generate pT7Luc/3'UTR and pT7Luc/5' and 3'UTR, respectively.

9.1.2. Generation of Her-2 In Vivo Expression Constructs

Constructs for cell-based expression were generated by isolation of Her-2 containing fragments of pT7Luc/5'UTR, pT7Luc/3'UTR and pT7Luc/5' and 3'UTR digested with HindIII and KpnI and cloned into pcDNA (+) (Invitrogen).

9.1.3. Generation of Her-2 uORF Mutants

The uORF contained within the Her-2 5' UTR was removed by extending the overlapping long primers. The overlapping sequence is underlined. The sense minus uORF HindIII primer is: cccaagcttcgcgcccggccccccacccctcgcag-caccccgcgccccgcgccctccc (SEQ ID NO: 90) and the antisense minus uORF NcoI primer is: ggccccatggctccggctg-gacccggctgggacccggctgggagggcgcgggagggcgcgg (SEQ ID NO: 91). The primers (10 micrograms) were denatured at 95 C for 2 minutes, annealed at 60 C for 5 minutes and extended at 72 C for 10 minutes using Taq polymerase (Clontech). After buffer-exchange, the product was digested with NcoI and HindIII and cloned in the HindIII/NcoI sites of the in vitro expression vector pT7Luc and pT7Luc/3'UTR, yielding pT7Luc/5'UTR minus uORF and pT7Luc/5'UTR minus uORF and 3' UTR. Both plasmids were digested with HindIII and KpnI and the Her-2 containing fragment was subcloned into the HindIII/KpnI site of pcDNA (+) (Invitrogen) for cell-based studies.

9.2. Stable Cell Line Production

Stable cell lines were generated in HeLa, 293T, and MCF-7. First, transient transfection was carried out using the Fugene 6 transfection reagent (Roche) according to manufacturer's instructions. Untranslated region-dependent firefly luciferase activity was monitored forty-eight hours post-transient transfection with the luciferase reporter assay system (Promega) according to manufacture's instructions.

Next, stable cell lines were generated by first transiently transfecting the above cell lines. Instead of lysing the transiently transfected 293T cells (or other), the cells were trypsinized, counted and seeded (10 ml) in 10 cm petri dishes at a concentration of 5000 cells/ml. The following day, hygromycin B was added in culture media to a final concentration of 100 mg/ml for 293T cells and 200 mg/ml for MCF-7 and Hela, to select for cells in which the transiently-transfected plasmid has stably integrated into the genome. Following ten to fourteen days of hygromycin B selection, individual hygromycin-resistant clones were expanded by transferring the cells from the petri dish to a single well in a six or twenty-four well plate using trypsin-soaked filter discs according to manufacture's instructions. Individual cell lines are then selected for further studies based on firefly luciferase expression levels.

9.3. In Vitro High Throughput Screen

Construct pT7Luc/5' and 3'UTR is utilized as a template for large-scale T7 polymerase transcription according to the manufacturer's protocol (Ambion). The mRNA template containing the Her-2 5' and 3' UTR and the Luciferase ORF is uncapped and used at 100 nanograms/reaction for a typical in vitro HTS. The number of samples run determines the amount of transcription yield that must be obtained. For example, for 100,000 reactions, using 100 nanograms of RNA/reaction, 10 milligrams of RNA must be produced. Typical yields from the Ambion T7 Transcription Kit for this template are 5 mg/ml of transcription.

Screening of compounds is done using one hundred 384-well plates per day. Each 384-well plate contains a standard puromycin titration curve that is used as a reference to calculate % inhibition and the statistical significance of the data points generated in the assay. This curve occurs in wells from column 3 and 4 of the 384-well plate. The concentration of puromycin is 20 mM serially diluted 2-fold to 0.078 mM plated in quadruplicate. Columns 1 and 2 contain 16 standards each of a positive control of 4% DMSO and a negative control consisting of the puromycin at 20 mM. The difference between the two controls is used as the window to calculate the percentage of inhibition of luciferase expression in the presence of a compound. Columns 5 through 24 contain compounds from a library of small molecules.

The in vitro translation reaction of the Her-2 driven Luciferase ORF consists of four microliters of rabbit reticulocyte lysate (Green Hectares) supplemented with 0.013 mgs/ml hemin (Sigma), 0.05 mgs/ml creatine kinase (Roche), and 0.125 mgs/ml tRNA (Sigma Type XII, rabbit liver), 100 nanograms uncapped mRNA and buffer containing 100 mM KOAc, 0.5 mM Mg(OAc)$_2$, 10 mM creatine phosphate, 0.03 mM amino acid mix, in a reaction volume of 20 ml. The reaction is then incubated at 30 C for 45 minutes. At the end of incubation, 20 mL of LucLite (Packard) is added to the reaction and the light output resulting from luciferase catalyzed conversion of luciferin, is monitored on a ViewLux uHTS Plate reader (Perkin Elmer).

10. EXAMPLE

Cell Expression Vectors

Stable cell line expression vectors (pCMR1 and pCMR2) are shown in FIGS. 8A and 8C. pCMR1, a high-level stable and transient mammalian expression vector designed to randomly integrate into the genome and pCMR2 is an episomal mammalian expression vector. pMCP1 (FIG. 8B) is a high level stable and transient mammalian expression vector designed to site-specifically integrate into the genome of cells genetically engineered to contain the FRT site-specific recombination site via the Flp recombinase (see, e.g., Craig, 1988, Ann. Rev. Genet. 22: 77-105; and Sauer, 1994, Curr. Opin. Biotechnol. 5: 521-527). The nucleotide sequences are presented below.

pCMR1

(SEQ ID NO: 92)

```
gacggatcgggagatctcccgatcccctatggtgcactctcagtacaatctgctctgatgccgcatagttaagccagtatctgctccct
gcttgtgtgttggaggtcgctgagtagtgcgcgagcaaaatttaagctacaacaaggcaaggcttgaccgacaattgcatgaagaat
ctgcttagggttaggcgttttgcgctgcttcgcgatgtacgggccagatatacgcgttgacattgattattgactagttattaatagtaatc
aattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattt
acggtaaactgcccacttggcagtacatcaagtgtatcatatgccaagtacgccccctattgacgtcaatgacggtaaatggcccgc
ctggcattatgcccagtacatgaccttatgggactttcctacttggcagtacatctacgtattagtcatcgctattaccatggtgatgcgg
ttttggcagtacatcaatgggcgtggatagcggtttgactcacggggatttccaagtaccacccattgacgtcaatgggagtttgttt
tggcaccaaaatcaacgggactttccaaaatgtcgtaacaactccgcccattgacgcaaatgggcggtaggcgtgtacggtggga
ggtctatataagcagagctctctggctaactaagctttcggcgcgccgaggtaccatgggatccgaagacgccaaaaacataaaga
aaggcccggcgccattctatcctctagaggatggaaccgctggagagcaactgcataaggctatgaagagatacgccctggttcct
ggaacaattgcttttacagatgcacatatcgaggtgaacatcacgtacgcggaatacttcgaaatgtccgttcggttggcagaagctat
gaaacgatatgggctgaatacaaatcacagaatcgtcgtatgcagtgaaaactctcttcaattctttatgccggtgttgggcgcgttattt
atcggagttgcagttgcgcccgcgaacgacatttataatgaacgtgaattgctcaacagtatgaacatttcgcagcctaccgtagtgtt
tgtttccaaaaaggggttgcaaaaaattttgaacgtgcaaaaaaaattaccaataatccagaaaattattatcatggattctaaaacgga
ttaccagggatttcagtcgatgtacacgttcgtcacatctcatctacctcccggttttaatgaatacgattttgtaccagagtcctttgatcg
tgacaaaacaattgcactgataatgaattcctctggatctactgggttacctaagggtgtggcccttccgcatagaactgcctgcgtca
gattctcgcatgccagagatcctatttttggcaatcaaatcattccggatactgcgattttaagtgttgttccattccatcacggttttggaa
tgtttactacactcggatatttgatatgtggatttcgagtcgtcttaatgtatagatttgaagaagagctgtttttacgatcccttcaggatta
caaaattcaaagtgcgttgctagtaccaaccctattttcattcttcgccaaaagcactctgattgacaaatacgatttatctaatttacacg
aaattgcttctggggcgcacctctttcgaaagaagtcggggaagcggttgcaaaacgcttccatcttccagggatacgacaaggat
atgggctcactgagactacatcagctattctgattacacccgaggggatgataaaccgggcgcggtcggtaaagttgttccattttt
gaagcgaaggttgtggatctggataccgggaaaacgctgggcgttaatcagagaggcgaattatgtgtcagaggacctatgattat
gtccggttatgtaaacaatccggaagcgaccaacgccttgattgacaaggatggatggctacattctggagacatagcttactggga
cgaagacgaacacttcttcatagttgaccgcttgaagtctttaattaaatacaaaggatatcaggtggcccccgctgaattggaatcga
tattgttacaacaccccaacatcttcgacgcgggcgtggcaggtcttcccgacgatgacgccggtgaacttcccgccgccgttgttgt
tttggagcacggaaagacgatgacggaaaaagagatcgtggattacgtcgccagtcaagtaacaaccgcgaaaaagttgcgcgg
aggagttgtgtttgtggacgaagtaccgaaaggtcttaccggaaaactcgacgcaagaaaaatcagagagatcctcataaaggcca
agaagggcggaaagtccaaattgcgcggccgctaactcgagaataaaatgaggaaattgcatcgcattgtctgagtaggtgtcattc
```

-continued

```
tattctggggggtggggtggggcaggacagcaaggggaggattgggaagacaatagcaggcatgctggggatgcggtgggct ctatggcttctgaggcggaaagaaccagctggggctctagggggtatccccacgcgcccgtgagcggcgcattaagcgcggcgg gtgtggtggttacgcgcagcgtgaccgctacacttgccagcgccctagcgcccgctccttttcgctttcttcccttcctttctcgccacgt tcgccggctttccccgtcaagctctaaatcggggggctccctttagggttccgatttagtgctttacggcacctcgacccccaaaaaactt gattagggtgatggttcacgtagtgggccatcgccctgatagacggttttttcgcccttttgacgttggagtccacgttctttaatagtgga ctcttgttccaaactggaacaacactcaaccctatctcggtctattcttttgatttataagggattttgccgatttcggcctattggttaaaaa atgagctgatttaacaaaaatttaacgcgaattaattctgtggaatgtgtgtcagttagggtgtggaaagtccccaggctccccagcag gcagaagtatgcaaagcatgcatctcaattagtcagcaaccaggtgtggaaagtccccaggctccccagcaggcagaagtatgca aagcatgcatctcaattagtcagcaaccatagtcccgcccctaactccgcccatcccgccctaactccgcccagttccgcccattct ccgcccatggctgactaatttttttttatttatgcagaggccgaggccgcctctgcctctgagctattccagaagtagtgaggaggcttt tttggaggcctaggcttttgcaaaaagctcccgggagcttgtatatccattttcggatctgatcagcacgtgatgaaaaagcctgaact caccgcgacgtctgtcgagaagtttctgatcgaaaagttcgacagcgtctccgacctgatgcagctctcggagggcgaagaatctc gtgctttcagcttcgatgtaggagggcgtggatatgtcctgcgggtaaatagctgcgccgatggtttctacaaagatcgttatgtttatc ggcactttgcatcggccgcgctcccgattccggaagtgcttgacattggggaattcagcgagagcctgacctattgcatctcccgcc gtgcacagggtgtcacgttgcaagacctgcctgaaaccgaactgcccgctgttctgcagccggtcgcggaggccatggatgcgat cgctgcggccgatcttagccagacgagcgggttcggcccattcggaccgcaaggaatcggtcaatacactacatggcgtgatttca tatgcgcgattgctgatccccatgtgtatcactggcaaactgtgatggacgacaccgtcagtgcgtccgtcgcgcaggctctcgatg agctgatgctttgggccgaggactgccccgaagtccggcacctcgtgcacgcggatttcggctccaacaatgtcctgacggacaat ggccgcataacagcggtcattgactggagcgaggcgatgttcggggattcccaatacgaggtcgccaacatcttcttctggaggcc gtggttggcttgtatggagcagcagacgcgctacttcgagcggaggcatccggagcttgcaggatcgccgcggctccgggcgtat atgctccgcattggtcttgaccaactctatcagagcttggttgacggcaatttcgatgatgcagcttgggcgcagggtcgatgcgacg caatcgtccgatccggagccgggactgtcgggcgtacacaaatcgcccgcagaagcgcggccgtctggaccgatggctgtgtag aagtactcgccgatagtggaaaccgacgccccagcactcgtccgagggcaaaggaatagcacgtgctacgagatttcgattccac cgccgccttctatgaaaggttgggcttcggaatcgttttccgggacgccggctggatgatcctccagcgcggggatctcatgctgga gttcttcgcccaccccaacttgtttattgcagcttataatggttacaaataaagcaatagcatcacaaatttcacaaataaagcattttttttc actgcattctagttgtggtttgtccaaactcatcaatgtatcttatcatgtctgtataccgtcgacctctagctagagcttggcgtaatcatg gtcatagctgtttcctgtgtgaaattgttatccgctcacaattccacacaacatacgagccggaagcataaagtgtaaagcctggggtg cctaatgagtgagctaactcacattaattgcgttgcgctcactgcccgctttccagtcgggaaacctgtcgtgccagctgcattaatga atcggccaacgcgcggggagaggcggtttgcgtattgggcgctcttccgcttcctcgctcactgactcgctgcgctcggtcgttcgg ctgcggcgagcggtatcagctcactcaaaggcggtaatacggttatccacagaatcaggggataacgcaggaaagaacatgtgag caaaaggccagcaaaaggccaggaaccgtaaaaaggccgcgttgctggcgtttttccataggctccgcccccctgacgagcatca caaaaatcgacgctcaagtcagaggtggcgaaacccgacaggactataaagataccaggcgtttccccctggaagctccctcgtg cgctctcctgttccgaccctgccgcttaccggatacctgtccgcctttctcccttcgggaagcgtggcgctttctcatagctcacgctgt aggtatctcagttcggtgtaggtcgttcgctccaagctgggctgtgtgcacgaaccccccgttcagcccgaccgctgcgccttatcc ggtaactatcgtcttgagtccaacccggtaagacacgacttatcgccactggcagcagccactggtaacaggattagcagagcgag gtatgtaggcggtgctacagagttcttgaagtggtggcctaactacggctacactagaagaacagtatttggtatctgcgctctgctga agccagttaccttcggaaaaagagttggtagctcttgatccggcaaacaaaccaccgctggtagcggttttttgtttgcaagcagca gattacgcgcagaaaaaaggatctcaagaagatcctttgatcttttctacggggtctgacgctcagtggaacgaaaactcacgttaa gggattttggtcatgagattatcaaaaaggatcttcacctagatccttttaaattaaaaatgaagttttaaatcaatctaaagtatatatgag taaacttggtctgacagttaccaatgcttaatcagtgaggcacctatctcagcgatctgtctatttcgttcatccatagttgcctgactccc cgtcgtgtagataactacgatacgggagggcttaccatctggccccagtgctgcaatgataccgcgagacccacgctcaccggctc
```

-continued cagatttatcagcaataaaccagccagccggaagggccgagcgcagaagtggtcctgcaactttatccgcctccatccagtctatta attgttgccgggaagctagagtaagtagttcgccagttaatagtttgcgcaacgttgttgccattgctacaggcatcgtggtgtcacgct cgtcgtttggtatggcttcattcagctccggttcccaacgatcaaggcgagttacatgatccccatgttgtgcaaaaaagcggttagc tccttcggtcctccgatcgttgtcagaagtaagttggccgcagtgttatcactcatggttatggcagcactgcataattctcttactgtcat gccatccgtaagatgcttttctgtgactggtgagtactcaaccaagtcattctgagaatagtgtatgcggcgaccgagttgctcttgccc ggcgtcaatacgggataataccgcgccacatagcagaactttaaaagtgctcatcattggaaaacgttcttcggggcgaaaactctc aaggatcttaccgctgttgagatccagttcgatgtaacccactcgtgcacccaactgatcttcagcatcttttactttcaccagcgtttctg ggtgagcaaaaacaggaaggcaaaatgccgcaaaaaagggaataagggcgacacggaaatgttgaatactcatactcttcctttt caatattattgaagcatttatcagggttattgtctcatgagcggatacatatttgaatgtatttagaaaaataaacaatagggggttccgcg cacatttccccgaaaagtgccacctgacgtc pCMR2

(SEQ ID NO: 93)
gttgacattgattattgactagttattaatagtaatcaattacgggtcattagttcatagcccatatatggagttccgcgttacataactta cggtaaatggcccgcctggctgaccgcccaacgacccccgcccattgacgtcaataatgacgtatgttcccatagtaacgccaata gggactttccattgacgtcaatgggtggagtatttacggtaaactgcccacttggcagtacatcaagtgtatcatatgccaagtccgcc ccctattgacgtcaatgacggtaaatggcccgcctggcattatgcccagtacatgaccttacgggactttcctacttggcagtacatct acgtattagtcatcgctattaccatggtgatgcggttttggcagtacaccaatgggcgtggatagcggtttgactcacggggatttcca agtctccacccccattgacgtcaatgggagtttgttttggcaccaaaatcaacgggactttccaaaatgtcgtaataaccccgccccgtt gacgcaaatgggcggtaggcgtgtacggtgggaggtctatataagcagagctcgtttagtgaaccgtaagctttcggcgcgccacg gtaccatgggatccgaagacgccaaaaacataaagaaaggcccggcgccattctatcctctagaggatggaaccgctggagagc aactgcataaggctatgaagagatacgccctggttcctggaacaattgcttttacagatgcacatatcgaggtgaacatcacgtacgc ggaatacttcgaaatgtccgttcggttggcagaagctatgaaacgatatgggctgaatacaaatcacagaatcgtcgtatgcagtgaa aactctcttcaattctttatgccggtgttgggcgcgttatttatcggagttgcagttgcgcccgcgaacgacatttataatgaacgtgaatt gctcaacagtatgaacatttcgcagcctaccgtagtgtttgtttccaaaaaggggttgcaaaaaattttgaacgtgcaaaaaaaattacc aataatccagaaaattattatcatggattctaaaacggattaccagggatttcagtcgatgtacacgttcgtcacatctcatctacctccc ggttttaatgaatacgattttgtaccagagtcctttgatcgtgacaaaacaattgcactgataatgaattcctctggatctactgggttacc taagggtgtggcccttccgcatagaactgcctgcgtcagattctcgcatgccagagatcctattttggcaatcaaatcattccggatac tgcgattttaagtgttgttccattccatcacggttttggaatgtttactacactcggatatttgatatgtggatttcgagtcgtcttaatgtata gatttgaagaagagctgtttttacgatcccttcaggattacaaaattcaaagtgcgttgctagtaccaaccctattttcattcttcgccaaa agcactctgattgacaaatacgatttatctaatttacacgaaattgcttctgggggcgcacctctttcgaaagaagtcggggaagcggt tgcaaaacgcttccatcttccagggatacgacaaggatatgggctcactgagactacatcagctattctgattacacccgaggggat gataaaccgggcgcggtcggtaaagttgttccatttttgaagcgaaggttgtggatctggataccgggaaaacgctgggcgttaatc agagaggcgaattatgtgtcagaggacctatgattatgtccggttatgtaaacaatccggaagcgaccaacgccttgattgacaagg atggatggctacattctggagacatagcttactgggacgaagacgaacacttcttcatagttgaccgcttgaagtctttaattaaataca aaggatatcaggtgccccgctgaattggaatcgatattgttacaacaccccaacatcttcgacgcgggcgtggcaggtcttcccg acgatgacgccggtgaacttcccgccgccgttgttgtttggagcacggaaagacgatgacggaaaaagagatcgtggattacgtc gccagtcaagtaacaaccgcgaaaaagttgcgcggaggagttgtgtttgtggacgaagtaccgaaaggtcttaccggaaaactcg acgcaagaaaaatcagagagatcctcataaaggccaagaagggcggaaagtccaaattgcgcggccgctaactcgagaataaac aagttaacaacaacaattgcattcattttatgtttcaggttcaggggaggtgtgggaggttttttaaagcaagtaaaacctctacaaatg tggtatggctgattatgatccggctgcctcgcgcgtttcggtgatgacggtgaaaacctctgacacatgcagctcccggagacggtc acagcttgtctgtaagcggatgccgggagcagacaagcccgtcagggcgtcagcgggtgttggcgggtgtcggggcgcagccatg -continued

```
aggtcgactctagaggatcgatgccccgccccggacgaactaaacctgactacgacatctctgccccttcttcgcggggcagtgca
tgtaatcccttcagttggttggtacaacttgccaactgggccctgttccacatgtgacacggggggggacccaaacacaaagggggttc
tctgactgtagttgacatccttataaatggatgtgcacatttgccaacactgagtggcttttcatcctggagcagactttgcagtctgtgga
ctgcaacacaacattgcctttatgtgtaactcttggctgaagctcttacaccaatgctggggggacatgtacctcccaggggcccagga
agactacggggaggctacaccaacgtcaatcagaggggcctgtgtagctaccgataagcggaccctcaagagggcattagcaata
gtgtttataaggccccccttgttaaccctaaacgggtagcatatgcttcccgggtagtagtatatactatccagactaaccctaattcaata
gcatatgttacccaacgggaagcatatgctatcgaattagggttagtaaaagggtcctaaggaacagcgatatctcccacccccatga
gctgtcacggttttattttacatgggggtcaggattccacgagggtagtgaaccattttagtcacaagggcagtggctgaagatcaagga
gcgggcagtgaactctcctgaatcttcgcctgcttcttcattctccttcgtttagctaatagaataactgctgagttgtgaacagtaaggt
gtatgtgaggtgctcgaaaacaaggtttcaggtgacgccccagaataaaatttggacgggggggttcagtggtggcattgtgctatg
acaccaatataaccctcacaaaccccttgggcaataaatactagtgtaggaatgaaacattctgaatatctttaacaatagaaatccatg
gggtggggacaagccgtaaagactggatgtccatctcacacgaatttatggctatgggcaacacataatcctagtgcaatatgatact
ggggttattaagatgtgtcccaggcagggaccaagacaggtgaaccatgttgttacactctatttgtaacaaggggaaagagagtgg
acgccgacagcagcggactccactggttgtctctaacaccccccgaaaattaaacggggctccacgccaatggggcccataaacaa
agacaagtggccactctttttttttgaaattgtggagtggggcacgcgtcagcccccacacgccgccctgcggttttggactgtaaaa
taagggtgtaataacttggctgattgtaaccccgctaaccactgcggtcaaaccacttgcccacaaaaccactaatggcaccccggg
gaatacctgcataagtaggtgggcgggccaagataggggcgcgattgctgcgataggaggacaaattacacacacttgcgcctg
agcgccaagcacagggttgttggtcctcatattcacgaggtcgctgagagcacggtgggctaatgttgccatgggtagcatatacta
cccaaatatctggatagcatatgctatcctaatctatatctgggtagcataggctatcctaatctatatctgggtagcatatgctatcctaa
tctatatctgggtagtatatgctatcctaatttatatctgggtagcataggctatcctaatctatatctgggtagcatatgctatcctaatctat
atctgggtagtatatgctatcctaatctgtatccgggtagcatatgctatcctaatagagattagggtagtatatgctatcctaatttatatct
gggtagcatatactacccaaatatctggatagcatatgctatcctaatctatatctgggtagcatatgctatcctaatctatatctgggtag
cataggctatcctaatctatatctgggtagcatatgctatcctaatctatatctgggtagtatatgctatcctaatttatatctgggtagcata
ggctatcctaatctatatctgggtagcatatgctatcctaatctatatctgggtagtatatgctatcctaatctgtatccgggtagcatatgc
tatcctcatgcatatacagtcagcatatgatacccagtagtagagtgggagtgctatcctttgcatatgccgccacctcccaagggg
cgtgaattttcgctgcttgtccttttcctgctggttgctcccattcttaggtgaatttaaggaggccaggctaaagccgtcgcatgtctgat
tgctcaccaggtaaatgtcgctaatgattccaacgcgagaaggtgttgagcgcggagctgagtgacgtgacaacatgggtatgccc
aattgccccatgttgggaggacgaaaatggtgacaagacagatggccagaaatacaccaacagcacgcatgatgtctactgggga
tttattctttagtgcggggaatacacggcttttaatacgattgagggcgtctcctaacaagttacatcactcctgcccttcctcaccctc
atctccatcacctccttcatctccgtcatctccgtcatcaccctccgcggcagcccttccaccataggtggaaaccagggaggcaaa
tctactccatcgtcaaagctgcacacagtcaccctgatattgcaggtaggagcgggctttgtcataacaaggtccttaatcgcatcctt
caaaacctcagcaaatatgagtttgtaaaaagaccatgaaataacagacaatggactcccttagcgggccaggttgtgggccgg
gtccaggggccattccaaaggggagacgactcaatggtgtaagacgacattgtggaatagcaagggcagttcctcgccttaggttg
taaagggaggtcttactacctccatatacgaacacaccggcgacccaagttcatcgtcggtagtcatttctacgtgactcctagccag
gagagctataaaccttctgcaatgttctcaaatttcgggttggaacctccttgaccacgatgatttccaaaccaccctcctttttttgcgc
cctgcctccatcaccctgaccccggggtccagtgcttgggccttctcctgggtcatctgcggggccctgctctatcgctcccggggg
cacgtcaggctcaccatctgggccaccttcttggtggtattcaaaataatcggctcccctacagggtggaaaaatggcatctacctg
gagggggcctgcgcggtggagaccggatgatgatgactgactactgggactcctgggcctatttctccacgtccacgacctctc
cccctggctctttcacgacttcccccctggctcttcacgtcctctaccccggcggcctccactacctcctcgaccccggcctccact
acctcctcgaccccggcctccactgcctcctcgaccccggcctccacctcctgctcctgcccctcctgacctgccctcacctgct
cctgcccctcctgccctcctgctcctgccctcctgccctcctgctcctgccctcctgccctcctgctcctgccctcctgcccct
```

```
cctcctgctcctgccctcctgccctcctcctgctcctgccctcctgccctcctgctcctgccctcctgccctcctgctcctgcc
cctcctgccctcctgctcctgccctcctgctcctgccctcctgctcctgccctcctgctcctgccctcctgccctcctgcccct
cctcctgctcctgccctcctgatcctgccctcctgccctcctgccctcctgctcctgccctcctcctgctcctgccctcctgcc
cctcctgccctcctcctgctcctgccctcctgccctcctcctgctcctgccctcctcctgctcctgccctcctgccctcctgcc
cctcctcctgctcctgccctcctgccctcctcctgctcctgccctcctcctgctcctgccctcctgccctcctgccctcctcct
gctcctgccctcctcctgctcctgccctcctgccctcctgccctcctcctgctcctgccctcctcctgacctgcc
cctcctgctcctgccctcccgctcctgctcctgctcctgttccaccgtgggtcccttttgcagccaatgcaacttggacgtttttggggt
ctccggacaccatctctatgtcttggccctgatcctgagccgccggggctcctggtcttccgcctcctcgtcctcgtcctcttcccgt
cctcgtccatggttatcacccctcttctttgaggtccactgccgccggagccttctggtccagatgtgtctcccttctctcctaggccat
ttccaggtcctgtacctggccccctcgtcagacatgattcacactaaaagagatcaatagacatctttattagacgacgctcagtaata
cagggagtgcagactcctgccccctccaacagccccccaccctcatcccttcatggtcgctgtcagacagatccaggtctgaaa
attcccatcctccgaaccatcctcgtcctcatcaccaattactcgcagcccggaaaactcccgctgaacatcctcaagatttgcgtcc
tgagcctcaagccaggcctcaaattcctcgtccccttttttgctggacggtagggatggggattctcgggacccctcctcttcctcttc
aaggtcaccagacagagatgctactggggcaacgaagaaaagctgggtgcggcctgtgaggatcagcttatcgatgataagctg
tcaaacatgagaattcttgaagacgaaagggcctcgtgatacgcctattttataggttaatgtcatgataataatggtttcttagacgtca
ggtggcacttttcggggaaatgtgcgcggaaccctatttgtttatttttctaaatacattcaaatatgtatccgctcatgagacaataacc
ctgataaatgcttcaataatattgaaaaaggaagagtatgagtattcaacatttccgtgtcgcccttattcccttttttgcggcattttgcctt
cctgttttgctcacccagaaacgctggtgaaagtaaaagatgctgaagatcagttgggtgcacgagtgggttacatcgaactggatc
tcaacagcggtaagatccttgagagttttcgccccgaagaacgttttccaatgatgagcacttttaaagttctgctatgtggcgcggtat
tatcccgtgttgacgccgggcaagagcaactcggtcgccgcatacactattctcagaatgacttggttgagtactcaccagtcacaga
aaagcatcttacggatggcatgacagtaagagaattatgcagtgctgccataaccatgagtgataacactgcggccaacttacttctg
acaacgatcggaggaccgaaggagctaaccgcttttttgcacaacatgggggatcatgtaactcgccttgatcgttgggaaccgga
gctgaatgaagccataccaaacgacgagcgtgacaccacgatgcctgcagcaatggcaacaacgttgcgcaaactattaactggc
gaactacttactctagcttcccggcaacaattaatagactggatggaggcggataaagttgcaggaccacttctgcgctcggcccttc
cggctggctggtttattgctgataaatctggagccggtgagcgtgggtctcgcggtatcattgcagcactggggccagatggtaagc
cctcccgtatcgtagttatctacacgacggggagtcaggcaactatggatgaacgaaatagacagatcgctgagataggtgcctcac
tgattaagcattggtaactgtcagaccaagtttactcatatatactttagattgatttaaaacttcatttttaatttaaaaggatctaggtgaa
gatccttttgataatctcatgaccaaaatcccttaacgtgagttttcgttccactgagcgtcagaccccgtagaaaagatcaaaggatc
ttcttgagatccttttttctgcgcgtaatctgctgcttgcaaacaaaaaaaccaccgctaccagcggtggtttgtttgccggatcaagag
ctaccaactctttttccgaaggtaactggcttcagcagagcgcagataccaaatactgtccttctagtgtagccgtagttaggccacca
cttcaagaactctgtagcaccgcctacatacctcgctctgctaatcctgttaccagtggctgctgccagtggcgataagtcgtgtcttac
cgggttggactcaagacgatagttaccggataaggcgcagcggtcgggctgaacggggggttcgtgcacacagcccagcttgga
gcgaacgacctacaccgaactgagatacctacagcgtgagctatgagaaagcgccacgcttcccgaagggagaaaggcggaca
ggtatccggtaagcggcagggtcggaacaggagagcgcacgagggagcttccaggggaaacgcctggtatctttatagtcctgt
cgggtttcgccacctctgacttgagcgtcgatttttgtgatgctcgtcaggggcggagcctatgaaaaacgccagcaacgcgg
ccttttacggttcctggccttttgctggccttgaagctgtccctgatggtcgtcatctacctgcctggacagcatggcctgcaacgcgg
gcatcccgatgccgccggaagcgagaagaatcataatggggaaggccatccagcctcgcgtcgcgaacgccagcaagacgtag
cccagcgcgtcggccccgagatgcgccgcgtgcggctgctggagatggcggacgcgatggatatgttctgccaagggttggtttg
cgcattcacagttctccgcaagaattgattggctccaattcttggagtggtgaatccgttagcgaggtgccgccctgcttcatcccgt
ggcccgttgctcgcgtttgctggcggtgtccccggaagaaatatatttgcatgtctttagttctatgatgacacaaacccgcccagcg
```

-continued

```
tcttgtcattggcgaattcgaacacgcagatgcagtcggggcggcgcggtccgaggtccacttcgcatattaaggtgacgcgtgtg
gcctcgaacaccgagcgaccctgcagcgacccgcttaacagcgtcaacagcgtgccgcagatcccgggggggcaatgagatatg
aaaaagcctgaactcaccgcgacgtctgtcgagaagtttctgatcgaaaagttcgacagcgtctccgacctgatgcagctctcggag
ggcgaagaatctcgtgctttcagcttcgatgtaggagggcgtggatatgtcctgcgggtaaatagctgcgccgatggtttctacaaag
atcgttatgtttatcggcactttgcatcggccgcgctcccgattccggaagtgcttgacattggggaattcagcgagagcctgacctat
tgcatctcccgccgtgcacagggtgtcacgttgcaagacctgcctgaaaccgaactgcccgctgttctgcagccggtcgcggagg
ccatggatgcgatcgctgcggccgatcttagccagacgagcgggttcggcccattcggaccgcaaggaatcggtcaatacactac
atggcgtgatttcatatgcgcgattgctgatcccatgtgtatcactggcaaactgtgatggacgacaccgtcagtgcgtccgtcgcg
caggctctcgatgagctgatgctttgggccgaggactgccccgaagtccggcacctcgtgcacgcggatttcggctccaacaatgt
cctgacggacaatggccgcataacagcggtcattgactggagcgaggcgatgttcggggattcccaatacgaggtcgccaacatc
ttcttctggaggccgtggttggcttgtatggagcagcagacgcgctacttcgagcggaggcatccggagcttgcaggatcgccgcg
gctccgggcgtatatgctccgcattggtcttgaccaactctatcagagcttggttgacggcaatttcgatgatgcagcttgggcgcag
ggtcgatgcgacgcaatcgtccgatccggagccgggactgtcgggcgtacacaaatcgcccgcagaagcgcggccgtctggac
cgatggctgtgtagaagtactcgccgatagtggaaaccgacgcccagcactcgtccggatcgggagatggggaggctaactg
aaacacggaaggagacaataccggaaggaacccgcgctatgacggcaataaaaagacagaataaaacgcacgggtgttgggtc
gtttgttcataaacgcggggttcggtcccagggctggcactctgtcgatacccaccgagacccattggggccaatacgcccgcg
tttcttccttttccccaccccaccccccaagttcgggtgaaggcccagggctcgcagccaacgtcggggcggcaggccctgccata
gccactggccccgtgggttagggacggggtccccatggggaatggtttatggttcgtgggggttattattttgggcgttgcgtggg
gtcaggtccacgactggactgagcagacagacccatggttttggatggcctgggcatgaccgcatgtactggcgcgacacgaa
caccgggcgtctgtggctgccaaacaccccgaccccaaaaaccaccgcgcggatttctggcgtgccaagctagtcgaccaatt
ctcatgtttgacagcttatcatcgcagatccgggcaacgttgttgccattgctgcaggcgcagaactggtaggtatggaagatctatac
attgaatcaatattggcaattagccatattagtcattggttatatagcataaatcaatattggctattggccattgcatacgttgtatctatat
cataatatgtacatttatattggctcatgtccaatatgaccgccat
``` pMCP1

(SEQ ID NO: 94)

```
gacggatcgggagatctcccgatcccctatggtgcactctcagtacaatctgctctgatgccgcatagttaagccagtatctgctccct
gcttgtgtgttggagtcgctgagtagtgcgcgagcaaaatttaagctacaacaaggcaaggcttgaccgacaattgcatgaagaat
ctgcttagggttaggcgttttgcgctgcttcgcgatgtacgggccagatatacgcgttgacattgattattgactagttattaatagtaatc
aattacggggtcattagttcatagcccatatatggagttccgcgttacataacttacggtaaatggcccgcctggctgaccgcccaac
gacccccgcccattgacgtcaataatgacgtatgttcccatagtaacgccaatagggactttccattgacgtcaatgggtggagtattt
acggtaaactgcccacttggcagtacatcaagtgtatcatatgccaagtacgccccctattgacgtcaatgacggtaaatggcccgc
ctggcattatgcccagtacatgaccttatgggactttcctacttggcagtacatctacgtattagtcatcgctattaccatggtgatgcgg
ttttggcagtacatcaatgggcgtggatagcggtttgactcacggggatttccaagtctccaccccattgacgtcaatgggagtttgttt
tggcaccaaaatcaacgggactttccaaaatgtcgtaacaactccgccccattgacgcaaatgggcggtaggcgtgtacggtggga
ggtctatataagcagagctctctggctaactaagctttcggcgcgccgaggtaccatgggatccgaagacgccaaaaacataaga
aaggcccggcgccattctatcctctagaggatggaaccgctggagagcaactgcataaggctatgaagagatacgccctggttcct
ggaacaattgcttttacagatgcacatatcgaggtgaacatcacgtacgcggaatacttcgaaatgtccgttcggttggcagaagctat
gaaacgatatgggctgaatacaaatcacagaatcgtcgtatgcagtgaaaactctcttcaattctttatgccggtgttgggcgcgttattt
atcggagttgcagttgcgcccgcgaacgacatttataatgaacgtgaattgctcaacagtatgaacatttcgcagcctaccgtagtgtt
tgtttccaaaaaggggttgcaaaaaattttgaacgtgcaaaaaaaattaccaataatccagaaaattattatcatggattctaaaacgga
ttaccagggatttcagtcgatgtacacgttcgtcacatctcatctacctcccggttttaatgaatacgattttgtaccagagtccctttgatcg
tgacaaaacaattgcactgataatgaattcctctggatctactgggttacctaagggtgtggcccttccgcatagaactgcctgcgtca
```

-continued

```
gattctcgcatgccagagatcctattttggcaatcaaatcattccggatactgcgattttaagtgttgttccattccatcacggttttggaa tgtttactacactcggatatttgatatgtggatttcgagtcgtcttaatgtatagatttgaagaagagctgtttttacgatcccttcaggatta caaaattcaaagtgcgttgctagtaccaaccctattttcattcttcgccaaaagcactctgattgacaaatacgatttatctatttacacg aaattgcttctgggggcgcacctctttcgaaagaagtcggggaagcggttgcaaaacgcttccatcttccagggatacgacaaggat atgggctcactgagactacatcagctattctgattacacccgaggggatgataaaccgggcgcggtcggtaaagttgttccatttttt gaagcgaaggttgtggatctggataccgggaaaacgctgggcgttaatcagagaggcgaattatgtgtcagaggacctatgattat gtccggttatgtaaacaatccggaagcgaccaacgccttgattgacaaggatggatggctacattctggagacatagcttactggga cgaagacgaacacttcttcatagttgaccgcttgaagtctttaattaaatacaaaggatatcaggtggcccccgctgaattggaatcga tattgttacaacaccccaacatcttcgacgcgggcgtggcaggtcttcccgacgatgacgccggtgaacttcccgccgccgttgttgt tttggagcacgaaagacgatgacggaaaagagatcgtggattacgtcgccagtcaagtaacaaccgcgaaaaagttgcgcgg aggagttgtgtttgtggacgaagtaccgaaaggtcttaccggaaaactcgacgcaagaaaaatcagagagatcctcataaaggcca agaagggcggaaagtccaaattgcgcggccgctaactcgagaataaaatgaggaaattgcatcgcattgtctgagtaggtgtcattc tattctgggggtggggtgggcaggacagcaaggggaggattgggaagacaatagcaggcatgctggggatgcggtgggct ctatggcttctgaggcggaaagaaccagctggggctctaggggtatccccacgcgccctgtagcggcgcattaagcgcggcgg gtgtggtggttacgcgcagcgtgaccgctacacttgccagcgccctagcgccgctccttcgctttcttcccttcctttctcgccacgt tcgccggctttccccgtcaagctctaaatcggggtcccctttagggttccgatttagtgctttacggcacctcgaccccaaaaaacttg attagggtgatggttcacgtacctagaagttcctattccgaagttcctattctctagaaagtataggaacttccttggccaaaaagcctg aactcaccgcgacgtctgtcgagaagtttctgatcgaaaagttcgacagcgtctccgacctgatgcagctctcggagggcgaagaa tctcgtgctttcagcttcgatgtaggagggcgtggatatgtcctgcgggtaaatagctgcgccgatggtttctacaaagatcgttatgttt atcggcactttgcatcggccgcgctcccgattccggaagtgcttgacattggggaattcagcgagagcctgacctattgcatctcccg ccgtgcacagggtgtcacgttgcaagacctgcctgaaaccgaactgcccgctgttctgcagccggtcgcggaggccatggatgcg atcgctgcggccgatcttagccagacgagcgggttcggcccattcggaccgcaaggaatcggtcaatacactacatggcgtgattt catatgcgcgattgctgatccccatgtgtatcactggcaaactgtgatgacgacaccgtcagtgcgtccgtcgcgcaggctctcgat gagctgatgctttgggccgaggactgccccgaagtccggcacctcgtgcagcaaacaaaccaccgctggtagcggttttttttgtttg caagcagcagattacgcgcagaaaaaaggatctcaagaagatcctttgatcttttctacggggtctgacgctcagtggaacgaaaa ctcacgttaagggattttggtcatgagattatcaaaaaggatcttcacctagatccttttaaattaaaaatgaagttttaaatcaatctaaag tatatatgagtaaacttggtctgacagttaccaatgcttaatcagtgaggcacctatctcagcgatctgtctatttcgttcatccatagttgc ctgactccccgtcgtgtagataactacgatacggagggcttaccatctggccccagtgctgcaatgataccgcgagacccacgct caccggctccagatttatcagcaataaaccagccagccggaagggccgagcgcagaagtggtcctgcaactttatccgcctccatc cagtctattaattgttgccgggaagctagagtaagtagttcgccagttaatagtttgcgcaacgttgttgccattgctacaggcatcgtg gtgtcacgctcgtcgtttggtatggcttcattcagctccggttcccaacgatcaaggcgagttacatgatcccccatgttgtgcaaaaa agcggttagctccttcggtcctccgatcgttgtcagaagtaagttggccgcagtgttatcactcatggttatggcagcactgcataattc tcttactgtcatgccatccgtaagatgcttttctgtgactggtgagtactcaaccaagtcattctgagaatagtgtatgcggcgaccgag ttgctcttgcccggcgtcaatacgggataataccgcgccacatagcagaactttaaaagtgctcatcattggaaaacgttatcgggg cgaaaactctcaaggatcttaccgctgttgagatccagttcgatgtaacccactcgtgcacccaactgatcttcagcatcttttactttca ccagcgtttctgggtgagcaaaaacaggaaggcaaaatgccgcaaaaaagggaataagggcgacacggaaatgttgaatactcat actatccttttcaatattattgaagcatttatcagggttattgtctcatgagcggatacatatttgaatgtatttagaaaaataaacaaata ggggttccgcgcacatttccccgaaaagtgccacctgacgtc
```

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for screening for a compound that modulates K-ras mRNA translation that is regulated by the untranslated regions (UTRs) of K-ras mRNA, said method comprising:
(a) contacting a compound with a first cell engineered to express a first reporter protein translated from a first mRNA transcript comprising a first reporter gene coding sequence operably linked to a first 5' UTR and a first 3' UTR of K-ras mRNA, wherein the first 5' UTR is upstream of the first reporter gene coding sequence and the first 3' UTR is downstream of the first reporter gene coding sequence and, wherein the first reporter gene coding sequence is not the coding sequence of K-ras mRNA, wherein the 5' UTR of K-ras mRNA is encoded by the nucleotide sequence of SEQ ID NO: 59 and the 3' UTR of K-ras mRNA is encoded by the nucleotide sequence of SEQ ID NO: 60 and wherein the expression of the first mRNA transcript is driven by transcriptional elements from a first expression vector;

(b) contacting the compound with a second cell engineered to express a second reporter protein translated from a second mRNA transcript comprising the first reporter gene coding sequence operably linked to a second 5' UTR and a second 3' UTR of a mRNA, wherein the second 5' UTR is upstream of the first reporter gene coding sequence and the second 3' UTR is downstream of the first reporter gene coding sequence, wherein the second 5' UTR and the second 3' UTR are each from a mRNA different than the 5' UTR and the 3' UTR of K-ras mRNA; and wherein the expression of the second mRNA transcript is driven by the same transcriptional elements as the first expression vector;

(c) contacting the compound with a third cell engineered to express a third reporter protein translated from a third mRNA transcript comprising the first reporter gene coding sequence operably linked to the first 5' UTR and the first 3' UTR of the K-ras mRNA, wherein the first 5' UTR is upstream of the first reporter gene coding sequence and the first 3' UTR is downstream of the first reporter gene coding sequence, and wherein the expression of the third mRNA transcript is driven from a second expression vector comprising different transcriptional elements than the first expression vector; and (d) detecting the amount or activity of the first, second, and third reporter proteins, wherein (i) an alteration in the amount or activity of the first reporter protein in the presence of the compound relative to the amount or activity of the first reporter protein in the absence of the compound or the presence of a negative control, (ii) no alteration in or not substantially altered amount or activity of the second reporter protein in the presence of the compound relative to the amount or activity of the second reporter protein in the absence of the compound or the presence of the negative control, and (iii) an alteration in the amount or activity of the third reporter protein in the presence of the compound relative to the amount or activity of the third reporter protein in the absence of the compound or the presence of a negative control indicates that the compound modulates K-ras mRNA translation that is regulated by the UTRs of K-ras mRNA.

2. A method for screening for a compound that modulates K-ras mRNA translation that is regulated by the untranslated regions (UTRs) of K-ras mRNA, said method comprising:

(a) contacting a compound with a first cell engineered to express a first reporter protein translated from a first mRNA transcript comprising a first reporter gene coding sequence operably linked to a first 5' UTR and a first 3' UTR of K-ras mRNA, wherein the first 5' UTR is upstream of the first reporter gene coding sequence and the first 3' UTR is downstream of the first reporter gene coding sequence, and wherein the first reporter gene coding sequence is not the coding sequence of K-ras mRNA, wherein the 5' UTR of K-ras mRNA is encoded by the nucleotide sequence of SEQ ID NO: 59 and the 3' UTR of K-ras mRNA is encoded by the nucleotide sequence of SEQ ID NO: 60 and wherein the expression of the first mRNA transcript is driven by transcriptional elements from a first expression vector;

(b) contacting the compound with cells in a plurality of wells, wherein each well is isolated from another well and the cells in each well are engineered to express a reporter protein translated from a mRNA transcript comprising the first reporter gene coding sequence operably linked to a second 5' UTR and a second 3' UTR of a mRNA, wherein the second 5' UTR is upstream of the first reporter gene coding sequence and the second 3' UTR is downstream of the first reporter gene coding sequence, and wherein the second 5' UTR and the second 3' UTR are each from a mRNA different than the 5' UTR and the 3' UTR of K-ras mRNA; and wherein the expression of the mRNA transcript is driven by the same transcriptional elements as the first expression vector;

(c) contacting the compound with a second cell engineered to express a second reporter protein translated from a second mRNA transcript comprising the first reporter gene coding sequence operably linked to the first 5' UTR and the first 3' UTR of the K-ras mRNA, wherein the first 5' UTR is upstream of the first reporter gene coding sequence and the first 3' UTR is downstream of the first reporter gene coding sequence, wherein the expression of the second mRNA transcript is driven from a second expression vector comprising different transcriptional elements than the first expression vector; and (d) detecting the amount or activity of the first and second reporter proteins and each reporter protein in each well, wherein a compound that modulates K-ras mRNA translation that is regulated by the UTRs of K-ras mRNA is identified if (i) the amount or activity of the first reporter protein in the presence of the compound is altered relative to the amount or activity of the first reporter protein in the absence of the compound or the presence of a negative control, (ii) the amount or activity of each reporter protein in each well in the presence of the compound is not altered or not substantially altered relative to the amount or activity of each reporter protein in each well in the absence of the compound or the presence of a negative control, and (iii) the amount or activity of the second reporter protein is altered relative to the amount or activity of the second reporter protein in the absence of the compound or the presence of a negative control.

3. A method for screening for a compound that modulates K-ras mRNA translation that is regulated by the untranslated regions (UTRs) of K-ras mRNA, said method comprising:

(a) contacting a compound with a first composition comprising a first cell-free translation mixture and a first mRNA transcript comprising a first reporter gene coding sequence operably linked to a first 5' UTR and a first 3' UTR of K-ras mRNA, wherein the first 5' UTR is upstream of the first reporter gene coding sequence and the first 3' UTR is downstream of the first reporter gene coding sequence, wherein the first reporter gene coding sequence is not the coding sequence of K-ras mRNA, wherein the 5' UTR of K-ras mRNA is encoded by the nucleotide sequence of SEQ ID NO: 59 and the 3' UTR of K-ras mRNA is encoded by the nucleotide sequence of SEQ ID NO: 60 and wherein the expression of the first mRNA transcript is driven by transcriptional elements from a first expression vector;

(b) contacting the compound with a second composition comprising a second cell-free translation mixture and a second mRNA transcript comprising the first reporter gene coding sequence operably linked to a second 5' UTR and a second 3' UTR of a mRNA, wherein the second 5' UTR is upstream of the first reporter gene coding sequence and the second 3' UTR is downstream of the first reporter gene coding sequence, wherein the second 5' UTR and the second 3' UTR are each from a mRNA different than the 5' UTR and 3' UTR of K-ras mRNA; and wherein the expression of the second mRNA transcript is driven by the same transcriptional elements as the first expression vector;

(c) contacting the compound with a third composition comprising a third cell-free translation mixture and a third mRNA transcript comprising the first reporter gene coding sequence operably linked to the first 5' UTR and the first 3' UTR of the K-ras mRNA, wherein the first 5' UTR is upstream of the first reporter gene coding sequence and the first 3' UTR is downstream of the first reporter gene coding sequence, wherein the expression of the third mRNA transcript is driven from a second expression vector comprising different transcriptional elements than the first expression vector; and (d) detecting the amount or activity of a first, second, and third reporter proteins translated from the first, second, and third mRNA transcripts, respectively, wherein (i) an alteration in the amount or activity of the first reporter protein in the presence of the compound relative to the amount or activity of the first reporter protein in the absence of the compound or the presence of a negative control, (ii) no alteration in or not substantially altered amount or activity of the second reporter protein in the presence of the compound relative to the amount or activity of the second reporter protein in the absence of the compound or the presence of the negative control, and (iii) an alteration in the amount or activity of the third reporter protein in the presence of the compound relative to the amount or activity of the third reporter protein in the absence of the compound or the presence of a negative control indicates that the compound modulates K-ras mRNA translation that is regulated by the UTRs of the K-ras mRNA.

4. The method of claim 1, wherein the compound does not alter K-ras mRNA levels.

5. The method of claim 2, wherein the compound does not alter K-ras mRNA levels.

6. The method of claim 3, wherein the compound does not alter K-ras mRNA levels.

7. The method of claim 1, wherein the first reporter protein is firefly luciferase, *renilla* luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, or alkaline phosphatase.

8. The method of claim 2, wherein the first reporter protein is firefly luciferase, *renilla* luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, or alkaline phosphatase.

9. The method of claim 3, wherein the first reporter protein is firefly luciferase, *renilla* luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase, or alkaline phosphatase.

10. The method of claim 1, wherein the first cell is engineered to stably or transiently express the first reporter protein.

11. The method of claim 2, wherein the first cell is engineered to stably or transiently express the first reporter protein.

12. The method of claim 1, wherein the first, second, and third cells are human cells.

13. The method of claim 12, wherein the first, second, and third human cells are HeLa cells or 293 cells.

14. The method of claim 3, wherein the first, second, and third cell-free translation mixtures are cell extracts derived from a human cell, a yeast cell, a mouse cell, a rat cell, a Chinese hamster ovary ("CHO") cell, a *Xenopus* oocyte, a primary cell, an undifferentiated cancer cell, or a rye embryo.

15. The method of claim 1, wherein the elements necessary for transcription comprise a promoter or enhancer element.

16. The method of claim 15, wherein said promoter is a constitutive promoter, a tissue-specific promoter, an inducible promoter, a SV40 early promoter region, a promoter contained in the 3' long terminal repeat of Rous sarcoma virus, a herpes thymidine kinase promoter, a β-lactamase promoter, a tac promoter, a nopaline synthetase promoter region, a cauliflower mosaic virus 35S RNA promoter, a promoter of the photosynthetic enzyme ribulose biphosphate carboxylase, a Gal 4 promoter, an alcohol dehydrogenase promoter, a phosphoglycerol kinase promoter, an alkaline phosphatase promoter, a CMV promoter, or a T7 promoter.

17. The method of claim 2, wherein the elements necessary for transcription comprise a promoter or enhancer element.

18. The method of claim 17, wherein said promoter is a constitutive promoter, a tissue-specific promoter, an inducible promoter, a SV40 early promoter region, a promoter contained in the 3' long terminal repeat of Rous sarcoma virus, a herpes thymidine kinase promoter, a β-lactamase promoter, a tac promoter, a nopaline synthetase promoter region, a cauliflower mosaic virus 35S RNA promoter, a promoter of the photosynthetic enzyme ribulose biphosphate carboxylase, a Gal 4 promoter, an alcohol dehydrogenase promoter, a phosphoglycerol kinase promoter, an alkaline phosphatase promoter, a CMV promoter, or a T7 promoter.

19. The method of claim 3, wherein the elements necessary for transcription comprise a promoter or enhancer element.

20. The method of claim 19, wherein said promoter is a constitutive promoter, a tissue-specific promoter, an inducible promoter, a SV40 early promoter region, a promoter contained in the 3' long terminal repeat of Rous sarcoma virus, a herpes thymidine kinase promoter, a β-lactamase promoter, a tac promoter, a nopaline synthetase promoter region, a cauliflower mosaic virus 35S RNA promoter, a promoter of the photosynthetic enzyme ribulose biphosphate carboxylase, a Gal 4 promoter, an alcohol dehydrogenase promoter, a phosphoglycerol kinase promoter, an alkaline phosphatase promoter, a CMV promoter, or a T7 promoter.

* * * * *

```
                           SEQUENCE LISTING

<160> NUMBER OF SEQ ID NOS: 90

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: consensus
      G-quartet element from synthetic sequences
<220> FEATURE:
<221> NAME/KEY: misc_feature
<222> LOCATION: 3, 7, 8, 11
<223> OTHER INFORMATION: n = a, t, c, or g
<220> FEATURE:
<221> NAME/KEY: misc_feature
<222> LOCATION: (7)..(8)
<223> OTHER INFORMATION: This represents one form of the sequence as
      described, other forms described may have up to five nucleotides
      in this variable region

<400> SEQUENCE: 1
ggntggnngg ntgg                                                          14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: synthetic
      G-quartet oligonucleotide
<220> FEATURE:
<221> NAME/KEY: misc_feature
<222> LOCATION: 3, 4, 7, 8, 11, 12
<223> OTHER INFORMATION: n = a, t, g or c
<220> FEATURE:
<221> NAME/KEY: misc_feature
<222> LOCATION: 3, 4, 7, 8, 11, 12
<223> OTHER INFORMATION: This represents one form of the sequence as
      described, other forms described have longer variable regions,
      typical is 2 - 10 nucleotides

<400> SEQUENCE: 2
ggnnggnngg nngg                                                          14

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence: Antisense
      minus uORF NcoI primer

<400> SEQUENCE: 3
ggccccatgg ctccggctgg acccggctgg gacccggctg ggagggcgcg ggagggcgcg        60
g                                                                        61

<210> SEQ ID NO 4
<211> LENGTH: 19
<212> TYPE: RNA
<213> ORGANISM: Oryctolagus cuniculus
<220> FEATURE:
<223> OTHER INFORMATION: subunit of 15-LOX-DICE
```

```
<400> SEQUENCE: 4
ccccrccctc uucccaag                                                    19

<210> SEQ ID NO 5
<211> LENGTH: 152
<212> TYPE: DNA
<213> ORGANISM: Homo sapiens

<400> SEQUENCE: 5
gcagaggacc agctaagagg gagagaagca actacagacc ccccctgaaa acaaccctca      60
gacgccacat cccctgacaa gctgccaggc aggttctctt cctctcacat actgacccac    120
ggctccaccc tctctcccct ggaaaggaca cc                                   152

<210> SEQ ID NO 6
<211> LENGTH: 792
<212> TYPE: DNA
<213> ORGANISM: Homo sapiens

<400> SEQUENCE: 6
tgaggaggac gaacatccaa ccttcccaaa cgcctcccct gccccaatcc ctttattacc      60
ccctccttca gacaccctca acctcttctg gctcaaaaag agaattgggg gcttagggtc    120
ggaacccaag cttagaactt taagcaacaa gaccaccact tcgaaacctg ggattcagga    180
atgtgtggcc tgcacagtga attgctggca accactaaga attcaaactg ggcctccag     240 aactcactgg ggcctacagc tttgatccct gacatctgga atctggagac cagggagcct    300
ttggttctgg ccagaatgct gcaggacttg agaagacctc acctagaaat tgacacaagt    360
ggaccttagg ccttcctctc tccagatgtt tccagacttc cttgagacac ggagcccagc    420
cctccccatg gagccagctc cctctattta tgtttgcact tgtgattatt tattatttat    480
ttattattta tttatttaca gatgaatgta tttatttggg agaccggggt atcctggggg    540
acccaatgta ggagctgcct tggctcagac atgttttccg tgaaaacgga gctgaacaat    600
aggctgttcc catgtagccc cctggcctct gtgccttctt ttgattatgt ttttttaaaat    660 atttatctga ttaagttgtc taaacaatgc tgatttggtg accaactgtc actcattgct    720
gagcctctgc tccccagggg agttgtgtct gtaatcgccc tactattcag tggcgagaaa    780
taaagtttgc tt                                                         792

<210> SEQ ID NO 7
<211> LENGTH: 21
<212> TYPE: RNA
<213> ORGANISM: Homo sapiens
<220> FEATURE:
<223> OTHER INFORMATION: Group I AU-Rich element(ARE) cluster of
      3'untranslated region

<400> SEQUENCE: 7
auuuauuuau uuauuuauuu a                                                21

<210> SEQ ID NO 8
<211> LENGTH: 40
<212> TYPE: DNA
<213> ORGANISM: Homo sapiens

<400> SEQUENCE: 8
kctggaggat gtggctgcag agcctgctgc tcttgggcac                            40

<210> SEQ ID NO 9
```

<211> LENGTH: 289
<212> TYPE: DNA
<213> ORGANISM: Homo sapiens

<400> SEQUENCE: 9

```
gccggggagc tgctctctca tgaaacaaga gctagaaact caggatggtc atcttggagg    60
gaccaagggg tgggccacag ccatggtggg agtggcctgg acctgccctg ggccacactg   120
accctgatac aggcatggca gaagaatggg aatattttat actgacagaa atcagtaata   180
tttatatatt tatattttta aaatatttat ttatttattt atttaagttc atattccata   240
tttattcaag atgttttacc gtaataatta ttattaaaaa tatgcttct               289
```

<210> SEQ ID NO 10
<211> LENGTH: 7008
<212> TYPE: DNA
<213> ORGANISM: Artificial Sequence
<220> FEATURE:
<223> OTHER INFORMATION: Description of Artificial Sequence: Expression Vector pCMRI

<400> SEQUENCE: 10

```
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca tgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgc cccattgacg caaatgggcg   780
gtaggcgtgt acggtgggag gtctatataa gcagagctct ctggctaact aagctttcgg   840
cgcgccgagg taccatggga tccgaagacg ccaaaaacat aaagaaaggc ccggcgccat   900
tctatcctct agaggatgga accgctggag agcaactgca taaggctatg aagagatacg   960
ccctggttcc tggaacaatt gcttttacag atgcacatat cgaggtgaac atcacgtacg  1020
cggaatactt cgaaatgtcc gttcggttgg cagaagctat gaaacgatat gggctgaata  1080
caaatcacag aatcgtcgta tgcagtgaaa actctcttca attctttatg ccggtgttgg  1140
gcgcgttatt tatcggagtt gcagttgcgc ccgcgaacga catttataat gaacgtgaat  1200
tgctcaacag tatgaacatt tcgcagccta ccgtagtgtt tgtttccaaa aagggggttgc  1260
aaaaaatttt gaacgtgcaa aaaaaattac caataatcca gaaaattatt atcatggatt  1320
ctaaaacgga ttaccaggga tttcagtcga tgtacacgtt cgtcacatct catctacctc  1380
ccggttttaa tgaatacgat tttgtaccag agtcctttga tcgtgacaaa acaattgcac  1440
tgataatgaa ttcctctgga tctactgggt tacctaaggg tgtggccctt ccgcatagaa  1500
ctgcctgcgt cagattctcg catgccagag atcctatttt tggcaatcaa atcattccgg  1560
```

```
atactgcgat tttaagtgtt gttccattcc atcacggttt tggaatgttt actacactcg    1620
gatatttgat atgtggattt cgagtcgtct taatgtatag atttgaagaa gagctgtttt    1680
tacgatccct tcaggattac aaaattcaaa gtgcgttgct agtaccaacc ctattttcat    1740
tcttcgccaa aagcactctg attgacaaat acgatttatc taatttacac gaaattgctt    1800
ctggggggcgc acctctttcg aaagaagtcg gggaagcggt tgcaaaacgc ttccatcttc    1860
cagggatacg acaaggatat gggctcactg agactacatc agctattctg attacacccg    1920
aggggggatga taaaccgggc gcggtcggta aagttgttcc attttttgaa gcgaaggttg    1980
tggatctgga taccgggaaa acgctgggcg ttaatcagag aggcgaatta tgtgtcagag    2040
gacctatgat tatgtccggt tatgtaaaca atccggaagc gaccaacgcc ttgattgaca    2100
aggatggatg gctacattct ggagacatag cttactggga cgaagacgaa cacttcttca    2160
tagttgaccg cttgaagtct ttaattaaat acaaaggata tcaggtggcc cccgctgaat    2220
tggaatcgat attgttacaa caccccaaca tcttcgacgc gggcgtggca ggtcttcccg    2280
acgatgacgc cggtgaactt cccgccgccg ttgttgtttt ggagcacgga aagacgatga    2340
cggaaaaaga gatcgtggat tacgtcgcca gtcaagtaac aaccgcgaaa aagttgcgcg    2400
gaggagttgt gtttgtggac gaagtaccga aaggtcttac cggaaaactc gacgcaagaa    2460
aaatcagaga gatcctcata aaggccaaga agggcggaaa gtccaaattg cgcggccgct    2520
aactcgagaa taaaatgagg aaattgcatc gcattgtctg agtaggtgtc attctattct    2580
ggggggtggg gtgggcagg acagcaaggg ggaggattgg gaagacaata gcaggcatgc    2640
tggggatgcg gtgggctcta tggcttctga ggcggaaaga accagctggg gctctagggg    2700
gtatccccac gcgccctgta gcggcgcatt aagcgcggcg ggtgtggtgg ttacgcgcag    2760
cgtgaccgct acacttgcca gcgccctagc gcccgctcct ttcgctttct tcccttcctt    2820
tctcgccacg ttcgccggct ttccccgtca agctctaaat cggggggctcc ctttagggtt    2880
ccgatttagt gctttacggc acctcgaccc caaaaaactt gattagggtg atggttcacg    2940
tagtgggcca tcgccctgat agacggtttt tcgccctttg acgttggagt ccacgttctt    3000
taatagtgga ctcttgttcc aaactggaac aacactcaac cctatctcgg tctattcttt    3060
tgatttataa gggattttgc cgatttcggc ctattggtta aaaaatgagc tgatttaaca    3120
aaaatttaac gcgaattaat tctgtggaat gtgtgtcagt tagggtgtgg aaagtccccca    3180
ggctccccag caggcagaag tatgcaaagc atgcatctca attagtcagc aaccaggtgt    3240
ggaaagtccc caggctcccc agcaggcaga agtatgcaaa gcatgcatct caattagtca    3300
gcaaccatag tcccgcccct aactccgccc atcccgcccc taactccgcc cagttccgcc    3360
cattctccgc cccatggctg actaattttt tttatttatg cagaggccga ggccgcctct    3420
gcctctgagc tattccagaa gtagtgagga ggcttttttg gaggcctagg cttttgcaaa    3480
aagctcccgg gagcttgtat atccattttc ggatctgatc agcacgtgat gaaaaagcct    3540
gaactcaccg cgacgtctgt cgagaagttt ctgatcgaaa agttcgacag cgtctccgac    3600
ctgatgcagc tctcggaggg cgaagaatct cgtgctttca gcttcgatgt aggagggcgt    3660
ggatatgtcc tgcgggtaaa tagctgcgcc gatggtttct acaaagatcg ttatgtttat    3720
cggcactttg catcggccgc gctcccgatt ccggaagtgc ttgacattgg ggaattcagc    3780
gagagcctga cctattgcat ctcccgccgt gcacagggtg tcacgttgca agacctgcct    3840
gaaaccgaac tgcccgctgt tctgcagccg gtcgcggagg ccatggatgc gatcgctgcg    3900
gccgatctta gccagacgag cgggttcggc ccattcggac cgcaaggaat cggtcaatac    3960
```

```
actacatggc gtgatttcat atgcgcgatt gctgatcccc atgtgtatca ctggcaaact    4020
gtgatggacg acaccgtcag tgcgtccgtc gcgcaggctc tcgatgagct gatgctttgg    4080
gccgaggact gccccgaagt ccggcacctc gtgcacgcgg atttcggctc caacaatgtc    4140
ctgacggaca atggccgcat aacagcggtc attgactgga gcgaggcgat gttcggggat    4200
tcccaatacg aggtcgccaa catcttcttc tggaggccgt ggttggcttg tatggagcag    4260
cagacgcgct acttcgagcg gaggcatccg gagcttgcag atcgccgcg gctccgggcg    4320 tatatgctcc gcattggtct tgaccaactc tatcagagct tggttgacgg caatttcgat    4380
gatgcagctt gggcgcaggg tcgatgcgac gcaatcgtcc gatccggagc cgggactgtc    4440 ggcgtacac aaatcgcccg cagaagcgcg gccgtctgga ccgatggctg tgtagaagta    4500
ctcgccgata gtgaaaccg acgcccagc actcgtccga gggcaaagga atagcacgtg    4560
ctacgagatt tcgattccac cgccgccttc tatgaaaggt tgggcttcgg aatcgttttc    4620
cgggacgccg gctggatgat cctccagcgc ggggatctca tgctggagtt cttcgcccac    4680
cccaacttgt ttattgcagc ttataatggt tacaaataaa gcaatagcat cacaaatttc    4740
acaaataaag catttttttc actgcattct agttgtggtt tgtccaaact catcaatgta    4800
tcttatcatg tctgtatacc gtcgacctct agctagagct tggcgtaatc atggtcatag    4860
ctgtttcctg tgtgaaattg ttatccgctc acaattccac acaacatacg agccggaagc    4920
ataaagtgta aagcctgggg tgcctaatga gtgagctaac tcacattaat tgcgttgcgc    4980
tcactgcccg ctttccagtc gggaaacctg tcgtgccagc tgcattaatg aatcggccaa    5040
cgcgcgggga gaggcggttt gcgtattggg cgctcttccg cttcctcgct cactgactcg    5100
ctgcgctcgg tcgttcggct gcggcgagcg gtatcagctc actcaaaggc ggtaatacgg    5160
ttatccacag aatcagggga taacgcagga agaacatgt gagcaaaagg ccagcaaaag    5220
gccaggaacc gtaaaaaggc cgcgttgctg gcgttttttcc ataggctccg ccccctgac    5280 gagcatcaca aaaatcgacg ctcaagtcag aggtggcgaa acccgacagg actataaaga    5340
taccaggcgt ttccccctgg aagctccctc gtgcgctctc ctgttccgac cctgccgctt    5400
accggatacc tgtccgcctt tctcccttcg ggaagcgtgg cgctttctca tagctcacgc    5460
tgtaggtatc tcagttcggt gtaggtcgtt cgctccaagc tgggctgtgt gcacgaaccc    5520
cccgttcagc ccgaccgctg cgccttatcc ggtaactatc gtcttgagtc aacccggta    5580 agacacgact tatcgccact ggcagcagcc actggtaaca ggattagcag agcgaggtat    5640
gtaggcggtg ctacagagtt cttgaagtgg tggcctaact acggctacac tagaagaaca    5700
gtatttggta tctgcgctct gctgaagcca gttaccttcg gaaaaagagt tggtagctct    5760
tgatccggca aacaaaccac cgctggtagc ggttttttg tttgcaagca gcagattacg    5820
cgcagaaaaa aaggatctca agaagatcct ttgatctttt ctacggggtc tgacgctcag    5880
tggaacgaaa actcacgtta agggattttg gtcatgagat tatcaaaaag gatcttcacc    5940
tagatccttt taaattaaaa atgaagtttt aaatcaatct aaagtatata tgagtaaact    6000
tggtctgaca gttaccaatg cttaatcagt gaggcaccta tctcagcgat ctgtctattt    6060
cgttcatcca tagttgcctg actccccgtc gtgtagataa ctacgatacg ggagggctta    6120
ccatctggcc ccagtgctgc aatgataccg cgagacccac gctcaccggc tccagattta    6180
tcagcaataa accagccagc cggaagggcc gagcgcagaa gtggtcctgc aactttatcc    6240
gcctccatcc agtctattaa ttgttgccgg gaagctagag taagtagttc gccagttaat    6300
```

```
agtttgcgca acgttgttgc cattgctaca ggcatcgtgg tgtcacgctc gtcgtttggt    6360
atggcttcat tcagctccgg ttcccaacga tcaaggcgag ttacatgatc ccccatgttg    6420
tgcaaaaaag cggttagctc cttcggtcct ccgatcgttg tcagaagtaa gttggccgca    6480
gtgttatcac tcatggttat ggcagcactg cataattctc ttactgtcat gccatccgta    6540
agatgctttt ctgtgactgg tgagtactca accaagtcat tctgagaata gtgtatgcgg    6600
cgaccgagtt gctcttgccc ggcgtcaata cgggataata ccgcgccaca tagcagaact    6660
ttaaaagtgc tcatcattgg aaaacgttct tcggggcgaa aactctcaag gatcttaccg    6720
ctgttgagat ccagttcgat gtaacccact cgtgcaccca actgatcttc agcatctttt    6780
actttcacca gcgtttctgg gtgagcaaaa acaggaaggc aaaatgccgc aaaaaaggga    6840
ataagggcga cacggaaatg ttgaatactc atactcttcc tttttcaata ttattgaagc    6900
atttatcagg gttattgtct catgagcgga tacatatttg aatgtattta gaaaaataaa    6960
caaatagggg ttccgcgcac atttccccga aaagtgccac ctgacgtc                 7008
```

```
<210> SEQ ID NO 11
<211> LENGTH: 47
<212> TYPE: DNA
<213> ORGANISM: Homo sapiens

<400> SEQUENCE: 11
atcactctct ttaatcacta ctcacattaa cctcaactcc tgccaca                  47
```

```
<210> SEQ ID NO 12
<211> LENGTH: 307
<212> TYPE: DNA
<213> ORGANISM: Homo sapiens

<400> SEQUENCE: 12
taattaagtg cttcccactt aaaacatatc aggccttcta tttatttatt taaatattta    60
aattttatat ttattgttga atgtatggtt gctacctatt gtaactatta ttcttaatct   120
taaaactata aatatggatc ttttatgatt cttttttgtaa gccctagggg ctctaaaatg   180
gtttacctta tttatcccaa aaatatttat tattatgttg aatgttaaat atagtatcta   240
tgtagattgg ttagtaaaac tatttaataa atttgataaa tataaaaaaa aaaaacaaaa   300
aaaaaaa                                                              307
```

```
<210> SEQ ID NO 13
<211> LENGTH: 15
<212> TYPE: RNA
<213> ORGANISM: Homo sapiens
<220> FEATURE:
<223> OTHER INFORMATION: Group III AU-Rich element(ARE) cluster of
      3'untranslated region
<220> FEATURE:
<221> NAME/KEY: misc_feature
<222> LOCATION: (1)..(15)
<223> OTHER INFORMATION: n = a, u, g or c

<400> SEQUENCE: 13
nauuuauuua uuuan                                                     15
```

```
<210> SEQ ID NO 14
<211> LENGTH: 62
<212> TYPE: DNA
<213> ORGANISM: Homo sapiens

<400> SEQUENCE: 14
```

```
ttctgccctc gagcccaccg ggaacgaaag agaagctcta tctcgcctcc aggagcccag    60
ct                                                                   62

<210> SEQ ID NO 15
<211> LENGTH: 427
<212> TYPE: DNA
<213> ORGANISM: Homo sapiens

<400> SEQUENCE: 15
tagcatgggc acctcagatt gttgttgtta atgggcattc cttcttctgg tcagaaacct    60
gtccactggg cacagaactt atgttgttct ctatggagaa ctaaaagtat gagcgttagg   120
acactatttt aattatttt  aatttattaa tatttaaata tgtgaagctg agttaattta   180
tgtaagtcat atttatattt ttaagaagta ccacttgaaa cattttatgt attagtttg    240 aaataataat ggaaagtggc tatgcagttt gaatatcctt tgtttcagag ccagatcatt   300
tcttggaaag tgtaggctta cctcaaataa atggctaact tatacatatt tttaaagaaa   360
tatttatatt gtatttatat aatgtataaa tggttttat  accaataaat ggcattttaa   420
aaaattc                                                             427

<210> SEQ ID NO 16
<211> LENGTH: 11693
<212> TYPE: DNA
<213> ORGANISM: Artificial Sequence
<220> FEATURE:
<223> OTHER INFORMATION: Description of Artificial Sequence: Expression
      Vector pCMR2

<400> SEQUENCE: 16
gttgacattg attattgact agttattaat agtaatcaat tacgggtca ttagttcata     60 gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtccgcccc ctattgacgt caatgacggt aaatggcccg   300
cctggcatta tgcccagtac atgaccttac ggactttcc  tacttggcag tacatctacg   360
tattagtcat cgctattacc atggtgatgc ggttttggca gtacaccaat gggcgtggat   420
agcggtttga ctcacgggga tttccaagtc tccaccccat tgacgtcaat gggagtttgt   480
tttggcacca aaatcaacgg gactttccaa aatgtcgtaa taaccccgcc ccgttgacgc   540
aaatgggcgg taggcgtgta cggtgggagg tctatataag cagagctcgt ttagtgaacc   600
gtaagctttc ggcgcgccac ggtaccatgg gatccgaaga cgccaaaaac ataaagaaag   660
gcccggcgcc attctatcct ctagaggatg gaaccgctgg agagcaactg cataaggcta   720
tgaagagata cgccctggtt cctggaacaa ttgcttttac agatgcacat atcgaggtga   780
acatcacgta cgcggaatac ttcgaaatgt ccgttcggtt ggcagaagct atgaaacgat   840
atgggctgaa tacaaatcac agaatcgtcg tatgcagtga aaactctctt caattcttta   900
tgccggtgtt gggcgcgtta tttatcggag ttgcagttgc gcccgcgaac gacatttata   960
atgaacgtga attgctcaac agtatgaaca tttcgcagcc taccgtagtg tttgtttcca  1020
aaaaggggtt gcaaaaaatt ttgaacgtgc aaaaaaaatt accaataatc cagaaaatta  1080
ttatcatgga ttctaaaacg gattaccagg gatttcagtc gatgtacacg ttcgtcacat  1140
ctcatctacc tcccggtttt aatgaatacg attttgtacc agagtccttt gatcgtgaca  1200
```

```
aaacaattgc actgataatg aattcctctg gatctactgg gttacctaag ggtgtggccc    1260
ttccgcatag aactgcctgc gtcagattct cgcatgccag agatcctatt tttggcaatc    1320
aaatcattcc ggatactgcg atttaagtg ttgttccatt ccatcacggt tttggaatgt     1380
ttactacact cggatatttg atatgtggat ttcgagtcgt cttaatgtat agatttgaag    1440
aagagctgtt tttacgatcc cttcaggatt acaaaattca aagtgcgttg ctagtaccaa    1500
ccctattttc attcttcgcc aaaagcactc tgattgacaa atacgattta tctaatttac    1560
acgaaattgc ttctgggggc gcacctcttt cgaaagaagt cggggaagcg gttgcaaaac    1620
gcttccatct tccagggata cgacaaggat atgggctcac tgagactaca tcagctattc    1680
tgattacacc cgagggggat gataaaccgg gcgcggtcgg taaagttgtt ccattttttg    1740
aagcgaaggt tgtggatctg gataccggga aaacgctggg cgttaatcag agaggcgaat    1800
tatgtgtcag aggacctatg attatgtccg gttatgtaaa caatccggaa gcgaccaacg    1860
ccttgattga caaggatgga tggctacatt ctggagacat agcttactgg gacgaagacg    1920
aacacttctt catagttgac cgcttgaagt ctttaattaa atacaaagga tatcaggtgg    1980
cccccgctga attggaatcg atattgttac aacaccccaa catcttcgac gcgggcgtgg    2040
caggtcttcc cgacgatgac gccggtgaac ttcccgccgc cgttgttgtt ttggagcacg    2100
gaaagacgat gacggaaaaa gagatcgtgg attacgtcgc cagtcaagta acaaccgcga    2160
aaaagttgcg cggaggagtt tgtttgtgg acgaagtacc gaaaggtctt accggaaaac     2220
tcgacgcaag aaaaatcaga gagatcctca taaaggccaa gaagggcgga agtccaaat    2280 tgcgcggccg ctaactcgag aataaacaag ttaacaacaa caattgcatt cattttatgt    2340
ttcaggttca gggggaggtg tgggaggttt tttaaagcaa gtaaaacctc tacaaatgtg    2400
gtatggctga ttatgatccg gctgcctcgc gcgtttcggt gatgacggtg aaaacctctg    2460
acacatgcag ctcccggaga cggtcacagc ttgtctgtaa gcggatgccg ggagcagaca    2520
agcccgtcag gcgtcagcgg gtgttggcgg gtgtcggggc gcagccatga ggtcgactct    2580
agaggatcga tgccccgccc cggacgaact aaacctgact acgacatctc tgcccttct     2640 tcgcggggca gtgcatgtaa tcccttcagt tggttggtac aacttgccaa ctgggccctg    2700
ttccacatgt gacacggggg gggaccaaac acaaggggt tctctgactg tagttgacat     2760
ccttataaat ggatgtgcac atttgccaac actgagtggc tttcatcctg gagcagactt    2820
tgcagtctgt ggactgcaac acaacattgc ctttatgtgt aactcttggc tgaagctctt    2880
acaccaatgc tgggggacat gtacctccca ggggcccagg aagactacgg gaggctacac    2940
caacgtcaat cagaggggcc tgtgtagcta ccgataagcg gaccctcaag agggcattag    3000
caatagtgtt tataaggccc ccttgttaac cctaaacggg tagcatatgc ttcccgggta    3060
gtagtatata ctatccagac taaccctaat tcaatagcat atgttaccca acgggaagca    3120
tatgctatcg aattagggtt agtaaaaggg tcctaaggaa cagcgatatc tcccacccca    3180
tgagctgtca cggtttattt acatggggt caggattcca cgagggtagt gaaccatttt     3240
agtcacaagg gcagtggctg aagatcaagg agcgggcagt gaactctcct gaatcttcgc    3300
ctgcttcttc attctccttc gtttagctaa tagaataact gctgagttgt gaacagtaag    3360
gtgtatgtga ggtgctcgaa acaaggtttt caggtgacgc ccccagaata aatttggac    3420 ggggggttca gtggtggcat tgtgctatga caccaatata accctcacaa accccttggg    3480
caataaatac tagtgtagga atgaaacatt ctgaatatct ttaacaatag aaatccatgg    3540
ggtggggaca agccgtaaag actggatgtc catctcacac gaatttatgg ctatgggcaa    3600
```

```
cacataatcc tagtgcaata tgatactggg gttattaaga gtgtgtcccag gcagggacca      3660 agacaggtga accatgttgt tacactctat ttgtaacaag gggaaagaga gtggacgccg      3720
acagcagcgg actccactgg ttgtctctaa caccccgaa aattaaacgg ggctccacgc       3780
caatggggcc cataaacaaa gacaagtggc cactcttttt tttgaaattg tggagtgggg      3840
gcacgcgtca gccccacac gccgccctgc ggttttggac tgtaaaataa gggtgtaata      3900
acttggctga ttgtaacccc gctaaccact gcggtcaaac cacttgccca caaaaccact      3960
aatggcaccc cggggaatac ctgcataagt aggtgggcgg gccaagatag gggcgcgatt      4020
gctgcgatct ggaggacaaa ttacacacac ttgcgcctga gcgccaagca cagggttgtt      4080
ggtcctcata ttcacgaggt cgctgagagc acggtgggct aatgttgcca tgggtagcat      4140
atactaccca aatatctgga tagcatatgc tatcctaatc tatatctggg tagcataggc      4200
tatcctaatc tatatctggg tagcatatgc tatcctaatc tatatctggg tagtatatgc      4260
tatcctaatt tatatctggg tagcataggc tatcctaatc tatatctggg tagcatatgc      4320
tatcctaatc tatatctggg tagtatatgc tatcctaatc tgtatccggg tagcatatgc      4380
tatcctaata gagattaggg tagtatatgc tatcctaatt tatatctggg tagcatatac      4440
tacccaaata tctggatagc atatgctatc ctaatctata tctgggtagc atatgctatc      4500
ctaatctata tctgggtagc ataggctatc ctaatctata tctgggtagc atatgctatc      4560
ctaatctata tctgggtagt atatgctatc ctaatttata tctgggtagc ataggctatc      4620
ctaatctata tctgggtagc atatgctatc ctaatctata tctgggtagt atatgctatc      4680
ctaatctgta tccgggtagc atatgctatc ctcatgcata tacagtcagc atatgatacc      4740
cagtagtaga gtgggagtgc tatcctttgc atatgccgcc acctcccaag ggggcgtgaa      4800
ttttcgctgc ttgtccttttt cctgctggtt gctcccattc ttaggtgaat ttaaggaggc      4860
caggctaaag ccgtcgcatg tctgattgct caccaggtaa atgtcgctaa tgttttccaa      4920
cgcgagaagg tgttgagcgc ggagctgagt gacgtgacaa catgggtatg cccaattgcc      4980
ccatgttggg aggacgaaaa tggtgacaag acagatggcc agaaatacac caacagcacg      5040
catgatgtct actggggatt tattctttag tgcggggaa tacacggctt ttaatacgat      5100
tgagggcgtc tcctaacaag ttacatcact cctgcccttc ctcaccctca tctccatcac      5160
ctccttcatc tccgtcatct ccgtcatcac cctccgcggc agcccttcc accataggtg       5220 gaaaccaggg aggcaaatct actccatcgt caaagctgca cacagtcacc ctgatattgc      5280
aggtaggagc gggctttgtc ataacaaggt ccttaatcgc atccttcaaa acctcagcaa      5340
atatatgagt ttgtaaaaag accatgaaat aacagacaat ggactccctt agcgggccag      5400
gttgtgggcc gggtccaggg gccattccaa aggggagacg actcaatggt gtaagacgac      5460
attgtggaat agcaagggca gttcctcgcc ttaggttgta aagggaggtc ttactacctc      5520
catatacgaa cacaccggcg acccaagttc cttcgtcggt agtcctttct acgtgactcc      5580
tagccaggag agctcttaaa ccttctgcaa tgttctcaaa tttcgggttg gaacctcctt      5640
gaccacgatg cttttccaaa ccaccctcct tttttgcgcc ctgcctccat caccctgacc      5700
ccggggtcca gtgcttgggc cttctcctgg gtcatctgcg gggccctgct ctatcgctcc      5760
cgggggcacg tcaggctcac catctgggcc accttcttgg tggtattcaa aataatcggc      5820
ttcccctaca gggtggaaaa atggccttct acctggaggg ggcctgcgcg gtggagaccc      5880
ggatgatgat gactgactac tgggactcct gggcctcttt tctccacgtc cacgacctct      5940
```

```
cccctggct ctttcacgac ttccccccct ggctcttca cgtcctctac cccggcggcc      6000
tccactacct cctcgacccc ggcctccact acctcctcga ccccggcctc cactgcctcc      6060
tcgaccccgg cctccacctc ctgctcctgc ccctcctgct cctgcccctc ctcctgctcc      6120
tgcccctcct gcccctcctg ctcctgcccc tcctgcccct cctgctcctg ccctcctgc      6180
ccctcctgct cctgcccctc ctgcccctcc tcctgctcct gccctcctg ccctcctcc      6240
tgctcctgcc cctcctgccc ctcctgctcc tgccctcct gccctcctg ctcctgcccc      6300
tcctgcccct cctgctcctg ccctcctgc tcctgcccct cctgctcctg ccctcctgc      6360
tcctgcccct cctgcccctc ctgcccctcc tcctgctcct gccctcctg ctcctgcccc      6420
tcctgcccct cctgcccctc ctgctcctgc ccctcctcct gctcctgccc ctcctgcccc      6480
tcctgcccct cctcctgctc ctgcccctcc tgccctcct cctgctcctg ccctcctcc      6540
tgctcctgcc cctcctgccc ctcctgcccc tcctcctgct cctgcccctc ctgccctcc      6600
tcctgctcct gccctccctc ctgctcctgc cctcctgcc cctcctgccc ctcctcctgc      6660
tcctgcccct cctcctgctc ctgcccctcc tgccctcct gccctcctg ccctcctcc      6720
tgctcctgcc cctcctcctg ctcctgcccc tcctgctcct gccctcccg cctcctgctcc      6780
tgctcctgtt ccaccgtggg tccctttgca gccaatgcaa cttggacgtt tttgggtct      6840
ccggacacca tctctatgtc ttggccctga tcctgagccg cccggggctc ctggtcttcc      6900
gcctcctcgt cctcgtcctc ttccccgtcc tcgtccatgg ttatcacccc ctcttctttg      6960
aggtccactg ccgccggagc cttctggtcc agatgtgtct cccttctctc ctaggccatt      7020
tccaggtcct gtacctggcc cctcgtcaga catgattcac actaaaagag atcaatagac      7080
atctttatta gacgacgctc agtgaataca gggagtgcag actcctgccc cctccaacag      7140
cccccccacc ctcatcccct tcatggtcgc tgtcagacag atccaggtct gaaaattccc      7200
catcctccga accatcctcg tcctcatcac caattactcg cagcccggaa aactcccgct      7260
gaacatcctc aagatttgcg tcctgagcct caagccaggc ctcaaattcc tcgtcccct      7320
ttttgctgga cggtagggat ggggattctc gggaccccctc ctcttcctct tcaaggtcac      7380
cagacagaga tgctactggg gcaacggaag aaaagctggg tgcggcctgt gaggatcagc      7440
ttatcgatga taagctgtca aacatgagaa ttcttgaaga cgaaagggcc tcgtgatacg      7500
cctatttta taggttaatg tcatgataat aatggttct tagacgtcag gtggcacttt      7560
tcggggaaat gtgcgcggaa ccctatttg tttatttttc taaatacatt caaatatgta      7620
tccgctcatg agacaataac cctgataaat gcttcaataa tattgaaaaa ggaagagtat      7680
gagtattcaa catttccgtg tcgcccttat ccctttttt gcggcatttt gccttcctgt      7740
ttttgctcac ccagaaacgc tggtgaaagt aaaagatgct gaagatcagt tgggtgcacg      7800
agtgggttac atcgaactgg atctcaacag cggtaagatc cttgagagtt ttcgccccga      7860
agaacgtttt ccaatgatga gcacttttaa agttctgcta tgtggcgcgg tattatcccg      7920
tgttgacgcc gggcaagagc aactcggtcg ccgcatacac tattctcaga atgacttggt      7980
tgagtactca ccagtcacag aaaagcatct tacggatggc atgacagtaa gagaattatg      8040
cagtgctgcc ataaccatga gtgataacac tgcggccaac ttacttctga caacgatcgg      8100
aggaccgaag gagctaaccg cttttttgca acatggggg gatcatgtaa ctcgccttga      8160
tcgttgggaa ccggagctga atgaagccat accaaacgac gagcgtgaca ccacgatgcc      8220
tgcagcaatg gcaacaacgt tgcgcaaact attaactggc gaactactta ctctagcttc      8280
ccggcaacaa ttaatagact ggatggaggc ggataaagtt gcaggaccac ttctgcgctc      8340
```

```
ggcccttccg gctggctggt ttattgctga taaatctgga gccggtgagc gtgggtctcg   8400
cggtatcatt gcagcactgg ggccagatgg taagccctcc cgtatcgtag ttatctacac   8460
gacgggagt caggcaacta tgatgaacg aaatagacag atcgctgaga taggtgcctc    8520
actgattaag cattggtaac tgtcagacca agtttactca tatatacttt agattgattt   8580
aaaacttcat ttttaattta aaaggatcta ggtgaagatc cttttttgata atctcatgac   8640
caaaatccct taacgtgagt tttcgttcca ctgagcgtca gaccccgtag aaaagatcaa   8700
aggatcttct tgagatcctt ttttttctgcg cgtaatctgc tgcttgcaaa caaaaaaacc   8760
accgctacca gcggtggttt gtttgccgga tcaagagcta ccaactcttt ttccgaaggt   8820
aactggcttc agcagagcgc agataccaaa tactgtcctt ctagtgtagc cgtagttagg   8880
ccaccacttc aagaactctg tagcaccgcc tacataccte gctctgctaa tcctgttacc   8940
agtggctgct gccagtggcg ataagtcgtg tcttaccggg ttggactcaa gacgatagtt   9000
accggataag gcgcagcggt cgggctgaac ggggggttcg tgcacacagc ccagcttgga   9060
gcgaacgacc tacaccgaac tgagatacct acagcgtgag ctatgagaaa gcgccacgct   9120
tcccgaaggg agaaaggcgg acaggtatcc ggtaagcggc agggtcggaa caggagagcg   9180
cacgagggag cttccagggg gaaacgcctg gtatctttat agtcctgtcg ggtttcgcca   9240
cctctgactt gagcgtcgat ttttgtgatg ctcgtcaggg gggcggagcc tatgaaaaa   9300
cgccagcaac gcggcctttt tacggttcct ggccttttgc tggccttgaa gctgtccctg   9360
atggtcgtca tctacctgcc tggacagcat ggcctgcaac gcgggcatcc cgatgccgcc   9420
ggaagcgaga agaatcataa tggggaaggc catccagcct cgcgtcgcga acgccagcaa   9480
gacgtagccc agcgcgtcgg ccccgagatg cgccgcgtgc ggctgctgga gatggcggac   9540
gcgatggata tgttctgcca agggttggtt tgcgcattca cagttctccg caagaattga   9600
ttggctccaa ttcttggagt ggtgaatccg ttagcgaggt gccgcccctgc ttcatccccg   9660
tggcccgttg ctcgcgtttg ctggcggtgt ccccggaaga aatatatttg catgtcttta   9720
gttctatgat gacacaaacc ccgcccagcg tcttgtcatt ggcgaattcg aacacgcaga   9780
tgcagtcggg gcggcgcggt ccgaggtcca cttcgcatat taaggtgacg cgtgtggcct   9840
cgaacaccga gcgaccctgc agcgaccccgc ttaacagcgt caacagcgtg ccgcagatcc   9900
cgggggggcaa tgagatatga aaaagcctga actcaccgcg acgtctgtcg agaagtttct   9960
gatcgaaaag ttcgacagcg tctccgacct gatgcagctc tcggagggcg aagaatctcg  10020
tgctttcagc ttcgatgtag gagggcgtgg atatgtcctg cgggtaaata gctgcgccga  10080
tggtttctac aaagatcgtt atgtttatcg gcactttgca tcggccgcgc tcccgattcc  10140
ggaagtgctt gacattgggg aattcagcga gagcctgacc tattgcatct cccgccgtgc  10200
acagggtgtc acgttgcaag acctgcctga aaccgaactg cccgctgttc tgcagccggt  10260
cgcggaggcc atggatgcga tcgctgcggc cgatcttagc cagacgagcg ggttcggccc  10320
attcggaccg caaggaatcg gtcaatacac tacatggcgt gatttcatat gcgcgattgc  10380
tgatccccat gtgtatcact ggcaaactgt gatggacgac accgtcagtg cgtccgtcgc  10440
gcaggctctc gatgagctga tgctttgggc cgaggactgc cccgaagtcc ggcacctcgt  10500
gcacgcggat ttcggctcca acaatgtcct gacggacaat ggccgcataa cagcggtcat  10560
tgactggagc gaggcgatgt tcggggattc ccaatacgag gtcgccaaca tcttcttctg  10620
gaggccgtgg ttggcttgta tggagcagca gacgcgctac ttcgagcgga ggcatccgga  10680
```

| | | | |
|---|---|---|---|
| gcttgcagga | tcgccgcggc | tccgggcgta tatgctccgc | attggtcttg accaactcta | 10740 |
| tcagagcttg | gttgacggca | atttcgatga tgcagcttgg | gcgcagggtc gatgcgacgc | 10800 |
| aatcgtccga | tccggagccg | ggactgtcgg gcgtacacaa | atcgcccgca gaagcgcggc | 10860 |
| cgtctggacc | gatggctgtg | tagaagtact cgccgatagt | ggaaaccgac gccccagcac | 10920 |
| tcgtccggat | cgggagatgg | gggaggctaa ctgaaacacg | gaaggagaca ataccggaag | 10980 |
| gaacccgcgc | tatgacggca | ataaaaagac agaataaaac | gcacgggtgt tgggtcgttt | 11040 |
| gttcataaac | gcggggttcg | gtcccagggc tggcactctg | tcgataccc accgagaccc | 11100 |
| cattggggcc | aatacgcccg | cgtttcttcc ttttccccac | cccaccccc aagttcgggt | 11160 |
| gaaggcccag | ggctcgcagc | caacgtcggg gcggcaggcc | ctgccatagc cactggcccc | 11220 |
| gtgggttagg | gacggggtcc | cccatgggga atggtttatg | gttcgtgggg gttattattt | 11280 |
| gggcgttgcg | tggggtcagg | tccacgactg gactgagcag | acagacccat ggttttgga | 11340 |
| tggcctgggc | atggaccgca | tgtactggcg cgacacgaac | accggcgtc tgtggctgcc | 11400 |
| aaacacccc | gacccccaaa | aaccaccgcg cggatttctg | gcgtgccaag ctagtcgacc | 11460 |
| aattctcatg | tttgacagct | tatcatcgca gatccgggca | acgttgttgc cattgctgca | 11520 |
| ggcgcagaac | tggtaggtat | ggaagatcta tacattgaat | caatattggc aattagccat | 11580 |
| attagtcatt | ggttatatag | cataaatcaa tattggctat | tggccattgc atacgttgta | 11640 |
| tctatatcat | aatatgtaca | tttatattgg ctcatgtcca | atatgaccgc cat | 11693 |

<210> SEQ ID NO 17
<211> LENGTH: 701
<212> TYPE: DNA
<213> ORGANISM: Homo sapiens

<400> SEQUENCE: 17

| | | | |
|---|---|---|---|
| aagagctcca | gagagaagtc | gaggaagaga gagacggggt | cagagagagc gcgcgggcgt | 60 |
| gcgagcagcg | aaagcgacag | gggcaaagtg agtgacctgc | ttttgggggt gaccgccgga | 120 |
| gcgcggcgtg | agccctcccc | cttgggatcc cgcagctgac | cagtcgcgct gacggacaga | 180 |
| cagacagaca | ccgcccccag | ccccagttac cacctcctcc | ccggccggcg gcggacagtg | 240 |
| gacgcggcgg | cgagccgcgg | gcaggggccg gagcccgccc | ccggaggcgg ggtggagggg | 300 |
| gtcggagctc | gcgcgtcgc | actgaaactt ttcgtccaac | ttctgggctg ttctcgcttc | 360 |
| ggaggagccg | tggtccgcgc | gggggaagcc gagccgagcg | gagccgcgag aagtgctagc | 420 |
| tcgggccggg | aggagccgca | gccggaggag gggaggagg | aagaagagaa ggaagaggag | 480 |
| aggggccgc | agtggcgact | cggcgctcgg aagccgggct | catggacggg tgaggcggcg | 540 |
| gtgtgcgcag | acagtgctcc | agcgcgcgcg ctccccagcc | ctggcccggc ctcgggccgg | 600 |
| gaggaagagt | agctcgccga | ggcgccgagg agagcgggcc | gccccacagc ccgagccgga | 660 |
| gagggacgcg | agccgcgcgc | cccggtcggg cctccgaaac c | | 701 |

<210> SEQ ID NO 18
<211> LENGTH: 1892
<212> TYPE: DNA
<213> ORGANISM: Homo sapiens

<400> SEQUENCE: 18

| | | | |
|---|---|---|---|
| tgagccgggc | aggaggaagg | agcctccctc agggtttcgg | gaaccagatc tctctccagg | 60 |
| aaagactgat | acagaacgat | cgatacagaa accacgctgc | cgccaccaca ccatcaccat | 120 |
| cgacagaaca | gtccttaatc | cagaaacctg aaatgaagga | agaggagact ctgcgcagag | 180 |

```
cactttgggt ccggagggcg agactccggc ggaagcattc ccgggcgggt gacccagcac      240
ggtccctctt ggaattggat tcgccatttt attttcttg ctgctaaatc accgagcccg       300
gaagattaga gagttttatt tctgggattc ctgtagacac acccacccac atacatacat      360
ttatatatat atatattata tatatataaa aataaatatc tctattttat atatataaaa      420
tatatatatt ctttttttaa attaacagtg ctaatgttat tggtgtcttc actggatgta      480
tttgactgct gtggacttga gttgggaggg gaatgttccc actcagatcc tgacagggaa      540
gaggaggaga tgagagactc tggcatgatc ttttttttgt cccacttggt ggggccaggg      600
tcctctcccc tgcccaagaa tgtgcaaggc cagggcatgg gggcaaatat gacccagttt      660
tgggaacacc gacaaaccca gccctggcgc tgagcctctc taccccaggt cagacggaca      720
gaaagacaaa tcacaggttc cgggatgagg acaccggctc tgaccaggag tttggggagc      780
ttcaggacat tgctgtgctt tggggattcc ctccacatgc tgcacgcgca tctcgccccc      840
aggggcactg cctggaagat tcaggagcct gggcggcctt cgcttactct cacctgcttc      900
tgagttgccc aggaggccac tggcagatgt cccggcgaag agaagagaca cattgttgga      960
agaagcagcc catgacagcg ccccttcctg ggactcgccc tcatcctctt cctgctcccc     1020
ttcctggggt gcagcctaaa aggacctatg tcctcacacc attgaaacca ctagttctgt     1080
ccccccagga aacctggttg tgtgtgtgtg agtggttgac cttcctccat cccctggtcc     1140
ttcccttccc ttcccgaggc acagagagac agggcaggat ccacgtgccc attgtggagg     1200
cagagaaaag agaaagtgtt ttatatacgg tacttattta atatcccttt ttaattagaa     1260
attagaacag ttaatttaat taaagagtag ggttttttt cagtattctt ggttaatatt      1320
taatttcaac tatttatgag atgtatcttt tgctctctct tgctctctta tttgtaccgg     1380
tttttgtata taaaattcat gtttccaatc tctctctccc tgatcggtga cagtcactag     1440
cttatcttga acagatattt aattttgcta acactcagct ctgccctccc cgatcccctg     1500
gctccccagc acacattcct ttgaaagagg gtttcaatat acatctacat actatatata     1560
tattgggcaa cttgtatttg tgtgtatata tatatatata tgtttatgta tatatgtgat     1620
cctgaaaaaa taaacatcgc tattctgttt tttatatgtt caaaccaaac aagaaaaaat     1680
agagaattct acatactaaa tctctctcct ttttaattt taatatttgt tatcatttat      1740
ttattggtgc tactgtttat ccgtaataat tgtggggaaa agatattaac atcacgtctt     1800
tgtctctagt gcagttttc gagatattcc gtagtacata tttattttta aacaacgaca      1860
aagaaataca gatatatctt aaaaaaaaaa aa                                   1892
```

<210> SEQ ID NO 19
<211> LENGTH: 249
<212> TYPE: RNA
<213> ORGANISM: Homo sapiens

<400> SEQUENCE: 19

```
ccgggcucau ggacggguga ggcggcggug ugcgcagaca gugcuccagc gcgcgcgcuc       60
cccagcccug gccggccuc gggccgggag gaagaguagc ucgccgaggc gccgaggaga       120
gcgggccgcc ccacagcccg agccggagag ggacgcgagc cgcgcgcccc ggucgggccu      180
ccgaaaccau gaacuuucug cugucuuggg ugcauggag ccuugccuug cugcucuacc       240
uccaccaug                                                              249
```

<210> SEQ ID NO 20

<211> LENGTH: 4825
<212> TYPE: DNA
<213> ORGANISM: Artificial Sequence
<220> FEATURE:
<223> OTHER INFORMATION: Description of Artificial Sequence: Expression vector pMCP1

<400> SEQUENCE: 20

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact aagctttcgg    840
cgcgccgagg taccatggga tccgaagacg ccaaaaacat aaagaaaggc ccggcgccat    900
tctatcctct agaggatgga accgctggag agcaactgca taaggctatg aagagatacg    960
ccctggttcc tggaacaatt gcttttacag atgcacatat cgaggtgaac atcacgtacg   1020
cggaatactt cgaaatgtcc gttcggttgg cagaagctat gaaacgatat gggctgaata   1080
caaatcacag aatcgtcgta tgcagtgaaa actctcttca attctttatg ccggtgttgg   1140
gcgcgttatt tatcggagtt gcagttgcgc ccgcgaacga catttataat gaacgtgaat   1200
tgctcaacag tatgaacatt tcgcagccta ccgtagtgtt tgtttccaaa aagggggttgc   1260
aaaaaatttt gaacgtgcaa aaaaattac caataatcca gaaaattatt atcatggatt   1320
ctaaaacgga ttaccaggga tttcagtcga tgtacgttc gtcacatct catctacctc   1380
ccggttttaa tgaatacgat tttgtaccag agtccttga tcgtgacaaa acaattgcac   1440
tgataatgaa ttcctctgga tctactgggt tacctaaggg tgtggccctt ccgcatagaa   1500
ctgcctgcgt cagattctcg catgccagag atcctatttt tggcaatcaa atcattccgg   1560
atactgcgat tttaagtgtt gttccattcc atcacggttt tggaatgttt actacactcg   1620
gatatttgat atgtggattt cgagtcgtct taatgtatag atttgaagaa gagctgtttt   1680
tacgatccct tcaggattac aaaattcaaa gtgcgttgct agtaccaacc ctattttcat   1740
tcttcgccaa aagcactctg attgacaaat acgatttatc taatttacac gaaattgctt   1800
ctggggcgc acctctttcg aaagaagtcg gggaagcggt tgcaaaacgc ttccatcttc   1860
cagggatacg acaaggatat gggctcactg agactacatc agctattctg attacacccg   1920
aggggatga taaaccgggc gcggtcggta agttgttcc atttttgaa gcgaaggttg   1980
tggatctgga taccgggaaa acgctgggcg ttaatcagag aggcgaatta tgtgtcagag   2040
gacctatgat tatgtccggt tatgtaaaca atccggaagc gaccaacgcc ttgattgaca   2100
```

```
aggatggatg gctacattct ggagacatag cttactggga cgaagacgaa cacttcttca    2160
tagttgaccg cttgaagtct ttaattaaat acaaaggata tcaggtggcc cccgctgaat    2220
tggaatcgat attgttacaa caccccaaca tcttcgacgc gggcgtggca ggtcttcccg    2280
acgatgacgc cggtgaactt cccgccgccg ttgttgtttt ggagcacgga aagacgatga    2340
cggaaaaaga gatcgtggat tacgtcgcca gtcaagtaac aaccgcgaaa aagttgcgcg    2400
gaggagttgt gtttgtggac gaagtaccga aaggtcttac cggaaaactc gacgcaagaa    2460
aaatcagaga gatcctcata aggccaaga agggcggaaa gtccaaattg cgcggccgct    2520
aactcgagaa taaaatgagg aaattgcatc gcattgtctg agtaggtgtc attctattct    2580
gggggtggg gtggggcagg acagcaaggg ggaggattgg gaagacaata gcaggcatgc    2640
tggggatgcg gtgggctcta tggcttctga ggcggaaaga accagctggg gctctagggg    2700
gtatccccac gcgccctgta gcggcgcatt aagcgcggcg ggtgtggtgg ttacgcgcag    2760
cgtgaccgct acacttgcca gcgccctagc gcccgctcct ttcgctttct tcccttcctt    2820
tctcgccacg ttcgccggct ttccccgtca gctctaaat cggggtccc tttagggttc      2880
cgatttagtg ctttacgca cctcgacccc aaaaaacttg attagggtga tggttcacgt      2940
acctagaagt tccattccg aagttcctat tctctagaaa gtataggaac ttccttggcc      3000
aaaaagcctg aactcaccgc gacgtctgtc gagaagtttc tgatcgaaaa gttcgacagc    3060
gtctccgacc tgatgcagct ctcggagggc gaagaatctc gtgctttcag cttcgatgta    3120
ggagggcgtg gatatgtcct gcgggtaaat agctgcgccg atggtttcta caaagatcgt    3180
tatgtttatc ggcactttgc atcggccgcg ctcccgattc cggaagtgct tgacattggg    3240
gaattcagcg agagcctgac ctattgcatc tcccgccgtg cacagggtgt cacgttgcaa    3300
gacctgcctg aaaccgaact gcccgctgtt ctgcagccgg tcgcggaggc catggatgcg    3360
atcgctgcgg ccgatcttag ccagacgagc gggttcggcc cattcggacc gcaaggaatc    3420
ggtcaataca ctacatggcg tgatttcata tgcgcgattg ctgatcccca tgtgtatcac    3480
tggcaaactg tgatggacga caccgtcagt gcgtccgtcg cgcaggctct cgatgagctg    3540
atgctttggg ccgaggactg ccccgaagtc cggcacctcg tgcagcaaac aaaccaccgc    3600
tggtagcggt tttttgttt gcaagcagca gattacgcgc agaaaaaaag gatctcaaga    3660
agatcctttg atcttttcta cggggtctga cgctcagtgg aacgaaaact cacgttaagg    3720
gattttggtc atgagattat caaaaaggat cttcacctag atccttttaa attaaaaatg    3780
aagttttaaa tcaatctaaa gtatatatga gtaaacttgg tctgacagtt accaatgctt    3840
aatcagtgag gcacctatct cagcgatctg tctatttcgt tcatccatag ttgcctgact    3900
ccccgtcgtg tagataacta cgatacggga gggcttacca tctggcccca gtgctgcaat    3960
gataccgcga gacccacgct caccggctcc agatttatca gcaataaacc agccagccgg    4020
aagggccgag cgcagaagtg gtcctgcaac tttatccgcc tccatccagt ctattaattg    4080
ttgccgggaa gctagagtaa gtagttcgcc agttaatagt ttgcgcaacg ttgttgccat    4140
tgctacaggc atcgtggtgt cacgctcgtc gtttggtatg gcttcattca gctccggttc    4200
ccaacgatca aggcgagtta catgatcccc catgttgtgc aaaaaagcgg ttagctcctt    4260
cggtcctccg atcgttgtca gaagtaagtt ggccgcagtg ttatcactca tggttatggc    4320
agcactgcat aattctctta ctgtcatgcc atccgtaaga tgcttttctg tgactggtga    4380
gtactcaacc aagtcattct gagaatagtg tatgcggcga ccgagttgct cttgcccggc    4440
gtcaatacgg gataataccg cgccacatag cagaacttta aaagtgctca tcattggaaa    4500
```

```
acgttcttcg gggcgaaaac tctcaaggat cttaccgctg ttgagatcca gttcgatgta    4560
acccactcgt gcacccaact gatcttcagc atctttact ttcaccagcg tttctgggtg    4620
agcaaaaaca ggaaggcaaa atgccgcaaa aagggaata agggcgacac ggaaatgttg    4680
aatactcata ctcttccttt ttcaatatta ttgaagcatt tatcagggtt attgtctcat    4740
gagcggatac atatttgaat gtatttagaa aaataaacaa ataggggttc cgcgcacatt    4800
tccccgaaaa gtgccacctg acgtc                                          4825
```

```
<210> SEQ ID NO 21
<211> LENGTH: 49
<212> TYPE: DNA
<213> ORGANISM: Homo sapiens

<400> SEQUENCE: 21
ccgccagatt tgaatcgcgg gacccgttgg cagaggtggc ggcggcggc              49

<210> SEQ ID NO 22
<211> LENGTH: 1141
<212> TYPE: DNA
<213> ORGANISM: Homo sapiens

<400> SEQUENCE: 22
ggcctctggc cggagctgcc tggtcccaga gtggctgcac cacttccagg gtttattccc      60
tggtgccacc agccttcctg tgggcccctt agcaatgtct taggaaagga gatcaacatt     120
ttcaaattag atgtttcaac tgtgctcctg ttttgtcttg aaagtggcac cagaggtgct     180
tctgcctgtg cagcgggtgc tgctggtaac agtggctgct tctctctctc tctctcttt     240 ttgggggctc attttgctg ttttgattcc cgggcttacc aggtgagaag tgagggagga     300
agaaggcagt gtccctttg ctagagctga cagctttgtt cgcgtgggca gagccttcca     360
cagtgaatgt gtctggacct catgttgttg aggctgtcac agtcctgagt gtggacttgg     420
caggtgcctg ttgaatctga gctgcaggtt ccttatctgt cacacctgtg cctcctcaga     480
ggacagtttt ttgttgttg tgtttttttg tttttttttt ttggtagatg catgacttgt     540
gtgtgatgag agaatggaga cagagtccct ggctcctcta ctgtttaaca acatggcttt     600
cttattttgt ttgaattgtt aattcacaga atagcacaaa ctacaattaa aactaagcac     660
aaagccattc taagtcattg gggaaacggg gtgaacttca ggtggatgag gagacagaat     720
agagtgatag gaagcgtctg gcagatactc cttttgccac tgctgtgtga ttagacaggc     780
ccagtgagcc gcggggcaca tgctggccgc tcctccctca gaaaaaggca gtggcctaaa     840 tccttttttaa atgacttggc tcgatgctgt ggggactgg ctgggctgct gcaggccgtg      900
tgtctgtcag cccaaccttc acatctgtca cgttctccac acgggggaga gacgcagtcc     960
gcccaggtcc ccgctttctt tggaggcagc agctcccgca gggctgaagt ctggcgtaag    1020
atgatggatt tgattcgccc tcctccctgt catagagctg cagggtggat tgttacagct    1080
tcgctggaaa cctctggagg tcatctcggc tgttcctgag aaataaaaag cctgtcattt    1140
c                                                                    1141

<210> SEQ ID NO 23
<211> LENGTH: 247
<212> TYPE: DNA
<213> ORGANISM: Homo sapiens

<400> SEQUENCE: 23
```

```
cccccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240
gcagcag                                                              247

<210> SEQ ID NO 24
<211> LENGTH: 1716
<212> TYPE: DNA
<213> ORGANISM: Homo sapiens

<400> SEQUENCE: 24
tgaccacgga ggatagtatg agccctaaaa atccagactc tttcgatacc caggaccaag      60
ccacagcagg tcctccatcc caacagccat gcccgcatta gctcttagac ccacagactg     120
gttttgcaac gtttacaccg actagccagg aagtacttcc acctcgggca cattttggga     180
agttgcattc ctttgtcttc aaactgtgaa gcatttacag aaacgcatcc agcaagaata     240
ttgtcccttt gagcagaaat ttatctttca aagaggtata tttgaaaaaa aaaaaaaaag     300
tatatgtgag gattttattt gattggggat cttggagttt ttcattgtcg ctattgattt     360
ttacttcaat gggctcttcc aacaaggaag aagcttgctg gtagcacttg ctaccctgag     420
ttcatccagg cccaactgtg agcaaggagc acaagccaca agtcttccag aggatgcttg     480
attccagtgg ttctgcttca aggcttccac tgcaaaacac taaagatcca agaaggcctt     540
catggcccca gcaggccgga tcggtactgt atcaagtcat ggcaggtaca gtaggataag     600
ccactctgtc ccttcctggg caaagaagaa acggagggga tgaattcttc cttagactta     660
cttttgtaaa aatgtcccca cggtacttac tccccactga tggaccagtg gtttccagtc     720
atgagcgtta gactgacttg tttgtcttcc attccattgt tttgaaactc agtatgccgc     780
ccctgtcttg ctgtcatgaa atcagcaaga gaggatgaca catcaaataa taactcggat     840
tccagcccac attggattca tcagcatttg gaccaatagc ccacagctga aatgtggaa      900 tacctaagga taacaccgct tttgttctcg caaaaacgta tctcctaatt tgaggctcag     960
atgaaatgca tcaggtcctt tggggcatag atcagaagac tacaaaaatg aagctgctct    1020
gaaatctcct ttagccatca ccccaacccc ccaaaattag tttgtgttac ttatggaaga    1080 tagtttttctc cttttacttc acttcaaaag ctttttactc aaagagtata tgttccctcc    1140
aggtcagctg ccccccaaacc ccctccttac gctttgtcac acaaaaagtg tctctgcctt    1200
gagtcatcta ttcaagcact tacagctctg gccacaacag ggcattttac aggtgcgaat    1260
gacagtagca ttatgagtag tgtgaattca ggtagtaaat atgaaactag ggtttgaaat    1320
tgataatgct ttcacaacat ttgcagatgt tttagaagga aaaagttcc ttcctaaaat      1380 aatttctcta caattggaag attggaagat tcagctagtt aggagcccat ttttccctaa    1440
tctgtgtgtg ccctgtaacc tgactggtta acagcagtcc tttgtaaaca gtgttttaaa    1500
ctctcctagt caatatccac cccatccaat ttatcaagga agaaatggtt cagaaaatat    1560
tttcagccta cagttatgtt cagtcacaca cacatacaaa atgttccttt tgcttttaaa    1620 gtaattttttg actcccagat cagtcagagc ccctacagca ttgttaagaa agtatttgat    1680
ttttgtctca atgaaaataa aactatattc atttcc                              1716

<210> SEQ ID NO 25
<211> LENGTH: 160
```

```
<212> TYPE: DNA
<213> ORGANISM: Homo sapiens

<400> SEQUENCE: 25
tataaaagct gggccggcgc gggccgggcc attcgcgacc cggaggtgcg cgggcgcggg    60
cgagcagggt ctccgggtgg gcggcgcgac gccccgcgca ggctggaggc cgccgaggct   120
cgccatgccg ggagaactct aactccccca tggagtcggc                         160

<210> SEQ ID NO 26
<211> LENGTH: 1306
<212> TYPE: DNA
<213> ORGANISM: Homo sapiens

<400> SEQUENCE: 26
tgaggcgcgc ggctgtggga ccgccctggg ccagcctccg gcggggaccc agggagtggt    60
ttggggtcgc cggatctcga ggcttgccca gaccgtgcga gccaggacta ggagattccg   120
gtgcctcctg aaagcctggc ctgctccgcg tgtcccctcc cttcctctgc gccggacttg   180
gtgcgtctaa gatgaggggg ccaggcggtg gcttctccct gcgaggaggg gagaattctt   240
ggggctgagc tgggagcccg gcaactctag tatttaggat aacttgtgcc ttggaaatgc   300
aaactcaccg ctccaatgcc tactgagtag ggggagcaaa tcgtgccttg tcattttatt   360
tggaggtttc ctgcctcctt cccgaggcta cagcagaccc ccatgagaga aggaggggag   420
caggcccgtg gaggagggg gctcagggag ctgagatccc gacaagcccg ccagcccag    480 ccgctcctcc acgcctgtcc ttagaaaggg gtggaaacat agggacttgg ggcttggaac   540
ctaaggttgt tccctagttc tacatgaagg tggaggtctc tagttccacg cctctcccac   600
ctccctccgc acacacccca cccagcctgc tataggctgg ctttcccttg gggctggaac   660
tcactgcgat ggggtcacca ggtgaccagt ggagcccca ccccgagtca gaccagaaag   720
ctaggtcgtg ggtcagctct gaggatgtat acccctggtg ggagagggag acctagagat   780
ctggctgtgg ggcgggcatg gggggtgaag ggccactggg accctcagcc ttgtttgtac   840
tgtatgcctt cagcattgcc taggaacacg aagcacgatc agtccatcca gagggaccgg   900
agttatgaca agcttcccaa atattttgct ttatcagccg atatcaacac ttgtatctgg   960
cctctgtgcc cagcagtgcc ttgtgcaatg tgaatgtacc gtctctgcta aaccaccatt  1020
ttatttggtt ttgttttgtt tggttttctc ggatacttgc caaaatgaga ctctccgtcg  1080
gcagctgggg gaagggtctg agactctctt tccttttggt tttgggatta cttttgatcc  1140
tgggggacca atgaggtgag gggggttctc ctttgccctc agctttccca gccctccggc  1200
ctgggctgcc cacaaggctt ctcccccaga ggccctggct cctggtcggg aagggaggtg  1260
cctcccgcca acgcatcact ggggctggga gcagggaagg gaattc                 1306

<210> SEQ ID NO 27
<211> LENGTH: 216
<212> TYPE: DNA
<213> ORGANISM: Homo sapiens

<400> SEQUENCE: 27
agcgagagcg cccccgagca gcgcccgcgc cctccgcgcc ttctccgccg ggacctcgag    60
cgaaagacgc ccgcccgccg cccagccctc gcctccctgc ccaccgggca caccgcgccg   120
ccaccccgac cccgctgcgc acggcctgtc cgctgcacac cagcttgttg gcgtcttcgt   180
cgccgcgctc gccccgggct actcctgcgc gccaca                             216
```

<210> SEQ ID NO 28
<211> LENGTH: 687
<212> TYPE: DNA
<213> ORGANISM: Homo sapiens

<400> SEQUENCE: 28

```
taaatgctac ctgggtttcc agggcacacc tagacaaaca rgggagaaga gtgtcagaat      60
cagaatcatg gagaaaatgg gcggggtgg tgtgggtgat gggactcatt gtagaaagga     120
agccttgctc attcttgagg agcattaagg tatttcgaaa ctgccaaggg tgctggtgcg     180
gatggacact aatgcagcca cgattggaga atactttgct tcatagtatt ggagcacatg     240
ttactgcttc attttggagc ttgtggagtt gatgactttc tgttttctgt ttgtaaatta     300
tttgctaagc atattttctc taggctttt tccttttggg gttctacagt cgtaaaagag     360
ataataagat tagttggaca gtttaaagct tttattcgtc ctttgacaaa agtaaatggg     420
agggcattcc atcccttcct gaaggggac actccatgag tgtctgtgag aggcagctat      480
ctgcactcta aactgcaaac agaaatcagg tgttttaaga ctgaatgttt tatttatcaa     540
aatgtagctt tggggaggg aggggaaatg taatactgga ataatttgta aatgatttta      600
attttatatt cagtgaaaag attttattta tggaattaac catttaataa agaaatattt     660
acctaaaaaa aaaaaaaaa aaaaaaa                                         687
```

<210> SEQ ID NO 29
<211> LENGTH: 310
<212> TYPE: DNA
<213> ORGANISM: Homo sapiens

<400> SEQUENCE: 29

```
cggcccccaga aaacccgagc gagtaggggg cggcgcgcag gagggaggag aactgggggc     60
gcgggaggct ggtgggtgtc gggggtggag atgtagaaga tgtgacgccg cggcccggcg    120
ggtgccagat tagcgacggg ctgcccgcgg ttgcaacggg atcccgggcg ctgcagcttg    180
ggaggcggct ctccccaggc ggcgtccgcg gagacaccca tccgtgaacc ccaggtcccg    240
ggccgccggc tcgccgcgca ccaggggccg gcggacagaa gagcggccga gcggctcgag    300
gctgggggac                                                           310
```

<210> SEQ ID NO 30
<211> LENGTH: 5882
<212> TYPE: DNA
<213> ORGANISM: Homo sapiens

<400> SEQUENCE: 30

```
ctgctaagag ctgattttaa tggccacatc taatctcatt tcacatgaaa gaagaagtat      60
attttagaaa tttgttaatg agagtaaaag aaaataaatg tgtatagctc agtttggata     120
attggtcaaa caatttttta tccagtagta aaatatgtaa ccattgtccc agtaaagaaa     180
aataacaaaa gttgtaaaat gtatattctc ccttttatat tgcatctgct gttacccagt     240
gaagcttacc tagagcaatg atcttttttca cgcatttgct ttattcgaaa agaggctttt     300
aaaatgtgca tgtttagaaa caaaattttct tcatggaaat catatacatt agaaaatcac     360
agtcagatgt ttaatcaatc caaaatgtcc actatttctt atgtcattcg ttagtctaca     420
tgtttctaaa catataaatg tgaatttaat caattccttt catagtttta taattctctg     480
gcagttcctt atgatagagt ttataaaaca gtcctgtgta aactgctgga agttcttcca     540
cagtcaggtc aattttgtca aacccttctc tgtacccata cagcagcagc ctagcaactc     600
```

-continued

```
tgctggtgat gggagttgta ttttcagtct tcgccaggtc attgagatcc atccactcac    660
atcttaagca ttcttcctgg caaaaattta tggtgaatga atatggcttt aggcggcaga    720
tgatatacat atctgacttc ccaaaagctc caggatttgt gtgctgttgc cgaatactca    780
ggacggacct gaattctgat tttataccag tctcttcaaa aacttctcga accgctgtgt    840
ctcctacgta aaaaagaga tgtacaaatc aataataatt acacttttag aaactgtatc    900
atcaaagatt ttcagttaaa gtagcattat gtaaaggctc aaaacattac cctaacaaag    960
taaagttttc aatacaaatt ctttgccttg tggatatcaa gaaatcccaa aatattttct   1020
taccactgta aattcaagaa gcttttgaaa tgctgaatat ttctttggct gctacttgga   1080
ggcttatcta cctgtacatt tttggggtca gctcttttta acttcttgct gctctttttc   1140
ccaaaaggta aaaatataga ttgaaaagtt aaaacatttt gcatggctgc agttcctttg   1200
tttcttgaga taagattcca agaacttag attcatttct tcaacaccga aatgctggag   1260
gtgtttgatc agttttcaag aaacttggaa tataaataat tttataattc aacaaaggtt   1320
ttcacatttt ataaggttga ttttcaatt aaatgcaaat ttgtgtggca ggattttat   1380
tgccattaac atattttgt ggctgctttt tctacacatc cagatggtcc ctctaactgg   1440
gctttctcta attttgtgat gttctgtcat tgtctcccaa agtatttagg agaagccctt   1500
taaaagctg ccttcctcta ccactttgct ggaaagcttc acaattgtca cagacaaaga   1560
tttttgttcc aatactcgtt ttgcctctat ttttcttgtt tgtcaaatag taaatgatat   1620
ttgcccttgc agtaattcta ctggtgaaaa acatgcaaag aagaggaagt cacagaaaca   1680
tgtctcaatt cccatgtgct gtgactgtag actgtcttac catagactgt cttacccatc   1740
ccctggatat gctcttgttt tttccctcta atagctatgg aaagatgcat agaaagagta   1800
taatgtttta aaacataagg cattcatctg ccattttca attacatgct gacttccctt   1860
acaattgaga tttgcccata ggttaaacat ggttagaaac aactgaaagc ataaagaaa   1920
aatctaggcc gggtgcagtg gctcatgcct atattccctg cactttggga ggccaaagca   1980
ggaggatcgc ttgagcccag gagttcaaga ccaacctggt gaaacccctgt ctctacaaaa   2040
aaacacaaaa aatagccagg catggtggcg tgtacatgtg gtctcagata cttgggaggc   2100
tgaggtggga gggttgatca cttgaggctg agaggtcaag gttgcagtga gccataatcg   2160
tgccactgca gtccagccta ggcaacagag tgagactttg tctcaaaaaa agagaaattt   2220
tccttaataa gaaagtaat ttttactctg atgtgcaata catttgttat taaatttatt   2280
atttaagatg gtagcactag tcttaaattg tataaaatat cccctaacat gtttaaatgt   2340
ccatttttat tcattatgct ttgaaaaata attatgggga aatacatgtt tgttattaaa   2400
tttattatta aagatagtag cactagtctt aaatttgata taacatctcc taacttgttt   2460
aaatgtccat ttttattctt tatgcttgaa aataaattat ggggatccta tttagctctt   2520
agtaccacta atcaaaagtt cggcatgtag ctcatgatct atgctgtttc tatgtcgtgg   2580
aagcaccgga tgggggtagt gagcaaatct gccctgctca gcagtcacca tagcagctga   2640
ctgaaaatca gcactgcctg agtagttttg atcagttttaa cttgaatcac taactgactg   2700
aaaattgaat gggcaaataa gtgctttgt ctccagtgta tgcggagac ccttccacct   2760
caagatggat atttcttccc caaggatttc aagatgaatt gaaattttta atcaagatag   2820
tgtgctttat tctgttgtat ttttttattat tttaatatac tgtaagccaa actgaaataa   2880
catttgctgt tttataggtt tgaagaacat aggaaaaact aagaggtttt gttttattt   2940
```

```
ttgctgatga agagatatgt ttaaatatgt tgtattgttt tgtttagtta caggacaata    3000
atgaaatgga gtttatattt gttatttcta ttttgttata tttaataata gaattagatt    3060
gaaataaaat ataatgggaa ataatctgca gaatgtgggt ttcctggtgt ttcctctgac    3120
tctagtgcac tgatgatctc tgataaggct cagctgcttt atagttctct ggctaatgca    3180
gcagatactc ttcctgccag tggtaatacg attttttaag aaggcagttt gtcaatttta    3240
atcttgtgga tacctttata ctcttagggt attattttat acaaaagcct tgaggattgc    3300
attctatttt ctatatgacc ctcttgatat ttaaaaaaca ctatggataa caattcttca    3360
tttacctagt attatgaaag aatgaaggag ttcaaacaaa tgtgtttccc agttaactag    3420
ggtttactgt ttgagccaat ataaatgttt aactgtttgt gatggcagta ttcctaaagt    3480
acattgcatg ttttcctaaa tacagagttt aaataatttc agtaattctt agatgattca    3540
gcttcatcat taagaatatc ttttgtttta tgttgagtta gaaatgcctt catatagaca    3600
tagtctttca gacctctact gtcagttttc atttctagct gctttcaggg ttttatgaat    3660
tttcaggcaa agctttaatt tatactaagc ttaggaagta tggctaatgc caacggcagt    3720
ttttttcttc ttaattccac atgactgagg catatatgat ctctgggtag gtgagttgtt    3780
gtgacaacca caagcacttt ttttttttt aagaaaaaa aggtagtgaa ttttaatca    3840
tctggacttt aagaaggatt ctggagtata cttaggcctg aaattatata tatttggctt    3900
ggaaatgtgt ttttcttcaa ttacatctac aagtaagtac agctgaaatt cagaggaccc    3960
ataagagttc acatgaaaaa aatcaattca tttgaaaagg caagatgcag gagagaggaa    4020
gccttgcaaa cctgcagact gcttttttgcc caatatagat tgggtaaggc tgcaaaacat    4080
aagcttaatt agctcacatg ctctgctctc acgtggcacc agtggatagt gtgagagaat    4140
taggctgtag aacaaatggc cttctctttc agcattcaca ccactacaaa atcatctttt    4200
atatcaacag aagaataagc ataaactaag caaaaggtca ataagtacct gaaaccaaga    4260
ttggctagag atatatctta atgcaatcca ttttctgatg gattgttacg agttggctat    4320
ataatgtatg tatggtattt tgatttgtgt aaaagtttta aaaatcaagc tttaagtaca    4380
tggacatttt taaataaaat atttaaagac aatttagaaa attgccttaa tatcattgtt    4440
ggctaaatag aataggggac atgcatatta aggaaaaggt catggagaaa taatattggt    4500
atcaaacaaa tacattgatt tgtcatgata cacattgaat ttgatccaat agtttaagga    4560
ataggtagga aaatttggtt tctattttc gatttcctgt aaatcagtga cataaataat    4620
tcttagctta ttttatattt ccttgtctta aatactgagc tcagtaagtt gtgttagggg    4680
attatttctc agttgagact ttcttatatg acatttact atgttttgac ttcctgacta    4740
ttaaaaataa atagtagaaa caattttcat aaagtgaaga attatataat cactgcttta    4800
taactgactt tattatattt atttcaaagt tcatttaaag gctactattc atcctctgtg    4860
atggaatggt caggaatttg ttttctcata gtttaattcc aacaacaata ttagtcgtat    4920
ccaaaataac ctttaatgct aaactttact gatgtatatc caaagcttct ccttttcaga    4980
cagattaatc cagaagcagt cataaacaga agaataggtg gtatgttcct aatgatatta    5040
tttctactaa tggaataaac tgtaatatta gaaattatgc tgctaattat atcagctctg    5100
aggtaatttc tgaaatgttc agactcagtc ggaacaaatt ggaaaattta aatttttatt    5160
cttagctata aagcaagaaa gtaaacacat taatttcctc aacatttttta agccaattaa    5220
aaatataaaa gatacacacc aatatcttct tcaggctctg acaggcctcc tggaaacttc    5280
cacatatttt tcaactgcag tataaagtca gaaaataaag ttaacataac tttcactaac    5340
```

| | |
|---|---|
| acacacatat gtagatttca caaaatccac ctataattgg tcaaagtggt tgagaatata | 5400 |
| tttttttagta attgcatgca aaatttttct agcttccatc ctttctccct cgtttcttct | 5460 |
| tttttttgggg gagctggtaa ctgatgaaat cttttcccac cttttctctt caggaaatat | 5520 |
| aagtggtttt gttggttaa cgtgatacat tctgtatgaa tgaaacattg gagggaaaca | 5580 |
| tctactgaat ttctgtaatt taaaatattt tgctgctagt taactatgaa cagatagaag | 5640 |
| aatcttacag atgctgctat aaataagtag aaaatataaa tttcatcact aaaatatgct | 5700 |
| atttttaaaat ctatttccta tattgtattt ctaatcagat gtattactct tattatttct | 5760 |
| attgtatgtg ttaatgattt tatgtaaaaa tgtaattgct tttcatgagt agtatgaata | 5820 |
| aaattgatta gtttgtgttt tcttgtctcc cgaaaaaaa aaaaaaaaa aaaaaaaa | 5880 |
| aa | 5882 |

<210> SEQ ID NO 31
<211> LENGTH: 310
<212> TYPE: DNA
<213> ORGANISM: Homo sapiens
<400> SEQUENCE: 31

| | |
|---|---|
| cggcccaga aaacccgagc gagtaggggg cggcgcgcag gagggaggag aactgggggc | 60 |
| gcgggaggct ggtgggtgtc gggggtggag atgtagaaga tgtgacgccg cggcccggcg | 120 |
| ggtgccagat tagcggacgg ctgcccgcgg ttgcaacggg atcccgggcg ctgcagcttg | 180 |
| ggaggcggct ctccccaggc ggcgtccgcg gagacaccca tccgtgaacc ccaggtcccg | 240 |
| ggccgccggc tcgccgcgca ccaggggccg gcggacagaa gagcggccga gcggctcgag | 300 |
| gctgggggac | 310 |

<210> SEQ ID NO 32
<211> LENGTH: 3212
<212> TYPE: DNA
<213> ORGANISM: Homo sapiens
<400> SEQUENCE: 32

| | |
|---|---|
| tgagggcgcc aggcaggcgg gcgccaccgc cacccgcagc gagggcggag ccggccccag | 60 |
| gtgctcccct gacagtccct cctctccgga gcattttgat accagaaggg aaagcttcat | 120 |
| tctccttgtt gttggttgtt ttttcctttg ctctttcccc cttccatctc tgacttaagc | 180 |
| aaaagaaaaa gattacccaa aaactgtctt taaagagag agagagaaaa aaaaaatagt | 240 |
| atttgcataa ccctgagcgg tgggggagga gggttgtgct acagatgata gaggatttta | 300 |
| taccccaata atcaactcgt ttttatatta atgtacttgt ttctctgttg taagaatagg | 360 |
| cattaacaca aaggaggcgt ctcgggagag gattaggttc catcctttac gtgtttaaaa | 420 |
| aaaagcataa aaacatttta aaaacataga aaaattcagc aaaccatttt taaagtagaa | 480 |
| gagggttta ggtagaaaaa catattcttg tgctttcct gataaagcac agctgtagtg | 540 |
| gggttctagg catctctgta ctttgcttgc tcatatgcat gtagtcactt tataagtcat | 600 |
| tgtatgttat tatattccgt aggtagatgt gtaacctctt caccttattc atggctgaag | 660 |
| tcacctcttg gttacagtag cgtagcgtgg ccgtgtgcat gtcctttgcg cctgtgacca | 720 |
| ccaccccaac aaaccatcca gtgacaaacc atccagtgga ggtttgtcgg gcaccagcca | 780 |
| gcgtagcagg gtcgggaaag gccacctgtc ccactcctac gatacgctac tataaagaga | 840 |
| agacgaaata gtgacataat atattctatt tttatactct tcctattttt gtagtgacct | 900 |

```
gtttatgaga tgctggtttt ctacccaacg ccctgcagc cagctcacgt ccaggttcaa      960
cccacagcta cttggtttgt gttcttcttc atattctaaa accattccat ttccaagcac    1020
tttcagtcca ataggtgtag gaaatagcgc tgttttttgtt gtgtgtgcag ggagggcagt   1080
tttctaatgg aatggtttgg gaatatccat gtacttgttt gcaagcagga ctttgaggca   1140
agtgtgggcc actgtggtgg cagtggaggt ggggtgtttg ggaggctgcg tgccagtcaa   1200
gaagaaaaag gtttgcattc tcacattgcc aggatgataa gttcctttcc ttttctttaa   1260
agaagttgaa gtttaggaat cctttggtgc caactggtgt ttgaaagtag ggacctcaga   1320
ggtttaccta gagaacaggt ggttttttaag ggttatctta gatgtttcac accggaaggt  1380
ttttaaacac taaaatatat aatttatagt taaggctaaa aagtatattt attgcagagg   1440
atgttcataa ggccagtatg atttataaat gcaatctccc cttgatttaa acacacagat   1500
acacacacac acacacacac acacacaaac cttctgcctt tgatgttaca gatttaatac   1560
agtttatttt taaagataga tcctttttata ggtgagaaaa aaacaatctg gaagaaaaaa  1620
accacacaaa gacattgatt cagcctgttt ggcgtttccc agagtcatct gattggacag   1680
gcatgggtgc aaggaaaatt agggtactca acctaagttc ggttccgatg aattcttatc   1740
ccctgccccct tcctttaaaa aacttagtga caaaatagac aatttgcaca tcttggctat  1800
gtaattcttg taatttttat ttaggaagtg ttgaagggag gtggcaagag tgtggaggct   1860
gacgtgtgag ggaggacagg cgggaggagg tgtgaggagg aggctcccga ggggaagggg   1920
cggtgcccac accggggaca ggccgcagct ccatttttctt attgcgctgc taccgttgac  1980
ttccaggcac ggtttggaaa tattcacatc gcttctgtgt atctctttca cattgtttgc   2040
tgctattgga ggatcagttt tttgttttac aatgtcatat actgccatgt actagtttta   2100
gttttctctt agaacattgt attacagatg ccttttttgt agtttttttt tttttatgt    2160
gatcaatttt gacttaatgt gattactgct ctattccaaa aaggttgctg tttcacaata   2220
cctcatgctt cacttagcca tggtggaccc agcgggcagg ttctgcctgc tttggcgggc   2280
agacacgcgg gcgcgatccc acacaggctg gcggggccg gccccgaggc cgcgtgcgtg    2340
agaaccgcgc cggtgtcccc agagaccagg ctgtgtccct cttctcttcc ctgcgcctgt   2400
gatgctgggc acttcatctg atcggggcg tagcatcata gtagttttta cagctgtgtt   2460
attctttgcg tgtagctatg gaagttgcat aattattatt attattatta taacaagtgt   2520
gtcttacgtg ccaccacggc gttgtacctg taggactctc attcgggatg attggaatag   2580
cttctggaat ttgttcaagt tttgggtatg tttaatctgt tatgtactag tgttctgttt   2640
gttattgttt tgttaattac accataatgc taatttaaag agactccaaa tctcaatgaa   2700
gccagctcac agtgctgtgt gccccggtca cctagcaagc tgccgaacca aaagaatttg   2760
caccccgctg cgggcccacg tggttgggc cctgccctgg cagggtcatc ctgtgctcgg    2820
aggccatctc gggcacaggc ccaccccgcc ccacccctcc agaacacggc tcacgcttac   2880
ctcaaccatc ctggctgcgg cgtctgtctg aaccacgcgg gggccttgag ggacgctttg   2940
tctgtcgtga tggggcaagg gcacaagtcc tggatgttgt gtgtatcgag aggccaaagg   3000
ctggtggcaa gtgcacgggg cacagcggag tctgtcctgt gacgcgcaag tctgagggtc   3060
tgggcggcgg gcggctgggt ctgtgcattt ctggttgcac cgcggcgctt cccagcacca   3120
acatgtaacc ggcatgtttc cagcagaaga caaaaagaca aacatgaaag tctagaaata   3180
aaactggtaa aaccccaaaa aaaaaaaaaa aa                                  3212
```

```
<210> SEQ ID NO 33
<211> LENGTH: 1043
<212> TYPE: DNA
<213> ORGANISM: Homo sapiens
<220> FEATURE:
<221> NAME/KEY: misc_feature
<222> LOCATION: (409)..(444)
<223> OTHER INFORMATION: n = a, t, g or c

<400> SEQUENCE: 33
gcaccgcggc gagcttggct gcttctgggg cctgtgtggc cctgtgtgtc ggaaagatgg      60
agcaagaagc cgagcccgag gggcggccgc gaccctctg accgagatcc tgctgctttc     120
gcagccagga gcaccgtccc tccccggatt agtgcgtacg agcgcccagt gccctggccc     180
ggagagtgga atgatccccg aggcccaggg cgtcgtgctt ccgcgcgccc cgtgaaggaa     240
actggggagt cttgagggac ccccgactcc aagcgcgaaa accccggatg gtgaggagca     300
ggtactggcc cggcagcgag cggtcacttt tgggtctggg ctctgacggt gtccctcta      360 tcgctggttc ccagcctctg cccgttcgca gcctttgtgc ggttcgtgnc tggggctcg      420 gggcgcgggg cgcggggcat gggncacgtg gctttgcgga ggttttgttg gactggggct     480
agacagtccc cgccagggag gagggcggga tttcggacgg ctctcgcggc ggtgggggtg     540
ggggtggttc ggaggtctcc gcgggagttc agggtaaagg tcacggggcc ggggctgcgg     600
gccgcttcgg cgcgggaggt ccggatgatc gcagtgcctg tcgggtcact agtgtgaacg     660
ctgcgcgtag tctgggcggg attgggccgg ttcagtgggc aggttgactc agcttttcct     720
cttgagctgg tcaagttcag acacgttccg aaactgcagt aaaaggagtt aagtcctgac     780
ttgtctccag ctggggctat ttaaaccatg catttcccca gctgtgttca gtggcgattg     840
gagggtagac ctgtgggcac ggacgcacgc cactttttct ctgctgatcc aggtaagcac     900
cgacttgctt gtagctttag ttttaactgt tgtttatgtt ctttatatat gatgtatttt     960
ccacagatgt ttcatgattt ccagttttca tcgtgtcttt ttttccttg taggcaaatg     1020 tgcaatacca acatgtctgt acc                                           1043

<210> SEQ ID NO 34
<211> LENGTH: 1153
<212> TYPE: DNA
<213> ORGANISM: Homo sapiens

<400> SEQUENCE: 34
tagttgacct gtctataaga gaattatata tttctaacta tataaccta ggaatttaga      60 caacctgaaa tttattcaca tatatcaaag tgagaaaatg cctcaattca catagatttc     120
ttctctttag tataattgac ctactttggt agtggaatag tgaatactta ctataatttg     180
acttgaatat gtagctcatc ctttacacca actcctaatt ttaaataatt tctactctgt     240
cttaaatgag aagtacttgg ttttttttt cttaaatatg tatatgacat ttaaatgtaa      300
cttattattt ttttttgagac cgagtcttgc tctgttaccc aggctggagt gcagtgggtg     360
atcttggctc actgcaagct ctgccctccc cgggttcgca ccattctcct gcctcagcct     420
cccaattagc ttggcctaca gtcatctgcc accacacctg gctaattttt tgtactttta     480
gtagagacag ggtttcaccg tgttagccag gatggtctcg atctcctgac ctcgtgatcc     540
gcccacctcg gcctcccaaa gtgctgggat tacaggcatg agccaccgtg ctctccagcc     600
taggcaacag agtgagactc tgtctccaaa aaaaaaaaa aaaaaagggg actaaacac     660 ccccagggaa agggacaggt gggacattct tattcttaat ttaaataaat tgacagggga     720
```

```
aagttgggcc actcttgagc ttgtgggtgc tcaccaggtt gaccccaaaa aaagaagcct      780
tccacaaaac attaatttat ttccctaata tacccgcctc tgtgagttaa gggataatgc      840
atcaggactc ttgcaaccag acaaaattat ttaaaaacgc cacttggggg ggaggcgggt      900
ccctcctggg gattcgcctt tgtgggagag aaaactgcac agacttgggc aaataatgtt      960
ttttgtcacc ccaaaacgta ttcgcgagac atttcattag aacgaagctt taccctaata     1020
ttgaactccc catttaaaca gtttccacac acacttaggg agattttcc ctctgtgagt      1080 tccgcagaac aatagttgga cgggaataga accctgaaac actttagttc accacgaact     1140
attatagggc ggg                                                        1153

<210> SEQ ID NO 35
<211> LENGTH: 334
<212> TYPE: DNA
<213> ORGANISM: Homo sapiens

<400> SEQUENCE: 35
tgactatcca gctctgagag acgggagttt ggagttgccc gctttacttt ggttgggttg       60
gggggggcgg cgggctgttt tgttcctttt cttttttaag agtttggtttt tctttttttaa    120 ttatccaaac agtgggcagc ttcctccccc acacccaagt atttgcacaa tatttgtgcg      180
gggtatgggg gtgggttttt aaatctcgtt tctcttggac aagcacaggg atctcgttct      240
cctcattttt tgggggtgtg tggggacttc tcaggtcgtg tccccagcct tctctgcagt      300
cccttctgcc ctgccgggcc cgtcgggagg cgcc                                  334

<210> SEQ ID NO 36
<211> LENGTH: 543
<212> TYPE: DNA
<213> ORGANISM: Homo sapiens

<400> SEQUENCE: 36
tagctcagga ccttggctgg gcctggtcgt catgtaggtc aggaccttgg ctggacctgg       60
aggccctgcc cagccctgct ctgcccagcc cagcaggggc tccaggcctt ggctggcccc      120
acatcgcctt ttcctccccg acacctccgt gcacttgtgt ccgaggagcg aggagccccct    180 cgggccctgg gtggcctctg ggcccttct cctgtctccg ccactccctc tggcggcgct      240
ggccgtggct ctgtctctct gaggtgggtc gggcgccctc tgcccgcccc ctcccacacc     300
agccaggctg gtctcctcta gcctgtttgt tgtgggtgg gggtatattt tgtaaccact      360
gggcccccag cccctctttt gcgacccctt gtcctgacct gttctcggca ccttaaatta     420
ttagaccccg gggcagtcag gtgctccgga cacccgaagg caataaaaca ggagccgtga     480
aaaaaaaaaa aaaaaaaaa aaaaaaaaa aaaaaaaaa aaaaaaaaa aaaaaaaaa          540 aaa                                                                    543

<210> SEQ ID NO 37
<211> LENGTH: 511
<212> TYPE: DNA
<213> ORGANISM: Homo sapiens

<400> SEQUENCE: 37
gctcagcaag gggtccgtcc ttctctgtca ctgtctcttt tgcctgttgt aattctgtct       60
gcctctctgg gactctgcct gtctcactct ttctgtctgt gcctctcctc actcttgttc      120 tttctgcctag aatcacagcc ctcagttttt ctgtcctcat gcatttgtct ttgtggctct     180 ttccgtctttt ctgcccttga caccatcccc tctcccagtg cttcccctct gcttccagat    240
```

-continued

```
cgcttcatga cttaggcagg gaaacagagg tcagggcctc cttccaggct tccctctgca        300
tcttactgag tatgcaggtc ggaagagcct cgggtcctgc ctccgcgggt ggcctagagc        360
caaaggaagg cggagcccgt cggggcggga ttggccctta gggccacctc ataaagcctg        420
gggcgagggg cacaacggcc ttgggaagga gccctgctgg ggccgtccag tcccccagac        480
ctcacaggct cagtcgcgga tctgcagtgt c                                       511
```

<210> SEQ ID NO 38
<211> LENGTH: 458
<212> TYPE: DNA
<213> ORGANISM: Homo sapiens

<400> SEQUENCE: 38

```
tagtagggac cagtgaccat cacatccctt caagagtcct gaagatcaag ccagttctcc         60
ttccctgcag agctttggcc attaccacct gacctcttgc tgccagctaa taagaagtgc        120
caagtggaca gtctggccac tgtcaaggca gggaaggggc catgactttt ctgccctgcc        180
ctcagcctgt tgccctgcct cccaaacccc attagtctag ccttgtagct gttactgcaa        240
gtgtttcttc tggcttagtc tgttttctaa agccaggact attcccttt c ctccccagga        300 atatgtgttt tcctttgtct taatcgatct ggtaggggag aaatggcgaa tgtcatacac        360
atgagatggt atatccttgc gatgtacaga atcagaaggt ggtttgacag catcataaac        420
aggctgactg gcaggaatga aaaaaaaaaa aaaaaaa                                 458
```

<210> SEQ ID NO 39
<211> LENGTH: 270
<212> TYPE: DNA
<213> ORGANISM: Homo sapiens

<400> SEQUENCE: 39

```
ggggccgccg agagccgcag cgccgctcgc ccgccgcccc ccaccccgcc gccccgcccg         60
gcgaattgcg ccccgcgccc tccctcgcg ccccgagac aaagaggaga gaaagtttgc        120
gcggccgagc gggcaggtga ggagggtgag ccgcgcggag gggcccgcct cggccccggc        180
tcagcccccg cccgcgcccc cagcccgccg ccgcgagcag cgcccggacc ccccagcggc        240
ggccccgccc gcccagcccc ccggcccgcc                                        270
```

<210> SEQ ID NO 40
<211> LENGTH: 751
<212> TYPE: DNA
<213> ORGANISM: Homo sapiens
<220> FEATURE:
<221> NAME/KEY: misc_feature
<222> LOCATION: (535)..(734)
<223> OTHER INFORMATION: n = a, t, g or c

<400> SEQUENCE: 40

```
taagcaggcc tccaacgccc ctgtggccaa ctgcaaaaaa agcctccaag ggtttcgact         60
ggtccagctc tgacatccct tcctggaaac agcatgaata aaacactcat cccatgggtc        120
caaattaata tgattctgct ccccccttct ccttttagac atggttgtgg gtctggaggg        180
agacgtgggt ccaaggtcct catcccatcc tccctctgcc aggcactatg tgtctggggc        240
ttcgatcctt gggtgcaggc agggctggga cacgcggctt ccctcccagt cctgccttg        300 gcaccgtcac agatgccaag caggcagcac ttagggatct cccagctggg ttagggcagg        360
gcctggaaat gtgcattttg cagaaacttt tgagggtcgt tgcaagactg tgtagcaggc        420
```

```
ctaccaggtc cctttcatct tgagagggac atggcccctt gttttctgca gcttccacgc    480
ctctgcactc cctgcccctg gcaagtgctc ccatcgcccc cggtgcccac catgnagctc    540
cccgcacctg actcccccca catccaaggg cagccctgga accagtgggc tagttccttg    600
aaggaagccc cactcattcc tattaatccc tcagaattcc cggggggagc cttccctcct    660
gaaccttggt aaaaatggg gaacgagaaa accccccgct tggagctgtg cgtttccagc     720
ccctacttga gagncttttt tttgggggcc g                                    751

<210> SEQ ID NO 41
<211> LENGTH: 229
<212> TYPE: DNA
<213> ORGANISM: Homo sapiens

<400> SEQUENCE: 41
cgcgccgggc ccggctcggc ccgacccggc tccgcgcggg caggcggggc ccagcgcact     60
cggagcccga gcccgagccg cagccgccgc ctggggcgct tgggtcggcc tcgaggacac    120
cggagagggg cgccacgccg ccgtggccgc agatttgaaa gaagccgaca ctaaaccacc    180
aatatacaac aaggccattt tgtcaaacga gagtcagcct ttaacgaaa               229

<210> SEQ ID NO 42
<211> LENGTH: 233
<212> TYPE: DNA
<213> ORGANISM: Homo sapiens

<400> SEQUENCE: 42
tagcagagag tcctgagcca ctgccaacat ttcccttctt ccagttgcac tattctgagg     60
gaaaatctga cacctaagaa atttactgtg aaaaagcatt ttaaaagaa aaggttttag     120 aatatgatct attttatgca tattgtttat aaagacacat ttacaattta cttttaatat    180
taaaaattac catattatga aaaaaaaaaa aaaaaaaaa aaaaaaaaaa aaa             233

<210> SEQ ID NO 43
<211> LENGTH: 349
<212> TYPE: DNA
<213> ORGANISM: Homo sapiens

<400> SEQUENCE: 43
ggcacgaggg gcgagaggaa gcagggagga gagtgatttg agtagaaaag aaacacagca     60
ttccaggctg gccccacctc tatattgata agtagccaat gggagcgggt agccctgatc    120
cctggccaat ggaaactgag gtaggcgggt catcgcgctg gggtctgtag tctgagcgct    180
acccggttgc tgctgcccaa ggaccgcgga gtcggacgca ggcagaccat gtggaccctg    240
gtgagctggg tggccttaac agcagggctg gtggctggaa cgcggtgccc agatggtcag    300
ttctgccctg tggcctgctg cctggacccc ggaggagcca gctacagct                349

<210> SEQ ID NO 44
<211> LENGTH: 337
<212> TYPE: DNA
<213> ORGANISM: Homo sapiens

<400> SEQUENCE: 44
tgagggacag tactgaagac tctgcagccc tcgggacccc actcggaggg tgccctctgc     60
tcaggcctcc ctagcacctc cccctaacca aattctccct ggaccccatt ctgagctccc    120
catcaccatg ggaggtgggg cctcaatcta aggccttccc tgtcagaagg gggttgtggc    180
aaaagccaca ttacaagctg ccatcccctc cccgtttcag tggaccctgt ggccaggtgc    240
```

-continued

```
tttccctat ccacagggt gtttgtgtgt gtgcgcgtgt gcgtttcaat aaagtttgta    300
cactttcaaa aaaaaaaaaa aaaaaaaaaa aaaaaa                           337
```

<210> SEQ ID NO 45
<211> LENGTH: 1700
<212> TYPE: DNA
<213> ORGANISM: Homo sapiens

<400> SEQUENCE: 45

```
tgtttgcatt aagttcatag attataattt gtaatggaat caacaccaaa tgcaaattag    60
aaagagagcc cactttgctc acccagtcac gtcttcccat gtaaccatag aacgttgggg   120
tcctgtgtct ttctagatcc acagtcttgc tctcagaaca ggctagccac accacaggcc   180
tagtgccagg acccatggcc ttttttttaag ctcagactcc cttctgtgaa cagcaatatc  240
cccacaactt gtacaacatt ggtgcttcct gcaagggcta cagaactatt tgatacgaaa   300
atgttcattg acttacacac aagagaagca caaaataaaa aattaataat taatttaatg   360
tctttgaaaa tgtaccattt atttttacat ttggggtcat aagaattgta ttacacttaa   420
gaatgcaata caatttgaag atcagatttt tctcccttg tgagaatttc tcagtatgtg    480
tgatgactac caagaaatca tagccagtca taaattcagt gagttactca taaacgaaca   540
agaaccacct acttcttggg gaggtaggtc tgcttccctt caactcagga tacaactgct   600
ttcaactgct ttcttcacat tagctgacta attagctaga agcctgtcgt aaacaatttt   660
atggttgact cctccctgg gctcagggtt ccctagaaca gagaggtccc caaatcccgg    720
tctgtggcct gtccgcctaa gctctgcctc ctgccagatc agcaggcagc attagattct   780
cataggagct ggacgcctat tgtgaactgc gcatgtgcgg gatccagatt gtgcactctt   840
tatgagaatc taactaatgc ttgatgatct atctgaacca gaacaattc atcctgaaac    900
catcccccac caatccatag aaatactgtc ttccacaaaa atgatccctg gtgccaaaaa   960
tgttagagac cactcccca aaactctctt cttagctctc acctcctgta ttactatctc   1020
atctcagtac attgaagccc ccatctttc cccatggatg cctcatttcc tattagggag   1080
gcatttttt attttttgtt tttattttt tccgagacgg agtctcgctc tgtcgccaag    1140
gctggagtgc agtggcgcga tctcggctca ctgcaagctc cgcctcccgg gttcacgcca   1200
ttctcctgcc tcagcctccc aagtagctgg gactacaggc gcccgcacta cgcccggcta   1260
attttttgta tttttagtag agacggggtt tcaccgtggt agccaggatg gtctcgatct   1320
cctgacctcg tgatccgccc gccttggcct cccaaagtgc tgggattaca ggcgtgagac   1380
cgcgcccggc cgtcatttgg tatgtcttaa tgtgcctcag gacctagcac agtccctggt   1440
acccagtaga gacctatgta atgttcgtta ttcaataata aatacatgaa ttaaagagtg   1500
agagtggatt ttgtaatgtt acgactgata gagaaatact cagtgattct aagggatggg   1560
gaagaacggt tggagctaga ggttgtgctc aggaaactat taaatagacg ttccgcagga   1620
agggattgac gaagtgtgag gttaatgagg aagggaaaat agaatataaa atttggtggt   1680
ggaaaagatc tgattcatga                                              1700
```

<210> SEQ ID NO 46
<211> LENGTH: 2419
<212> TYPE: DNA
<213> ORGANISM: Homo sapiens

<400> SEQUENCE: 46

-continued

```
taaccagcgg gccccctggtc aagtgctggc tctgctgtcc ttgccttcca tttcccctct      60
gcacccagaa cagtggtggc aacattcatt gccaagggcc caaagaaaga gctacctgga     120
ccttttgttt tctgtttgac aacatgttta ataaataaaa atgtcttgat atcagtaaga     180
atcagagtct tctcactgat tctgggcata ttgatctttc ccccatttc tctacttggc      240
tgctccctga gaggactgca taggatagaa atgcctttt cttttctttt cgttttttt      300
tttttttttt tttgagatgg agtctcactc tgtcgcccag gcttaagtgc aatggcacaa     360
tctcggctca ctgcaacctc tctctcctgg gttcaagtga ttctcctgcc tcagcctccc     420
aaatagctga gattacaggc atgcaccacc acacctggct aatttttgtg ttttagtag      480
agacagggtt tcaccgtttt ggccaggttg gtcttgaact cctgacctcg ggagatccgc     540
ccaccttggc ctctctttgt gctgggatta caggcatgag ccactgagcc gggccacttt     600
ttccttatca gtcagttttt acaagtcatt agggaggtag actttacctc tctgtgaagg     660
aaagtatggt atgttgatct acagagagag atggaaaaat tccagggctc gtagctacta     720
agcagaattt ccaagatagg caaattgttt tttctgtcaa ataataagct aatattactt     780
ctacaaatat gagaccttgg agagaagttt ccaaggacca agtaccaaca taccaacaga     840
ttattatagt ttctctcact cttacacaca cacacacaca tatacacata tgtaatccag     900
catgaatacc aaaattcatt cagggtagcc accttttgtc ttaatcgaga gataattttg     960
atgtttgaat ggaatgctcc caggatattc tcttgtcatg gttattttat ataaaattca    1020
aaaaccaatt acattattc ctctgtaatc tttactttta tcaactaatg tctggcaagt     1080
gtgatgtttt ggggaagtta tagaagattc cggccaggcg cttatctcac gcttgtaatc    1140
cagcactttg ggaagctgag gcggacagat cacgaggtca agagatcaag accatcctgg    1200
acaacatggt gaaaccttgt ctctactaaa aatgtgaaaa ttagctgggc gtggtggcac    1260
acacctatag tcccagctac tcgggaggct gaggcaggag aatcgcttga acctaggagg    1320
cggaggttgc actgagccga gatcacgcca ctgcactcca gcctgggcga cagagcgaga    1380
ctccatctca aaaaaaaaa aaaagaaag atcccagttt atcccagttt atcccttatt      1440
cttcctcaat tctcaagatt tgttttaag ttaacataac ttaggttaac acactctttg     1500
taaaatacac tgttcaatct acagactcag tggttagctt cctgttaact aatttctgtt    1560
gacaggtact tggatatttt atttagaaag tggttgccaa taaattagtt ataagtcgcc    1620
agtttcactg ccttgtgaac acataattat tgtggtctca gtattcccta tggtggcttc    1680
tcctgctcct ggtattgccc tgaaatgggc caaaagccgt ggctccccaa tgctcaggtt    1740
atagaacatt gtccaggtac cacctaggag agcccagcct cactgaaagt attcaaattt    1800
aggaatgggt tgagaagta ggtagctggt atgtgcttag cacaagaatc tctcttcctt     1860
gggttagtct gtttcaaaac tgaaaacact gtcattcctt aagaaaatag gaaaaagtat    1920
tccaaacctc tgtcactaga aaatttgcca tattaccaaa tctcaaaaac ctctcaggaa    1980
atgagaaagt cccagtttct ggtaaactat ttgggcccct ttctcaagtt ctccttccag    2040
tgctatttcc ttgaggtgag gcaaagttac tcaagatcat cgctgccact caaggccttg    2100
atagggcaag tgaaaggcat ggaccattat tatattgatc acagcataag ctgtgaaaac    2160
ccacatcttc tccaaacatc tgcttggagc attatcatcg catagtttgc tctggtgttc    2220
agggaaatcg ctgtttcata ggaaatcaca tggcagtggg atgggagtgt tcctgacct     2280
gccgatggta ctggcacctg agcaagcatt cctagtcctt tttggtctgg gcctcttgtt    2340
ctatcacaac cacaagctgt ttaaaataaa aacgtcaagt cacaggcagg tcattttatc    2400
```

```
ctgcgtgaat caattgaag                                              2419
```

<210> SEQ ID NO 47
<211> LENGTH: 297
<212> TYPE: DNA
<213> ORGANISM: Homo sapiens

<400> SEQUENCE: 47

```
tcctcagtgc acagtgctgc ctcgtctgag gggacaggag gatcaccctc ttcgtcgctt    60
cggccagtgt gtcgggctgg gccctgacaa gccacctgag gagaggctcg gagccgggcc   120
cggaccccgg cgattgccgc ccgcttctct ctagtctcac gaggggtttc ccgcctcgca   180
cccccacctc tggacttgcc tttccttctc ttctccgcgt gtggagggag ccagcgctta   240
ggccggagcg agcctggggg ccgcccgccg tgaagacatc gcggggaccg attcacc      297
```

<210> SEQ ID NO 48
<211> LENGTH: 1192
<212> TYPE: DNA
<213> ORGANISM: Homo sapiens

<400> SEQUENCE: 48

```
tgagcttttt cttaatttca ttccttttt tggacactgg tggctcacta cctaaagcag     60
tctatttata ttttctacat ctaattttag aagcctggct acaatactgc acaaacttgg   120
ttagttcaat ttttgatccc cttctactt aatttacatt aatgctcttt tttagtatgt    180
tctttaatgc tggatcacag acagctcatt ttctcagttt tttggtattt aaaccattgc   240
attgcagtag catcatttta aaaaatgcac ctttttattt atttattttt ggctagggag   300
tttatccctt tttcgaatta tttttaagaa gatgccaata taattttttgt aagaaggcag  360
taaccttca tcatgatcat aggcagttga aaaatttta cacctttttt ttcacatttt    420
acataaataa taatgctttg ccagcagtac gtggtagcca caattgcaca atatattttc   480
ttaaaaaata ccagcagtta ctcatggaat atattctgcg tttataaaac tagtttttaa   540
gaagaaattt tttttggcct atgaaattgt taaacctgga acatgacatt gttaatcata   600
taataatgat tcttaaatgc tgtatggttt attatttaaa tgggtaaagc catttacata   660
atatagaaag atatgcatat atctagaagg tatgtggcat ttatttggat aaaattctca   720
attcagagaa atcatctgat gtttctatag tcactttgcc agctcaaaag aaaacaatac   780
cctatgtagt tgtggaagtt tatgctaata ttgtgtaact gatattaaac ctaaatgttc   840
tgcctaccct gttggtataa agatattttg agcagactgt aaacaagaaa aaaaaaatca   900
tgcattctta gcaaaattgc ctagtatgtt aatttgctca aaatacaatg tttgattta    960
tgcactttgt cgctattaac atccttttt tcatgtagat ttcaataatt gagtaatttt   1020
agaagcatta ttttaggaat atatagttgt cacagtaaat atcttgtttt ttctatgtac   1080
attgtacaaa ttttttcattc cttttgctct ttgtggttgg atctaacact aactgtattg  1140
ttttgttaca tcaaataaac atcttctgtg gaccaggaaa aaaaaaaaaa aa          1192
```

<210> SEQ ID NO 49
<211> LENGTH: 197
<212> TYPE: DNA
<213> ORGANISM: Homo sapiens

<400> SEQUENCE: 49

```
agacagcctt aacccacggg cgcgggcgag tcgtatgggc aggggcaggc gggagcgacg    60
```

-continued

| | |
|---|---|
| tggggcgacg ctcacgaacg atcagagctg cgggcgacgc aacgaagccc ggaggccgca | 120 |
| ggctgcgcgc tccctcgcag cagccgggcg ggcaaaagcc cccagtcctc ggcccccgcg | 180 |
| caagcgacgc cgggaaa | 197 |

<210> SEQ ID NO 50
<211> LENGTH: 3293
<212> TYPE: DNA
<213> ORGANISM: Homo sapiens

<400> SEQUENCE: 50

| | |
|---|---|
| taattattta tattgtaaag aattttaaca gtcctgggga cttccttgaa ggatcatttt | 60 |
| cacttttgct cagaagaaag ctctggatct atcaaataaa gaagtccttc gtgtgggcta | 120 |
| catatataga tgttttcatg aagaggagtg aaaagccaga aggatataga caaatgaggc | 180 |
| ctaagacctt tcctgccagt aactatactg tcagtagccg gcaaatgtta caagaaattc | 240 |
| gggaatccct taggaattta tctaaaccat ctgatgctgc taaggctgag cataacatga | 300 |
| gtaaaatgtc aaccgaagat cctcgacaag tcagaaatcc acccaaattt gggacgcatc | 360 |
| ataaagcctt gcaggaaatt cgaaactctc tgcttccatt tgcaaatgaa acaaattctt | 420 |
| ctcggagtac ttcagaagtt aatccacaaa tgcttcaaga cttgcaagct gctggatttg | 480 |
| atgaggatat ggttatacaa gctcttcaga aaactaacaa cagaagtata aagcagcaa | 540 |
| ttgaattcat tagtaaaatg agttaccaag atcctcgacg agagcagatg gctgcagcag | 600 |
| ctgccagacc tattaatgcc agcatgaaac cagggaatgt gcagcaatca gttaaccgca | 660 |
| aacagagctg gaaggttct aaagaatcct tagttcctca gaggcatggc ccgccactag | 720 |
| gagaaagtgt ggcctatcat tctgagagtc ccaactcaca gacagatgta ggaagacctt | 780 |
| tgtctggatc tggtatatca gcatttgttc aagctcaccc tagcaacgga cagagagtga | 840 |
| accccccacc accacctcaa gtaaggagtg ttactcctcc accacctcca agaggccaga | 900 |
| ctcccccctcc aagaggtaca actccacctc cccttcatg ggaaccaaac tctcaaacaa | 960 |
| agcgctattc tggaaacatg gaatacgtaa tctcccgaat ctctcctgtc ccacctgggg | 1020 |
| catggcaaga gggctatcct ccaccacctc tcaacacttc ccccatgaat cctcctaatc | 1080 |
| aaggacagag aggcattagt tctgttcctg ttggcagaca accaatcatc atgcagagtt | 1140 |
| ctagcaaatt taacttttcca tcagggagac tggaatgca gaatggtact ggacaaactg | 1200 |
| atttcatgat acaccaaaat gttgtccctg ctggcactgt gaatcggcag ccaccacctc | 1260 |
| catatcctct gacagcagct aatggacaaa gcccttctgc tttacaaaca gggggatctg | 1320 |
| ctgctccttc gtcatataca aatggaagta ttcctcagtc tatgatggtg ccaaacagaa | 1380 |
| atagtcataa catggaacta tataacatta gtgtacctgg actgcaaaca aattggcctc | 1440 |
| agtcatcttc tgctccagcc cagtcatccc cgagcagtgg gcatgaaatc cctacatggc | 1500 |
| aacctaacat accagtgagg tcaaattctt ttaataaccc attaggaaat agagcaagtc | 1560 |
| actctgctaa ttctcagcct tctgctacaa cagtcactgc aattacacca gctcctattc | 1620 |
| aacagcctgt gaaaagtatg cgtgtattaa aaccagagct acagactgct ttagcaccta | 1680 |
| cacacccttc ttggatacca cagccaattc aaactgttca acccagtcct tttcctgagg | 1740 |
| gaaccgcttc aaatgtgact gtgatgccac tgttgctga agctccaaac tatcaaggac | 1800 |
| caccaccacc ctacccaaaa catctgctgc accaaaaccc atctgttcct ccatacgagt | 1860 |
| caatcagtaa gcctagcaaa gaggatcagc caagcttgcc caaggaagat gagagtgaaa | 1920 |
| agagttatga aaatgttgat agtggggata agaaaagaa acagattaca acttcaccta | 1980 |

```
ttactgttag gaaaaacaag aaagatgaag agcgaaggga atctcgtatt caaagttatt    2040
ctcctcaagc atttaaattc tttatggagc aacatgtaga aaatgtactc aaatctcatc    2100
agcagcgtct acatcgtaaa aaacaattag agaatgaaat gatgcgggtt ggattatctc    2160
aagatgccca ggatcaaatg agaaagatgc tttgccaaaa agaatctaat tacatccgtc    2220
ttaaaagggc taaaatggac aagtctatgt ttgtgaagat aaagacacta ggaataggag    2280
catttggtga agtctgtcta gcaagaaaag tagatactaa ggctttgtat gcaacaaaaa    2340
ctcttcgaaa gaaagatgtt cttcttcgaa atcaagtcgc tcatgttaag gctgagagag    2400
atatcctggc tgaagctgac aatgaatggg tagttcgtct atattattca ttccaagata    2460
aggacaattt atactttgta atggactaca ttcctggggg tgatatgatg agcctattaa    2520
ttagaatggg catcttttcca gaaagtctgg cacgattcta catagcagaa cttacctgtg    2580
cagttgaaag tgttcataaa atgggtttta ttcatagaga tattaaacct gataatattt    2640
tgattgatcg tgatggtcat attaaattga ctgactttgg cctctgcact ggcttcagat    2700
ggacacacga ttctaagtac tatcagagtg gtgaccatcc acggcaagat agcatggatt    2760
tcagtaatga atggggggat ccctcaagct gtcgatgtgg agacagactg aagccattag    2820
agcggagagc tgcacgccag caccagcgat gtctagcaca ttctttggtt gggactccca    2880
attatattgc acctgaagtg ttgctacgaa caggatacac acagtgtgt gattggtgga    2940 gtgttggtgt tattcttttt gaaatgttgg tgggacaacc tcctttcttg gcacaaacac    3000
cattagaaac acaaatgaag gtcacctgct gctatataca tcattggctc gagaagaaac    3060
tactgaacac cctgcgagag agaagcctag aaaagaaaga aagggccaaa aggttttgaa    3120
ctcttcatcc ctaatttgct acactgatca aaaccaagta agggctcctg aagtccatga    3180
gtctatcatc aatcagcaca aatgctatac tagtttgtaa ctgcggggtc agttgtgaag    3240
gggaaggaca gcagtcttat ccatattcca ggaagccaca gtaaactgct cga           3293

<210> SEQ ID NO 51
<211> LENGTH: 424
<212> TYPE: DNA
<213> ORGANISM: Homo sapiens

<400> SEQUENCE: 51
cctactctat tcagatattc tccagattcc taaagattag agatcatttc tcattctcct     60
aggagtactc acttcaggaa gcaaccagat aaaagagagg tgcaacggaa gccagaacat    120
tcctcctgga aattcaacct gtttcgcagt ttctcgagga atcagcattc agtcaatccg    180
ggccgggagc agtcatctgt ggtgaggctg attggctggg caggaacagc gccggggcgt    240
gggctgagca cagcgcttcg ctctctttgc cacaggaagc tgagctcat tcgagtagcg    300 gctcttccaa gctcaaagaa gcagaggccg ctgttcgttt cctttaggtc tttccactaa    360
agtcggagta tcttcttcca agatttcacg tcttggtggc cgttccaagg agcgcgaggt    420
cggg                                                                 424

<210> SEQ ID NO 52
<211> LENGTH: 706
<212> TYPE: DNA
<213> ORGANISM: Homo sapiens

<400> SEQUENCE: 52
tgaactctga ctgtatgaga tgttaaatac tttttaatat ttgtttagat atgacattta     60
```

```
ttcaaagtta aaagcaaaca cttacagaat tatgaagagg tatctgttta acatttcctc    120
agtcaagttc agagtcttca gagacttcgt aattaaagga acagagtgag agacatcatc    180
aagtggagag aaatcatagt ttaaactgca ttataaattt tataacagaa ttaaagtaga    240
ttttaaaaga taaatgtgt aattttgttt atattttccc atttggactg taactgactg    300
ccttgctaaa agattataga agtagcaaaa agtattgaaa tgtttgcata aagtgtctat    360
aataaaacta aactttcatg tgactggagt catcttgtcc aaactgcctg tgaatatatc    420
ttctctcaat tggaatattg tagataactt ctgctttaaa aaagttttct ttaaatatac    480
ctactcattt ttgtgggaat ggttaagcag tttaaataat tcctgtgtat atgtctatca    540 catagggtc taacagaaca atctggattc attatttcta ggacttgatc ctgctgatgc     600
tgaatttgca cattaaggtg tgttaacaac caaaacacag atcgatataa aagtaagga     660 ggtggggaga ggcaaattat gatgtgctat gagttagatg tatagt                  706
```

<210> SEQ ID NO 53
<211> LENGTH: 239
<212> TYPE: DNA
<213> ORGANISM: Homo sapiens

<400> SEQUENCE: 53

```
agtccgcggc gttccccggc tgcagccggg agggggccga ggagtgactg agccccgggc     60
tgtgcagtcc gacgccgact gaggcacgag cgggtgacgc tgggcctgca gcgcggagca    120
gaaagcagaa cccgcagagt cctccctgct gctgtgtgga cgacacgtgg gcacaggcag    180
aagtgggccc tgtgaccagc tgcactggtt tcgtggaagg aagctccagg actggcggg    239
```

<210> SEQ ID NO 54
<211> LENGTH: 641
<212> TYPE: DNA
<213> ORGANISM: Homo sapiens

<400> SEQUENCE: 54

```
tgaggcagct gctatcccca tctccctgcc tggcccccaa cctcagggct cccaggggtc     60
tccctggctc cctcctccag gcctgcctcc cacttcactg cgaagaccct cttgcccacc    120
ctgactgaaa gtaggggggct ttctggggcc tagcgatctc tcctggccta tccgctgcca    180
gccttgagcc ctggctgttc tgtggttcct ctgctcaccg cccatcaggg ttctcttatc    240
aactcagaga aaaatgctcc ccacagcgtc cctggcgcag gtgggctgga cttctacctg    300
ccctcaaggg tgtgtatatt gtataggggc aactgtatga aaaattgggg aggaggggc    360 cgggcgcggt gctcacgcct gtaatcccag cactttggga ggccgaggcg ggtggatcac    420
gaggtcagga gatcgagacc atcctggcta acatggtgaa accccgtctc tactaaaaat    480
acaaaaaaaa tttagccggg cgcggtggcg ggcacctgta gtcccagcta cttgggaggc    540
tgaggcagga aatggtgtg aacccggag cggaggttgc agtgagctga atcgtgcta    600 ctgcactcca gcctggggga cagaaagaga ctccgtctca a                        641
```

<210> SEQ ID NO 55
<211> LENGTH: 493
<212> TYPE: DNA
<213> ORGANISM: Homo sapiens

<400> SEQUENCE: 55

```
tttctgtgaa gcagaagtct gggaatcgat ctggaaatcc tcctaatttt tactccctct     60 cccccccgact cctgattcat tgggaagttt caaatcagct ataactggag agagctgaag    120
```

| | |
|---|---|
| attgatggga tcgttgcctt atgcctttgt tttggtttta caaaaaggaa acttgacaga | 180 |
| ggatcatgct atacttaaaa aatacaacat cgcagaggaa gtagactcat attaaaaata | 240 |
| cttactaata ataacgtgcc tcatgaagta aagatccgaa aggaattgga ataaaacttt | 300 |
| cctgcatctc aagccaaggg ggaaacacca gaatcaagtg ttccgcgtga ttgaagacac | 360 |
| cccctcgtcc aagaatgcaa agcacatcca ataaagagc tggattataa ctcctcttct | 420 |
| ttctctgggg gccgtgggt gggagctggg gcgagaggtg ccgttggccc ccgttgcttt | 480 |
| tcctctggga ggg | 493 |

<210> SEQ ID NO 56
<211> LENGTH: 5282
<212> TYPE: DNA
<213> ORGANISM: Homo sapiens

<400> SEQUENCE: 56

| | |
|---|---|
| tgaagtcaac atgcctgccc caaacaaata tgcaaaaggt tcactaaagc agtagaaata | 60 |
| atatgcattg tcagtgatgt tccatgaaac aaagctgcag gctgtttaag aaaaaataac | 120 |
| acacatataa acatcacaca cacagacaga cacacacaca caacaatt aacagtcttc | 180 |
| aggcaaaacg tcgaatcagc tatttactgc caaagggaaa tatcatttat tttttacatt | 240 |
| attaagaaaa aaagatttat ttatttaaga cagtcccatc aaaactcctg tctttggaaa | 300 |
| tccgaccact aattgccaag caccgcttcg tgtggctcca cctggatgtt ctgtgcctgt | 360 |
| aaacatagat tcgcttttcca tgttgttggc cggatcacca tctgaagagc agacggatgg | 420 |
| aaaaaggacc tgatcattgg ggaagctggc tttctggctg ctggaggctg gggagaaggt | 480 |
| gttcattcac ttgcattct ttgccctggg ggctgtgata ttaacagagg gagggttcct | 540 |
| gtggggggaa gtccatgcct ccctggcctg aagaagagac tctttgcata tgactcacat | 600 |
| gatgcatacc tggtgggagg aaaagagttg ggaacttcag atggacctag tacccactga | 660 |
| gatttccacg ccgaaggaca gcgatgggaa aaatgcccctt aaatcatagg aaagtatttt | 720 |
| tttaagctac caattgtgcc gagaaaagca ttttagcaat ttatacaata tcatccagta | 780 |
| ccttaagccc tgattgtgta tattcatata ttttggatac gcaccccca actcccaata | 840 |
| ctggctctgt ctgagtaaga aacagaatcc tctggaactt gaggaagtga acatttcggt | 900 |
| gacttccgca tcaggaaggc tagagttacc cagagcatca ggccgccaca agtgcctgct | 960 |
| tttaggagac cgaagtccgc agaacctgcc tgtgtcccag cttggaggcc tggtcctgga | 1020 |
| actgagccgg ggccctcact ggcctcctcc agggatgatc aacagggcag tgtggtctcc | 1080 |
| gaatgtctgg aagctgatgg agctcagaat tccactgtca agaaagagca gtagagggt | 1140 |
| gtggctgggc ctgtcaccct ggggccctcc aggtaggccc gttttcacgt ggagcatggg | 1200 |
| agccacgacc cttcttaaga catgtatcac tgtagaggga aggaacagag gccctgggcc | 1260 |
| cttcctatca gaaggacatg gtgaaggctg gaacgtgag gagaggcaat ggccacggcc | 1320 |
| cattttggct gtagcacatg gcacgttggc tgtgtggcct tggcccacct gtgagtttaa | 1380 |
| agcaaggctt taaatgactt tggagagggt cacaaatcct aaaagaagca ttgaagtgag | 1440 |
| gtgtcatgga ttaattgacc cctgtctatg gaattacatg taaaacatta tcttgtcact | 1500 |
| gtagtttggt tttatttgaa aacctgacaa aaaaaaagtt ccaggtgtgg aatatggggg | 1560 |
| ttatctgtac atcctggggc attaaaaaaa aaatcaatgg tggggaacta taagaagta | 1620 |
| acaaaagaag tgacatcttc agcaaataaa ctaggaaatt ttttttttctt ccagtttaga | 1680 |

```
atcagccttg aaacattgat ggaataactc tgtggcatta ttgcattata taccatttat    1740
ctgtattaac tttggaatgt actctgttca atgtttaatg ctgtggttga tatttcgaaa    1800
gctgctttaa aaaatacat gcatctcagc gttttttgt ttttaattgt atttagttat     1860
ggcctataca ctatttgtga gcaaaggtga tcgttttctg tttgagattt ttatctcttg    1920
attcttcaaa agcattctga gaaggtgaga taagccctga gtctcagcta cctaagaaaa   1980
acctggatgt cactggccac tgaggagctt tgtttcaacc aagtcatgtg catttccacg   2040
tcaacagaat tgtttattgt gacagttata tctgttgtcc ctttgacctt gtttcttgaa   2100
ggtttcctcg tccctgggca attccgcatt taattcatgg tattcaggat tacatgcatg   2160
tttggttaaa cccatgagat tcattcagtt aaaaatccag atggcaaatg accagcagat   2220
tcaaatctat ggtggtttga cctttagaga gttgctttac gtggcctgtt tcaacacaga   2280
cccacccaga gccctcctgc cctccttccg cggggggcttt tcatggctg tccttcaggg    2340
tcttcctgaa atgcagtggt gcttacgctc caccaagaaa gcaggaaacc tgtggtatga   2400
agccagacct ccccggcggg cctcagggaa cagaatgatc agacctttga atgattctaa   2460
ttttttaagca aaatattatt ttatgaaagg tttacattgt caaagtgatg aatatggaat   2520
atccaatcct gtgctgctat cctgccaaaa tcattttaat ggagtcagtt tgcagtatgc   2580
tccacgtggt aagatcctcc aagctgcttt agaagtaaca atgaagaacg tggacgcttt   2640
taatataaag cctgttttgt cttctgttgt tgttcaaacg ggattcacag agtatttgaa   2700
aaatgtatat atattaagag gtcacggggg ctaattgctg gctggctgcc ttttgctgtg   2760
gggttttgtt acctggtttt aataacagta aatgtgccca gcctcttggc cccagaactg    2820
tacagtattg tggctgcact tgctctaaga gtagttgatg ttgcattttc cttattgtta   2880
aaaacatgtt agaagcaatg aatgtatata aaagcctcaa ctagtcattt ttttctcctc    2940
ttctttttt tcattatatc taattatttt gcagttgggc aacagagaac catccctatt    3000
ttgtattgaa gagggattca catctgcatc ttaactgctc tttatgaatg aaaaaacagt   3060
cctctgtatg tactcctctt tacactggcc agggtcagag ttaaatagag tatatgcact    3120
ttccaaattg gggacaaggg ctctaaaaaa agccccaaaa ggagaagaac atctgagaac    3180
ctcctcggcc ctcccagtcc ctcgctgcac aaatactccg caagagaggc cagaatgaca    3240
gctgacaggt ctatggcca tcgggtcgtc tccgaagatt tggcagggc agaaaactct      3300
ggcaggctta agatttggaa taaagtcaca gaatcaagga agcacctcaa tttagttcaa    3360
acaagacgcc aacattctct ccacagctca cttacctctc tgtgttcaga tgtggccttc    3420
catttatatg tgatctttgt tttattagta aatgcttatc atctaaagat gtagctctgg    3480
cccagtggga aaaattagga agtgattata aatcgagagg agttataata atcaagatta    3540
aatgtaaata atcagggcaa tcccaacaca tgtctagctt tcacctccag gatctattga   3600
gtgaacagaa ttgcaaatag tctctatttg taattgaact tatcctaaaa caaatagttt    3660
ataaatgtga acttaaactc taattaattc caactgtact tttaaggcag tggctgtttt    3720
tagactttct tatcacttat agttagtaat gtacacctac tctatcagag aaaaacagga    3780
aaggctcgaa atacaagcca ttctaaggaa attagggagt cagttgaaat tctattctga    3840
tcttattctg tggtgtcttt tgcagcccag acaaatgtgg ttacacactt tttaagaaat   3900
acaattctac attgtcaagc ttatgaaggt tccaatcaga tctttattgt tattcaattt   3960
ggatctttca gggatttttt ttttaaatta ttatgggaca aaggacattt gttggagggg    4020
tgggagggag gaacaatttt taaatataaa acattcccaa gtttggatca gggagttgga   4080
```

```
agttttcaga ataaccagaa ctaagggtat gaaggacctg tattggggtc gatgtgatgc    4140
ctctgcgaag aaccttgtgt gacaaatgag aaacattttg aagtttgtgg tacgacctttt   4200 agattccaga gacatcagca tggctcaaag tgcagctccg tttggcagtg caatggtata    4260
aatttcaagc tggatatgtc taatgggtat ttaaacaata aatgtgcagt tttaactaac    4320
aggatattta atgacaacct tctggttggt agggacatct gtttctaaat gtttattatg    4380
tacaatacag aaaaaaattt tataaaatta agcaatgtga aactgaattg gagagtgata    4440
atacaagtcc tttagtctta cccagtgaat cattctgttc catgtctttg gacaaccatg    4500
accttggaca atcatgaaat atgcatctca ctggatgcaa agaaaatcag atggagcatg    4560
aatggtactg taccggttca tctggactgc cccagaaaaa taacttcaag caaacatcct    4620
atcaacaaca aggttgttct gcataccaag ctgagcacag aagatgggaa cactggtgga    4680
ggatggaaag gctcgctcaa tcaagaaaat tctgagacta ttaataaata agactgtagt    4740
gtagatactg agtaaatcca tgcacctaaa ccttttggaa aatctgccgt gggccctcca    4800
gatagctcat tcattaagt ttttccctcc aaggtagaat ttgcaagagt gacagtggat    4860
tgcatttctt tggggaagc tttcttttgg tggttttgtt tattatacct tcttaagttt    4920
tcaaccaagg tttgcttttg ttttgagtta ctggggttat ttttgtttta aataaaaata    4980
agtgtacaat aagtgttttt gtattgaaag cttttgttat caagattttc atactttttac   5040 cttccatggc tcttttttaag attgatactt ttaagaggtg gctgatattc tgcaacactg   5100
tacacataaa aaatacggta aggatacttt acatggttaa ggtaaagtaa gtctccagtt    5160
ggccaccatt agctataatg gcactttgtt tgtgttgttg gaaaaagtca cattgccatt    5220
aaactttcct tgtctgtcta gttaatattg tgaagaaaaa taaagtacag tgtgagatac    5280
tg                                                                  5282

<210> SEQ ID NO 57
<211> LENGTH: 117
<212> TYPE: DNA
<213> ORGANISM: Homo sapiens

<400> SEQUENCE: 57
attcggggcg agggaggagg aagaagcgga ggaggcggct cccgctcgca gggccgtgca     60
cctgcccgcc cgcccgctcg ctcgctcgcc cgccgcgccg cgctgccgac cgccagc       117

<210> SEQ ID NO 58
<211> LENGTH: 430
<212> TYPE: DNA
<213> ORGANISM: Homo sapiens

<400> SEQUENCE: 58
tgatccaggg agcccccacc atccgggggg accccgagtg tcatctcttc tacaatgagc     60
agcaggaggc ttgcggggtg cacacccagc ggatgcagta gaccgcagcc agccggtgcc    120
tggcgcccct gccccccgcc cctctccaaa caccggcaga aaacggagag tgcttgggtg    180
gtgggtgctg gaggattttc cagttctgac cacgtatttt atatttggaa agagaccagc    240
accgagctcg gcacctcccc ggcctctctc ttcccagctg cagatgccac acctgctcct    300
tcttgctttc cccgggggag gaaggggtt gtggtcgggg agctggggta caggtttggg    360
gagggggaag agaaattttt atttttgaac ccctgtgtcc cttttgcata agattaaagg    420
aaggaaaagt                                                          430
```

<210> SEQ ID NO 59
<211> LENGTH: 192
<212> TYPE: DNA
<213> ORGANISM: Homo sapiens

<400> SEQUENCE: 59

```
tcctaggcgg cggccgcggc ggcggaggca gcagcggcgg cggcagtggc ggcggcgaag      60
gtggcggcgg ctcggccagt actcccggcc cccgccattt cggactggga gcagcgcgg     120
cgcaggcact gaaggcggcg gcggggccag aggctcagcg gctcccaggt gcgggagaga    180
ggcctgctga aa                                                        192
```

<210> SEQ ID NO 60
<211> LENGTH: 4172
<212> TYPE: DNA
<213> ORGANISM: Homo sapiens

<400> SEQUENCE: 60

```
taaatacaat ttgtactttt ttcttaaggc atactagtac aagtggtaat ttttgtacat      60
tacactaaat tattagcatt tgttttagca ttacctaatt ttttttcctgc tccatgcaga    120
ctgttagctt ttaccttaaa tgcttatttt aaaatgacag tggaagtttt ttttttcctcg   180
aagtgccagt attcccagag ttttggtttt tgaactagca atgcctgtga aaaagaaact    240
gaatacctaa gatttctgtc ttggggtttt tggtgcatgc agttgattac ttcttatttt    300
tcttaccaag tgtgaatgtt ggtgtgaaac aaattaatga agcttttgaa tcatccctat    360
tctgtgtttt atctagtcac ataaatggat taattactaa tttcagttga gaccttctaa    420
ttggttttta ctgaaacatt gagggacaca aatttatggg cttcctgatg atgattcttc    480
taggcatcat gtcctatagt ttgtcatccc tgatgaatgt aaagttacac tgttcacaaa    540
ggttttgtct cctttccact gctattagtc atggtcactc tccccaaaat attatatttt    600
ttctataaaa agaaaaaat ggaaaaaaat tacaaggcaa tggaaactat tataaggcca     660
tttcctttc acattagata aattactata aagactccta atagcttttt cctgttaagg     720
cagacccagt atgaatggga ttattatagc aaccattttg gggctatatt tacatgctac    780
taaattttta taataattga aaagatttta acaagtataa aaaaattctc ataggaatta    840
aatgtagtct ccctgtgtca gactgctctt tcatagtata actttaaatc ttttcttcaa    900
cttgagtctt tgaagatagt tttaattctg cttgtgacat aaaagatta tttgggccag     960
ttatagctta ttaggtgttg aagagaccaa ggttgcaagc caggccctgt gtgaaccttg    1020
agctttcata gagagtttca cagcatggac tgtgtgcccc acggtcatcc gagtggttgt    1080
acgatgcatt ggttagtcaa aaatgggag ggactagggc agtttggata gctcaacaag     1140
atacaatctc actctgtggt ggtcctgctg acaaatcaag agcattgctt tgtttctta     1200
agaaaacaaa ctctttttta aaaattactt ttaaatatta actcaaaagt tgagattttg    1260
gggtggtggt gtgccaagac attaattttt tttttaaaca atgaagtgaa aaagttttac    1320
aatctctagg tttggctagt tctcttaaca ctggttaaat taacattgca taaacactt     1380
tcaagtctga tccatatta ataatgcttt aaaataaaaa taaaaacaat ccttttgata     1440
aatttaaaat gttacttatt ttaaaataaa tgaagtgaga tggcatggtg aggtgaaagt    1500
atcactggac taggttgttg gtgacttagg ttctagatag gtgtctttta ggactctgat    1560
tttgaggaca tcacttacta tccatttctt catgttaaaa gaagtcatct caaactctta    1620
gttttttttt tttacactat gtgatttata ttccatttac ataaggatac acttatttgt    1680
```

-continued

```
caagctcagc acaatctgta aattttaac ctatgttaca ccatcttcag tgccagtctt    1740
gggcaaaatt gtgcaagagg tgaagtttat atttgaatat ccattctcgt tttaggactc    1800
ttcttccata ttagtgtcat cttgcctccc taccttccac atgccccatg acttgatgca    1860
gttttaatac ttgtaattcc cctaaccata agatttactg ctgctgtgga tatctccatg    1920
aagttttccc actgagtcac atcagaaatg ccctacatct tattttcctc agggctcaag    1980
agaatctgac agataccata aagggatttg acctaatcac taattttcag gtggtggctg    2040
atgctttgaa catctctttg ctgcccaatc cattagcgac agtaggattt ttcaaccctg    2100
gtatgaatag acagaaccct atccagtgga aggagaattt aataaagata gtgcagaaag    2160
aattccttag gtaatctata actaggacta ctcctggtaa cagtaataca ttccattgtt    2220
ttagtaacca gaaatcttca tgcaatgaaa aatactttaa ttcatgaagc ttactttttt    2280
ttttttggtg tcagagtctc gctcttgtca cccaggctgg aatgcagtgg cgccatctca    2340
gctcactgca accttccatc ttcccaggtt caagcgattc tcgtgcctcg gcctcctgag    2400
tagctgggat tacaggcgtg tgcactacac tcaactaatt tttgtatttt taggagagac    2460
ggggtttcac ctgttggcca ggctggtctc gaactcctga cctcaagtga ttcacccacc    2520
ttggcctcat aaacctgttt tgcagaactc atttattcag caaatattta ttgagtgcct    2580
accagatgcc agtcaccgca caaggcactg ggtatatggt atcccaaac aagagacata    2640 atcccggtcc ttaggtactg ctagtgtggt ctgtaatatc ttactaaggc ctttggtata    2700
cgacccagag ataacacgat gcgtatttta gttttgcaaa gaaggggttt ggtctctgtg    2760
ccagctctat aattgttttg ctacgattcc actgaaactc ttcgatcaag ctactttatg    2820
taaatcactt cattgtttta aaggaataaa cttgattata ttgttttttt atttggcata    2880
actgtgattc tttaggaca attactgtac acattaaggt gtatgtcaga tattcatatt    2940
gacccaaatg tgtaatattc cagttttctc tgcataagta attaaaatat acttaaaaat    3000
taatagtttt atctgggtac aaataaacag tgcctgaact agttcacaga caagggaaac    3060
ttctatgtaa aaatcactat gatttctgaa ttgctatgtg aaactacaga tctttggaac    3120
actgtttagg tagggtgtta agacttgaca cagtacctcg tttctacaca gagaaagaaa    3180
tggccatact tcaggaactg cagtgcttat gagggatat ttaggcctct tgaattttg    3240 atgtagatgg gcattttttt aaggtagtgg ttaattacct ttatgtgaac tttgaatggt    3300
ttaacaaaag atttgttttt gtagagattt taaaggggga gaattctaga ataaatgtt    3360 acctaattat tacagcctta aagacaaaaa tccttgttga agttttttta aaaaagact    3420 aaattacata gacttaggca ttaacatgtt tgtggaagaa tatagcagac gtatattgta    3480
tcatttgagt gaatgttccc aagtaggcat tctaggctct atttaactga gtcacactgc    3540
ataggaattt agaacctaac ttttataggt tatcaaaact gttgtcacca ttgcacaatt    3600
ttgtcctaat atatacatag aaactttgtg gggcatgtta agttacagtt tgcacaagtt    3660
catctcattt gtattccatt gatttttttt tttcttctaa acattttttc ttcaaaacag    3720
tatatataac ttttttttagg ggatttttt tagacagcaa aaaactatct gaagatttcc    3780
atttgtcaaa aagtaatgat ttcttgataa ttgtgtagtg aatgttttt agaacccagc    3840 agttaccttg aaagctgaat ttatatttag taacttctgt gttaatactg gatagcatga    3900
attctgcatt gagaaactga atagctgtca taaaatgctt ctttcctaa agaaagatac    3960 tcacatgagt tcttgaagaa tagtcataac tagattaaga tctgtgtttt agtttaatag    4020
```

```
tttgaagtgc ctgtttggga taatgatagg taatttagat gaatttaggg gaaaaaaaag    4080
ttatctgcag ttatgttgag ggcccatctc tcccccaca ccccacaga gctaactggg       4140 ttacagtgtt ttatccgaaa gtttccaatt cc                                    4172

<210> SEQ ID NO 61
<211> LENGTH: 238
<212> TYPE: DNA
<213> ORGANISM: Homo sapiens

<400> SEQUENCE: 61
ccattgtgct ggaaaggcgc gcaacggcgg cgacggcggc gaccccaccg cgcatcctgc      60
caggcctccg cgcccagccg cccacgcgcc cccgcgcccc gcgccccgac cctttcttcg    120 cgccccccgcc cctcggcccg ccaggccccc ttgccggcca cccgccaggc cccgcgccgg    180
cccgcccgcc gcccaggacc ggcccgcgcc ccgcaggccg ccgccgccc gcgccgcc       238

<210> SEQ ID NO 62
<211> LENGTH: 547
<212> TYPE: DNA
<213> ORGANISM: Homo sapiens

<400> SEQUENCE: 62
ggccccgcag ctctggccac agggacctct gcagtgcccc ctaagtgacc cggacacttc      60
cgagggggcc atcaccgcct gtgtatataa cgtttccggt attactctgc tacacgtagc    120 cttttttactt ttggggtttt gttttttgttc tgaactttcc tgttacctt tcagggctga    180 tgtcacatgt aggtggcgtg tatgagtgga gacgggcctg ggtcttgggg actggagggc    240
aggggtcctt ctgcccctgg ggtcccaggg tgctctgcct gctcagccag gcctctcctg    300
ggagccactc gcccagagac tcagcttggc caacttgggg ggctgtgtcc acccagcccg    360
cccgtcctgt gggctgcaca gctcaccttg ttccctcctg ccccggttcg agagccgagt    420
ctgtgggcac tctctgcctt catgcacctg tcctttctaa cacgtcgcct tcaactgtaa    480
tcacaacatc ctgactccgt catttaataa agaaggaaca tcaggcatgc taaaaaaaaa    540
aaaaaaa                                                              547

<210> SEQ ID NO 63
<211> LENGTH: 102
<212> TYPE: DNA
<213> ORGANISM: Homo sapiens

<400> SEQUENCE: 63
gaattccggc aaacatgagg cagctgccag ccggcctggg cagtcttgtc tgcctcggct      60
gtgaagtggg gaggctggca acagttttct tcagcgccca gg                      102

<210> SEQ ID NO 64
<211> LENGTH: 2017
<212> TYPE: DNA
<213> ORGANISM: Homo sapiens

<400> SEQUENCE: 64
gacacgtcca aaggagtgca tggccacagc cacctccacc cccaagaaac ctccatcctg      60
ccaggagcag cctccaagaa acttttaaaa aatagatttg caaaaagtga acagattgct    120
acacacacac acacacacac acacacacac acacacagcc attcatctgg gctggcagag    180
gggacagagt tcaggagggg gctgagtctg ctaggggcc gagtcagag gccccagcca    240 gcccttccca ggccagcgag gcgaggctgc ctctgggtga gtggctgaca gagcaggtct    300
```

```
gcaggccacc agctgctgga tgtcaccaag aagggctcg agtgccctgc aggagggtcc      360
aatcctccgg tcccacctcg tcccgttcat ccattctgct ttcttgccac acagtggccg      420
gcccaggctc ccctggtctc ctccccgtag ccactctctg cccactacct atgcttctag      480
aaagcccctc acctcaggac cccagaggac cagctggggg caggggggga gaggggtaa       540 tggaggccaa gcctgcagct ttctggaaat tcttccctgg ggtcccagt atcccctgct       600 actccactga cctggaagag ctgggtacca ggccacccac tgtggggcaa gcctgagtgg      660
tgagggccca ctggcatcat tctccctcca tggcaggaag gcgggggatt tcaagtttag      720
ggattgggtc gtggtggaga atctgagggc actctgccag ctccacaggt ggatgagcct      780
ctccttgccc cagtcctggt tcagtgggaa tgcagtgggt ggggctgtac acaccctcca      840
gcacagactg ttccctccaa ggtcctctta ggtcccgggg aggaacgtgg ttcagagact      900
ggcagccagg gagcccgggg cagagctcag aggagtctgg aaggggcgt gtccctcctc       960 ttcctgtagt gcccctccca tggcccagca gcttggctga ccccctctcc tgaagcagct     1020
gtgcgccgtc cctctgcctt gcacaaaaag cacaagacat tccttagcag ctcagcgcag     1080
ccctagtggg agcccagcac actgcttctc ggaggccagg ccctcctgct ggctgagctt     1140
gggcccggtg gccccaatat ggtggccctg gggaagaggc cttgggggtc tgctctgtgc     1200
ctgggatcag tggggcccca aagcccagcc cggctgacca acattcaaaa gcacaaaccc     1260
tggggactct gcttggctgt cccctccatc tggggatgga gaatgcagcc caaagctgga     1320
gccaatggtg agggctgaga gggctgtggc tgggtggtca gcagaaaccc caggaggaga     1380
gagatgctgc tcccgcctga ttggggcctc acccagaagg aacccggtcc cagccgcatg     1440
gcccctccag gaacattccc acataataca ttccatcaca gccagccag ctccactcag      1500 ggctggcccg gggagtcccc gtgtgcccca agaggctagc cccagggtga gcagggccct     1560
cagaggaaag gcagtatggc ggaggccatg ggggcccctc ggcattcaca cacagcctgg     1620
cctcccctgc ggagctgcat ggacgcctgg ctccaggctc caggctgact ggggcctctg     1680
cctccaggag ggcatcagct ttccctggct cagggatctt ctccctcccc tcacccgctg     1740
cccagccctc ccagctgatg tcactctgcc tctaagccaa ggcctcagga gagcatcacc     1800
accacaccct gcggccttgc cttggggcca gactggctgc acagcccaac caggaggggt     1860
ctgcctccca cgctgggaca cagaccggcc gcatgtctgc atggcagaag cgtctccctt     1920
gccacggcct gggagggtgg ttcctgttct cagcatccac taatattcag tcctgtatat     1980
tttaataaaa taaacttgac aaaggaaaaa aaaaccg                             2017

<210> SEQ ID NO 65
<211> LENGTH: 97
<212> TYPE: DNA
<213> ORGANISM: Homo sapiens

<400> SEQUENCE: 65
gtccaggaac tcctcagcag cgcctccttc agctccacag ccagacgccc tcagacagca       60
aagcctaccc ccgcgccgcg ccctgccccgc cgctgcg                                97

<210> SEQ ID NO 66
<211> LENGTH: 1474
<212> TYPE: DNA
<213> ORGANISM: Homo sapiens

<400> SEQUENCE: 66
```

```
aagtctaatg atcatattta tttatttata tgaaccatgt ctattaattt aattatttaa    60
taatatttat attaaactcc ttatgttact taacatcttc tgtaacagaa gtcagtactc   120
ctgttgcgga gaaggagtc atacttgtga agactttat gtcactactc taaagatttt    180
gctgttgctg ttaagtttgg aaaacagttt ttattctgtt ttataaacca gagagaaatg   240
agttttgacg tctttttact tgaatttcaa cttatattat aaggacgaaa gtaaagatgt   300
ttgaatactt aaacactatc acaagatgcc aaaatgctga agttttttac actgtcgatg   360
tttccaatgc atcttccatg atgcattaga agtaactaat gtttgaaatt ttaaagtact   420
tttgggtatt tttctgtcat caaacaaaac aggtatcagt gcattattaa atgaatattt   480
aaattagaca ttaccagtaa tttcatgtct actttttaaa atcagcaatg aaacaataat   540
ttgaaatttc taaattcata gggtagaatc acctgtaaaa gctgtttga tttcttaaag    600 ttattaaact tgtacatata ccaaaaagaa gctgtcttgg atttaaatct gtaaaatcag   660
atgaaatttt actacaattg cttgttaaaa tattttataa gtgatgttcc ttttcacca    720 agagtataaa cctttttagt gtgactgtta aaacttcctt ttaaatcaaa atgccaaatt   780
tattaaggtg gtggagccac tgcagtgtta tctcaaaata agaatatcct gttgagatat   840
tccagaatct gtttatatgg ctggtaacat gtaaaaaccc cataacccg ccaaaagggg    900 tcctacccctt gaacataaag caataaccaa aggagaaaag cccaaattat tggttccaaa   960
tttagggttt aaactttttg aagcaaactt ttttttagcc ttgtgcactg cagacctggt   1020
actcagattt tgctatgagg ttaatgaagt accaagctgt gcttgaataa cgatatgttt   1080
tctcagattt tctgttgtac agtttaattt agcagtccat atcacattgc aaaagtagca   1140
atgacctcat aaaataccctc ttcaaaatgc ttaaattcat ttcacacatt aattttatct   1200
cagtcttgaa gccaattcag taggtgcatt ggaatcaagc ctggctacct gcatgctgtt   1260
ccttttcttt tcttcttttta gccatttttgc taagagacac agtcttctca aacacttcgt   1320 ttctccctatt ttgttttact agttttaaga tcagagttca cttttctttgg actctgccta   1380 tattttctta cctgaacttt tgcaagtttt caggtaaacc tcagctcagg actgctattt   1440
agctcctctt aagaagatta aaaaaaaaaa aaaa                              1474

<210> SEQ ID NO 67
<211> LENGTH: 99
<212> TYPE: DNA
<213> ORGANISM: Homo sapiens

<400> SEQUENCE: 67
gcgcccggcc cccaccccctc gcagcacccc gcgccccgcg ccctcccagc cgggtccagc    60
cggagccatg gggccggagc cgcagtgagc accatggag                            99

<210> SEQ ID NO 68
<211> LENGTH: 614
<212> TYPE: DNA
<213> ORGANISM: Homo sapiens

<400> SEQUENCE: 68
tgaaccagaa ggccaagtcc gcagaagccc tgatgtgtcc tcagggagca gggaaggcct    60
gacttctgct ggcatcaaga ggtgggaggg ccctccgacc acttccaggg gaacctgcca   120
tgccaggaac ctgtcctaag gaaccttcct tcctgcttga gttcccagat ggctggaagg   180
ggtccagcct cgttggaaga ggaacagcac tgggagtct ttgtggattc tgaggccctg    240
cccaatgaga ctctagggtc cagtggatgc cacagcccag cttggcccctt tccttccaga   300
```

-continued

```
tcctgggtac tgaaagcctt agggaagctg gcctgagagg ggaagcggcc ctaagggagt    360
gtctaagaac aaaagcgacc cattcagaga ctgtccctga aacctagtac tgcccccat     420 gaggaaggaa cagcaatggt gtcagtatcc aggctttgta cagagtgctt ttctgtttag    480
tttttacttt ttttgttttg ttttttttaaa gacgaaataa agacccaggg gagaatgggt  540
gttgtatggg gaggcaagtg tgggggtcc ttctccacac ccactttgtc catttgcaaa    600
tatattttgg aaaa                                                      614
```

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Primer 1
      for amplify VEGF 5'UTR

<400> SEQUENCE: 69

```
aaagtcgacg taatcgcgga ggcttgggc agccgg                               35
```

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Primer 2
      for amplify VEGF 5'UTR

<400> SEQUENCE: 70

```
tttgcgactg gtcagctgcg ggatcccaag                                     30
```

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Primer 3
      for amplify VEGF 5'UTR

<400> SEQUENCE: 71

```
aagtcgacgt aagagctcca gagagaagtc gag                                 33
```

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence: Primer 4
      for amplify VEGF 5'UTR

<400> SEQUENCE: 72

```
aaacccgggc agcaaggcaa ggctccaatg cac                                 33
```

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Primer 5
      for amplify VEGF 3'UTR

<400> SEQUENCE: 73

```
gccgggcagg aggaaggagc ctccctcagg gtttgggga                           39
```

```
<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Primer 6
      for amplify VEGF 3'UTR

<400> SEQUENCE: 74
ctgcactaga gacaaagacg tgatgttaat                                  30

<210> SEQ ID NO 75
<211> LENGTH: 66
<212> TYPE: DNA
<213> ORGANISM: Artificial Sequence
<220> FEATURE:
<223> OTHER INFORMATION: Description of Artificial Sequence: Polylinker

<400> SEQUENCE: 75
gaacaaatgt cgacgggggc ccctaggaga tctagcgctg gatccccgg ggagctcaug  60 gaagac                                                            66

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Primer for
      luciferase amplification

<400> SEQUENCE: 76
cggtgttggg cgcgttattt atcggagttg                                  30

<210> SEQ ID NO 77
<211> LENGTH: 30
<212> TYPE: DNA
<213> ORGANISM: Artificial Sequence
<220> FEATURE:
<223> OTHER INFORMATION: Description of Artificial Sequence: Primer for
      luciferase amplification

<400> SEQUENCE: 77
ttggcgaaga atgaaaatag ggttggtact                                  30

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Primer for
      GAPDH amplification

<400> SEQUENCE: 78
ggtgaaggtc ggagtcaacg ga                                          22

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Primer for
      GAPDH amplification

<400> SEQUENCE: 79
gagggatctc gctcctggaa g                                           21
```

```
<210> SEQ ID NO 80
<211> LENGTH: 55
<212> TYPE: DNA
<213> ORGANISM: Artificial Sequence
<220> FEATURE:
<223> OTHER INFORMATION: Description of Artificial Sequence: 5'UTR
      forward oligo

<400> SEQUENCE: 80
aaagtcgacg taaccgccag atttgaatcg cgggacccgt tggcagaggt ggcgg        55

<210> SEQ ID NO 81
<211> LENGTH: 54
<212> TYPE: DNA
<213> ORGANISM: Artificial Sequence
<220> FEATURE:
<223> OTHER INFORMATION: Description of Artificial Sequence: 5'UTR
      reverse oligo

<400> SEQUENCE: 81
aaaggatccg ggcaacgtcg gggcacccat gccgccgccg ccacctctgc caac         54

<210> SEQ ID NO 82
<211> LENGTH: 40
<212> TYPE: DNA
<213> ORGANISM: Artificial Sequence
<220> FEATURE:
<223> OTHER INFORMATION: Description of Artificial Sequence: 3'UTR
      forward oligo

<400> SEQUENCE: 82
aaagcggccg cggcctctgc cggagctgcc tggtcccaga                         40

<210> SEQ ID NO 83
<211> LENGTH: 37
<212> TYPE: DNA
<213> ORGANISM: Artificial Sequence
<220> FEATURE:
<223> OTHER INFORMATION: Description of Artificial Sequence: 3'UTR
      reverse oligo

<400> SEQUENCE: 83
aaatctagac tcaggaacag ccgagatgac ctccaga                            37

<210> SEQ ID NO 84
<211> LENGTH: 67
<212> TYPE: DNA
<213> ORGANISM: Artificial Sequence
<220> FEATURE:
<223> OTHER INFORMATION: Description of Artificial Sequence: SL top
      oligonucleotide

<400> SEQUENCE: 84
ctagaagctt agggccgcgg atccgcgcgc ggttcgccgc gcgcggatcc gcggtagcaa   60
gttagtc                                                             67

<210> SEQ ID NO 85
<211> LENGTH: 68
<212> TYPE: DNA
<213> ORGANISM: Artificial Sequence
<220> FEATURE:
<223> OTHER INFORMATION: Description of Artificial Sequence: SL bottom
      oligonucleotide

<400> SEQUENCE: 85
gactaagctt gctaccgcgg atccgcgcgc ggcgaaccgc gcgcggatcc gcggccctaa   60
```

```
gcttctag                                                            68

<210> SEQ ID NO 86
<211> LENGTH: 32
<212> TYPE: DNA
<213> ORGANISM: Artificial Sequence
<220> FEATURE:
<223> OTHER INFORMATION: Description of Artificial Sequence: PCR primer
      (Sense/HindIII)

<400> SEQUENCE: 86
caagaagctt gcgcccggcc ccccacccct cg                                 32

<210> SEQ ID NO 87
<211> LENGTH: 31
<212> TYPE: DNA
<213> ORGANISM: Artificial Sequence
<220> FEATURE:
<223> OTHER INFORMATION: Description of Artificial Sequence: PCR primer
      (Antisense/NcoI)

<400> SEQUENCE: 87
agcccatggt gctcactgcg gctccggccc c                                  31

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: PCR primer
      (Sense/BglII)

<400> SEQUENCE: 88
agactctgaa ccagaaggcc aa                                            22

<210> SEQ ID NO 89
<211> LENGTH: 36
<212> TYPE: DNA
<213> ORGANISM: Artificial Sequence
<220> FEATURE:
<223> OTHER INFORMATION: Description of Artificial Sequence: PCR primer
      (Antisense/KpnI)

<400> SEQUENCE: 89
ctcggtacca gttttccaaa atatatttgc aaatgg                             36

<210> SEQ ID NO 90
<211> LENGTH: 58
<212> TYPE: DNA
<213> ORGANISM: Artificial Sequence
<220> FEATURE:
<223> OTHER INFORMATION: Description of Artificial Sequence: sense minus
      uORF HindIII primer

<400> SEQUENCE: 90
cccaagcttc gcgcccggcc ccccacccct cgcagcaccc cgcgcccgc gccctccc      58
```